US010004810B2

(12) United States Patent
Robillard et al.

(10) Patent No.: US 10,004,810 B2
(45) Date of Patent: *Jun. 26, 2018

(54) BIO-ORTHOGONAL DRUG ACTIVATION

(71) Applicant: TAGWORKS PHARMACEUTICALS B.V., Eindhoven (NL)

(72) Inventors: Marc Stefan Robillard, Eindhoven (NL); Hendricus Marie Janssen, Eindhoven (NL); Wolter Ten Hoeve, Assen (NL); Ronny Mathieu Versteegen, Helgelsom (NL)

(73) Assignee: TAGWORKS PHARMACEUTICALS B.V., Eindhoven (NL)

( * ) Notice: Subject to any disclaimer, the term of this patent is extended or adjusted under 35 U.S.C. 154(b) by 0 days. days.

This patent is subject to a terminal disclaimer.

(21) Appl. No.: 15/233,283

(22) Filed: Nov. 23, 2016

(65) Prior Publication Data

US 2017/0143840 A1    May 25, 2017

Related U.S. Application Data

(62) Division of application No. 14/117,246, filed as application No. PCT/IB2012/052445 on May 16, 2012, now Pat. No. 9,421,274.

(60) Provisional application No. 61/515,432, filed on Aug. 5, 2011, provisional application No. 61/515,458, filed on Aug. 5, 2011.

(30) Foreign Application Priority Data

May 16, 2011 (EP) ..................... 11166241
May 20, 2011 (EP) ..................... 11166942
Aug. 5, 2011 (EP) ..................... 11176736
Aug. 5, 2011 (EP) ..................... 11176741
Dec. 8, 2011 (EP) ..................... 11192572
Dec. 8, 2011 (EP) ..................... 11192577

(51) Int. Cl.
| C07D 257/08 | (2006.01) |
| C07D 237/26 | (2006.01) |
| A61K 47/48 | (2006.01) |
| C07C 33/16 | (2006.01) |
| B82Y 5/00 | (2011.01) |
| A61K 31/704 | (2006.01) |
| A61K 38/05 | (2006.01) |
| A61K 39/395 | (2006.01) |
| A61K 47/22 | (2006.01) |
| A61K 31/435 | (2006.01) |
| A61K 31/444 | (2006.01) |
| A61K 47/54 | (2017.01) |
| A61K 47/68 | (2017.01) |

(52) U.S. Cl.
CPC ...... A61K 47/48061 (2013.01); A61K 31/435 (2013.01); A61K 31/444 (2013.01); A61K 31/704 (2013.01); A61K 38/05 (2013.01); A61K 39/3955 (2013.01); A61K 39/39558 (2013.01); A61K 47/22 (2013.01); A61K 47/545 (2017.08); A61K 47/555 (2017.08); A61K 47/6803 (2017.08); A61K 47/6897 (2017.08); B82Y 5/00 (2013.01); C07C 33/16 (2013.01); C07D 237/26 (2013.01); C07D 257/08 (2013.01)

(58) Field of Classification Search
CPC . C07D 257/02; C07D 237/268; C07D 257/08
USPC ................................ 544/179, 235
See application file for complete search history.

(56) References Cited

U.S. PATENT DOCUMENTS

| 4,486,414 A | 12/1984 | Pettit |
| 4,486,444 A | 12/1984 | Shepard |
| 4,826,964 A | 5/1989 | Acton |
| 4,879,278 A | 11/1989 | Pettit |
| 4,986,988 A | 1/1991 | Pettit |
| 5,138,036 A | 8/1992 | Pettit |
| 5,198,560 A | 3/1993 | Kadow |
| 5,410,024 A | 4/1995 | Pettit |
| 5,504,191 A | 4/1996 | Pettit |

(Continued)

FOREIGN PATENT DOCUMENTS

| WO | 2010051530 A2 | 5/2010 |
| WO | 2010119382 A1 | 10/2010 |

(Continued)

OTHER PUBLICATIONS

Haun, Jered B. et al , "Bioorthogonal Chemistry Amplifies Nanoparticle Binding and Enhances the Sensitivity of Cell Detection", Nature Nanotechnology, vol. 5, Sep. 2010, pp. 660-665.
Rossin, Raffaella, et al "In vivo Chemistry for Pretargeted Tumor Imaging in Live Mice", Bioorganic Chemistry, Angewandte Chemie (INT ED) vol. 49, 2010, pp. 3375-3378.
Wolff Manfred E. "Burger's Medicinal Chemistry 5ed Part 1", John Wiley & Sons 1995, p. 975-977.
Banker G.S. et al "Modern Pharmaceutices 3ed", Marcel Dekker , NY 1996, p. 451 and 596.
Senter, P .D. et al. "Antibody-drug conjugates: targeted drug delivery for cancer." Current Opinion in Chemical Biology, (2010), 14:529-537.
Klopman, G. et al. "Computer automated log P calculations based on an extended group contribution approach". Journal Chem. Inf. Comput. Sci. (1994), 34, 752-781.

(Continued)

Primary Examiner — Venkataraman Balasubramanian
(74) Attorney, Agent, or Firm — Lucas & Mercanti, LLP

(57) ABSTRACT

The invention relates to a Prodrug activation method, for therapeutics, wherein use is made of abiotic reactive chemical groups that exhibit bio-orthogonal reactivity towards each other. The invention also relates to a Prodrug kit comprising at least one Prodrug and at least one Activator, wherein the Prodrug comprises a Drug and a first Bio-orthogonal Reactive Group (the Trigger), and wherein the Activator comprises a second Bio-orthogonal Reactive Group. The invention also relates to targeted therapeutics used in the above-mentioned method and kit. The invention particularly pertains to antibody-drug conjugates and to bi- and trispecific antibody derivatives.

4 Claims, 6 Drawing Sheets

(56) References Cited

U.S. PATENT DOCUMENTS

| | | | |
|---|---|---|---|
| 5,521,284 | A | 5/1996 | Pettit |
| 5,530,097 | A | 6/1996 | Pettit |
| 5,599,902 | A | 2/1997 | Pettit |
| 5,635,483 | A | 6/1997 | Pettit |
| 5,663,149 | A | 9/1997 | Pettit |
| 5,665,860 | A | 9/1997 | Pettit |
| 5,780,588 | A | 7/1998 | Pettit |
| 6,034,065 | A | 3/2000 | Pettit |
| 6,239,104 | B1 | 5/2001 | Pettit |
| 6,323,315 | B1 | 11/2001 | Pettit |
| 9,421,274 | B2 * | 8/2016 | Robillard ......... A61K 47/48746 |
| 2009/0023916 | A1 | 1/2009 | Fox |

FOREIGN PATENT DOCUMENTS

| | | |
|---|---|---|
| WO | 2010119389 A2 | 10/2010 |
| WO | 2012049624 A1 | 4/2012 |
| WO | 2012085789 A1 | 6/2012 |

OTHER PUBLICATIONS

Thakur, A. et al. "Cancer therapy with bispecific antibodies: Clinical experience". Current Opinion in Molecular Therapeutics, (2010), 12(3), 340-349.
Thalhammer, F. et al. "Reaktivitat Einfacher Offenkettiger Und Cyclischer Dienophile Bei Diels-alder-reaktionen mil inversem elektronenbedarf". Tetrahedron Letters (1990), 31 (47), 6851-6854.
Wijnen, J.W. et al. "Substitute effects on an inverse electron demand hetero diels-alder reaction in aqueous solution and organic solvents: cycloaddition of substituted styrenes to Di(2-pyridyl)-1,2,4,5-tetrazine". Journal of Organic D Chemistry, (1996), 61, 2001-2005.
Blackman, M.L. et al. "The tetrazine ligation: fast bioconjugation based on inverse-electron-demand Diels-Alder reactivity". Journal of American Chemical Society, (2008), 130(41), 13518-13519.
Rossin, R. et al. "In vivo chemistry for pretargeted tumor imaging in live mice". Angewandte Chemie International Edition, (2010), 49, 3375-3378.
Devaraj, N.K. et al. "Fast and sensitive pretargeted labeling of cancer cells via tetrazine/trans-cyclooctene cycloaddition". Angewandte Chemie International Edition, (2009), 48(38): 7013-1016.
Devaraj, N.K. et al. Angewandte Chemie International Edition (2009), 48, 1-5.
Tranoy-Opalinski, I. et al. "Design of self-Immolative linkers for tumour activated prodrug therapy". Anti-Cancer Agents in Medicinal Chemistry, (2008), 8, 618-637.
Greenwald, RB. et al. "Drug delivery systems employing 1,4-or 1,6-elimination: Poly( ethylene glycol) prodrugs of amine-containing compounds". Journal Med. Chem. (1999), 42, 3657-3667.
Blencowe, CA et al. "Self-immolative linkers in polymeric delivery systems". Polymer Chemistry, (2011 ), 2, 773-790.
Gere, V. et al. "Olefin Inversion. Protection of the sulfide function in the stereospecific synthesis of trans-Thiacyclooct-4-ene". Journal of Organic Chemistry, (1980), 45, 261-264.
Prevost, M. et al. "Insertions of silylenes into vinyl epoxides: Diastereoselective synthesis of functionalized, optically active trans-Dioxasilacyclooctenes". Journal of the American Chemical Society, (2009), 131, 14182-14182.
Devaraj, N.K. et al. "Tetrazine-based cycloadditions: Application to Pretargeted live cell imaging". Bioconjugate Chem., (2008), 19(12), 2297-2299.
Geldard, J.F. et al. "The organic chemistry of a new weak field tridentate chelating agent. 3,5-Di(2-pyridyl)-1,2,4-triazole". Journal Organic Chemistry. (1965), 30, 318-319.
Grakauskas, VA et al. "Some 3,6-unsymmetrically disubstituted 1,2,4,5-Tetrazines". Journal American Chemical Society, (1958), 80, 3155-3159.
Audebert, P. et al. "Synthesis of new substituted tetrazines: electrochemical and spectroscopic properties". New Journal Chem. (2004), 28, 387-392.
Kaim, W. et al. "The new tetrafunctional (pi) acceptor ligand 3,6-Bis(2'-pyrimidyl)-1,2,4,5-tetrazine(bmtz): Diruthenium complexes of bmtz and of its 1,4-Dihydro form". Z. Naturforsch, 50b, 123-127 (1995).
Choe, Y.H. et al. "Anticancer drug delivery systems: multi-loaded N4-acyl poly( ethylene glycol) prodrugs of ara-C. II. Efficacy in ascites and solid tumors". Journal of Controlled Release, (2002), 79, 55-70.
Haba, K. et al. "Single-triggered trimeric prodrugs". Angewandte Chemie International Edition. (2005), 44, 726-730.
Whitham, G.H. et al. "trans-Cycloalkenes. Part II. Application of the Dioxolan Olefin Synthesis to the Stereospecific Formation of trans-Cyclo-octene Derivatives. (1 SR,2RS)-Irans-Cyclo-oct-2-en-1-ol". Journal Chem. Society, (1971 ), D 886-890.
Whitham, G.H. et al. "trans-Cycloalkenes. Part I. (1 RS,2RS)-Irans-Cyclo-oct-2-en-1-ol". Journal Chem. Society, (1971 ), 883-886.
Whitham, G.H. et al. "trans-Cycloalkenes. Part III. Stereochemistry and Mechanism of Some Reactions of Diastereoisomeric 3-Substituted trans-Cyclo-octenes". Journal Chem. Society, (1971 ), 891-896.
Ingold, C.K. et al. "The Nature of the Alternating effect in carbon chains. Part XXII. An attempt further to define !eh probable mechanism of orientation in aromatic substitution". Journal Chem. Society. (1927), 2918-2926.
Mohsin, H. et al. "Radiolanthanide-labeled monoclonal antibody CC49 for radioimmunotherapy of cancer: biological comparison of DOTA conjugates and 149Pm, 166Ho, and 177Lu". Bioconjugate Chem. (2006), 17, 485-492.
Thompson, S. et al. "The construction and in vitro testing of photo-activalable cancer targeting folaled anti-CD3 conjugates". Biochemical and Biophysical Research Communications, (2008), 366, 526-531.
Brakel, van, R. et al. "A doxorubicin prodrug activated by the staudinger reaction". Bioconujugate Chem. (2008), 19, 714-718.
Viswanadhan, V.N. et al. "Atomic physicochemical parameters for three dimensional structure directed quantitative structure-activity relationships. 4. Additional parameters for hydrophobic and dispersive interactions and their application for an automated superposition of certain naturally occuring nucleoside antibiotics". Journal Chem. Inf. D Comput. Sci. (1989), 29, 163-172.

* cited by examiner

Scheme 1

Scheme 2

BIO-ORTHOGONAL DRUG ACTIVATION

CROSS-REFERENCE TO PRIOR APPLICATIONS

This application is a divisional of U.S. application Ser. No. 14/117,246 filed Nov. 12, 2013 which is the U.S. National Phase application under 35 U.S.C. § 371 of International Application No. PCT/IB2012/052445, filed on May 16, 2012, which claims the benefit of U.S. Provisional Patent Application No. 61/515,432, filed on Aug. 5, 2011; U.S. Provisional Patent Application No. 61/515,458, filed on Aug. 5, 2011; European Patent Application No. 11166241.7, filed on May 16, 2011; European Patent Application No. 11166942.0, filed on May 20, 2011; European Patent Application No. 11176741.4, filed on Aug. 5, 2011; European Patent Application No. 11176736.4, filed on Aug. 5, 2011; European Patent Application No. 11192572.3, filed on Dec. 8, 2011 and European Patent Application No. 11192577.2, filed on Dec. 8, 2011. All of these applications are hereby incorporated by reference herein.

FIELD OF THE INVENTION

The invention relates to therapeutical methods on the basis of inactivated drugs, such as prodrugs, that are activated by means of an abiotic, bio-orthogonal chemical reaction.

BACKGROUND OF THE INVENTION

In the medical arena the use of inactive compounds such as prodrugs which are activated in a specific site in the human or animal body is well known. Also targeted delivery of inactives such as prodrugs has been studied extensively. Much effort has been devoted to drug delivery systems that effect drug release selectivity at a target site and/or at a desired moment in time. One way is to selectively activate a (systemic) prodrug specifically by local and specific enzymatic activity. However, in many cases a target site of interest lacks a suitable overexpressed enzyme. An alternative is to transport an enzyme to target tissue via a technique called antibody-directed enzyme prodrug therapy (ADEPT). In this approach an enzyme is targeted to a tumor site by conjugation to an antibody that binds a tumor-associated antigen. After systemic administration of the conjugate, its localization at the target and clearance of unbound conjugate, a designed prodrug is administered systemically and locally activated. This method requires the catalysis of a reaction that must not be accomplished by an endogenous enzyme. Enzymes of non-mammalian origin that meet these needs are likely to be highly immunogenic, a fact that makes repeated administration impossible. Alternatively, prodrugs can be targeted to a disease site followed by disease-specific or -non-specific endogenous activation processes (eg pH, enzymes, thiol-containing compounds).

Targeted anticancer therapeutics are designed to reduce nonspecific toxicities and increase efficacy relative to conventional cancer chemotherapy. This approach is embodied by the powerful targeting ability of monoclonal antibodies (mAbs) to specifically deliver highly potent, conjugated small molecule therapeutics to a cancer cell. In an attempt to address the issue of toxicity, chemotherapeutic agents (drugs) have been coupled to targeting molecules such as antibodies or protein receptor ligands that bind with a high degree of specificity to tumor cell to form compounds referred to as antibody-drug conjugates (ADC) or immunoconjugates. Immunoconjugates in theory should be less toxic because they direct the cytotoxic drug to tumors that express the particular cell surface antigen or receptor. This strategy has met limited success in part because cytotoxic drugs tend to be inactive or less active when conjugated to large antibodies, or protein receptor ligands. Promising advancements with immunoconjugates has seen cytotoxic drugs linked to antibodies through a linker that is cleaved at the tumor site or inside tumor cells (Senter et al, Current Opinion in Chemical Biology 2010, 14:529-537). Ideally, the mAb will specifically bind to an antigen with substantial expression on tumor cells but limited expression on normal tissues. Specificity allows the utilization of drugs that otherwise would be too toxic for clinical application. Most of the recent work in this field has centered on the use of highly potent cytotoxic agents. This requires the development of linker technologies that provide conditional stability, so that drug release occurs after tumor binding, rather than in circulation.

As a conjugate the drug is inactive but upon target localization the drug is released by eg pH or an enzyme, which could be target specific but may also be more generic. The drug release may be achieved by an extracellular mechanism such as low pH in tumor tissue, hypoxia, certain enzymes, but in general more selective drug release can be achieved through intracellular, mostly lysosomal, release mechanisms (e.g. glutathione, proteases, catabolism) requiring the antibody conjugate to be first internalized. Specific intracellular release mechanisms (eg glutathione, cathepsin) usually result in the parent drug, which depending on its properties, can escape the cell and attack neighboring cells. This is viewed as an important mechanism of action for a range of antibody-drug conjugates, especially in tumors with heterogeneous receptor expression, or with poor mAb penetration. Examples of cleavable linkers are: hydrazones (acid labile), peptide linkers (cathepsin B cleavable), hindered disulfide moieties (thiol cleavable). Also non-cleavable linkers can be used in mAb-drug conjugates. These constructs release their drug upon catabolism, presumably resulting in a drug molecule still attached to one amino acid. Only a subset of drugs will regain their activity as such a conjugate. Also, these aminoacid-linked drugs cannot escape the cells. Nevertheless, as the linker is stable, these constructs are generally regarded as the safest and depending on the drug and target, can be very effective.

The current antibody-drug conjugate release strategies have their limitations. The extracellular drug release mechanisms are usually too unspecific (as with pH sensitive linkers) resulting in toxicity. Intracellular release depends on efficient (e.g receptor-mediated internalization) of the mAb-drug, while several cancers lack cancer-specific and efficiently internalizing targets that are present in sufficiently high copy numbers. Intracellular release may further depend on the presence of an activating enzyme (proteases) or molecules (thiols such as glutathione) in sufficiently high amount. Following intracellular release, the drug may, in certain cases, escape from the cell to target neighbouring cells. This effect is deemed advantageous in heterogeneous tumors where not every cell expresses sufficiently high amounts of target receptor. It is of further importance in tumors that are difficult to penetrate due e.g. to elevated interstitial pressure, which impedes convectional flow. This is especially a problem for large constructs like mAb (conjugates). This mechanism is also essential in cases where a binding site barrier occurs. Once a targeted agent leaves the vasculature and binds to a receptor, its movement within the tumor will be restricted. The likelihood of a mAb conjugate being restricted in the perivascular space scales with its affinity for its target. The penetration can be improved by increasing the mAb dose, however, this approach is limited by dose limiting toxicity in e.g. the liver. Further, antigens that are shed from dying cells can be present in the tumor interstitial space where they can prevent mAb-conjugates of binding their target cell. Also, many targets are hampered by ineffective internalization, and different drugs cannot be linked to a mAb in the same way. Further, it has been proven cumbersome to design linkers to be selectively cleavable by endogenous elements in the target while stable to endogenous elements en route to the target (especially the case for slow clearing full mAbs). As a result, the optimal drug, linker, mAb, and target combination needs to be selected and optimized on a case by case basis.

Another application area that could benefit from an effective prodrug approach is the field of T-cell engaging antibody constructs (e.g., bi- or trispecific antibody fragments), which act on cancer by engaging the immune system. It has long been considered that bringing activated T-cells into direct contact with cancer cells offers a potent way of killing them (Thompson et al., Biochemical and Biophysical Research Communications 366 (2008) 526-531). Of the many bispecific antibodies that have been created to do this, the majority are composed of two antibody binding sites, one site targets the tumor and the other targets a T-cell (Thakur et al. Current Opinion in Molecular Therapeutics 2010, 12(3), 340-349). However, with bispecific antibodies containing an active T-cell binding site, peripheral T-cell binding will occur. This not only prevents the conjugate from getting to the tumor but can also lead to cytokine storms and T-cell depletion. Photo-activatable anti-T-cell antibodies, in which the anti-T-cell activity is only restored when and where it is required (i.e. after tumor localization via the tumor binding arm), following irradiation with UV light, has been used to overcome these problems. Antihuman CD3 (T-cell targeting) antibodies could be reversibly inhibited with a photocleavable 1-(2-nitrophenyl)ethanol (NPE) coating (Thompson et al., Biochemical and Biophysical Research Communications 366 (2008) 526-531). However, light based activation is limited to regions in the body where light can penetrate, and is not easily amendable to treating systemic disease such as metastatic cancer.

Strongly related constructs that could benefit from a prodrug approach are trispecific T-cell engaging antibody constructs with for example a CD3- and a CD28 T-cell engaging moiety in addition to a cancer targeting agent. Such constructs are too toxic to use as such and either the CD3 or the CD28 or both binding domains need to be masked.

It is desirable to be able to activate targeted drugs selectively and predictably at the target site without being dependent on homogenous penetration and targeting, and on endogenous parameters which may vary en route to and within the target, and from indication to indication and from patient to patient.

In order to avoid the drawbacks of current prodrug activation, it has been proposed in Bioconjugate Chem 2008, 19, 714-718, to make use of an abiotic, bio-orthogonal chemical reaction, viz. the Staudinger reaction, to provoke activation of the prodrug. Briefly, in the introduced concept, the Prodrug is a conjugate of a Drug and a Trigger, and this Drug-Trigger conjugate is not activated endogenously by e.g. an enzyme or a specific pH, but by a controlled administration of the Activator, i.e. a species that reacts with the Trigger moiety in the Prodrug, to induce release of the Drug from the Trigger (or vice versa, release of the Trigger from the Drug, however one may view this release process). The presented Staudinger approach for this concept, however, has turned out not to work well, and its area of applicability is limited in view of the specific nature of the release mechanism imposed by the Staudinger reaction. Other drawbacks for use of Staudinger reactions are their limited reaction rates, and the oxidative instability of the phosphine components of these reactions. Therefore, it is desired to provide reactants for an abiotic, bio-orthogonal reaction that are stable in physiological conditions, that are more reactive towards each other, and that are capable of inducing release of a bound drug by means of a variety of mechanisms, thus offering a greatly versatile activated drug release method.

The use of a biocompatible chemical reaction that does not rely on endogenous activation mechanisms (eg pH, enzymes) for selective Prodrug activation would represent a powerful new tool in cancer therapy. Selective activation of Prodrugs wvhen and where required allows control over many processes within the body, including cancer. Therapies, such as anti-tumor antibody therapy, may thus be made more specific, providing an increased therapeutic contrast between normal cells and tumour to reduce unwanted side effects. In the context of T-cell engaging anticancer antibodies, the present invention allows the systemic administration and tumor targeting of an inactive antibody construct (i.e. this is then the Prodrug), diminishing off-target toxicity. Upon sufficient tumor uptake and clearance from non target areas, the tumor-bound antibody is activated by administration of the Activator, which reacts with the Trigger or Triggers on the antibody or particular antibody domain, resulting in removal of the Trigger and restoration of the T-cell binding function. This results in T-cell activation and anticancer action (i.e. this is then the Drug release).

SUMMARY OF THE INVENTION

In order to better address one or more of the foregoing desires, the present invention, in one aspect, provides the use of a Diene as an activator for the release, in a physiological environment, of a substance linked to a trans-cyclooctene. In connection herewith, the invention also pertains to a Diene for use as an activator for the release, in a physiological environment, of a substance linked to a trans-cyclooctene, and to a method for activating, in a physiological environment, the release of a substance linked to a trans-cyclooctene, wherein a Diene is used as an activator.

In another aspect, the invention presents the use of the inverse electron-demand Diels-Alder reaction between a trans-cyclooctene and a Diene as a chemical tool for the release, in a physiological environment, of a bound substance.

In a still further aspect, the invention is a kit for the administration and activation of a Prodrug, the kit comprising a Drug linked, directly or indirectly, to a Trigger moiety, and an Activator for the Trigger moiety, wherein the Trigger moiety comprises a dienophile and the Activator comprises a diene, the dienophile comprising a trans-cyclooctene ring, the ring optionally including one or more hetero-atoms, and the diene being selected so as to be capable of reacting with the dienophile in an inverse electron-demand Diels-Alder reaction. Activation of the Prodrug by the retro Diels-Alder reaction of the Trigger with the Activator leads to release of the Drug.

In another aspect, the invention presents a Prodrug comprising a Drug compound linked, directly or indirectly, to a trans-cyclooctene moiety.

In yet another aspect, the invention provides a method of modifying a Drug compound into a Prodrug that can be triggered by an abiotic, bio-orthogonal reaction, the method comprising the steps of providing a Drug and chemically linking the Drug to a trans-cyclooctene moiety.

In a still further aspect, the invention provides a method of treatment wherein a patient suffering from a disease that can be modulated by a drug, is treated by administering, to said patient, a Prodrug comprising a Trigger moiety after activation of which by administration of an Activator the Drug will be released, wherein the Trigger moiety comprises a trans-cyclooctene ring, the ring optionally including one or more hetero-atoms, and the diene Activator being selected so as to be capable of reacting with the trans-cyclooctene dienophile in an inverse electron-demand Diels-Alder reaction.

In a still further aspect, the invention is a compound comprising an eight-membered non-aromatic cyclic mono-alkenylene moiety (preferably a cyclooctene moiety, and more preferably a trans-cyclooctene moiety), said moiety comprising a linkage to a Drug, for use in prodrug therapy in an animal or a human being.

THE RETRO DIELS-ALDER REACTION

Below a reaction scheme is given for a [4+2] Diels-Alder reaction between the (3,6)-di-(2-pyridyl)-s-tetrazine diene and a trans-cylcooctene dienophile, followed by a retro Diels Alder reaction in which the product and dinitrogen is formed. The reaction product may tautomerize, and this is also shown in the scheme. Because the trans cyclooctene derivative does not contain electron withdrawing groups as in the classical Diels Alder reaction, this type of Diels Alder reaction is distinguished from the classical one, and frequently referred to as an "inverse electron demand Diels Alder reaction". In the following text the sequence of both reaction steps, i.e. the initial Diels-Alder cyclo-addition (typically an inverse electron demand Diels Alder cyclo-addition) and the subsequent retro Diels Alder reaction will be referred to in shorthand as "retro Diels Alder reaction" or "retro-DA". It will sometimes be abbreviated as "rDA" reaction. The product of the reaction is then the retro Diels-Alder adduct, or the rDA adduct.

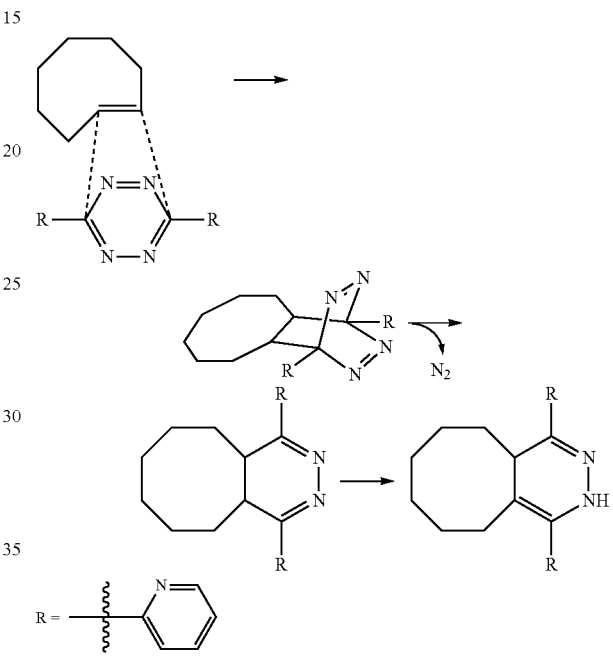

DETAILED DESCRIPTION OF THE INVENTION

In a general sense, the invention is based on the recognition that a drug can be released from trans-cyclooctene derivatives upon cyclooaddition with compatible dienes, such as tetrazine derivatives. Without wishing to be bound by theory, the inventors believe that the molecular structure of the retro Diels-Alder adduct can be such that a spontaneous elimination or cyclization reaction within this rDA adduct releases the drug. Particularly, the inventors believe that appropriately modified rDA components lead to rDA adducts wherein the bond to the drug on the dienophile is broken by the presence of a lone electron pair on the diene.

The present invention for the first time presents the use of the inverse electron-demand Diels-Alder reaction between a trans-cyclooctene and a Diene as a chemical tool for the release, in a physiological environment, of a bound substance. It will be understood, based on this description, that said substance is bound to the TCO. The invention, in this aspect, should be seen regardless of the specific chemical structure. Rather, it puts to use, in a general sense, proven bio-orthogonal chemistry, viz. the rDA reaction, for a new and unexpected purpose, viz. presenting a chemical substance, such as a drug, in a bound form in such a way that release thereof in a bio-orthogonal reaction can be triggered.

The term "using the inverse electron-demand Diels Alder reaction" should not be read in a strict sense as referring only to the stage wherein the two reaction partners for this reaction, the dienophile of which having the drug bound thereto, are brought together. Rather, it will be understood that "using the reaction" also implies that one should start with the drug being bound to one of the reaction partners (viz. the dienophile).

Figure 6:
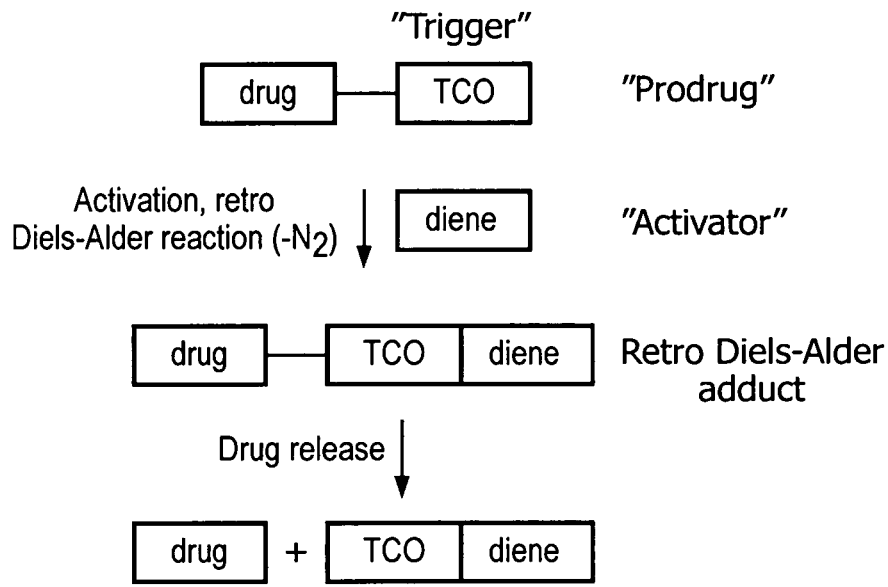
FIG. 6 illustrates the general concept of using the retro-Diels Alder reaction in prodrug activation.

The general concept of using the retro-Diels Alder reaction in Prodrug activation is illustrated in Scheme 1. See FIG. 6.

In the present invention, the term "Diene" (including the diene in the foregoing scheme) stands for a heterocyclic moiety comprising at least 2 conjugated double bonds. The Diene, as comprised in the Activator, can be part of a ring structure that comprises a third double bond, such as a tetrazine (which is a preferred Activator according to the invention.

In the foregoing scheme "TCO" stands for trans-cyclooctene. The term trans-cyclooctene is used here as possibly including one or more hetero-atoms, and particularly refers to a structure satisfying formula (1a). In a broad sense, the inventors have found that—other than the attempts made on the basis of the Staudinger reaction—the selection of a TCO as the trigger moiety for a prodrug, provides a versatile tool to render drug (active) moieties into prodrug (activatable) moieties, wherein the activation occurs through a powerful, abiotic, bio-orthogonal reaction of the dienophile (Trigger) with the diene (Activator), viz the aforementioned retro Diels-Alder reaction, and wherein the Prodrug is a Drug-dienophile conjugate.

It will be understood that in Scheme 1 in the retro Diels-Alder adduct as well as in the end product, the indicated TCO group and the indicated diene group are the residues of, respectively, the TCO and diene groups after these groups have been converted in the retro Diels-Alder reaction.

A requirement for the successful application of an abiotic bio-orthogonal chemical reaction is that the two participating functional groups have finely tuned reactivity so that interference with coexisting functionality is avoided. Ideally, the reactive partners would be abiotic, reactive under physiological conditions, and reactive only with each other while ignoring their cellular/physiological surroundings (bio-orthogonal). The demands on selectivity imposed by a biological environment preclude the use of most conventional reactions.

The inverse electron demand Diels Alder reaction, however, has proven utility in animals at low concentrations and semi-equimolar conditions (R. Rossin et al, *Angewandte Chemie Int Ed* 2010, 49, 3375-3378). The reaction partners subject to this invention are strained trans-cyclooctene (TCO) derivatives and suitable dienes, such as tetrazine derivatives. The cycloaddition reaction between a TCO and a tetrazine affords an intermediate, which then rearranges by expulsion of dinitrogen in a retro-Diels-Alder cycloaddition to form a dihydropyridazine conjugate. This and its tautomers is the retro Diels-Alder adduct.

The present inventors have come to the non-obvious insight, that the structure of the TCO, par excellence, is suitable to provoke the release of a drug linked to it, as a result of the reaction involving the double bond available in the TCO dienophile, and a diene. The features believed to enable this are (a) the nature of the rDA reaction, which involves a rearrangement of double bonds, which can be put to use in provoking an elimination cascade; (b) the nature of the rDA adduct that bears a dihydro pyridazine group that is non-aromatic (or another non-aromatic group) and that can rearrange by an elimination reaction to form conjugated double bonds or to form an (e.g. pyridazine) aromatic group, (c) the nature of the rDA adduct that may bear a dihydro pyridazine group that is weakly basic and that may therefore catalyze elimination reactions, and (d) the bicyclic nature of the rDA adduct, which allows the formation of a bridge (hence an additional ring) from the diene part of the resulting bicyclic moiety, to substituents on the TCO part of the bicyclic moiety.

It is to be emphasized that the invention is thus of a scope well beyond specific chemical structures. In a broad sense, the invention puts to use the recognition that the rDA reaction as well as the rDA adduct embody a versatile platform for enabling provoked drug release in a bioorthogonal reaction.

The fact that the reaction is bio-orthogonal, and that many structural options exist for the reaction pairs, will be clear to the skilled person. E.g., the rDA reaction is known in the art of pre-targeted medicine. Reference is made to, e.g., WO 2010/119382, WO 2010/119389, and WO 2010/051530. Whilst the invention presents an entirely different use of the reaction, it will be understood that the various structural possibilities available for the rDA reaction pairs as used in pre-targeting, are also available in the field of the present invention.

The dienophile trigger moiety used in the present invention comprises a trans-cyclooctene ring, the ring optionally including one or more hetero-atoms. Hereinafter this eight-membered ring moiety will be defined as a trans-cyclooctene moiety, for the sake of legibility, or abbreviated as "TCO" moiety. It will be understood that the essence resides in the possibility of the eight-membered ring to act as a dienophile and to be released from its conjugated drug upon reaction. The skilled person is familiar with the fact that the dienophile activity is not necessarily dependent on the presence of all carbon atoms in the ring, since also heterocyclic mono-alkenylene eight-membered rings are known to possess dienophile activity.

Thus, in general, the invention is not limited to strictly drug-substituted trans-cyclooctene. The person skilled in organic chemistry will be aware that other eight-membered ring-based dienophiles exist, which comprise the same endocyclic double bond as the trans-cyclooctene, but which may have one or more heteroatoms elsewhere in the ring. I.e., the invention generally pertains to eight-membered non-aromatic cyclic alkenylene moieties, preferably a cyclooctene moiety, and more preferably a trans-cyclooctene moiety, comprising a conjugated drug.

Other than is the case with e.g. medicinally active substances, where the in vivo action is often changed with minor structural changes, the present invention first and foremost requires the right chemical reactivity combined with an appropriate design of the drug-conjugate. Thus, the possible structures extend to those of which the skilled person is familiar with that these are reactive as dienophiles.

It should be noted that, depending on the choice of nomenclature, the TCO dienophile may also be denoted E-cyclooctene. With reference to the conventional nomenclature, it will be understood that, as a result of substitution on the cyclooctene ring, depending on the location and molecular weight of the substituent, the same cyclooctene isomer may formally become denoted as a Z-isomer. In the present invention, any substituted variants of the invention, whether or not formally "E" or "Z," or "cis" or "trans" isomers, will be considered derivatives of unsubstituted trans-cyclooctene, or unsubstituted E-cyclooctene. The terms "trans-cyclooctene" (TCO) as well as E-cyclooctene are used interchangeably and are maintained for all dienophiles according to the present invention, also in the event that substituents would formally require the opposite nomenclature. I.e., the invention relates to cyclooctene in which carbon atoms 1 and 6 as numbered below are in the E (entgegen) or trans position.

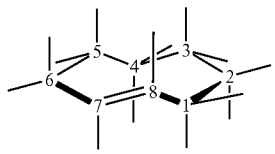

Formula (1)

The present invention will further be described with respect to particular embodiments and with reference to certain drawings but the invention is not limited thereto but only by the claims. Any reference signs in the claims shall not be construed as limiting the scope. The drawings described are only schematic and are non-limiting. In the drawings, the size of some of the elements may be exaggerated and not drawn on scale for illustrative purposes. Where an indefinite or definite article is used when referring to a singular noun e.g. "a" or "an", "the", this includes a plural of that noun unless something else is specifically stated.

It is furthermore to be noticed that the term "comprising", used in the description and in the claims, should not be interpreted as being restricted to the means listed thereafter; it does not exclude other elements or steps. Thus, the scope of the expression "a device comprising means A and B" should not be limited to devices consisting only of components A and B. It means that with respect to the present invention, the only relevant components of the device are A and B.

In several chemical formulae below reference is made to "alkyl" and "aryl." In this respect "alkyl", each independently, indicates an aliphatic, straight, branched, saturated, unsaturated and/or or cyclic hydrocarbyl group of up to ten carbon atoms, possibly including 1-10 heteroatoms such as O, N, or S, and "aryl", each independently, indicates an aromatic or heteroaromatic group of up to twenty carbon atoms, that possibly is substituted, and that possibly includes 1-10 heteroatoms such as O, N, P or S. "Aryl" groups also include "alkylaryl" or "arylalkyl" groups (simple example: benzyl groups). The number of carbon atoms that an "alkyl", "aryl", "alkylaryl" and "arylalkyl" contains can be indicated by a designation preceding such terms (i.e. $C_{1-10}$ alkyl means that said alkyl may contain from 1 to 10 carbon atoms). Certain compounds of the invention possess chiral centers and/or tautomers, and all enantiomers, diasteriomers and tautomers, as well as mixtures thereof are within the scope of the invention. In several formulae, groups or substituents are indicated with reference to letters such as "A", "B", "X", "Y", and various (numbered) "R" groups. The definitions of these letters are to be read with reference to each formula. i.e. in different formulae these letters, each independently, can have different meanings unless indicated otherwise.

In all embodiments of the invention as described herein, alkyl is preferably lower alkyl ($C_{1-4}$ alkyl), and each aryl preferably is phenyl.

Earlier work (R. Rossin et al. *Angewandte Chemie Int Ed* 2010, 49, 3375-3378) demonstrated the utility of the inverse-electron-demand Diels Alder reaction for pretargeted radioimmunoimaging. This particular cycloaddition example occurred between a (3,6)-di-(2-pyridyl)-s-tetrazine derivative and a E-cyclooctene, followed by a retro Diels Alder reaction in which the product and nitrogen is formed. Because the trans cyclooctene derivative does not contain electron withdrawing groups as in the classical Diels Alder reaction, this type of Diels Alder reaction is distinguished from the classical one, and frequently referred to as an "inverse electron demand Diels Alder reaction". In the following text the sequence of both reaction steps, i.e. the initial Diels-Alder cyclo-addition (typically an inverse electron demand Diels Alder cyclo-addition) and the subsequent retro Diels Alder reaction will be referred to in shorthand as "retro Diels Alder reaction."

Retro Diels-Alder Reaction

The Retro Diels-Alder coupling chemistry generally involves a pair of reactants that couple to form an unstable intermediate, which intermediate eliminates a small molecule (depending on the starting compounds this may be e.g. $N_2$, $CO_2$, RCN), as the sole by-product through a retro Diels-Alder reaction to form the retro Diels-Alder adduct. The paired reactants comprise, as one reactant (i.e. one Bio-orthogonal Reactive Group), a suitable diene, such as a derivative of tetrazine, e.g. an electron-deficient tetrazine and, as the other reactant (i.e. the other Bio-orthogonal Reactive Group), a suitable dienophile, such as a strained cyclooctene (TCO).

The exceptionally fast reaction of e.g. electron-deficient (substituted) tetrazines with a TCO moiety results in a ligation intermediate that rearranges to a dihydropyridazine retro Diels-Alder adduct by eliminating $N_2$ as the sole by-product in a [4+2] Retro Diels-Alder cycloaddition. In aqueous environment, the initially formed 4,5-dihydropyridazine product may tautomerize to a 1,4-dihydropyridazine product.

The two reactive species are abiotic and do not undergo fast metabolism or side reactions in vivo. They are bio-orthogonal, e.g. they selectively react with each other in physiologic media. Thus, the compounds and the method of the invention can be used in a living organism. Moreover, the reactive groups are relatively small and can be introduced in biological samples or living organisms without significantly altering the size of biomolecules therein. References on the Inverse electron demand Diels Alder reaction, and the behavior of the pair of reactive species include: Thalhammer, F; Wallfahrer, U; Sauer, J, Tetrahedron Letters, 1990, 31 (47), 6851-6854; Wijnen, J W; Zavarise, S; Engberts. JBFN, Journal Of Organic Chemistry, 1996, 61, 2001-2005; Blackman, M L; Royzen, M; Fox. J M, Journal Of The American Chemical Society, 2008, 130 (41), 13518-19), R. Rossin, P. Renart Verkerk, Sandra M. van den Bosch, R. C. M. Vulders, 1. Verel, J. Lub, M. S. Robillard, Angew Chem Int Ed 2010, 49, 3375, N. K. Devaraj, R. Upadhyay, J. B. Haun, S. A. Hilderbrand. R. Weissleder. Angew Chem Int Ed 2009, 48, 7013, and Devaraj et al., Angew. Chem. Int. Ed., 2009, 48, 1-5.

It will be understood that, in a broad sense, according to the invention the aforementioned retro Diels-Alder coupling and subsequent drug activation chemistry can be applied to basically any pair of molecules, groups, or moieties that are capable of being used in Prodrug therapy. I.e. one of such a pair will comprise a drug linked to a dienophile (the Trigger). The other one will be a complementary diene for use in reaction with said dienophile.

Trigger

The Prodrug comprises a Drug denoted as $D^D$ linked, directly or indirectly, to a Trigger moiety denoted as $T^R$, wherein the Trigger moiety is a dienophile. The dienophile, in a broad sense, is an eight-membered non-aromatic cyclic alkenylene moiety (preferably a cyclooctene moiety, and more preferably a trans-cyclooctene moiety). Optionally, the trans-cyclooctene (TCO) moiety comprises at least two exocyclic bonds fixed in substantially the same plane, and/or it optionally comprises at least one substituent in the axial position, and not the equatorial position. The person skilled in organic chemistry will understand that the term "fixed in substantially the same plane" refers to bonding theory according to which bonds are normally considered to be fixed in the same plane. Typical examples of such fixations in the same plane include double bonds and strained fused rings. E.g., the at least two exocyclic bonds can be the two bonds of a double bond to an oxygen (i.e. C=O). The at least two exocyclic bonds can also be single bonds on two adjacent carbon atoms, provided that these bonds together are part of a fused ring (i.e. fused to the TCO ring) that assumes a substantially flat structure, therewith fixing said two single bonds in substantially one and the same plane. Examples of the latter include strained rings such as cyclopropyl and cyclobutyl. Without wishing to be bound by theory, the inventors believe that the presence of at least two exocyclic bonds in the same plane will result in an at least partial flattening of the TCO ring, which can lead to higher reactivity in the retro-Diels-Alder reaction.

Preferably, the TCO satisfies the following formula (1a):

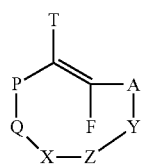

(1a)

For triggers $T^R$ that function via a cascade elimination mechanism, A and P each independently are $CR^a{}_2$ or $CR^aX^D$, provided that at least one is $CR^aX^D$. $X^D$ is (O—C(O))$_p$-(L$^D$)$_n$-(D$^D$), S—C(O)-(L$^D$)$_n$-(D$^D$), O—C(S)-(L$^D$)$_n$-(D$^D$), S—C(S)-(L$^D$)$_n$-(D$^D$), O—S(O)-(L$^D$)$_n$-(D$^D$), wherein p=0 or 1, (L$^D$)$_n$ is an optional linker, with n=0 or 1, preferably linked to $T^R$ via S, N, NH, or O, wherein these atoms are part of the linker, which may consist of multiple units arranged linearly and/or branched. $D^D$ is one or more therapeutic moieties or drugs, preferably linked via S, N, NH, or O, wherein these atoms are part of the therapeutic moiety. Preferably. $X^D$ is (O—C(O))$_p$-(L$^D$)$_n$-(D$^D$), where p=0 or 1, preferably 1, and n=0 or 1.

For triggers $T^R$ that function via a cyclization elimination mechanism, A and P each independently are $CR^a{}_2$ or $CR^aX^D$, provided that at least one is $CR^aX^D$. $X^D$ is O—C(O)-(L$^D$)$_n$-(D$^D$), S—C(O)-(L$^D$)$_n$-(D$^D$), O—C(S)-(L$^D$)$_n$-(D$^D$), S—C(S)-(L$^D$)$_n$-(D$^D$), NR$^d$—C(O)-(L$^D$)$_n$-(D$^D$), NR$^d$—C(S)-(L$^D$)$_n$-(D$^D$), C(O)-(L$^D$)$_n$-(D$^D$), C(S)-(L$^D$)$_n$-(D$^D$). (L$^D$)$_n$ is an optional linker with n=0 or 1, preferably linked to $T^R$ via S, N. NH, or O, and which may consist of multiple units arranged linearly and/or branched. $D^D$ is one or more therapeutic moieties or drugs, preferably linked via S, N, NH, or O, wherein these atoms are part of the therapeutic moiety. Preferably, $X^D$ is NR$^d$—C(O)-(L$^D$)$_n$-(D$^D$) or C(O)-(L$^D$)$_n$-(D$^D$), wherein n=0 or 1.

It is preferred that when $D^D$ is bound to $T^R$ or $L^D$ via NH, this NH is a primary amine (—NH$_2$) residue from $D^D$, and when $D^D$ is bound via N, this N is a secondary amine (—NH—) residue from $D^D$. Similarly, it is preferred that when $D^D$ is bound via O or S, said O or S are, respectively, a hydroxyl (—OH) residue or a sulfhydryl (—SH) residue from $D^D$.

It is further preferred that said S, N. NH, or O moieties comprised in $D^D$ are bound to an aliphatic or aromatic carbon of $D^D$.

It is preferred that when $L^D$ is bound to $T^R$ via NH, this NH is a primary amine (—NH$_2$) residue from $L^D$, and when $L^D$ is bound via N, this N is a secondary amine (—NH—) residue from $L^D$. Similarly, it is preferred that when $L^D$ is bound via O or S, said O or S are, respectively, a hydroxyl (—OH) residue or a sulfhydryl (—SH) residue from $L^D$ It is further preferred that said S, N, NH, or O moieties comprised in $L^D$ are bound to an aliphatic or aromatic carbon of $L^D$.

Where reference is made in the invention to a linker $L^D$ this can be self-immolative or not, or a combination thereof, and which may consist of multiple self-immolative units.

By way of further clarification, if p=0 and n=0 (for the cascade elimination mechanism), the drug species $D^D$ directly constitutes the leaving group of the elimination reaction, and if p=0 and n=1, the self-immolative linker constitutes the leaving group of the elimination. The position and ways of attachment of linkers $L^D$ and drugs $D^D$ are known to the skilled person (see for example Papot et al, *Anti-Cancer Agents in Medicinal Chemistry*, 2008, 8, 618-637). Nevertheless, typical but non-limiting examples of self-immolative linkers $L^D$ are benzyl-derivatives, such as those drawn below. On the right, an example of a self-immolative linker with multiple units is shown; this linker will degrade not only into $CO_2$ and one unit of 4-aminobenzyl alcohol, but also into one 1,3-dimethylimidazolidin-2-one unit.

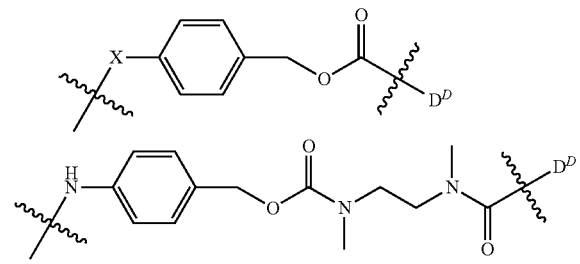

X = O or S or NH or NR with R = alkyl or aryl

In an interesting embodiment, Y,Z,X,Q each independently are selected from the group consisting of $CR^a{}_2$, C=$CR^a{}_2$, C=O, C=S, C=NR$^b$, S, SO, SO$_2$, O, NR$^b$, and SiR$^c{}_2$, with at most three of Y, Z, X, and Q being selected from the group consisting of C=$CR^a{}_2$, C=O, C=S, and C=NR$^b$, wherein two R moieties together may form a ring, and with the proviso that no adjacent pairs of atoms are present selected from the group consisting of O—O, O—NR$^b$, S—NR$^b$, O—S, O—S(O), O—S(O)$_2$, and S—S, and such that Si is only adjacent to $CR^a{}_2$ or O.

In a preferred embodiment, the TCO of formula (1a) is an all-carbon ring. In another preferred embodiment, the TCO of formula (1a) is a heterocyclic carbon ring, having of one to three oxygen atoms in the ring, and preferably a single oxygen atom.

In another interesting embodiment, one of the bonds PQ, QX, XZ, ZY, YA is part of a fused ring or consists of $CR^a$=$CR^a$, such that two exocyclic bonds are fixed in the same plane, and provided that PQ and YA are not part of an aromatic 5- or 6-membered ring, of a conjugated 7-membered ring, or of $CR^a$=$CR^a$; when not part of a fused ring P and A are independently $CR^a{}_2$ or $CR^aX^D$, provided that at least one is $CR^aX^D$; when part of a fused ring P and A are independently $CR^a$ or $CX^D$, provided that at least one is $CX^D$; the remaining groups (Y,Z,X,Q) being independently from each other $CR^a{}_2$, C=$CR^a{}_2$, C=O, C=S, C=$NR^b$, S, SO, $SO_2$, O, $NR^b$, $SiR^c{}_2$, such that at most 1 group is C=$CR^a{}_2$, C=O, C=S, C=$NR^b$, and no adjacent pairs of atoms are present selected from the group consisting of O—O, O—$NR^b$, S—$NR^b$, O—S, O—S(O), O—$S(O)_2$, and S—S, and such that Si, if present, is adjacent to $CR^a{}_2$ or O, and the $CR^a{}_2$=$CR^a{}_2$ bond, if present, is adjacent to $CR^a{}_2$ or C=$CR^a{}_2$ groups;

T, F each independently denotes H, or a substituent selected from the group consisting of alkyl, F, Cl, Br, or I.

In some embodiments fused rings are present that result in two exocyclic bonds being fixed in substantially the same plane. These are selected from fused 3-membered rings, fused 4-membered rings, fused bicyclic 7-membered rings, fused aromatic 5-membered rings, fused aromatic 6-membered rings, and fused planar conjugated 7-membered rings as defined below:

Fused 3-membered rings are:

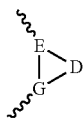

Therein E, G are part of the above mentioned 8-membered ring and can be fused to PQ, QP, QX, XQ, XZ, ZX, ZY, YZ, YA, AY, such that P, A are $CR^a$ or $CX^D$, and such that $CX^D$ can only be present in A and P.

E-G is $CR^a$—$CR^a$ or $CR^a$—$CX^D$, and D is $CR^a{}_2$, C=O, C=S, C=$NR^b$, $NR^b$, O, S, or E-G is $CR^a$—N or $CX^D$—N, and D is $CR^a{}_2$, C=O, C=S, C=$NR^b$, $NR^b$O, or S.

Fused 4-membered rings are:

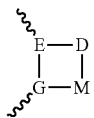

E-G is part of the above mentioned 8-membered ring and can be fused to PQ, QP, QX, XQ, XZ, ZX, ZY, YZ, YA, AY, such that P, A are C, $CR^a$ or $CX^D$, and such that $CX^D$ can only be present in A and P.

E and G are $CR^a$, $CX^D$ or N, and D, M independently from each other are $CR^a{}_2$, C=O, C=S, C=$NR^b$, C=$CR^a{}_2$, S, SO. $SO_2$, O, $NR^b$ but no adjacent O—O or S—S groups; or E-D is C=$CR^a$ and G is N, $CR^a$, $CX^D$ and M is $CR^a{}_2$, S, SO, $SO_2$, O, $NR^b$; or E-D is C=N and G is N, $CR^a$, $CX^D$ and M is $CR^a{}_2$, S, SO, $SO_2$, O; or D-M is $CR^a$=$CR^a$ and E and G each independently are $CR^a$, $CX^D$ or N; or D-M is $CR^a$=N and E is $CR^a$. $CX^D$, N, and G is $CR^a$ or $CX^D$; or E is C, G is $CR^a$, $CX^D$ or N, and D and M are $CR^a{}_2$, S, SO, $SO_2$, O, $NR^b$, or at most 1 of C=O, C=S, C=$NR^b$, C=$CR^a{}_2$, but no adjacent O—O or S—S groups; or E and G are C and D and M independently from each other are $CR^a{}_2$, S, SO, $SO_2$, O, $NR^b$ but no adjacent O—O, or S—S groups.

Fused bicyclic 7-membered rings are:

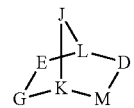

E-G is part of the above mentioned 8-membered ring and can be fused to PQ, QP, QX, XQ, XZ, ZX, ZY, YZ, YA, AY, such that P, A are C, $CR^a$ or $CX^D$, and such that $CX^D$ can only be present in A and P;

E,G are C, $CR^a$, $CX^D$ or N; K, L are $CR^a$; D,M form a $CR^a$=$CR^a$ or $CR^a$=N, or D,M independently from each other are $CR^a{}_2$, C=O, C=S, C=$NR^b$, C=$CR^a{}_2$, S, SO, $SO_2$, O, $NR^b$ but no adjacent O—O, S—S, N—S groups; J is $CR^a{}_2$, C=O, C=S, C=$NR^b$, C=$CR^a{}_2$, S, SO, $SO_2$, O, $NR^b$; at most 2 N groups; or E,G are C, $CR^a$, $CX^D$; K is N and L is $CR^a$; D,M form a $CR^a$=$CR^a$ bond or D,M independently from each other are $CR^a{}_2$, C=O, C=S, C=$NR^b$, C=$CR^a{}_2$, $NR^b$ but no adjacent O—O, S—S, N—S groups; J is $CR^a{}_2$, C=O, C=S, C=$NR^b$, C=$CR^a{}_2$, S. SO, $SO_2$, O, $NR^b$; at most 2 N groups; or E,G are C, $CR^a$, $CX^D$; K and L are N; D,M, J independently from each other are $CR^a{}_2$, C=O, C=S, C=$NR^b$, C=$CR^a{}_2$ groups;

Fused aromatic 5-membered rings are

E, G are part of the above mentioned 8-membered ring and can be fused to QX, XQ, XZ, ZX, ZY, YZ.

E,G is C. One of the groups L, K, or M are O, $NR^b$, S and the remaining two groups are independently from each other $CR^a$ or N; or, E is C and G is N, L, K, M are independently from each other $CR^a$ or N.

Fused aromatic 6-membered rings are:

E, G are part of the above mentioned 8-membered ring and can be fused to QX, XQ, XZ, ZX, ZY, YZ.

E,G is C, L K, D, M are independently from each other $CR^a$ or N.

Fused planar conjugated 7-membered rings are

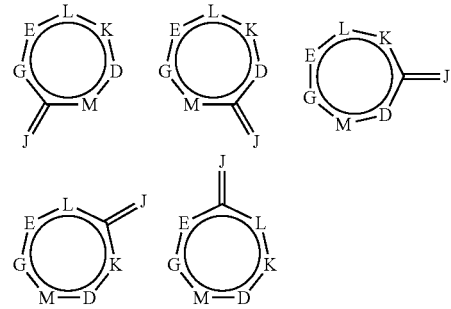

E, G are part of the above mentioned 8-membered ring and can be fused to QX, XQ, XZ, ZX, ZY, YZ E,G is C; L, K, D, M are $CR^a$; J is S, O, $CR^a{}_2$, $NR^b$.

Each $R^a$ as above-indicated can independently be H, alkyl, aryl, OR', SR', S(=O)''', S(=O)$_2$R''', S(=O)$_2$NR'R'', Si—R''', Si—O—R''', OC(=O)R''', SC(=O)R''', OC(=S)R''', SC(=S)R''', F, Cl, Br, I, N$_3$, SO$_2$H, SO$_3$H, SO$_4$H, PO$_3$H, PO$_4$H, NO, NO$_2$, CN, OCN, SCN, NCO, NCS, CF$_3$, CF$_2$—R', NR'R'', C(=O)R', C(=S)R', C(=O)O—R', C(=S)O—R', C(=O)S—R', C(=S)S—R', C(=O)NR'R'', C(=S)NR'R'', NR'C(=O)—R''', NR'C(=S)—R''', NR'C(=O)O—R''', NR'C(=S)O—R''', NR'C(=O)S—R''', NR'C(=S)S—R''', OC(=O)NR'—R''', SC(=O)NR'—R''', OC(=S)NR'—R''', SC(=S)NR'—R''', NR'C(=O)NR''—R'', NR'C(=S)NR''—R'', CR'NR'', with each R' and each R'' independently being H, aryl or alkyl and R''' independently being aryl or alkyl;

Each $R^b$ as above indicated is independently selected from the group consisting of H, alkyl, aryl, O-aryl, O-alkyl, OH, C(=O)NR'R'' with R' and R'' each independently being H, aryl or alkyl, R'CO-alkyl with R' being H, alkyl, and aryl;

Each $R^c$ as above indicated is independently selected from the group consisting of H, alkyl, aryl. O-alkyl, O-aryl, OH;

Each $R^d$ as above indicated is H, $C_{1-6}$ alkyl and $C_{1-6}$ aryl; wherein two or more $R^{a,b,c}$ moieties together may form a ring:

In all of the above embodiments, optionally one of A, P, Q, Y, X, and Z, or the substituents or fused rings of which they are part, or the self-immolative linker $L^D$, or the drug $D^D$, is bound, optionally via a spacer or spacers $S^P$, to one or more targeting agents $T^T$ or masking moieties $M^M$.

The synthesis of TCO's as described above is well available to the skilled person. This expressly also holds for TCO's having one or more heteroatoms in the strained cycloalkene rings. References in this regard include Cere et al. *Journal of Organic Chemistry* 1980, 45, 261 and Prevost et al. *Journal of the American Chemical Society* 2009, 131, 14182.

In a preferred embodiment, the trans-cyclooctene moiety satisfies formula (1b):

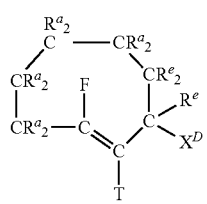

(1b)

wherein, in addition to the optional presence of at most two exocyclic bonds fixed in the same plane, each $R^a$ independently denotes H, or, in at most four instances, a substituent selected from the group consisting of alkyl, aryl, OR', SR', S(=O)R''', S(=O)$_2$R''', S(=O)$_2$NR'R'', Si—R''', Si—O—R''', OC(=O)R''', SC(=O)R''', OC(=S)R''', SC(=S)R''', F, Cl, Br, I, N$_3$, SO$_2$H, SO$_3$H, SO$_4$H, PO$_3$H, PO$_4$H, NO, NO$_2$, CN, OCN, SCN, NCO, NCS, CF$_3$, CF$_2$—R', NR'R'', C(=O)R', C(=S)R', C(=O)O—R', C(=S)O—R', C(=O)S—R', C(=S)S—R', C(=O)NR'R'', C(=S)NR'R'', NR'C(=O)—R''', NR'C(=S)—R''', NR'C(=O)O—R''', NR'C(=S)O—R''', NR'C(=O)S—R''', NR'C(=S)S—R''', OC(=O)NR'—R''', SC(=O)NR'—R''', OC(=S)NR'—R''', SC(=S)NR'—R''', NR'C(=O)NR''—R'', NR'C(=S)NR''—R'', CR'NR'', with each R' and each R'' independently being H, aryl or alkyl and R''' independently being aryl or alkyl;

Each $R^e$ as above indicated is independently selected from the group consisting of H, alkyl, aryl. OR', SR', S(=O)R''', S(=O)$_2$R''', Si—R''', Si—O—R''', OC(=O)R''', SC(=O)R''', OC(=S)R''', SC(=S)R''', F, Cl, Br, I, N$_3$, SO$_2$H, SO$_3$H, PO$_3$H, NO, NO$_2$, CN, CF$_3$, CF$_2$—R', C(=O)R', C(=S)R', C(=O)O—R', C(=S)O—R', C(=O)S—R', C(=S)S—R', C(=O)NR'R'', C(=S)NR'R'', NR'C(=O)—R''', NR'C(=S)—R''', NR'C(=O)O—R''', NR'C(=S)O—R''', NR'C(=O)S—R''', NR'C(=S)S—R''', NR'C(=O)NR''—R'', NR'C(=S)NR''—R'', CR'NR'', with each R' and each R'' independently being H, aryl or alkyl and R''' independently being aryl or alkyl; wherein two $R^{a,e}$ moieties together may form a ring:

with optionally one Rae comprised in a linker moiety, optionally via a spacer $S^P$, to a targeting agent $T^T$ or a masking moiety $M^M$, and wherein T and F each independently denote H, or a substituent selected from the group consisting of alkyl, F, Cl, Br, and I, and $X^D$ is as defined above for formula (1a).

Preferably, each $R^{a,e}$ is selected independently from the group consisting of H, alkyl, O-alkyl, O-aryl, OH, C(=O)NR'R'', NR'C(=O)—R''', with R' and R'' each independently being H, aryl or alkyl, and with R''' independently being alkyl or aryl.

In the foregoing dienophiles, it is preferred that the at least two exocyclic bonds fixed in the same plane are selected from the group consisting of (a) the single bonds of a fused cyclobutyl ring, (b) the hybridized bonds of a fused aromatic ring, (c) an exocyclic double bond to an oxygen, and (d) an exocyclic double bond to a carbon.

In a further preferred embodiment, the dienophile is a compound selected from the following structures:

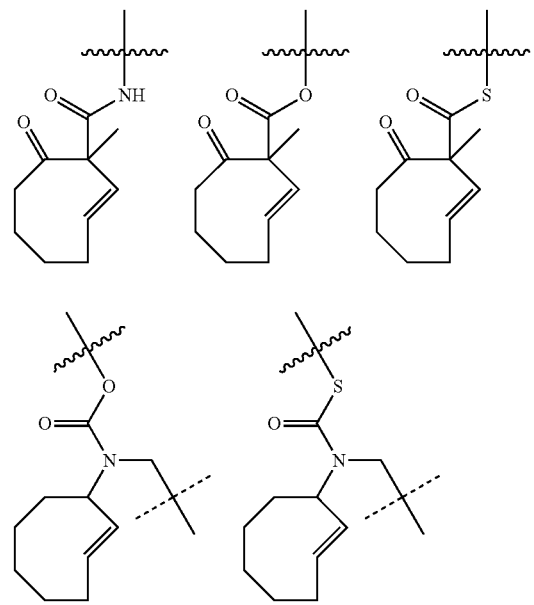

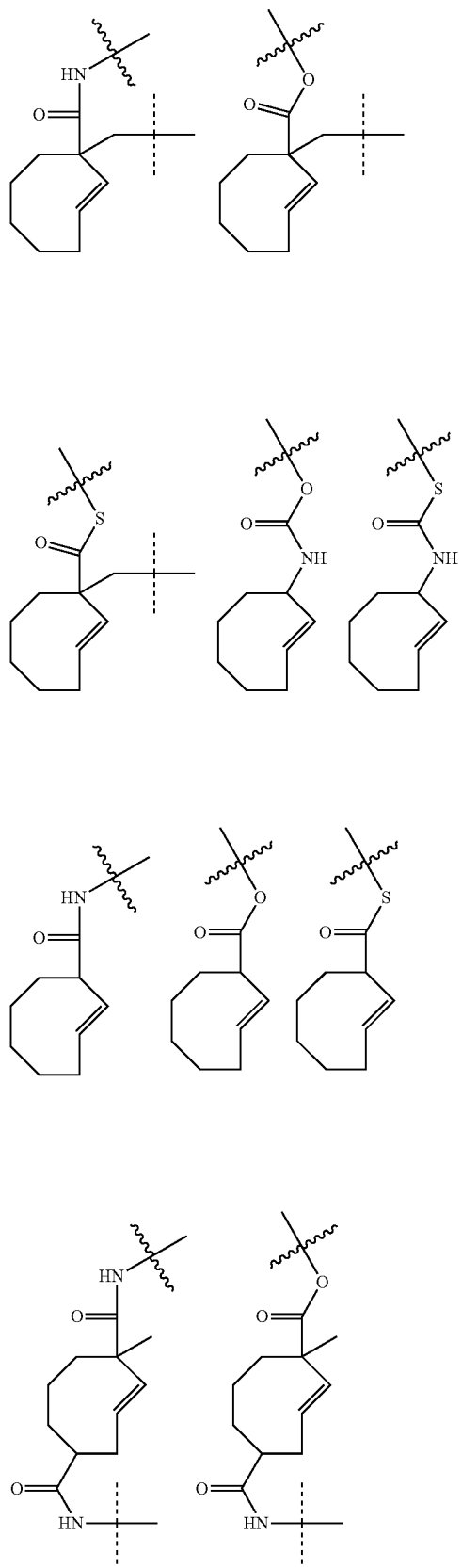
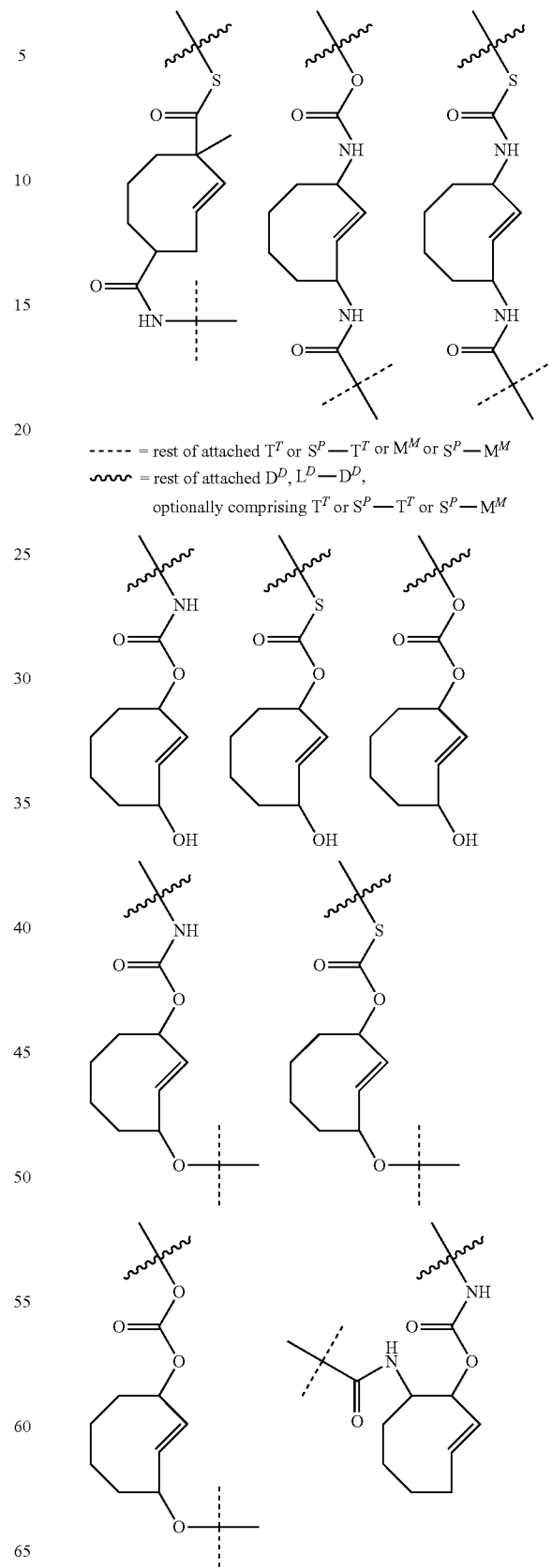
----- = rest of attached $T^T$ or $S^P$—$T^T$ or $M^M$ or $S^P$—$M^M$
∼∼∼ = rest of attached $D^D$, $L^D$—$D^D$, optionally comprising $T^T$ or $S^P$—$T^T$ or $S^P$—$M^M$

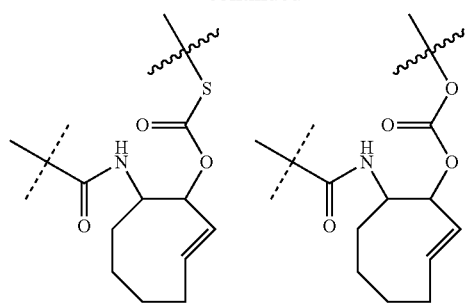
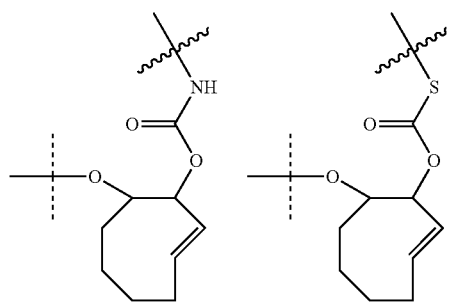
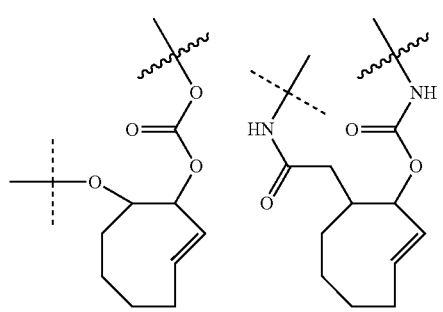
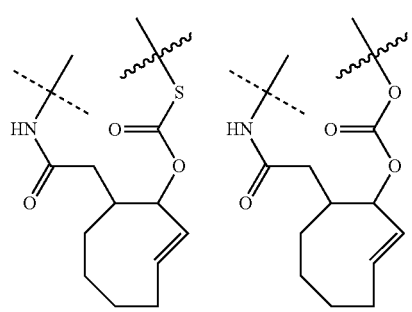
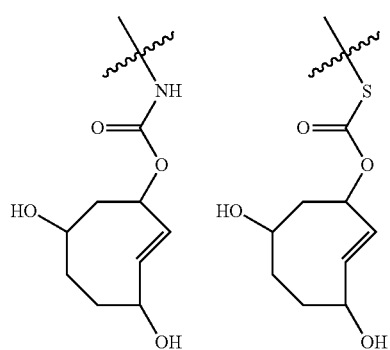
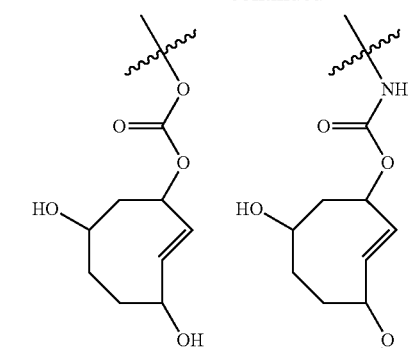
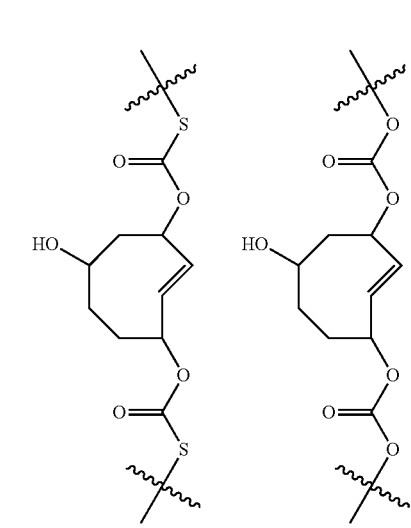

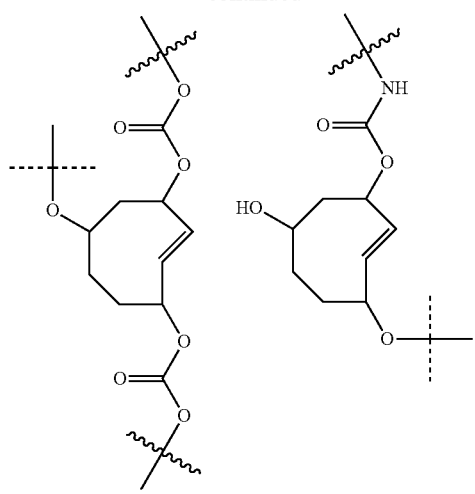
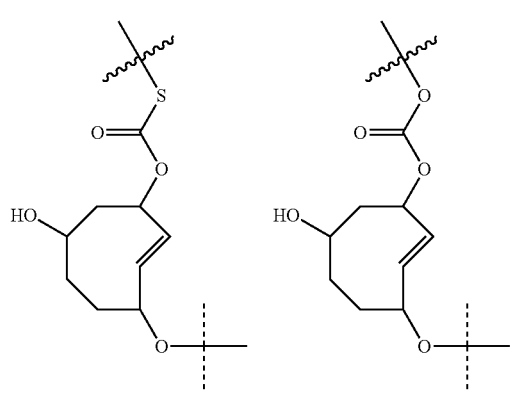
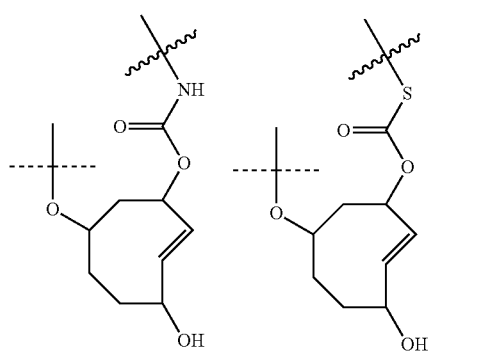
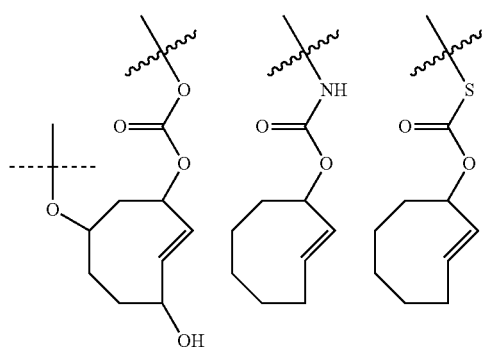
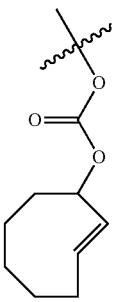
----- = rest of attached $T^T$ or $S^P$—$T^T$ or $M^M$ or $S^P$—$M^M$
~~~~ = rest of attached $D^D$, $L^D$—$D^D$, optionally comprising $T^T$ or $S^P$—$T^T$ or $S^P$—$M^M$
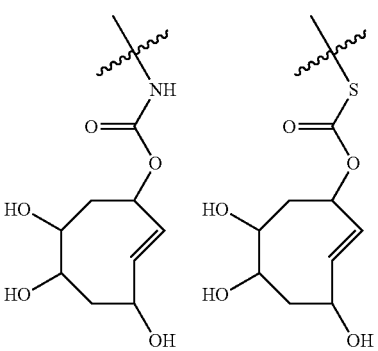
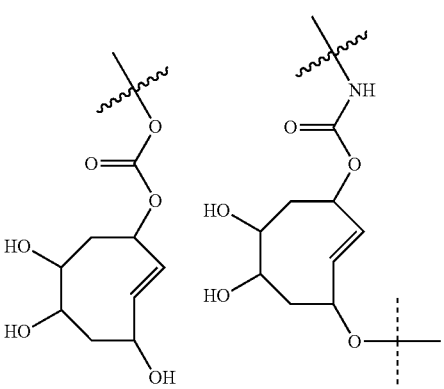
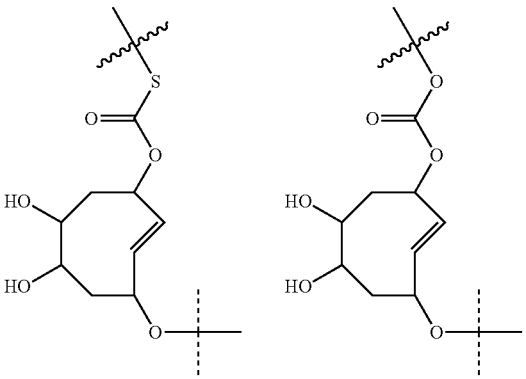

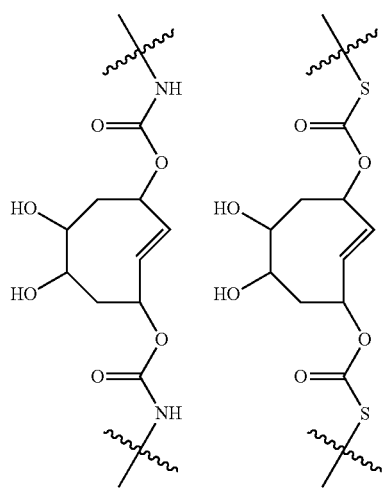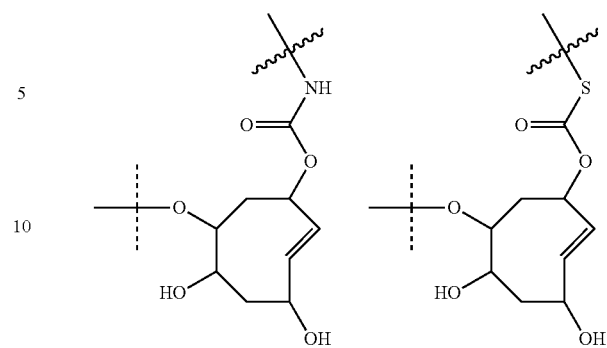

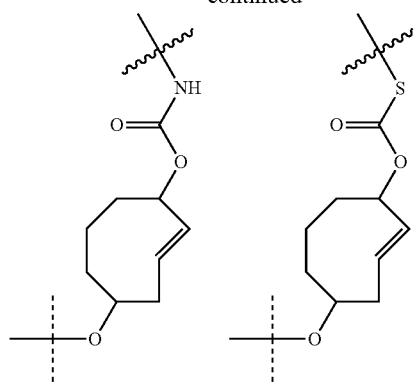
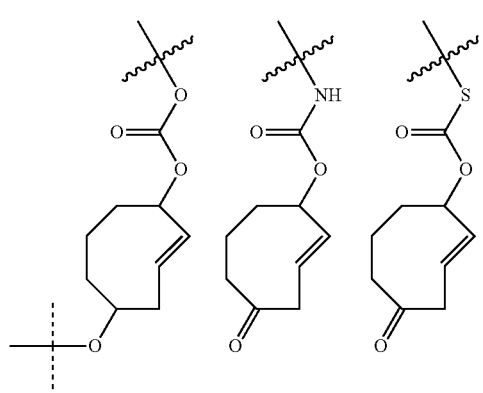
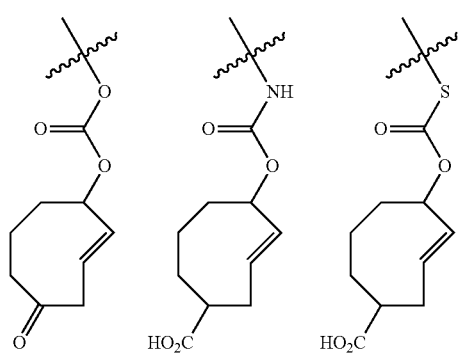
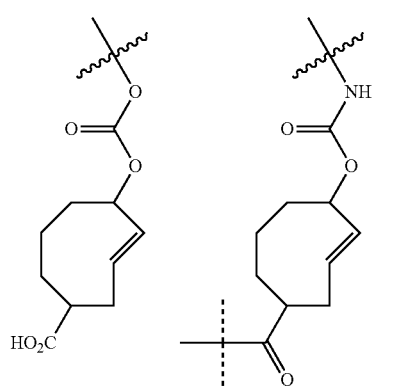
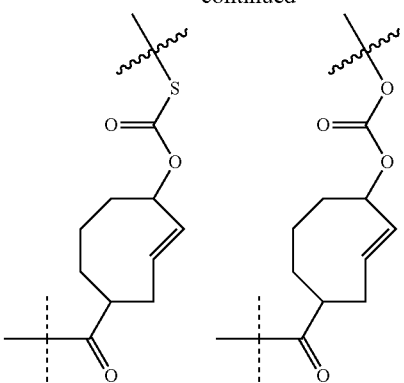
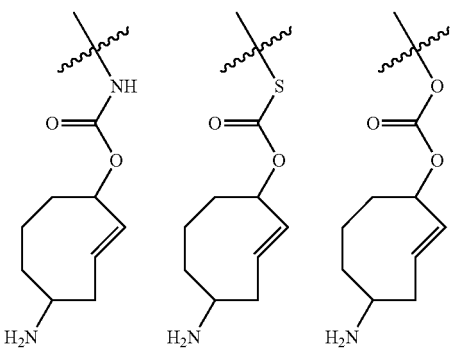
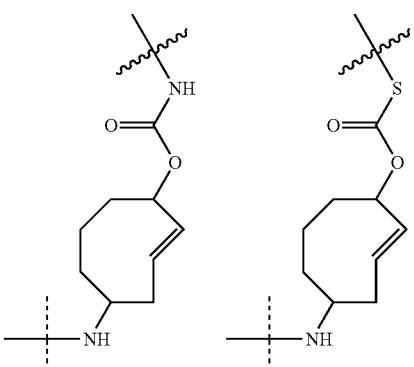
- - - - = rest of attached $T^T$ or $S^P$—$T^T$ or $M^M$ or $S^P$—$M^M$
∿∿∿ = rest of attached $D^D$, $L^D$—$D^D$, optionally comprising $T^T$ or $S^P$—$T^T$ or $S^P$—$M^M$

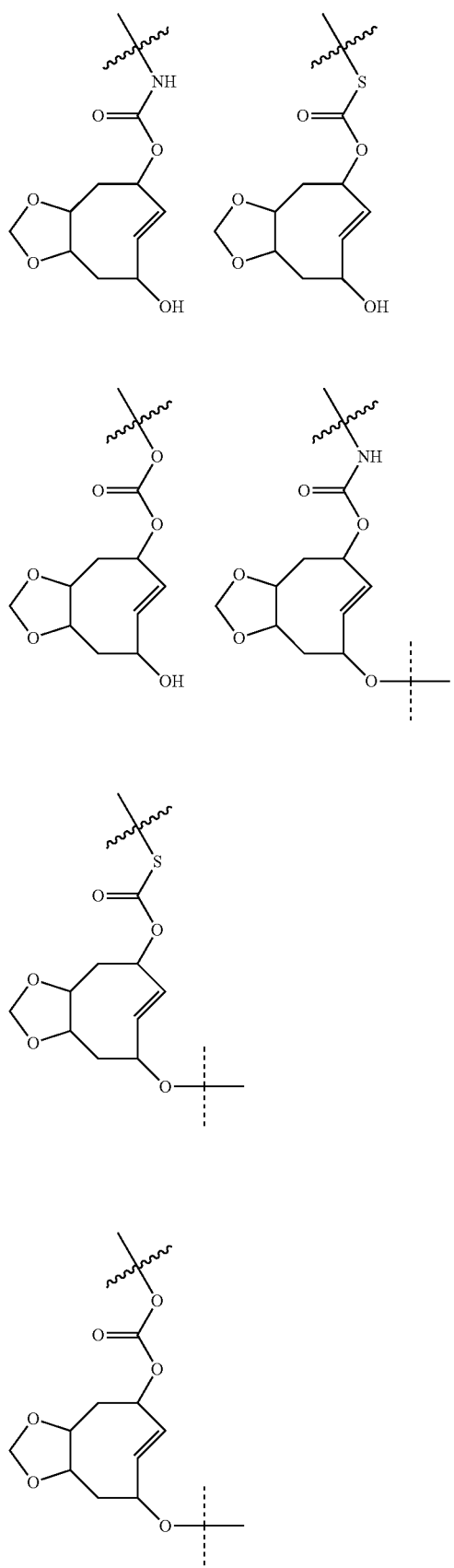
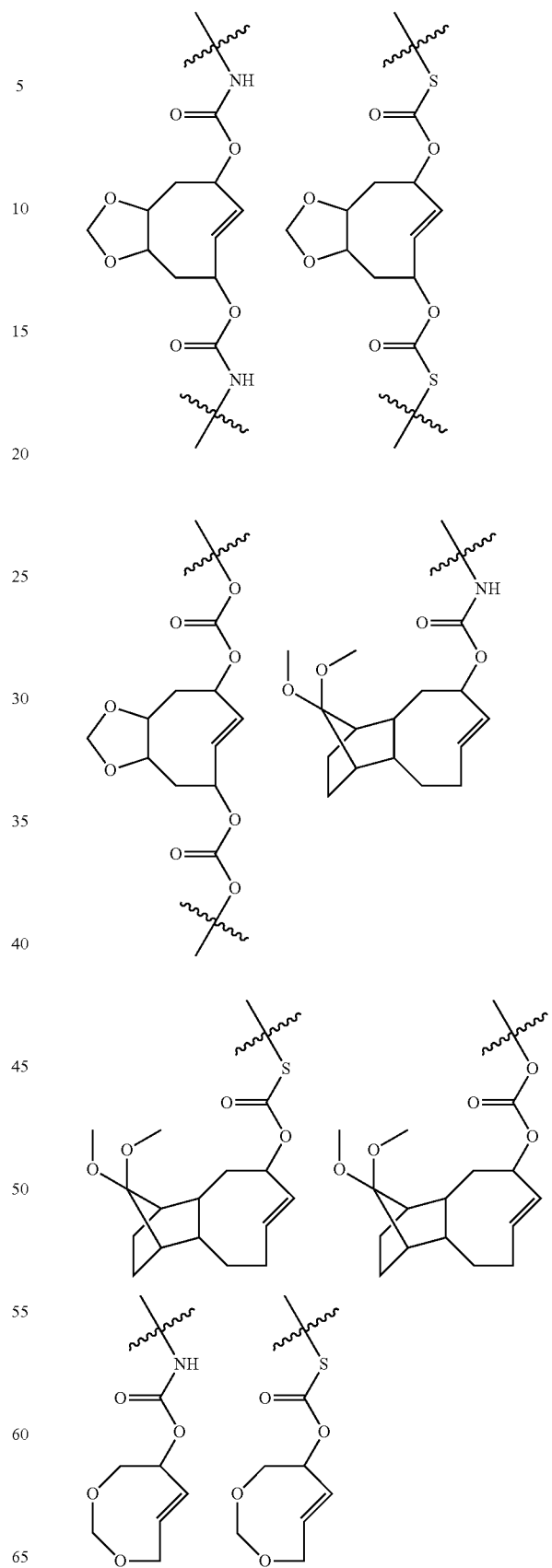

-continued
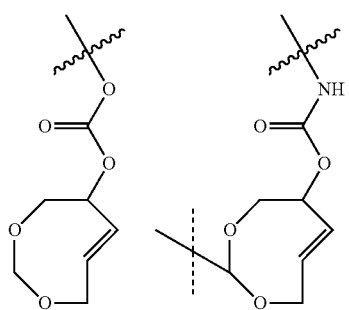 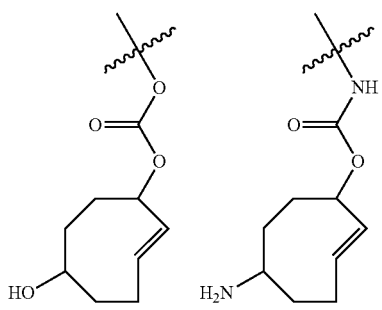
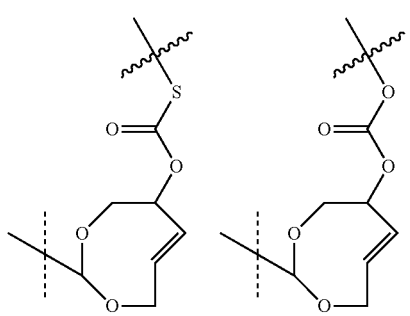 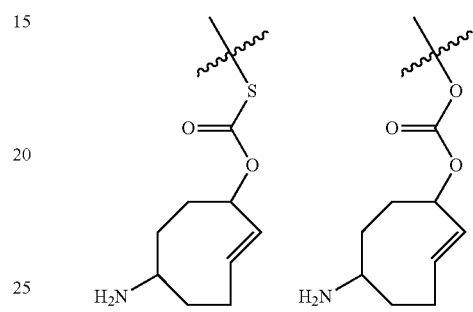
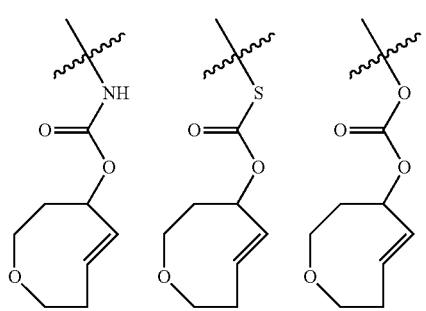 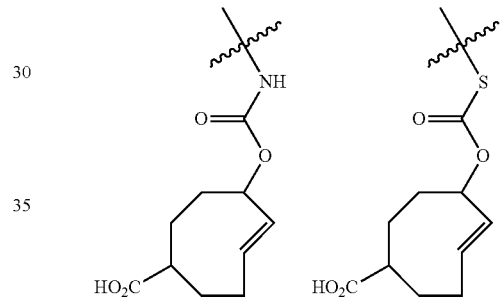
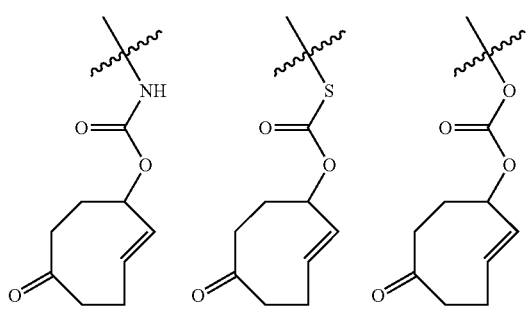 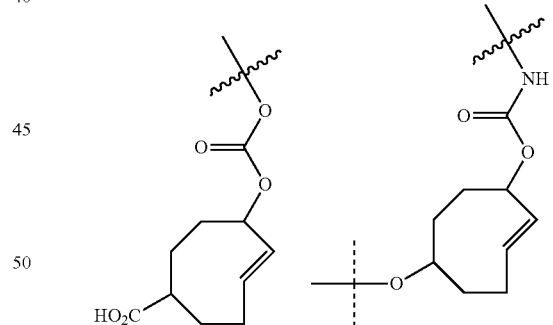
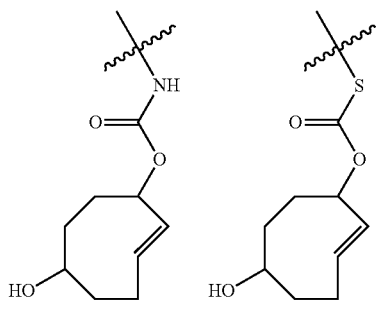 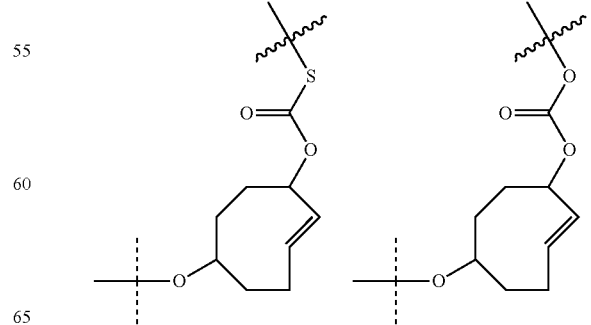

31
-continued
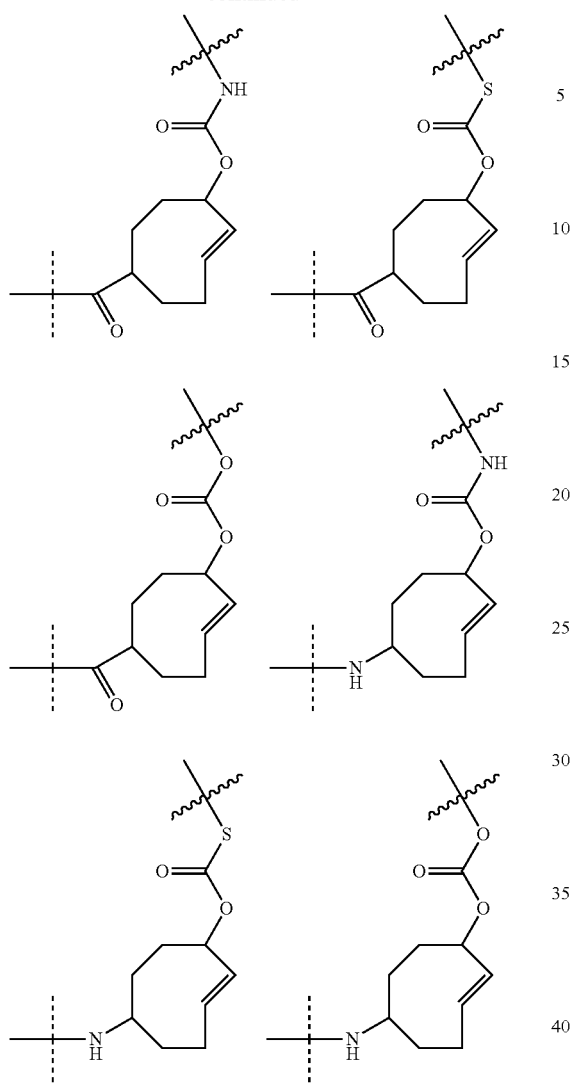
- - - - = rest of attached $T^T$ or $S^P$—$T^T$ or $M^M$ or $S^P$—$M^M$
〰〰 = rest of attached $D^D$, $L^D$—$D^D$, optionally comprising $T^T$ or $S^P$—$T^T$ or $S^P$—$M^M$
For activation via the cascade elimination mechanism as discussed below, preferred dienophiles are a subset of the above, viz.:
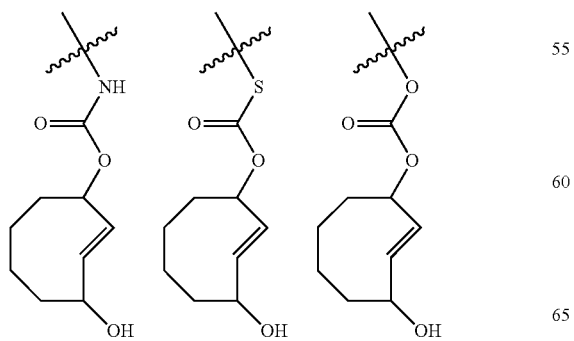
32
-continued
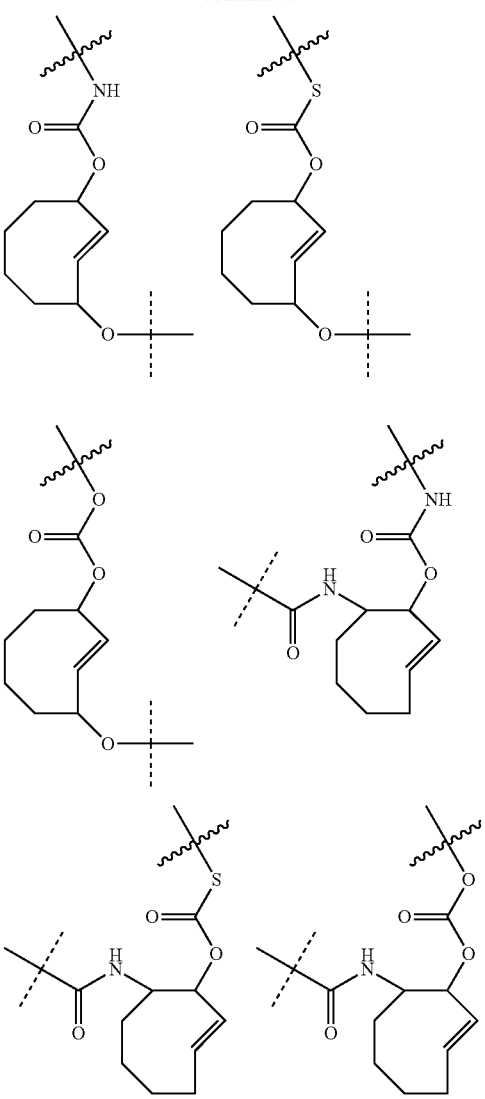
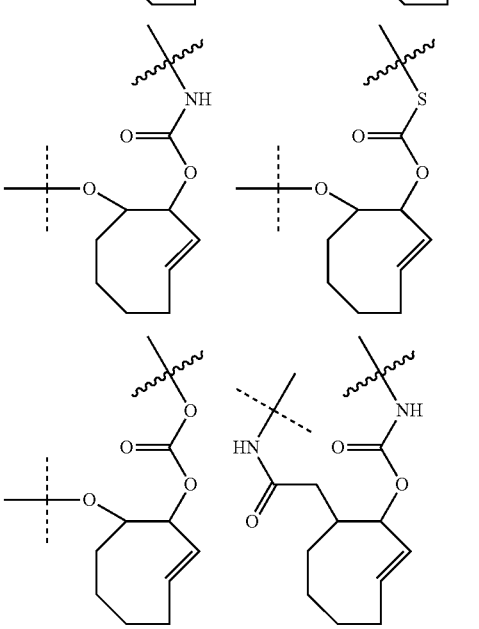

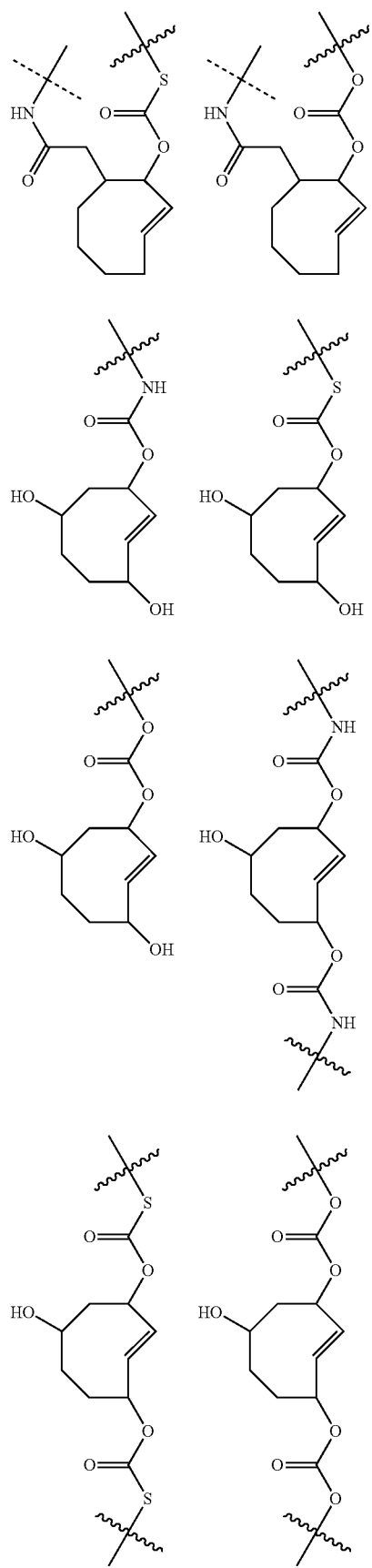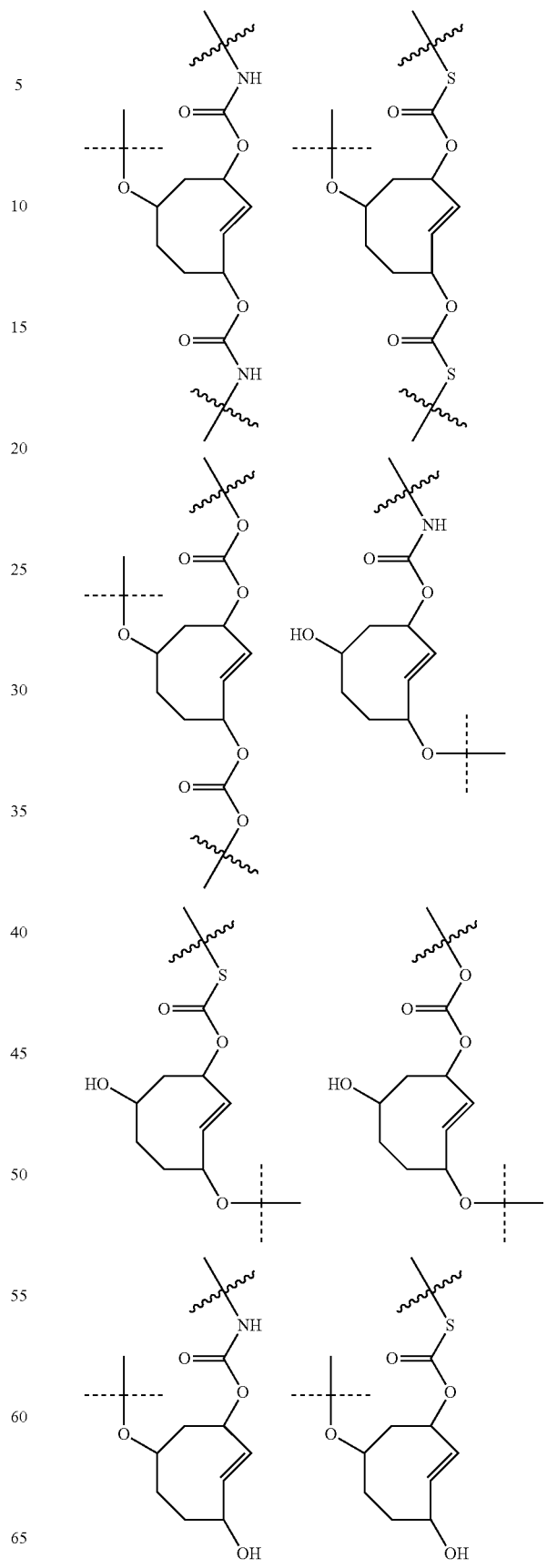

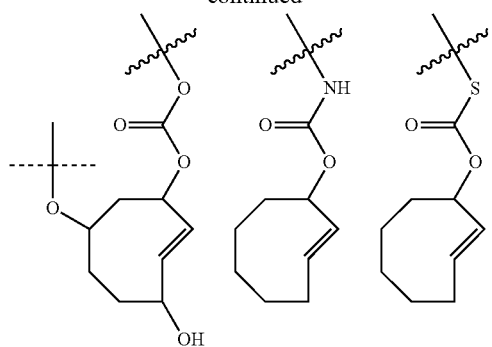
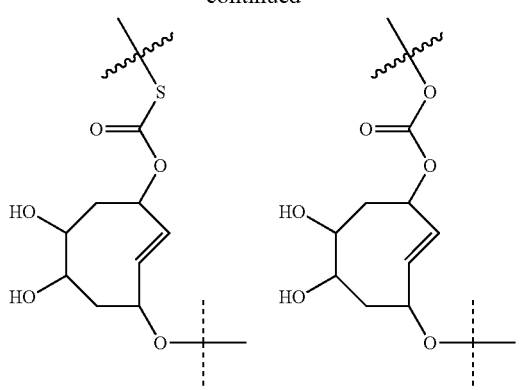
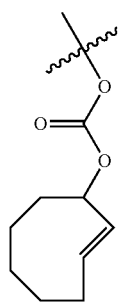
----- = rest of attached $T^T$ or $S^P$—$T^T$ or $M^M$ or $S^P$—$M^M$
∼∼∼ = rest of attached $D^D$, $L^D$—$D^D$, optionally comprising $T^T$ or $S^P$—$T^T$ or $S^P$—$M^M$
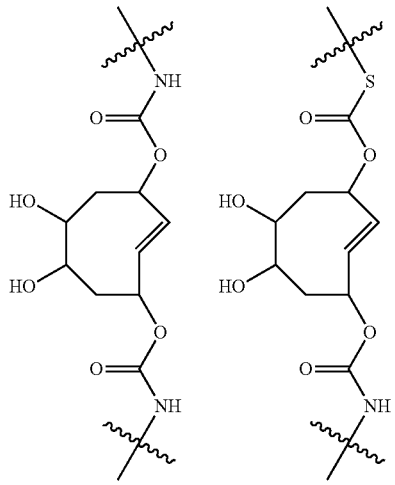
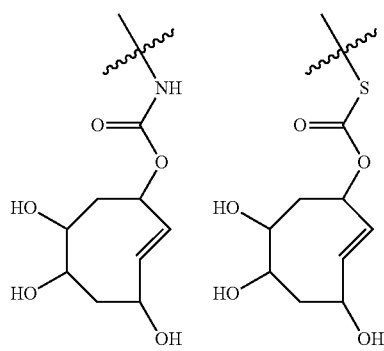
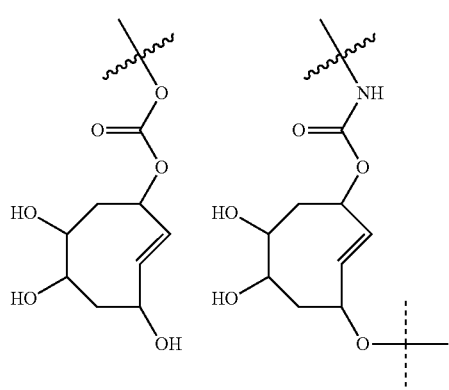
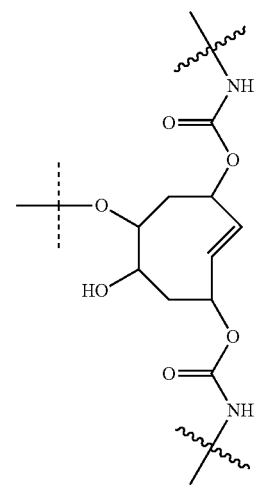

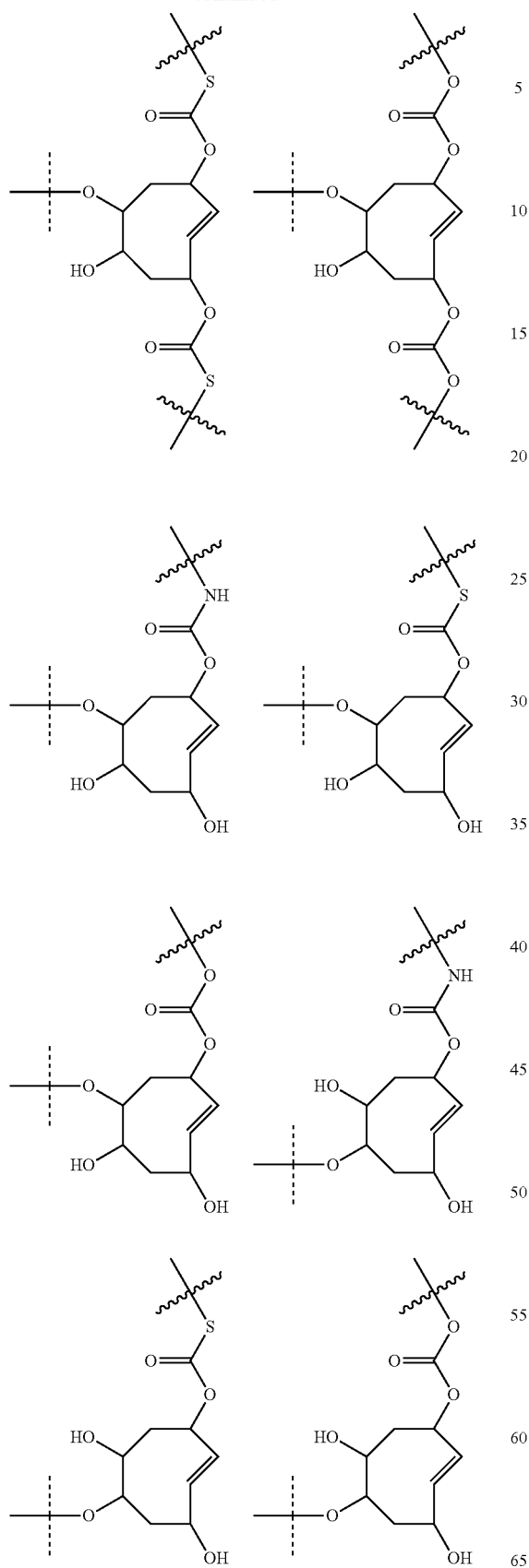
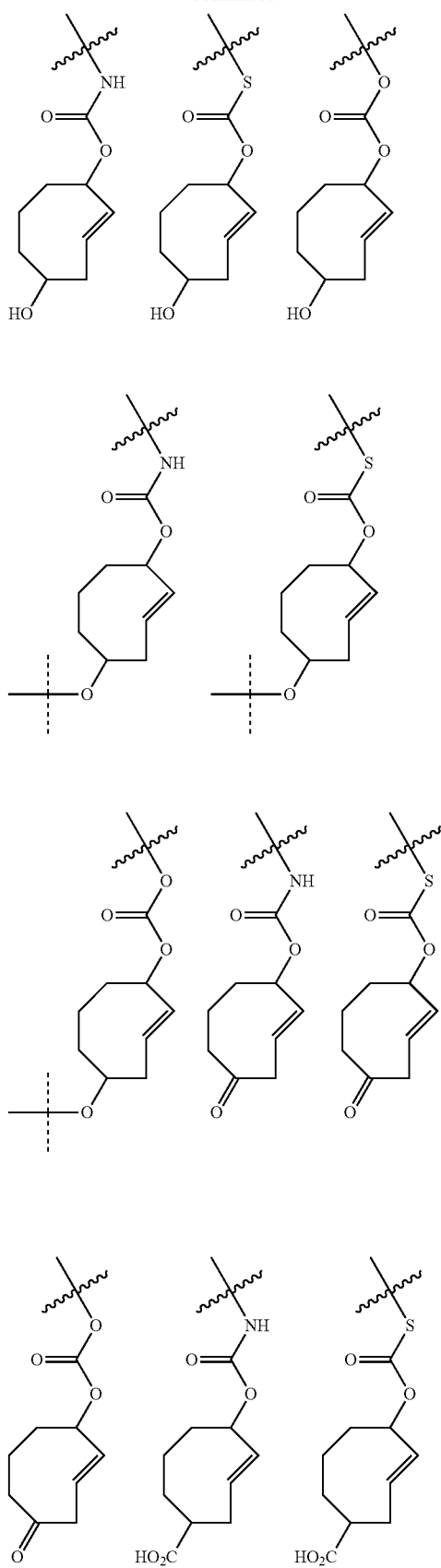

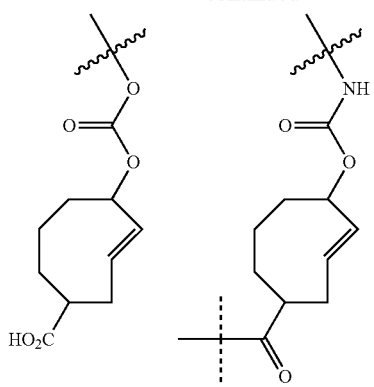
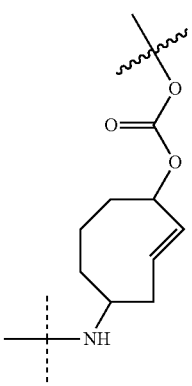
----- = rest of attached $T^T$ or $S^P$—$T^T$ or $M^M$ or $S^P$—$M^M$
∿∿∿ = rest of attached $D^D$, $L^D$—$D^D$, optionally comprising $T^T$ or $S^P$—$T^T$ or $S^P$—$M^M$

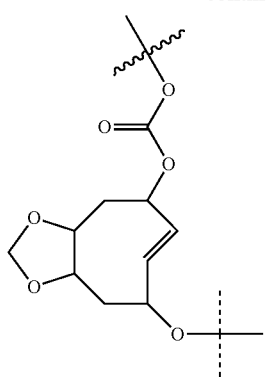
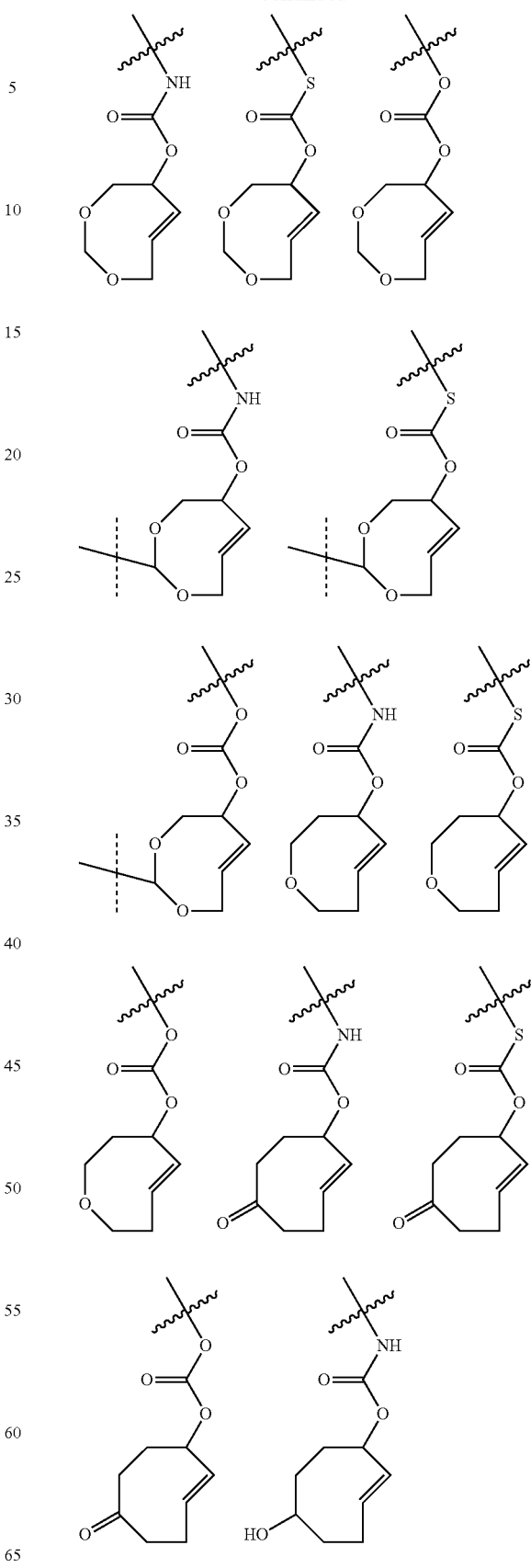

-continued

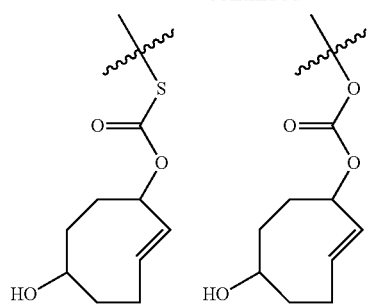
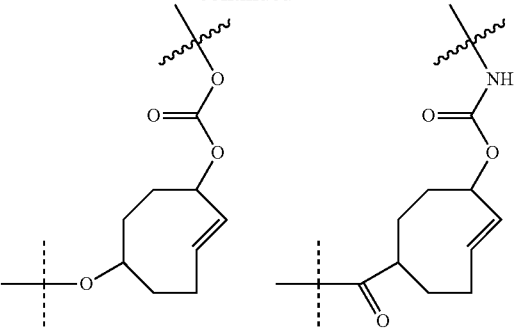
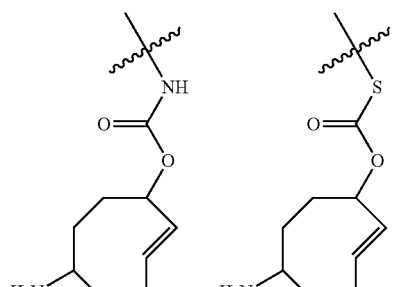
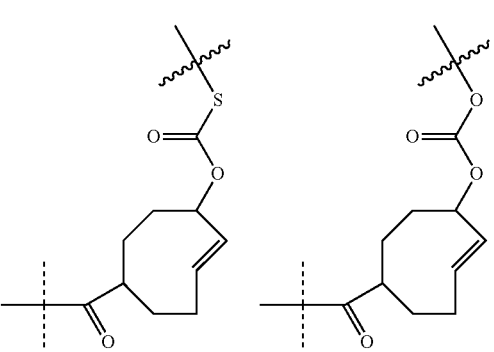
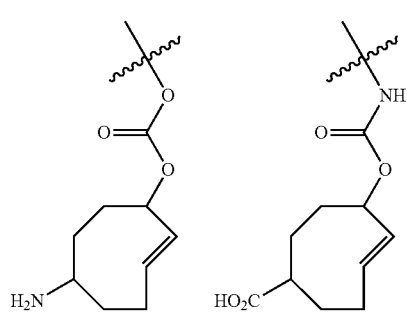
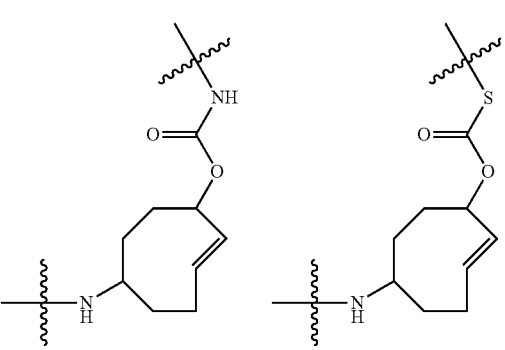
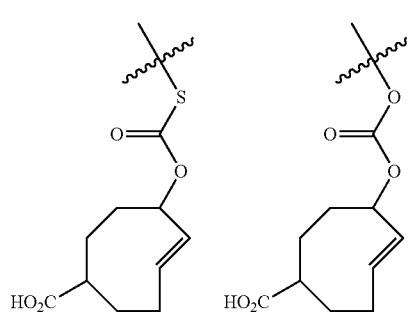
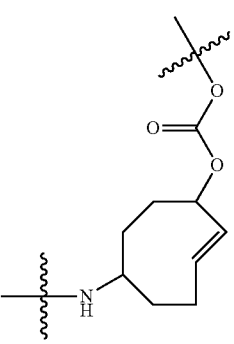
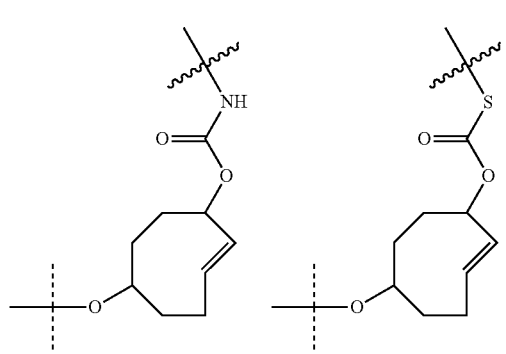

- - - - = rest of attached $T^T$ or $S^P$—$T^T$ or $M^M$ or $S^P$—$M^M$
∿∿∿ = rest of attached $D^D$, $L^D$—$D^D$,
optionally comprising $T^T$ or $S^P$—$T^T$ or $S^P$—$M^M$ Use of TCO as a Carrier The invention also pertains to the use of a trans-cyclooctene satisfying formula (1a), in all its embodiments, as a carrier for a therapeutic compound. The trans-cyclooctene is to be read as a TCO in a broad sense, as discussed above, preferably an all-carbon ring or including one or two heteroatoms. A therapeutic compound is a drug or other compound or moiety intended to have therapeutic application. The use of TCO as a carrier according to this aspect of the invention does not relate to the therapeutic activity of the therapeutic compound. In fact, also if the therapeutic compound is a drug substance intended to be developed as a drug, many of which will fail in practice, the application of TCO as a carrier still is useful in testing the drug. In this sense, the TCO in its capacity of a carrier is to be regarded in the same manner as a pharmaceutical excipient, serving as a carrier when introducing a drug into a subject.

The use of a TCO as a carrier has the benefit that it enables the administration, to a subject, of a drug carried by a moiety that is open to a bioorthogonal reaction, with a diene, particularly a tetrazine. This provides a powerful tool not only to affect the fate of the drug carried into the body, but also to follow its fate (e.g. by allowing a labeled diene to react with it), or to change its fate (e.g. by allowing pK modifying agents to bind with it). This is all based on the possibility to let a diene react with the TCO in the above-discussed rDA reaction. The carrier is preferably reacted with an Activator as discussed below, so as to provoke the release of the therapeutic compound from the TCO, as amply discussed herein.

Activator

The Activator comprises a Bio-orthogonal Reactive Group, wherein this Bio-orthogonal Reactive Group of the Activator is a diene. This diene reacts with the other Bio-orthogonal Reactive Group, the Trigger, and that is a dienophile (vide supra). The diene of the Activator is selected so as to be capable of reacting with the dienophile of the Trigger by undergoing a Diels-Alder cycloaddition followed by a retro Diels-Alder reaction, giving the Retro Diels-Alder adduct. This intermediate adduct then releases the drug or drugs, where this drug release can be caused by various circumstances or conditions that relate to the specific molecular structure of the retro Diels-Alder adduct.

In alternative, preferred embodiments, the Activator is selected such as to provoke either of two drug release mechanisms, one being via intramolecular cyclization, the other via an elimination or a cascade elimination.

Drug Release Via Intramolecular Cyclization

In one preferred embodiment of this invention, the release of the drug or drugs is caused by an intramolecular cyclization reaction within the Retro Diels-Alder adduct: a nucleophilic site that originates from the Activator (i.e. from the diene) reacts with an electrophilic site that originates from the Prodrug (i.e. from the dienophile trigger, particularly from the $X^D$ group in this trigger, vide supra) thereby forming a cycle and thereby releasing the drug as a leaving group. The intramolecular reaction takes place effectively and efficiently, as the nucleophilic site and the electrophilic site have been brought together in close proximity within the Retro Diels-Alder adduct. Additionally, the formation of the cyclic structure may also be a driving force for the intramolecular reaction taking place, and thus may also contribute to an effective release of the leaving group, i.e. release of the drug. Reaction between the nucleophilic site and the electrophilic site is not efficient prior to the Retro Diels-Alder reaction, as the reaction then is an intermolecular reaction that furthermore does not involve the formation of a cyclic structure.

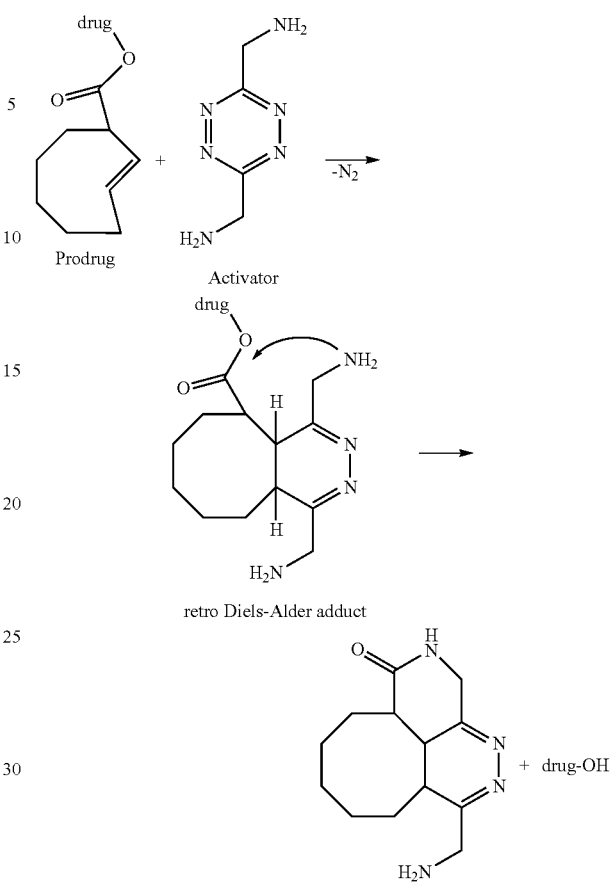

The above example illustrates how a cyclization reaction within the retro Diels-Alder adduct can result in release of a drug species. The driving force for the release of the drug is the close proximity of the nucleophilic site (here the amine groups in the 3- and 6-positions of the tetrazine Activator) and the electrophilic site (here an ester carbonyl moiety) within the retro Diels-Alder adduct, so that these reactive species have a high local concentration. Additionally, the formation of a stable 6-ring species may drive the cyclization, where this ring formation may further be augmented by the conformation of the fused cyclo-octane and dihydro pyridazine rings that pre-organizes 5 of the 6 atoms in the 6-ring that needs to be formed. In any case, and in whatever way the process is viewed, the drug species (here the alcohol 'drug-OH') is effectively expelled from the retro Diels-Alder adduct, while it does not get expelled from the Prodrug alone.

It may also be possible that the nucleophilic site assists in expelling the drug species by a nucleophilic attack on the electrophilic site with subsequent drug release, but without actually forming a (stable) cyclic structure. In this case, no ring structure is formed and the nucleophilic site remains intact, for example because the ring structure is shortlived and unstable and breaks down with reformation of the nucleophilic site.

In this first preferred embodiment of the invention, the Activator is a diene bearing one or more nucleophilic sites, where this nucleophilic site can be any nucleophilic moiety known in the art. One has to consider that the nucleophilic site must be able to act as a nucleophile under conditions that may exist inside the (human) body, so for example at physiological conditions where the pH=ca. 7.4, or for example at conditions that prevail in malignant tissue where pH-values may be lower than 7.4. Nonlimiting examples of nucleophilic sites are amine, alcohol (or hydroxy), thiol, carboxylate, amide, urea, thiourea, phosphine or N-oxide groups. From these, most preferred are amine, thiol or alcohol groups, as these are generally most nucleophilic in nature and therefore most effective.

Amine groups can be primary ($R^1$—$NH_2$), secondary ($R^1R^2NH$) or tertiary ($R^1R^2R^3N$) amine groups, preferably primary or secondary amine groups; more generally, the nitrogen atom preferably bears one or two hydrogen atoms. The amines can be aliphatic, benzylic, allylic or aromatic in nature. The amine nucleophilic site may be placed in a heterocycle or a heteroaromatic cycle, such as particularly in 5-, 6- or 7-membered ring structures. Examples are imidazole, triazole, pyrrole or pyridine heteroaromatic cycles. Furthermore, the nucleophilic nitrogen atom may be placed adjacent to another heteroatom such as an N, O. S or P atom, so that the amine group may be part of e.g. a hydroxyl-amine, a hydrazine or a phosphazene group.

Alcohol or hydroxy groups ($R^1$—OH) can be aliphatic, benzylic or allylic alcohols, and can then be primary, secondary or tertiary, preferably primary alcohols. The alcohol may also be aromatic in nature, so that the $R^1$ moiety may represent any (hetero)aromatic group; the alcohol is then a phenol group. The hydroxyl group may also be part of a hydroxyl-amine group, so that the nucleophilic oxygen atom is placed adjacent an N-atom.

Thiol or mercaptan groups ($R^1$—SH) can be aliphatic, benzylic or allylic thiols, and can then be primary, secondary or tertiary, preferably primary thiols. The thiols may also be aromatic in nature, so that the $R^1$ moiety may represent any (hetero)aromatic group. Thiols are attractive nucleophiles as under physiological conditions these groups are prone to be deprotonated making them more nucleophilic.

Carboxylate groups are deprotonated carboxylic acid groups ($R^1$—COOH), and indeed, under physiological conditions these groups exist as carboxylates, making these moieties somewhat nucleophilic. The $R^1$ groups may be aliphatic or aromatic in nature.

Amide groups can be regular amide groups ($R^1$—CO—NH—$R^2$) or sulfonamide groups ($R^1$—$SO_2$—NH—$R^2$) where the nitrogen atom bears a hydrogen atom and where it functions as the nucleophilic atom. Interesting amide groups are those where the $R^2$-group is aromatic; these groups may more easily be deprotonated, making the amide more nucleophilic. In a similar fashion, particularly interesting urea groups ($R^1$—$NR^3$—CX—NH—$R^2$) are those where the $R^2$-group is aromatic, as these groups may more easily deprotonate the proton on the adjacent nitrogen atom, making this site more nucleophilic. The $R^3$ group may be H, aliphatic or aromatic. X may be oxygen (regular ureas) or sulfur (thio-ureas). Thio-ureas are also particularly interesting ureas as the sulfur atom may serve as the nucleophilic site in these groups.

Phosphine groups ($PR^1R^2R^3$) are nucleophilic groups also. Preferred phosphines are those where at least 2, preferably all 3 of the $R^1$, $R^2$ and $R^3$ groups are aromatic in nature, as these phosphines are more stable and are least likely to oxidize.

N-oxides are also known as nucleophiles, where the oxygen atom is the nucleophilic atom. Particular examples are those where the nitrogen atom is part of an aromatic moiety, such as pyridine-oxides.

Dienes

The Activator is a diene. The person skilled in the art is aware of the wealth of dienes that are reactive in the Retro Diels-Alder reaction. The diene comprised in the Activator can be part of a ring structure that comprises a third double bond, such as a tetrazine (which is a preferred Activator according to the invention).

Generally, the Activator is a molecule comprising a heterocyclic ring structure, said ring structure comprising a diene moiety. A diene moiety is conceptually familiar to the skilled person, and consists of an array of four atoms (say PQRS), which are bonded such as to have two double bonds divided by a single bond (i.e. P=Q-R=S).

Preferred dienes are given below, with reference to formulae (2)-(4). The nucleophilic site or sites are present in these dienes, and they can be present in the given $R^1$ and/or $R^2$ and/or A and/or B and/or X and/or Y groups. The nucleophilic site(s) are preferably present in the $R^1$ and/or the $R^2$ groups.

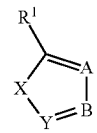

(2)

In formula (2) $R^1$ is selected from the group consisting of H, alkyl, aryl, $CF_3$, $CF_2$—R', OR', SR', C(=O)R', C(=S)R', C(=O)O—R', C(=O)S—R', C(=S)O—R', C(=S)S—R", C(=O)NR'R", C(=S)NR'R", NR'R", NR'C(=O)R", NR'C(=S)R", NR'C(=O)OR", NR'C(=S)OR", NR'C(=O)SR", NR'C(=S)SR", NR'C(=O)NR"R", NR'C(=S)NR"R" with each R' and each R" independently being H, aryl or alkyl; A and B each independently are selected from the group consisting of alkyl-substituted carbon, aryl substituted carbon, nitrogen, $N^+O^-$, $N^+R$ with R being alkyl, with the proviso that A and B are not both carbon; X is selected from the group consisting of O, N-alkyl, and C=O, and Y is CR with R being selected from the group consisting of H, alkyl, aryl, C(=O)OR', C(=O)SR', C(=S)OR', C(=S)SR', C(=O)NR'R" with R' and R" each independently being H, aryl or alkyl.

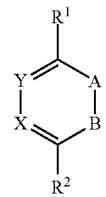

(3)

A diene particularly suitable as a reaction partner for cyclooctene is given in formula (3), wherein $R^1$ and $R^2$ each independently are selected from the group consisting of H, alkyl, aryl, $CF_3$, $CF_2$—R', $NO_2$, OR', SR', C(=O)R', C(=S)R', OC(=O)R''', SC(=O)R''', OC(=S)R''', SC(=S)R''', S(=O)R', S(=O)$_2$R-', S(=O)$_2$NR'R". C(=O)O—R', C(=O)S—R', C(=S)O—R', C(=S)S—R', C(=O)NR'R", C(=S)NR'R", NR'R", NR'C(=O)R", NR'C(=S)R", NR'C(=O)OR", NR'C(=S)OR", NR'C(=O)SR", NR'C(=S)SR", OC(=O)NR'R", SC(=O)NR'R", OC(=S)NR'R", SC(=S)NR'R", NR'C(=O)NR"R", NR'C(=S)NR"R" with each R' and each R" independently being H, aryl or alkyl, and R''' independently being aryl or alkyl; A is selected from the group consisting of N-alkyl, N-aryl. C=O, and CN-alkyl; B is O or S; X is selected from the group consisting of N, CH, C-alkyl, C-aryl, CC(=O)R', CC(=S)R', CS(=O) R, CS(=O)₂R''', CC(=O)O—R', CC(=O)S—R', CC(=S) O—R', CC(=S)S—R', CC(=O)NR'R''. CC(=S)NR'R'', R' and R'' each independently being H, aryl or alkyl and R''' independently being aryl or alkyl; Y is selected from the group consisting of CH, C-alkyl, C-aryl, N, and N⁺O⁻.

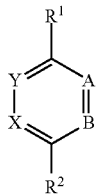
(4)

Another diene particularly suitable as a reaction partner for cyclooctene is diene (4), wherein R¹ and R² each independently are selected from the group consisting of H, alkyl, aryl, CF₃, CF₂—R', NO, NO₂, OR', SR', CN. C(=O)R', C(=S)R', OC(=O)R''', SC(=O)R''', OC(=S)R''', SC(=S) R''', S(=O)R', S(=O)₂R''', S(=O)₂OR', PO₃R'R'', S(=O)₂ NR'R'', C(=O)O—R', C(=O)S—R', C(=S)O—R', C(=S) S—R', C(=O)NR'R'', C(=S)NR'R'', NR'R'', NR'C(=O) R'', NR'C(=S)R'', NR'C(=O)OR'', NR'C(=S)OR'', NR'C (=O)SR'', NR'C(=S)SR'', OC(=O)NR'R'', SC(=O) NR'R'', OC(=S)NR'R'', SC(=S)NR'R'', NR'C(=O) NR''R'', NR'C(=S)NR''R'' with each R' and each R'' independently being H, aryl or alkyl, and R''' independently being aryl or alkyl; A is selected from the group consisting of N, C-alkyl, C-aryl, and N⁺O⁻; B is N; X is selected from the group consisting of N, CH, C-alkyl, C-aryl, CC(=O)R', CC(=S)R', CS(=O)R', CS(=O)₂R''', CC(=O)O—R', CC(=O)S—R, CC(=S)O—R', CC(=S)S—R', CC(=O) NR'R'', CC(=S)NR'R'', R' and R'' each independently being H, aryl or alkyl and R''' independently being aryl or alkyl; Y is selected from the group consisting of CH, C-alkyl, C-aryl, N, and N⁺O⁻.

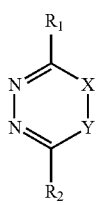
(5)

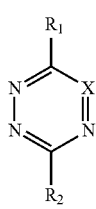
(6)

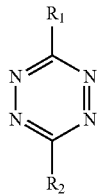
(7)

According to the invention, particularly useful dienes are 1,2-diazine, 1,2,4-triazine and 1,2,4,5-tetrazine derivatives, as given in formulas (5), (6) and (7), respectively. The nucleophilic site or sites are present in these di-, tri- or tetra-azines, and they can be present in the given R¹ and/or R² and/or X and/or Y groups. The nucleophilic site(s) are preferably present in the R¹ and/or the R² groups.

The 1,2-diazine is given in (5), wherein R¹ and R² each independently are selected from the group consisting of H, alkyl, aryl, CF₃, CF₂—R', NO₂, OR', SR', C(=O)R', C(=S) R', OC(=O)R''', SC(=O)R''', OC(=S)R''', SC(=S)R''', S(=O)R', S(=O)₂R''', S(=O)₂NR'R'', C(=O)O—R', C(=O)S—R', C(=S)O—R', C(=S)S—R', C(=O)NR'R'', C(=S)NR'R'', NR'R'', NR'C(=O)R'', NR'C(=S)R'', NR'C (=O)OR'', NR'C(=S)OR'', NR'C(=O)SR'', NR'C(=S) SR'', OC(=O)NR'R'', SC(=O)NR'R'', OC(=S)NR'R'', SC(=S)NR'R'', NR'C(=O)NR''R'', NR'C(=S)NR''R'' with each R' and each R'' independently being H, aryl or alkyl, and R''' independently being aryl or alkyl; X and Y each independently are selected from the group consisting of O, N-alkyl. N-aryl, C=O, CN-alkyl, CH, C-alkyl, C-aryl, CC(=O)R', CC(=S)R', CS(=O)R', CS(=O)₂R''', CC(=O)O—R', CC(=O)S—R', CC(=S)O—R', CC(=S) S—R', CC(=O)NR'R'', CC(=S)NR'R'', with R' and R'' each independently being H, aryl or alkyl and R''' independently being aryl or alkyl, where X—Y may be a single or a double bond, and where X and Y may be connected in a second ring structure apart from the 6-membered diazine. Preferably, X—Y represents an ester group (X=O and Y=C=O; X—Y is a single bond) or X—Y represents a cycloalkane group (X=CR' and Y=CR''; X—Y is a single bond; R' and R'' are connected), preferably a cyclopropane ring, so that R' and R'' are connected to each other at the first carbon atom outside the 1,2-diazine ring.

The 1,2,4-triazine is given in (6), wherein R¹ and R² each independently are selected from the group consisting of H, alkyl, aryl, CF₃, CF₂—R', NO₂, OR', SR', C(=O)R', C(=S) R', OC(=O)R''', SC(=O)R''', OC(=S)R''', SC(=S)R''', S(=O)R'. S(=O)₂R''', S(=O)₂NR'R'', C(=O)O—R', C(=O)S—R', C(=S)O—R', C(=S)S—R', C(=O)NR'R'', C(=S)NR'R'', NR'R'', NR'C(=O)R'', NR'C(=S)R'', NR'C (=O)OR'', NR'C(=S)OR'', NR'C(=O)SR'', NR'C(=S) SR'', OC(=O)NR'R'', SC(=O)NR'R'', OC(=S)NR'R'', SC(=S)NR'R'', NR'C(=O)NR''R'', NR'C(=S)NR''R'' with each R' and each R'' independently being H, aryl or alkyl, and R''' independently being aryl or alkyl; X is selected from the group consisting of CH, C-alkyl. C-aryl. CC(=O)R', CC(=S)R', CS(=O)R', CS(=O)₂R''', CC(=O)O—R', CC(=O)S—R', CC(=S)O—R', CC(=S)S—R', CC(=O) NR'R'', CC(=S)NR'R'', R' and R'' each independently being H, aryl or alkyl and R''' independently being aryl or alkyl.

The 1,2,4,5-tetrazine is given in (7), wherein R¹ and R² each independently are selected from the group consisting of H, alkyl, aryl, CF₃, CF₂—R', NO, NO₂, OR', SR', CN, C(=O)R', C(=S)R', OC(=O)R''', SC(=O)R''', OC(=S) R''', SC(=S)R''', S(=O)R', S(=O)₂R''', S(=O)₂OR', PO₃R'R", S(=O)₂NR'R", C(=O)O—R', C(=O)S—R', C(=S)O—R', C(=S)S—R', C(=O)NR'R", C(=S)NR'R", NR'R", NR'C(=O)R''', NR'C(=S)R''', NR'C(=O)OR''', NR'C(=S)OR", NR'C(=O)SR", NR'C(=S)SR", OC(=O)NR'R", SC(=O)NR'R", OC(=S)NR'R", SC(=S)NR'R", NR'C(=O)NR"R''', NR'C(=S)NR"R''' with each R' and each R" independently being H, aryl or alkyl, and R''' independently being aryl or alkyl.

Electron-deficient 1,2-diazines (5), 1,2,4-triazines (6) or 1,2,4,5-tetrazines (7) are especially interesting as such dienes are generally more reactive towards dienophiles. Di-tri- or tetra-azines are electron deficient when they are substituted with groups or moieties that do not generally hold as electron-donating, or with groups that are electron-withdrawing. For example, $R^1$ and/or $R^2$ may denote a substituent selected from the group consisting of H, alkyl, $NO_2$, F, Cl, $CF_3$, CN, COOR, CONHR, $CONR_2$, COR, $SO_2R$, $SO_2OR$, $SO_2NR_2$, $PO_3R_2$, NO, 2-pyridyl, 3-pyridyl, 4-pyridyl, 2,6-pyrimidyl, 3,5-pyrimidyl, 2,4-pyrimidyl, 2,4 imidazyl, 2,5 imidazyl or phenyl, optionally substituted with one or more electron-withdrawing groups such as $NO_2$, F, Cl, $CF_3$, CN, COOH, COOR, $CONH_2$, CONHR, $CONR_2$, COR, $SO_2R$, $SO_2OR$, $SO_2NR_2$, $PO_3R_2$, NO, Ar, wherein R is H or alkyl, and Ar stands for an aromatic group, particularly phenyl, pyridyl, or naphthyl.

The 1,2,4,5-tetrazines of formula (7) are most preferred as Activator dienes, as these molecules are most reactive in retro Diels-Alder reactions with dienophiles, such as the preferred TCO dienophiles, even when the $R^1$ and/or $R^2$ groups are not necessarily electron withdrawing, and even when $R^1$ and/or $R^2$ are in fact electron-donating. Electron donating groups are for example OH, OR', SH, SR', $NH_2$, NHR', NR'R", NHC(=O)R", NR'C(=O)R", NHC(=S)R", NR'C(=S)R", $NHSO_2R"$, $NR'SO_2R"$ with R' and R" each independently being alkyl or aryl groups. Examples of other electron donating groups are phenyl groups with attached to them one or more of the electron donating groups as mentioned in the list above, especially when substituted in the 2-, 4- and/or 6-position(s) of the phenyl group.

The 1,2,4,5-tetrazines can be asymmetric or symmetric in nature, i.e. the $R^1$ and $R^2$ groups in formula (7) may be different groups or may be identical groups, respectively. Symmetric 1,2,4,5-tetrazines are most preferred as then the Retro Diels-Alder reaction will lead to a Retro Diels-Alder dihydro-pyridazine adduct with both sides of the dihydro-pyridazine ring bearing nucleophilic sites that can be active in the cyclization reaction.

1,2,4,5-Tetrazines with one nucleophilic site per $R^1$ and $R^2$ group are preferred.

1,2,4,5-Tetrazines are preferred with the nucleophilic sites positioned such that the intramolecular cyclization reaction within the Retro Diels-Alder adduct produces a ring structure with a low ring strain. Ring strain is caused by high-energy bond angles that have to be adopted due the connectivity within a particular ring. As is known in the art, every type of ring structure, with heteroatoms or unsaturated bonds possibly being present, will have its own sequence of ring strains on going from smaller to larger rings. Nevertheless, as a rule of thumb, most 5-, 6- and possibly 7-membered rings as well as larger rings such as 12- and 13-membered rings are low in ring strain, while 3-, 4-, 9- and 10-membered rings are often high or higher in ring strain. For example, cyclopropane, cyclobutane and cyclononane have ring strains of 120, 110 and 50 kJ/mol, respectively, while cylcopentane and cyclohexane have ring strains of 25 and virtually 0 kJ/mol, respectively, with cyclododecane also being low in ring strain. Accordingly, 1,2,4,5-tetrazines with the nucleophilic atom positioned at the first (or alfa), second (or beta) or third (or gamma) position of the 3- and/or 6-substituents (i.e. the $R^1$ and/or the $R^2$ residues in formula (7)) of the 1,2,4,5-tetrazine as counted from the tetrazine ring are most preferred, as these situations enable cyclization to 5-, 6- or 7-membered rings. Nucleophilic sites at the seventh, eighth, or ninth atom of the $R^1$ and/or $R^2$ residues are also preferred as these situations are suited for cyclization to 12- or 13-membered rings. By way of clarification of this definition 3,6-diamino-1,2,4,5-tetrazine (the nitrogens are in the alfa position), 3,6-di-(2,5-imidazyl)-1,2,4,5-tetrazine (the nitrogens are in the beta position), 3,6-di-(2-aminoethyl)-1,2,4,5-tetrazine (the nitrogens are in the gamma position) and 3,6-di-(6-aminohexyloxy)-1,2,4,5-tetrazine (the nitrogens are in the eighth position) have been drawn below.

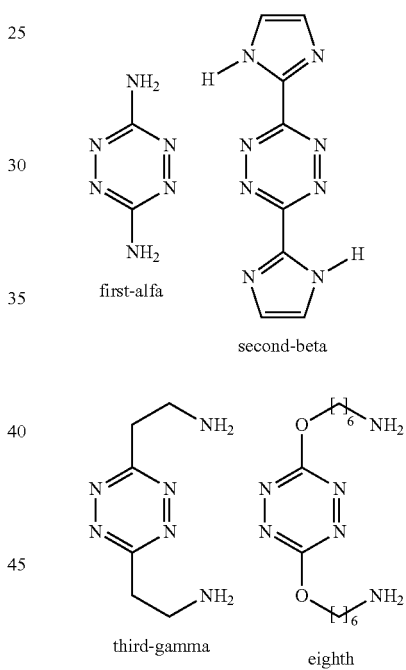

first-alfa second-beta third-gamma eighth

In the following paragraphs specific examples of 1,2,4,5-tetrazines that bear nucleophilic sites will be highlighted by defining the $R^1$ and $R^2$ residues in formula (7). First, symmetric tetrazines, i.e. $R^1$ is identical to $R^2$, will be listed. Thereafter comments will be made on and examples will be given of asymmetric 1,2,4,5-tetrazines, i.e. $R^1$ is then different from $R^2$.

Examples of symmetric tetrazines are: $R^1=R^2=$OH, SH, $NH_2$, NHR', NH—CO—R', NH—SO—R', NH—$SO_2$—R', where R' represents an alkyl or an aryl group, preferably a methyl, ethyl, phenyl or tolyl group. Symmetric tetrazines where $R^1=R^2=$OH, SH. $NH_2$ or NHR' are preferred. Note that in these examples the nucleophilic site is positioned at the first (alfa) atom of $R^1$ and $R^2$ residues, as counted from the tetrazine ring.

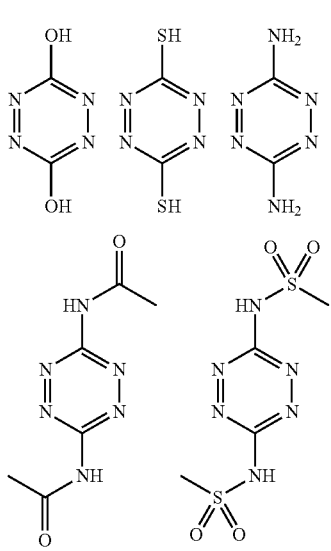

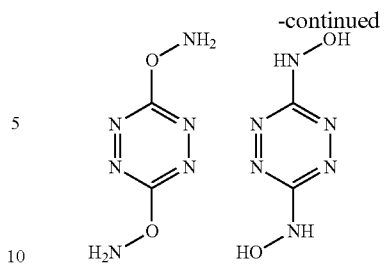

Further examples of symmetric tetrazines are those with attached hetero(aromatic) cycles that inherently bear nucleophilic sites, e.g. $R^1=R^2=$2,4-imidazyl, 2,5-imidazyl, 2,3-pyrazyl, 3,4-pyrazyl, 2-pyrryl, 3-pyrryl, 2,3,4-triazyl, 2,3,5-triazyl, 2,3,4,5-tetrazyl. These hetero(aromatic) cycles may optionally be substituted with $C_{1-6}$ alkyl moieties. Find below examples of these structures drawn; other tautomeric forms of these molecules are also included.

Other examples of symmetric tetrazines are those with attached benzylic alcohol, benzylic thiol or benzylic amine groups, where $R^1=R^2=CH_2OH$ (or CHR'OH, CR'R"OH), $CH_2SH$ (or CHR'SH, CR'R"SH), $CH_2NH_2$ (or CHR'NH$_2$, CR'R"'NH$_2$), $CH_2NHR'''$ (or CHR'NHR''', CR'R"NHR'''), where R' and R" each independently represent $C_1$-$C_6$ alkyl chains and where R''' represents $C_1$-$C_6$ alkyl chains or an aryl, preferably a phenyl group. From these $R^1=R^2=CH_2OH$, $CH_2SH$, $CH_2NH_2$ and $CH_2NHR'''$ are preferred, where R''' is then methyl, ethyl or phenyl. Yet other examples of symmetric tetrazines are those where $R^1=R^2=$NH—NH$_2$ (or NR'—NH$_2$, NR'—NHR"), O—NH$_2$ (or O—NHR'), NH—OH (or NR'—OH, NH—OR'), where R' and R" each independently represent $C_{1-6}$ alkyl chains or aryl groups, preferably each independently a methyl, ethyl, propyl or phenyl group. More preferred are the simple NH—NH$_2$, O—NH$_2$ and NH—OH groups. Note that in these examples the nucleophilic site is positioned at the second (beta) atom of $R^1$ and $R^2$ residues (or at the first alfa-atom) as counted from the tetrazine ring.

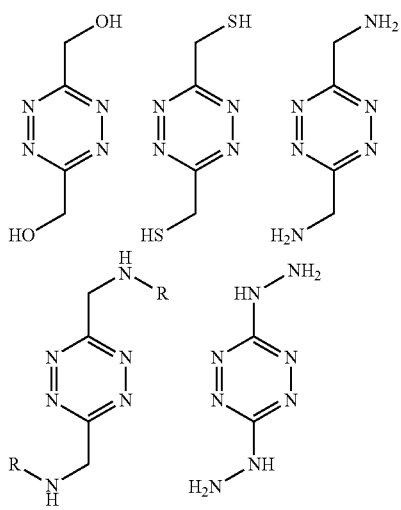

both R = methyl, or
both R = ethyl, or
both R = phenyl

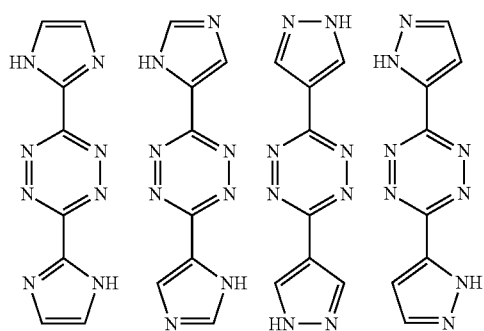

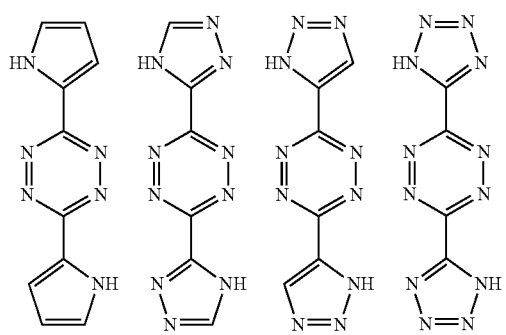

Yet other symmetric tetrazine examples are those where $R^1$ and $R^2$ are aryl groups, preferably phenyl, pyridyl or pyrimidyl groups, with attached nucleophilic sites. These aryls may optionally be substituted with $C_{1-6}$ alkyl moieties. Nucleophilic sites can for example be —NH$_2$, —NHR', —OH, —SH or —CH$_2$NH$_2$, CH$_2$NHR', —CH$_2$OH CH$_2$SH groups, where R' may represent $C_{1-6}$ alkyl or phenyl. Accordingly, specific examples are $R^1=R^2=$2-aminophenyl, 3-aminophenyl, 4-aminophenyl, 2-amino-6-pyridyl, 3-amino-6-pyridyl, 4-amino-6-pyridyl, or 2-hydroxyphenyl, 3-hydroxyphenyl, 4-hydroxyphenyl, 2-hydroxy-6-pyridyl, 3-hydroxy-6-pyridyl, 4-hydroxy-6-pyridyl, or 2-thiolphenyl, 3-thiolphenyl, 4-thiolphenyl, 2-thiol-6-pyridyl, 3-thiol-6-pyridyl, 4-thiol-6-pyridyl, or 2-(aminomethylene)-phenyl, 3-(aminomethylene)-phenyl, 4-(aminomethylene)-phenyl, 2-(aminomethylene)-6-pyridyl, 3-(aminomethylene)-6-pyridyl, 4-(aminomethylene)-6-pyridyl, or 2-(hydroxymethylene)-phenyl, 3-(hydroxymethylene)-phenyl, 4-(hydroxymethylene)-phenyl, 2-(hydroxymethylene)-6-pyridyl, 3-(hydroxymethylene)-6-pyridyl, 4-(hydroxymethylene)-6-pyridyl, or 2-(thiolmethylene)-phenyl, 3-(thiolmethylene)-phenyl, 4-(thiolmethylene)-phenyl, 2-(thiolmethylene)-6-pyridyl, 3-(thiolmethylene)-6-pyridyl, 4-(thiolmethylene)-6-pyridyl. See hereunder some of these structures with the nucleophilic group attached at the 2-position of the aryl group; alternatively, attachment at either one of the other positions is also possible.

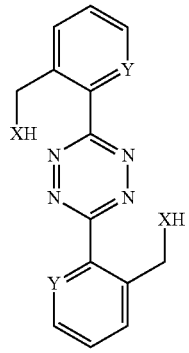

both X = O and both Y = C, or
both X = O and both Y = N, or
both X = S and both Y = C, or
both X = S and both Y = N

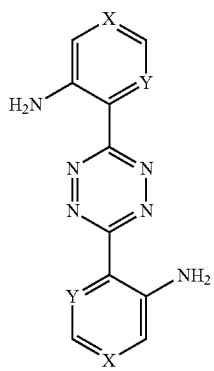

both Y = C and both X = C, or
both Y = C and both X = N, or
both Y = N and both X = C, or
both Y = N and both X = N

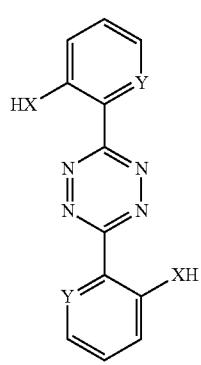

both X = O and both Y = C, or
both X = O and both Y = N, or
both X = S and both Y = C, or
both X = S and both Y = N Furthermore, other symmetric tetrazine examples are those where $R^1$ and $R^2$ are alkyl groups with attached nucleophilic sites. These alkyls may be $C_{2-12}$ linear, branched or cyclic and may contain 1 to 3 heteroatoms such as N, O or S. Nucleophilic sites can for example be —$NH_2$, —NHR', —OH, —SH groups, where R' may represent $C_{1-6}$ alkyl or phenyl. Accordingly, specific examples are $R^1=R^2$=2-amino-ethyl, 4-amino-butyl, 6-amino-hexyl, 2-amino-ethyloxy, 4-amino-butyloxy, 6-amino-hexyloxy, 2-amino-ethylthioxy, 4-amino-butylthioxy, 6-amino-hexylthioxy, or 2-hydroxy-ethyl, 4-hydroxy-butyl, 6-hydroxy-hexyl, 2-hydroxy-ethyloxy, 4-hydroxy-butyloxy, 6-hydroxy-hexyloxy, 2-hydroxy-ethylthioxy, 4-hydroxy-butylthioxy, 6-hydroxy-hexylthioxy, or 2-thiol-ethyl, 4-thiol-butyl, 6-thiol-hexyl, 2-thiol-ethyloxy, 4-thiol-butyloxy, 6-thiol-hexyloxy, 2-thiol-ethylthioxy, 4-thiol-butylthioxy, 6-thiol-hexylthioxy, or 2-pyrrolidinyl, or 2-piperidinyl, or N-piperazyl. By way of clarification, see the ethylene spaced structures drawn below. Other spacers than the drawn ethylene (or the mentioned butylene or hexylene) spacers are also possible of course.

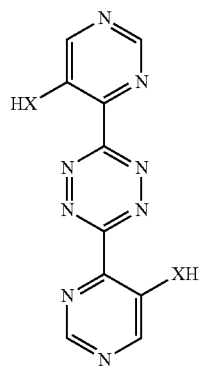

both Y = O, or
both X = S

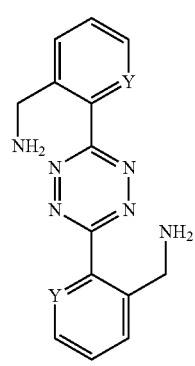

both Y = C, or
both Y = N

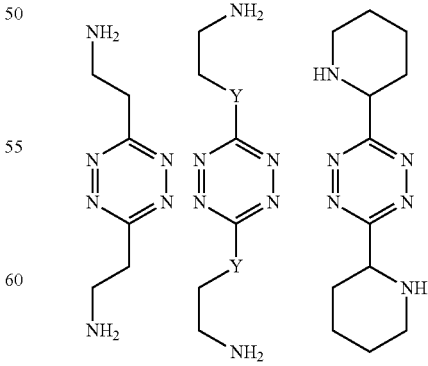

both Y = O, or
both Y = S

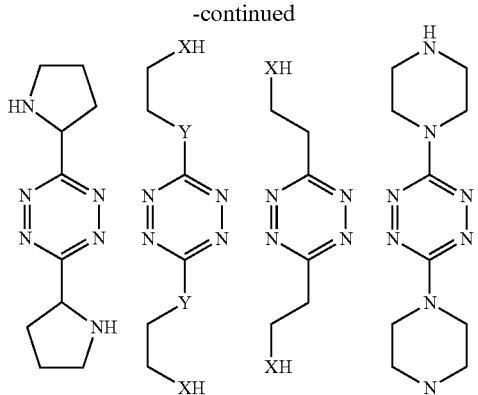

both X = O and both Y = O, or both X = O, or
both X = O and both Y = S, or both X = S
both X = S and both Y = O, or
both X = S and both Y = S In case asymmetric 1,2,4,5-tetrazines are considered, one can choose any combination of given $R^1$ and $R^2$ residues that have been highlighted and listed above for the symmetric tetrazines of formula (7), provided of course that $R^1$ and $R^2$ are different. Accordingly, both $R^1$ and $R^2$ have nucleophilic sites. Find below some example structures drawn.

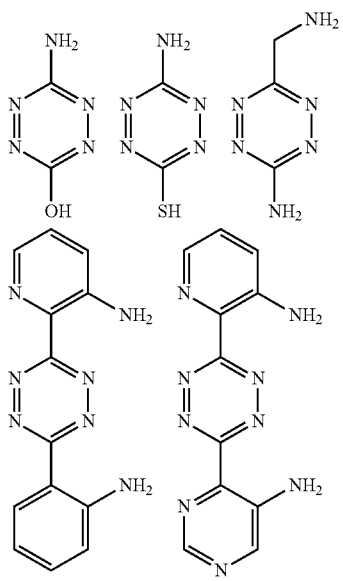

However, in case asymmetric 1,2,4,5-tetrazines are considered, it is preferred that the above listed $R^1$ residues for the symmetric 1,2,4,5-tetrazines are combined with an $R^2$ residue that not necessarily bears a nucleophilic site, that does not generally hold as electron-donating and that preferably is electron-withdrawing and that is chosen from residues of the group H, alkyl (preferably methyl), aryl (preferably 2-pyridyl, 3-pyridyl, 4-pyridyl, 2,6-pyrimidyl, 3,5-pyrimidyl, 2,4-pyrimidyl or phenyl optionally substituted with one or more electron-withdrawing groups such as $NO_2$, F, Cl, $CF_3$, CN, COOH, COOR', $CONH_2$, CONHR', CONR'R'', CHO, COR', $SO_2R'$, $SO_2OR'$, NO or R'), $CF_3$, $CF_2$—R', C(=O)R', C(=S)R', S(=O)R', S(=O)$_2$R', C(=O)O—R', C(=O)S—R', C(=S)O—R', C(=S)S—R', C(=O)NR'R'', C(=S)NR'R'' with R' and R'' each independently being aryl or alkyl. More preferably, the $R^2$ residue then is chosen from H, methyl, 2-pyridyl, 3-pyridyl, 4-pyridyl, 2,6-pyrimidyl, 3,5-pyrimidyl, 2,4-pyrimidyl, phenyl, $CONH_2$, CONHR', CONR'R'' with R' and R'' each independently being aryl or alkyl, preferably methyl or ethyl. Find below some example structures drawn.

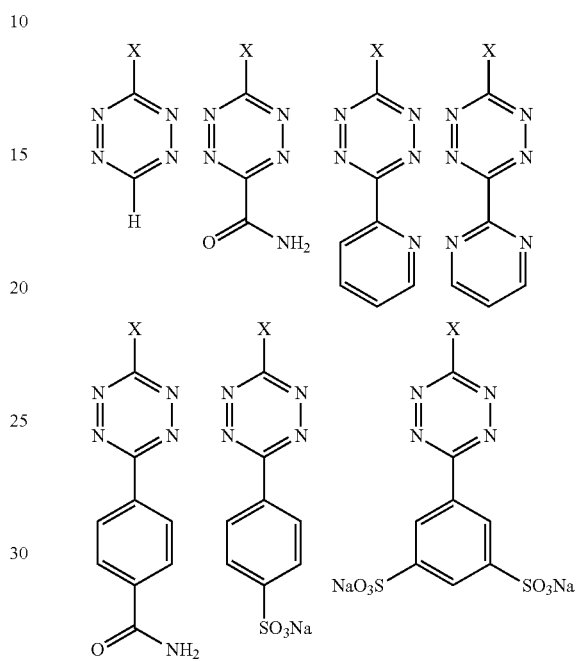

For all structures:
X = $NH_2$, or X = OH, or X = SH, or
X = $CH_2NH_2$, or X = 2,5-imidazyl, or
X = 2-aminophenyl, or X = $(CH_2)_7$—$NH_2$ Drug Release Via (Cascade) Elimination Reactions In another preferred embodiment of this invention, the release of the drug or drugs is caused by an intramolecular elimination reaction within the Retro Diels-Alder adduct. This elimination reaction can be a simple one step reaction, or it can be a multiple step reaction that involves one or more intermediate structures. These intermediates may be stable for some time or may immediately degrade to the thermodynamic end product or to the next intermediate structure. When several steps are involved, one can speak of a cascade reaction. In any case, whether it be a simple or a cascade process, the result of the elimination reaction is that the drug gets released from the retro Diels-Alder adduct. Without wishing to be bound by theory, the design of both components (i.e. the diene Activator and the dienophile Trigger) is such that the distribution of electrons within the retro Diels-Alder adduct is unfavorable, so that a rearrangement of these electrons must occur. This situation initiates the intramolecular (cascade) elimination reaction to take place, and it therefore induces the release of the drug or drugs. Occurrence of the elimination reaction in and drug release from the Prodrug is not efficient or cannot take place prior to the Retro Diels-Alder reaction, as the Prodrug itself is relatively stable as such. Elimination can only take place after the Activator and the Prodrug have reacted and have been assembled in the retro Diels-Alder adduct.

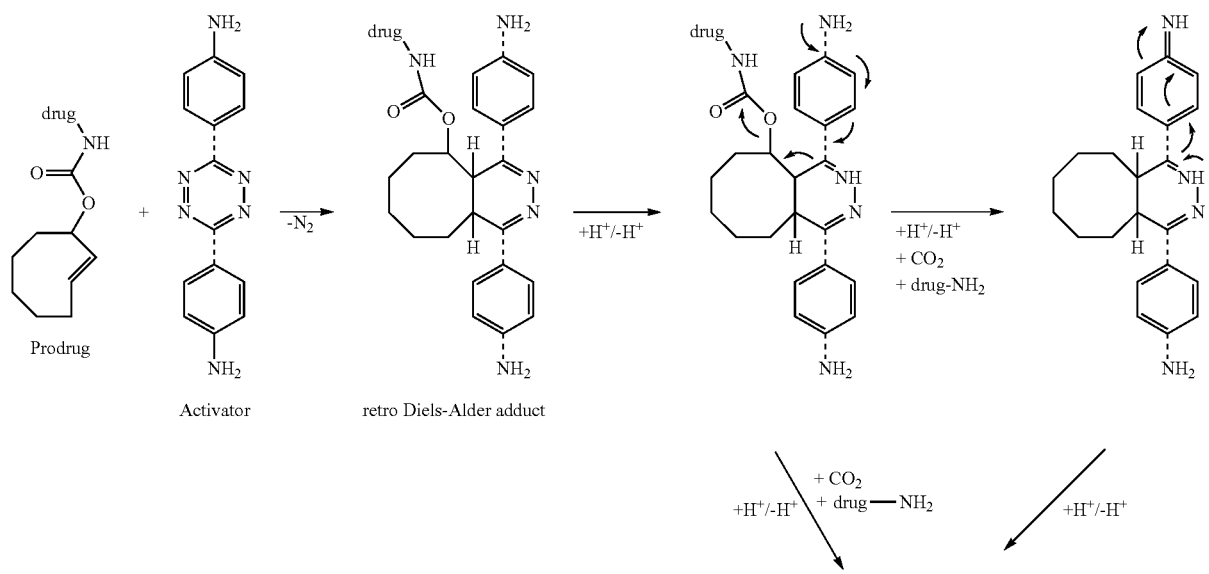
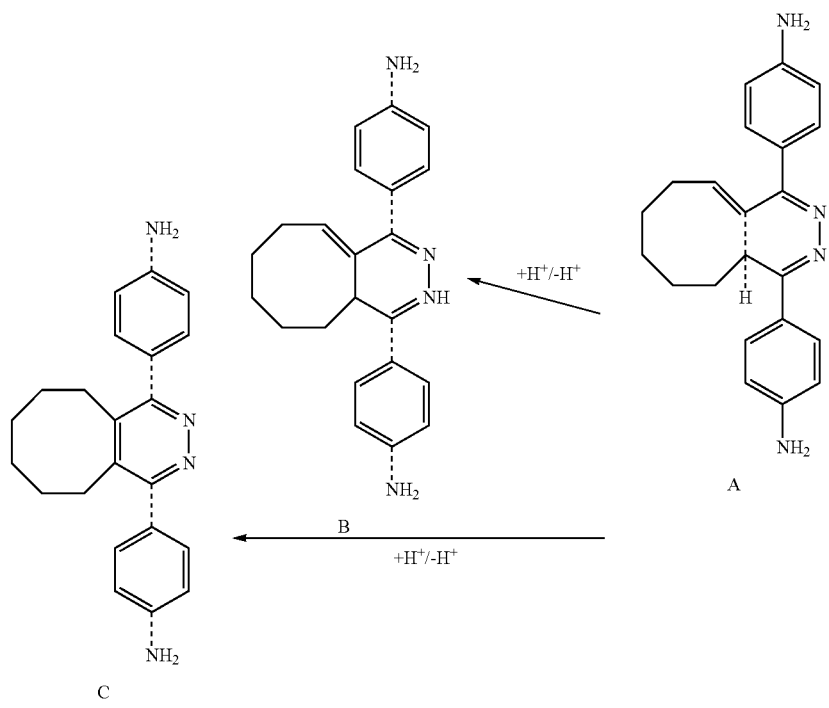

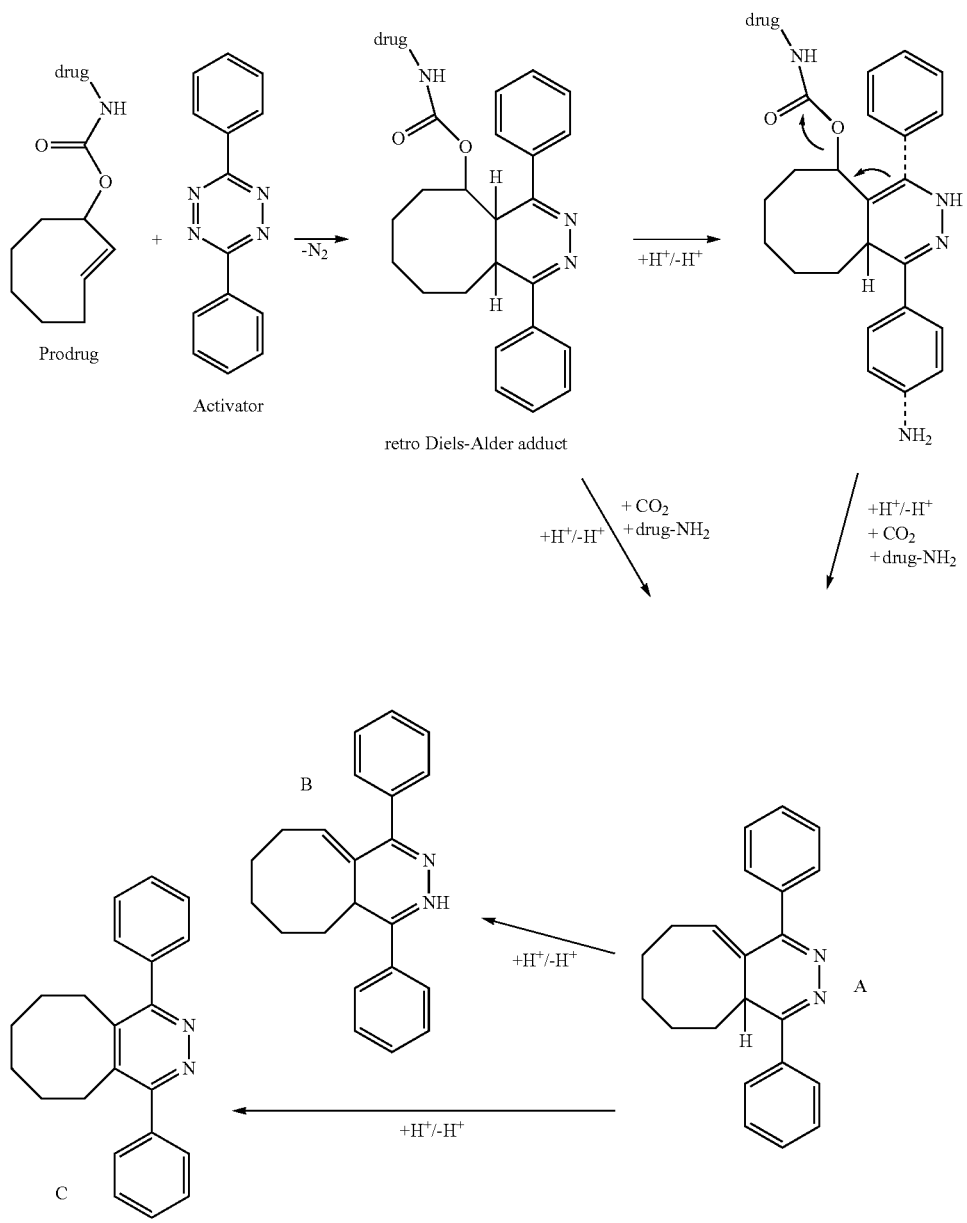

Without wishing to be bound by theory, the above two examples illustrate how the unfavorable distribution of electrons w,ithin the retro Diels-Alder adduct can be relieved by an elimination reaction, thereby releasing the drug. In one scenario, the elimination process produces end product A, where this product has a conjugation of double bonds that was not present in the retro Diels-Alder adduct yet. Species A may tautomerize to end product B, or may rearrange to form end product C. Then, the non-aromatic dihydro pyridazine ring in the retro Diels-Alder adduct has been converted to the aromatic pyridazine ring in the end product C. The skilled person will understand that the distribution of electrons in the retro Diels-Alder adduct is generally unfavorable relative to the distribution of the electrons in the end products, either species A or B or C. Thus, the formation of a species stabler than the retro Diels-Alder adduct is the driving force for the (cascade) elimination reaction. In any case, and in whatever way the process is viewed, the drug species (here the amine 'drug-$NH_2$') is effectively expelled from the retro Diels-Alder adduct, while it does not get expelled from the Prodrug alone.

Below scheme depicts a possible alternative release mechanism for the cascade elimination, in addition to the two discussed above. Without wishing to be bound by theory, the below examples illustrates how the unfavorable distribution of electrons within the retro Diels-Alder adduct may be relieved by an elimination reaction, thereby releasing the drug. This process may evolve via various tauromerisations that are all equilibria. Here, the rDA reaction produces tautomers A and B, which can interchange into one and other. Tautomer B can lead to the elimination into product C and thereafter into D.

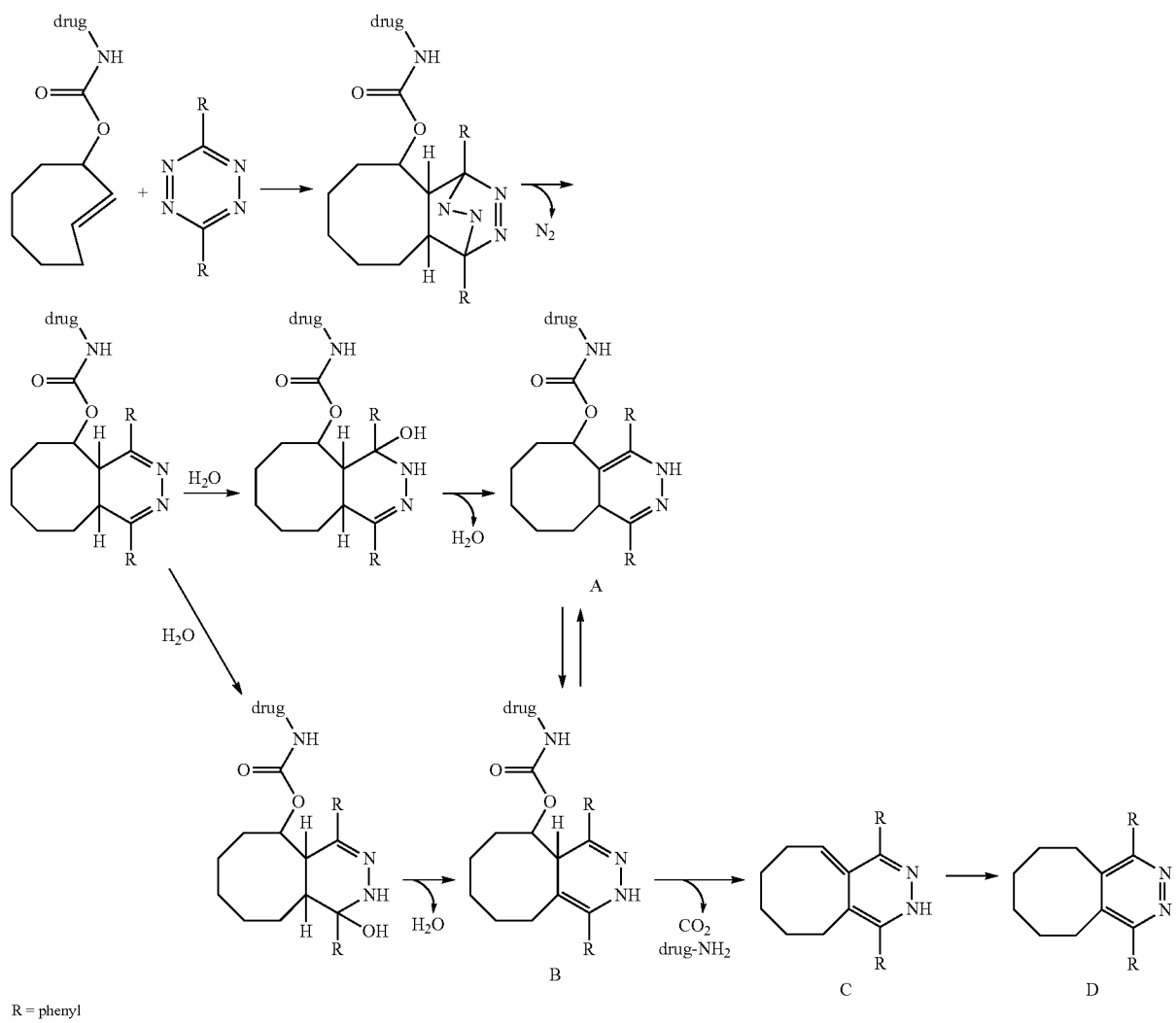

R = phenyl

Also in this second embodiment of the invention, the Activator is a diene. The person skilled in the art is aware of the wealth of dienes that are reactive in the Retro Diels-Alder reaction. Preferred dienes are given below, with reference to formulae (8)-(10).

$$\text{(8)}$$

In formula (8) $R^1$ is selected from the group consisting of H, alkyl, aryl, $CF_3$, $CF_2$—R', OR', SR', C(=O)R', C(=S)R', C(=O)O—R', C(=O)S—R', C(=S)O—R', C(=S)S—R", C(=O)NR'R''', C(=S)NR'R'', NR'R'', NR'C(=O)R'', NR'C(=S)R'', NR'C(=O)OR'', NR'C(=S)OR'', NR'C(=O)SR'', NR'C(=S)SR'', NR'C(=O)NR''R''', NR'C(=S)NR''R'' with each R' and each R'' independently being H, aryl or alkyl; A and B each independently are selected from the group consisting of alkyl-substituted carbon, aryl substituted carbon, nitrogen. $N^+O^-$, $N^+R$ with R being alkyl, with the proviso that A and B are not both carbon; X is selected from the group consisting of O, N-alkyl, and C=O, and Y is CR with R being selected from the group consisting of H, alkyl, aryl, C(=O)OR', C(=O)SR', C(=S)OR', C(=S)SR', C(=O)NR'R'' with R' and R'' each independently being H, aryl or alkyl.

$$\text{(9)}$$

A diene particularly suitable as a reaction partner for cyclooctene is given in formula (9), wherein $R^1$ and $R^2$ each independently are selected from the group consisting of H, alkyl, aryl, $CF_3$, $CF_2$—R', $NO_2$, OR', SR', C(=O)R', C(=S)R'. OC(=O)R''', SC(=O)R''', OC(=S)R''', SC(=S)R''', S(=O)R', S(=O)₂R''', S(=O)₂NR'R'', C(=O)O—R', C(=O)S—R', C(=S)O—R', C(=S)S—R', C(=O)NR'R'', C(=S)NR'R'', NR'R'', NR'C(=O)R'', NR'C(=S)R'', NR'C(=O)OR'', NR'C(=S)OR'', NR'C(=O)SR'', NR'C(=S)SR'', OC(=O)NR'R'', SC(=O)NR'R'', OC(=S)NR'R'', SC(=S)NR'R'', NR'C(=O)NR''R''', NR'C(=S)NR''R''' with each R' and each R'' independently being H, aryl or alkyl, and R''' independently being aryl or alkyl; A is selected from the group consisting of N-alkyl, N-aryl, C=O, and CN-alkyl; B is O or S; X is selected from the group consisting of N, CH, C-alkyl, C-aryl, CC(=O)R', CC(=S)R', CS(=O)R', CS(=O)₂R''', CC(=O)O—R', CC(=O)S—R', CC(=S)O—R', CC(=S)S—R', CC(=O)NR'R'', CC(=S)NR'R'', R' and R'' each independently being H, aryl or alkyl and R''' independently being aryl or alkyl; Y is selected from the group consisting of CH, C-alkyl, C-aryl, N, and N⁺O⁻.

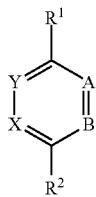

(10)

Another diene particularly suitable as a reaction partner for cyclooctene is diene (10), wherein $R^1$ and $R^2$ each independently are selected from the group consisting of H, alkyl, aryl, CF₃, CF₂—R', NO, NO₂, OR', SR', CN, C(=O)R', C(=S)R', OC(=O)R''', SC(=O)R''', OC(=S)R''', SC(=S)R'', S(=O)R', S(=O)₂R''', S(=O)₂OR', PO₃R'R'', S(=O)₂NR'R'', C(=O)O—R', C(=O)S—R', C(=S)O—R', C(=S)S—R', C(=O)NR'R'', C(=S)NR'R'', NR'R'', NR'C(=O)R'', NR'C(=S)R'', NR'C(=O)OR'', NR'C(=S)OR'', NR'C(=O)SR'', NR'C(=S)SR'', OC(=O)NR'R'', SC(=O)NR'R'', OC(=S)NR'R'', SC(=S)NR'R'', NR'C(=O)NR''R''', NR'C(=S)NR''R''' with each R' and each R'' independently being H, aryl or alkyl, and R''' independently being aryl or alkyl; A is selected from the group consisting of N, C-alkyl, C-aryl, and N⁺O⁻; B is N; X is selected from the group consisting of N, CH, C-alkyl, C-aryl, CC(=O)R', CC(=S)R', CS(=O)R', CS(=O)₂R''', CC(=O)O—R', CC(=O)S—R', CC(=S)O—R', CC(=S)S—R', CC(=O)NR'R'', CC(=S)NR'R'', R' and R'' each independently being H, aryl or alkyl and R''' independently being aryl or alkyl; Y is selected from the group consisting of CH, C-alkyl, C-aryl, N, and N⁺O⁻.

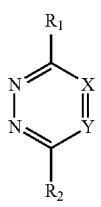

(11)

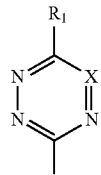

(12)

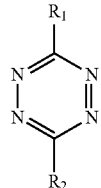

(13)

According to the invention, particularly useful dienes are 1,2-diazine, 1,2,4-triazine and 1,2,4,5-tetrazine derivatives, as given in formulas (11), (12) and (13), respectively.

The 1,2-diazine is given in (11), wherein $R^1$ and $R^2$ each independently are selected from the group consisting of H, alkyl, aryl, CF₃, CF₂—R', NO₂, OR', SR', C(=O)R', C(=S)R', OC(=O)R''', SC(=O)R''', OC(=S)R''', SC(=S)R''', S(=O)R', S(=O)₂R''', S(=O)₂NR'R'', C(=O)O—R', C(=O)S—R', C(=S)O—R', C(=S)S—R', C(=O)NR'R'', C(=S)NR'R'', NR'R'', NR'C(=O)R'', NR'C(=S)R'', NR'C(=O)OR'', NR'C(=S)OR'', NR'C(=O)SR'', NR'C(=S)SR'', OC(=O)NR'R'', SC(=O)NR'R'', OC(=S)NR'R'', SC(=S)NR'R'', NR'C(=O)NR''R''', NR'C(=S)NR''R''' with each R' and each R'' independently being H, aryl or alkyl, and R''' independently being aryl or alkyl; X and Y each independently are selected from the group consisting of O, N-alkyl, N-aryl, C=O, CN-alkyl, CH, C-alkyl, C-aryl, CC(=O)R', CC(=S)R', CS(=O)R', CS(=O)₂R''', CC(=O)O—R', CC(=O)S—R', CC(=S)O—R', CC(=S)S—R', CC(=O)NR'R'', CC(=S)NR'R'', with R' and R'' each independently being H, aryl or alkyl and R''' independently being aryl or alkyl, where X—Y may be a single or a double bond, and where X and Y may be connected in a second ring structure apart from the 6-membered diazine. Preferably, X—Y represents an ester group (X=O and Y=C=O; X—Y is a single bond) or X—Y represents a cycloalkane group (X=CR' and Y=CR''; X—Y is a single bond; R' and R'' are connected), preferably a cyclopropane ring, so that R' and R'' are connected to each other at the first carbon atom outside the 1,2-diazine ring.

The 1,2,4-triazine is given in (12), wherein $R^1$ and $R^2$ each independently are selected from the group consisting of H, alkyl, aryl, CF₃, CF₂—R', NO₂, OR', SR', C(=O)R', C(=S)R', OC(=O)R''', SC(=O)R''', OC(=S)R''', SC(=S)R''', S(=O)R', S(=O)₂R''', S(=O)₂NR'R'', C(=O)O—R', C(=O)S—R', C(=S)O—R', C(=S)S—R', C(=O)NR'R'', C(=S)NR'R'', NR'R'', NR'C(=O)R'', NR'C(=S)R'', NR'C(=O)OR'', NR'C(=S)OR'', NR'C(=O)SR'', NR'C(=S)SR'', OC(=O)NR'R'', SC(=O)NR'R'', OC(=S)NR'R'', SC(=S)NR'R'', NR'C(=O)NR''R''', NR'C(=S)NR''R''' with each R' and each R'' independently being H, aryl or alkyl, and R'' independently being aryl or alkyl; X is selected from the group consisting of CH, C-alkyl, C-aryl, CC(=O)R', CC(=S)R', CS(=O)R', CS(=O)₂R''', CC(=O)O—R', CC(=O)S—R', CC(=S)O—R', CC(=S)S—R', CC(=O)NR'R'', CC(=S)NR'R'', R' and R'' each independently being H, aryl or alkyl and R''' independently being aryl or alkyl.

The 1,2,4,5-tetrazine is given in (13), wherein $R^1$ and $R^2$ each independently are selected from the group consisting of H, alkyl, aryl, $CF_3$, $CF_2$—R', NO, $NO_2$, OR', SR', CN, C(=O)R', C(=S)R', OC(=O)R''', SC(=O)R''', OC(=S)R''', SC(=S)R''', S(=O)R', S(=O)$_2$R''', S(=O)$_2$OR', $PO_3$R'R'', S(=O)NR'R'', C(=O)O—R', C(=O)S—R', C(=S)O—R', C(=S)S—R', C(=O)NR'R'', C(=S)NR'R'', NR'R'', NR'C(=O)R'', NR'C(=S)R'', NR'C(=O)OR'', NR'C(=S)OR'', NR'C(=O)SR'', NR'C(=S)SR'', OC(=O)NR'R'', SC(=O)NR'R'', OC(=S)NR'R'', SC(=S)NR'R'', NR'C(=O)NR''R'', NR'C(=S)NR''R'' with each R' and each R'' independently being H, aryl or alkyl, and R''' independently being aryl or alkyl.

Electron-deficient 1,2-diazines (11), 1,2,4-triazines (12) or 1,2,4,5-tetrazines (13) are especially interesting as such dienes are generally more reactive towards dienophiles. Di-tri- or tetra-azines are electron deficient when they are substituted with groups or moieties that do not generally hold as electron-donating, or with groups that are electron-withdrawing. For example, $R^1$ and/or $R^2$ may denote a substituent selected from the group consisting of H, alkyl, $NO_2$, F, Cl, $CF_3$, CN, COOR, CONHR, $CONR_2$, COR, $SO_2R$, $SO_2OR$, $SO_2NR_2$, $PO_3R_2$, NO, 2-pyridyl, 3-pyridyl, 4-pyridyl, 2,6-pyrimidyl, 3,5-pyrimidyl, 2,4-pyrimidyl, 2,4 imidazyl, 2,5 imidazyl or phenyl, optionally substituted with one or more electron-withdrawing groups such as $NO_2$, F, Cl, $CF_3$, CN, COOR, CONHR, CONR, COR, $SO_2R$, $SO_2OR$, $SO_2NR_2$, $PO_3R_2$, NO, Ar, wherein R is H or $C_1$-$C_6$ alkyl, and Ar stands for an aromatic group, particularly phenyl, pyridyl, or naphthyl.

The 1,2,4,5-tetrazines of formula (13) are most preferred as Activator dienes, as these molecules are most reactive in retro Diels-Alder reactions with dienophiles, such as the preferred TCO dienophiles, even when the $R^1$ and/or $R^2$ groups are not necessarily electron withdrawing, and even when $R^1$ and/or $R^2$ are in fact electron donating. Electron donating groups are for example OH, OR', SH, SR', $NH_2$, NHR', NR'R'', NHC(=O)R'', NR'C(=O)R'', NHC(=S)R'', NR'C(=S)R'', $NHSO_2R''$, $NR'SO_2R''$ with R' and R'' each independently being alkyl or aryl groups. Examples of other electron donating groups are phenyl groups with attached to them one or more of the electron donating groups as mentioned in the list above, especially when substituted in the 2-, 4- and/or 6-position(s) of the phenyl group.

According to the invention, 1,2,4,5-tetrazines with two electron withdrawing residues, or those with one electron withdrawing residue and one residue that is neither electron withdrawing nor donating, are called electron deficient. In a similar way, 1,2,4,5-tetrazines with two electron donating residues, or those with one electron donating residue and one residue that is neither electron withdrawing nor donating, are called electron sufficient, 1,2,4,5-Tetrazines with two residues that are both neither electron withdrawing nor donating, or those that have one electron withdrawing residue and one electron donating residue, are neither electron deficient nor electron sufficient.

The 1,2,4,5-tetrazines can be asymmetric or symmetric in nature, i.e. the $R^1$ and $R^2$ groups in formula (13) may be different groups or may be identical groups, respectively. Symmetric 1,2,4,5-tetrazines are more convenient as these Activators are more easily accessible via synthetic procedures.

We have tested several 1,2,4,5-tetrazines with respect to their ability as Activator to release a model drug compound (i.e. benzyl amine) from a Prodrug via an elimination (cascade) process, and we have found that tetrazines that are electron deficient, electron sufficient or neither electron deficient nor electron sufficient are capable to induce the drug release. Furthermore, both symmetric as well as asymmetric tetrazines were effective.

Electron deficient 1,2,4,5 tetrazines and 1,2,4,5-tetrazines that are neither electron deficient nor electron sufficient are generally more reactive in retro Diels-Alder reactions with dienophiles (such as TCOs), so these two classes of 1,2,4,5-tetrazines are preferred over electron sufficient 1,2,4,5-tetrazines, even though the latter are also capable of inducing drug release in Prodrugs.

In the following paragraphs specific examples of 1,2,4,5-tetrazine Activators according to the second embodiment of this invention will be highlighted by defining the $R^1$ and $R^2$ residues in formula (13).

Symmetric electron deficient 1,2,4,5-tetrazines with electron withdrawing residues are for example those with $R^1$=$R^2$=H, 2-pyridyl, 3-pyridyl, 4-pyridyl, 2,4-pyrimidyl, 2,6-pyrimidyl, 3,5-pyrimidyl, 2,3,4-triazyl or 2,3,5-triazyl. Other examples are those with $R^1$=$R^2$=phenyl with COOH or COOMe carboxylate, or with CN nitrile, or with $CONH_2$, $CONHCH_3$ or $CON(CH_3)_2$ amide, or with $SO_3H$ or $SO_3Na$ sulfonate, or with $SO_2NH_2$, $SO_2NHCH_3$ or $SO_2N(CH_3)_2$ sulfonamide, or with $PO_3H_2$ or $PO_3Na_2$ phosphonate substituents in the 2-, 3- or 4-position of the phenyl group, or in the 3- and 5-positions, or in the 2- and 4-positions, or in the 2,- and 6-positions of the phenyl group. Other substitution patterns are also possible, including the use of different substituents, as long as the tetrazine remains symmetric. See below for some examples of these structures.

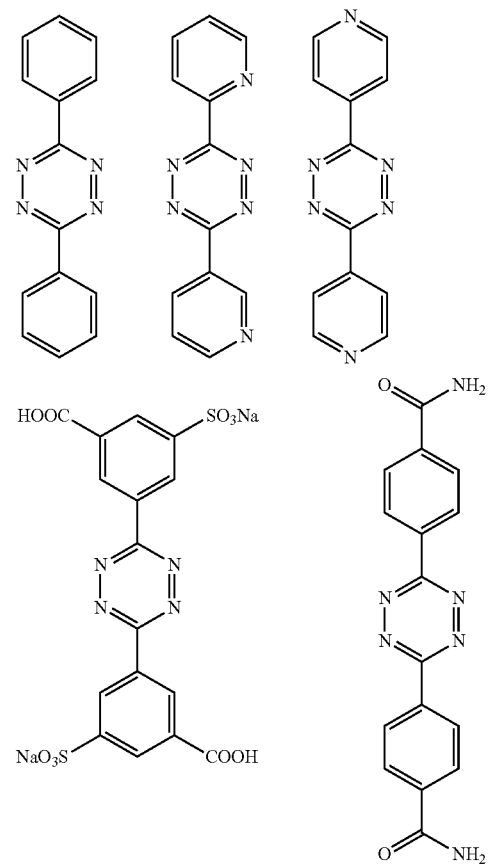

-continued

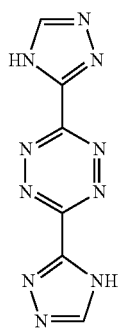

Symmetric electron sufficient 1,2,4,5-tetrazines with electron donating residues are for example those with $R^1=R^2=$OH, OR', SH, SR', NH$_2$, NHR', NR'$_2$, NH—CO—R', NH—SO—R', NH—SO$_2$—R', 2-pyrryl, 3-pyrryl, 2-thiophene, 3-thiophene, where R' represents a methyl, ethyl, phenyl or tolyl group. Other examples are those with $R^1=R^Z=$phenyl with OH, OR', SH. SR', NH$_2$, NHR', NR'$_2$, NH—CO—R', NR"—CO—R', NH—SO—R' or NH—SO$_2$—R' substituent(s), where R' represents a methyl, ethyl, phenyl or tolyl group, where R" represents a methyl or ethyl group, and where the substitution is done on the 2- or 3- or 4- or 2- and 3- or 2- and 4- or 2- and 5- or 2- and 6- or 3- and 4- or 3- and 5- or 3-, 4- and 5-position(s). See below for some examples of these structures.

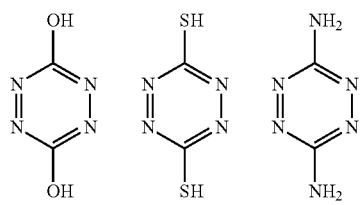

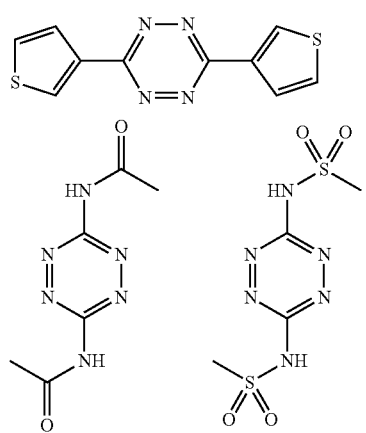

-continued

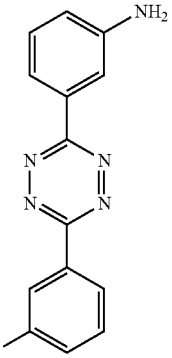 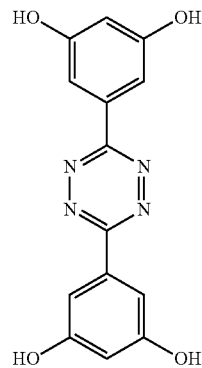

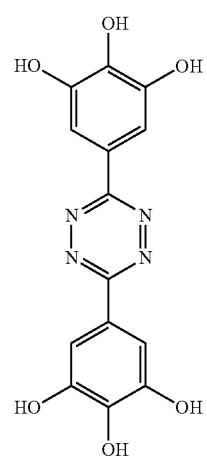

Symmetric 1,2,4,5-tetrazines with neither electron withdrawing nor electron donating residues are for example those with $R^1=R^2=$phenyl, methyl, ethyl, (iso)propyl, 2,4-imidazyl, 2,5-imidazyl, 2,3-pyrazyl or 3,4-pyrazyl. Other examples are those where $R'=R^2=$a hetero(aromatic) cycle such as a oxazole, isoxazole, thiazole or oxazoline cycle. Other examples are those where $R^1=R^2=$a phenyl with one electron withdrawing substituent selected from COOH, COOMe, CN, CONH$_2$. CONHCH$_3$, CON(CH$_3$)$_2$, SO$_3$H, SO$_3$Na, SO$_2$NH$_2$, SO$_2$NHCH$_3$, SO$_2$N(CH$_3$)$_2$. PO$_3$H$_2$ or PO$_3$Na$_2$ and one electron donating subsituent selected from OH, OR', SH, SR', NH$_2$, NHR', NR'$_2$, NH—CO—R', NR"—CO—R', NH—SO—R' or NH—SO$_2$—R' substituent(s), where R' represents a methyl, ethyl, phenyl or tolyl group and where R" represents a methyl or ethyl group. Substitutions can be done on the 2- and 3-, 2- and 4-, 2,- and 5-, 2- and 6, 3- and 4-, and the 3- and 5-positions. Yet other examples are those where $R^1=R^2=$a pyridyl or pyrimidyl moiety with one electron donating subsituent selected from OH, OR', SH, SR', NH$_2$, NHR', NR'$_2$, NH—CO—R', NR"—CO—R', NH—SO—R' or NH—SO$_2$—R' substituents, where R' represents a methyl, ethyl, phenyl or tolyl group and where R" represents a methyl or ethyl group. See below for some examples.

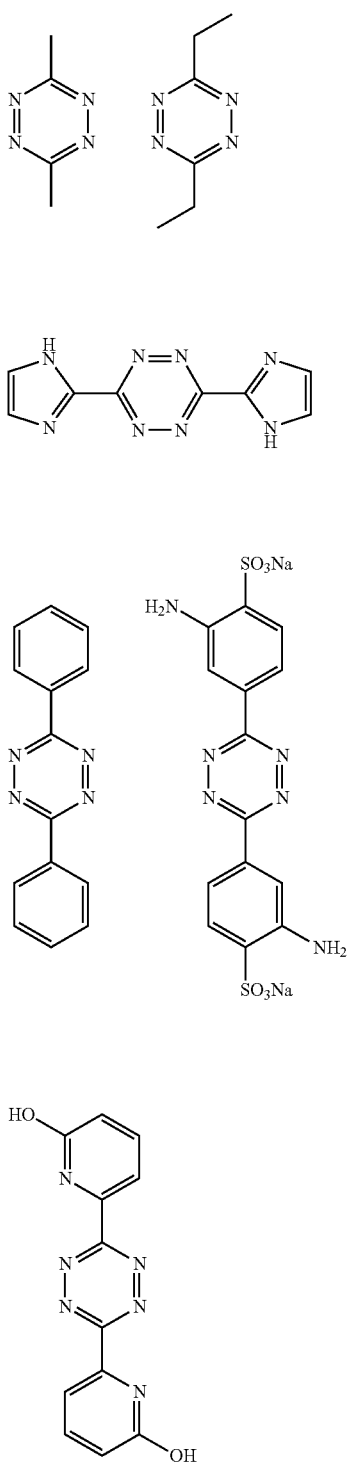

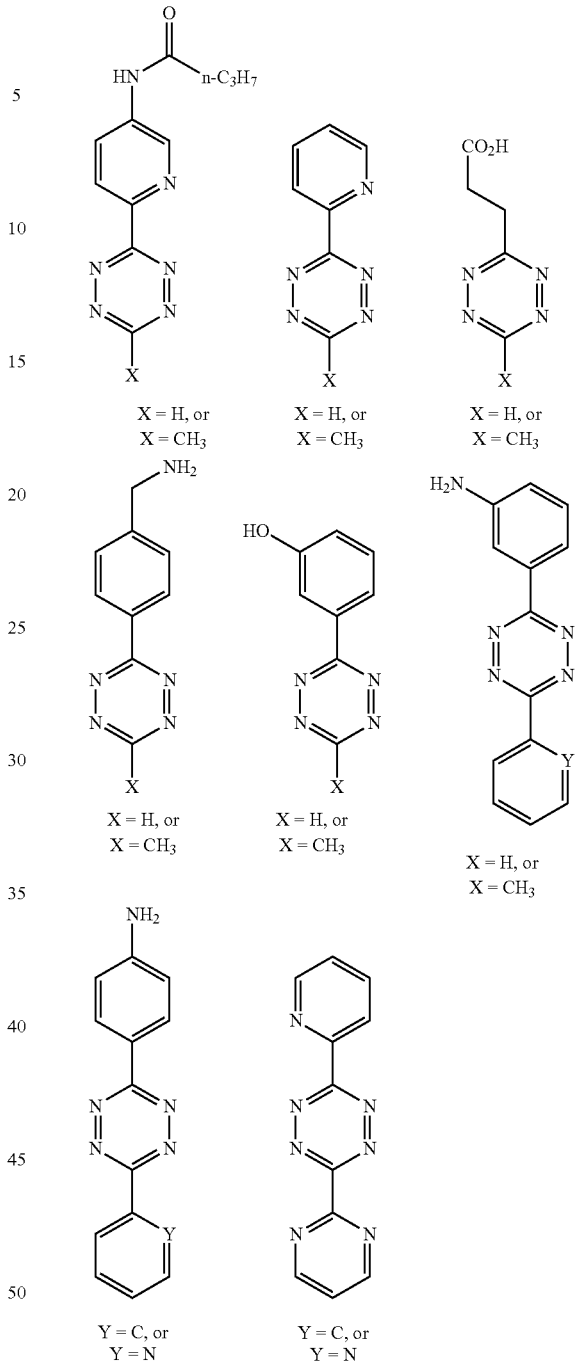

In case asymmetric 1,2,4,5-tetrazines are considered, one can choose any combination of given $R^1$ and $R^2$ residues that have been highlighted and listed above for the symmetric tetrazines according to formula (13), provided of course that $R^1$ and $R^2$ are different. Preferred asymmetric 1,2,4,5-tetrazines are those where at least one of the residues $R^1$ or $R^2$ is electron withdrawing in nature. Find below some example structures drawn.

Further Considerations Regarding the Activator

In the above the Activator has been described and defined with respect to either of two preferred embodiments of this invention, and for both embodiments 1,2-diazines, 1,2,4-triazines and 1,2,4,5-tetrazines, particularly 1,2,4,5-tetrazines, are the preferred diene Activators. In the below, some relevant features of the Activator will be highlighted, where it will also become apparent that there are plentiful options for designing the right Activator formulation for every specific application.

According to the invention, the Activator, e.g. a 1,2,4,5-tetrazine, has useful and beneficial pharmacological and pharmaco-kinetic properties, implying that the Activator is non-toxic or at least sufficiently low in toxicity, produces metabolites that are also sufficiently low in toxicity, is sufficiently soluble in physiological solutions, can be applied in aqueous or other formulations that are routinely used in pharmaceutics, and has the right log D value where this value reflects the hydrophilic/hydrophobic balance of the Activator molecule at physiological pH. As is known in the art, log D values can be negative (hydrophilic molecules) or positive (hydrophobic molecules), where the lower or the higher the log D values become, the more hydrophilic or the more hydrophobic the molecules are, respectively. Log D values can be predicted fairly adequately for most molecules, and log D values of Activators can be tuned by adding or removing polar or apolar groups in their designs. Find below some Activator designs with their corresponding calculated log D values (at pH=7.4). Note that addition of methyl, cycloalkylene, pyridine, amine, alcohol or sulfonate groups or deletion of phenyl groups modifies the log D value, and that a very broad range of log D values is accessible.

The Activator according to the invention has an appropriate reactivity towards the Prodrug, and this can be regulated by making the diene, particularly the 1,2,4,5-tetrazines, sufficiently electron deficient. Sufficient reactivity will ensure a fast retro Diels-Alder reaction with the Prodrug as soon as it has been reached by the Activator.

The Activator according to the invention has a good bio-availability, implying that it is available inside the (human) body for executing its intended purpose: effectively reaching the Prodrug at the Primary Target. Accordingly, the Activator does not stick significantly to blood components or to tissue that is non-targeted. The Activator may be designed to bind to albumin proteins that are present in the blood (so as to increase the blood circulation time, as is known in the art), but it should at the same time be released effectively from the blood stream to be able to reach the Prodrug. Accordingly, blood binding and blood releasing should then be balanced adequately. The blood circulation time of the Activator can also be increased by increasing the molecular weight of the Activator, e.g. by attaching poly-

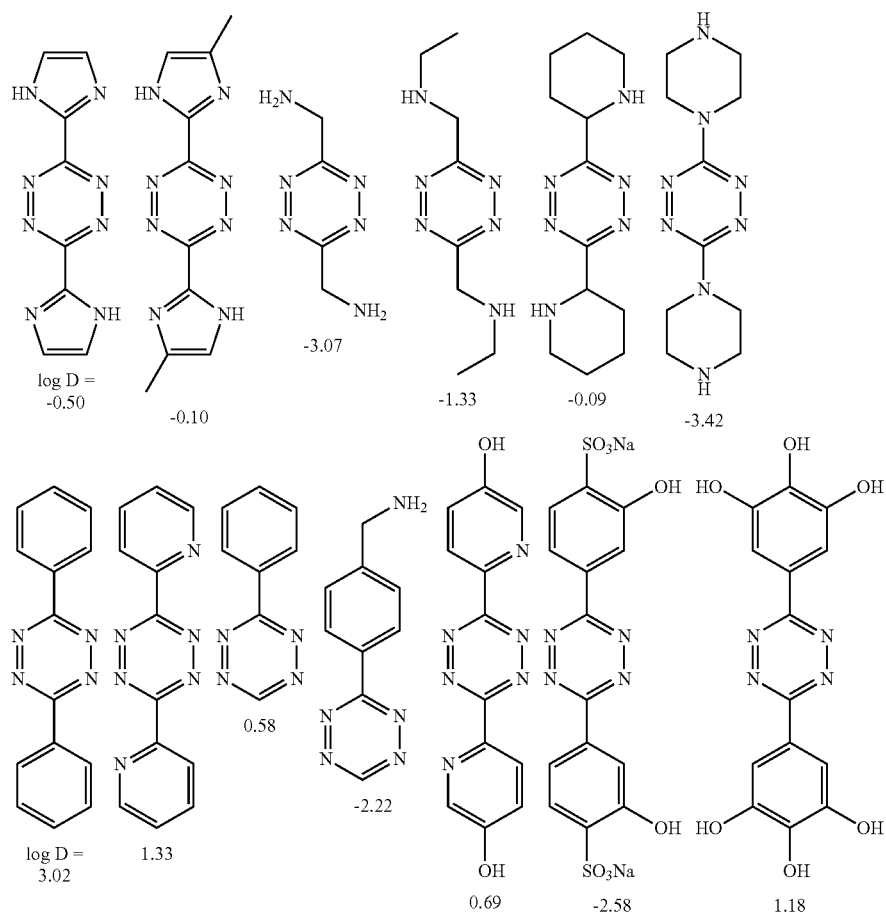

The given log D numbers have been calculated from a weighed method, with equal importance of the 'VG' (Viswanadhan. V. N.; Ghose, A. K.; Revankar, G. R; Robins, R. K., J. Chem. Inf. Comput. Sci., 1989, 29, 163-172), 'KLOP' (according to Klopman, G.; Li, Ju-Yun.; Wang, S.; Dimayuga, M.; J. Chem. Inf. Comput. Sci., 1994, 34, 752) and 'PHYS' (according to the PHYSPROP©, database) methods, based on an aqueous solution in 0.1 M in $Na^+K^+Cl^-$.

ethylene glycol (PEG) groups to the Activator ('pegylation'). Alternatively, the PKPD of the activator may be modulated by conjugating the activator to another moiety such as a polymer, protein, (short) peptide, carbohydrate.

The Activator according to the invention may be multimeric, so that multiple diene moieties may be attached to a molecular scaffold, particularly to e.g. multifunctional molecules, carbohydrates, polymers, dendrimers, proteins or peptides, where these scaffolds are preferably water soluble.

Examples of scaffolds that can be used are (multifunctional) polyethylene glycols, poly (propylene imine) (PPI) dendrimers, PAMAM dendrimers, glycol based dendrimers, heparin derivatives, hyaluronic acid derivatives or serum albumine proteins such as HSA.

Depending on the position of the Prodrug (e.g. inside the cell or outside the cell; specific organ that is targeted) the Activator is designed to be able to effectively reach this Prodrug. Therefore, the Activator can for example be tailored by varying its log D value, its reactivity or its charge. The Activator may even be engineered with a targeting agent (e.g. a protein, a peptide and/or a sugar moiety), so that the Primary Target can be reached actively instead of passively. In case a targeting agent is applied, it is preferred that it is a simple moiety (i.e. a short peptide or a simple sugar).

According to the invention, a mixture of different Activators can be applied. This may be relevant for regulation of the release profile of the drug.

The Activator that according to the invention will cause and regulate drug release at the Primary Target may additionally be modified with moieties giving extra function(s) to the Activator, either for in-vitro and/or for in-vivo studies or applications. For example, the Activator may be modified with dye moieties or fluorescent moieties (see e.g. S. Hilderbrand et al., Bioconjugate Chem., 2008, 19, 2297-2299 for 3-(4-benzylamino)-1,2,4,5-tetrazine that is amidated with the near-infrared (NIR) fluorophore VT680), or they may be functionalized with imaging probes, where these probes may be useful in imaging modalities, such as the nuclear imaging techniques PET or SPECT. In this way, the Activator will not only initiate drug release, but can also be localized inside the (human) body, and can thus be used to localize the Prodrug inside the (human) body. Consequently, the position and amount of drug release can be monitored. For example, the Activator can be modified with DOTA (or DTPA) ligands, where these ligands are ideally suited for complexation with $^{111}In^{3+}$-ions for nuclear imaging. In other examples, the Activator may be linked to $^{123}I$ or $^{18}F$ moieties, that are well established for use in SPECT or PET imaging, respectively. Furthermore, when used in combination with e.g. beta-emitting isotopes, such as Lu-177, or Y-90, prodrug activation can be combined with localized radiotherapy in a pretargeted format.

Synthesis routes to the above activators are readily available to the skilled person, based on standard knowledge in the art. References to tetrazine synthesis routes include Lions et al. *J. Org. Chem.,* 1965, 30, 318-319; Horwitz et al. *J. Am. Chem. Soc.,* 1958, 80, 3155-3159; Hapiot et al, *New. J. Chem.,* 2004, 28, 387-392, Kaim et al, *Z. Naturforsch.,* 1995, 50b, 123-127.

Prodrug

A Prodrug is a conjugate of the Drug $D^D$ and the Trigger $T^R$ and thus comprises a Drug that is capable of therapeutic action after its release from the Trigger. Such a Prodrug may optionally have specificity for disease targets.

The general formula of the Prodrug is shown below in Formula (14a) and (14b).

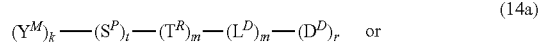
(14a)

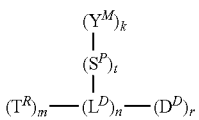
(14b)

The moiety $Y^M$ can either be a targeting agent $T^T$ or a masking moiety $M^M$; $S^P$ is spacer; $T^R$ is Trigger, $L^D$ is linker, and $D^D$ is drug.

For applications where drugs are released from a targeting agent: $Y^M$ is a targeting agent $T^T$;

k=1; m,r≥1; t,n≥0.   Formula (14a):

k=1; m,n,r≥1; t≥0.   Formula (14b):

For applications where masked drugs are unmasked: $Y^M$ is a masking moiety $M^M$;

r=1; m≥1; k,n,t≥0.   Formula (14a) and (14b):

Although it has been omitted for the sake of clarity in the above formula, $D^D$ can further comprise $T^T$ and/or $M^M$, optionally via $S^P$.

Drugs that can be used in a Prodrug relevant to this invention include but are not limited to: antibodies, antibody derivatives, antibody fragments, e.g. Fab2, Fab, scFV, diabodies, triabodies, antibody (fragment) fusions (eg bi-specific and trispecific mAb fragments), proteins, aptamers, oligopeptides, oligonucleotides, oligosaccharides, as well as peptides, peptoids, steroids, organic drug compounds, toxins, hormones, viruses, whole cells, phage. Typical drugs for which the invention is suitable include, but are not limited to: bi-specific and trispecific mAb fragments, immunotoxins, comprising eg ricin A, diphtheria toxin, cholera toxin. Other embodiments use auristatins, maytansines, calicheamicin, Duocarmycins, maytansinoids DM1 and DM4, auristatin MMAE, CC1065 and its analogs, camptothecin and its analogs. SN-38 and its analogs; antiproliferative/antitumor agents, antibiotics, cytokines, anti-inflammatory agents, anti-viral agents, antihypertensive agents, chemo-sensitizing and radiosensitizing agents. In other embodiments the released Drug $D^D$ is itself a prodrug designed to release a further drug $D^D$. Drugs optionally include a membrane translocation moiety (adamantine, poly-lysine argine, TAT) and/or a targeting agent (against eg a tumor cel receptor) optionally linked through a stable or labile linker.

Exemplary drugs for use as conjugates to the TCO derivative and to be released upon retro Diels Alder reaction with the Activator include but are not limited to: cytotoxic drugs, particularly those which are used for cancer therapy. Such drugs include, in general, DNA damaging agents, anti-metabolites, natural products and their analogs. Exemplary classes of cytotoxic agents include the enzyme inhibitors such as dihydrofolate reductase inhibitors, and thymidylate synthase inhibitors, DNA alkylators, radiation sensitizers, DNA intercalators, DNA cleavers, anti-tubulin agents, topoisomerases inhibitors, platinum-based drugs, the anthracycline family of drugs, the vinca drugs, the mitomycins, the bleomycins, the cytotoxic nucleosides, taxanes, lexitropsins, the pteridine family of drugs, diynenes, the podophyllotoxins, dolastatins, maytansinoids, differentiation inducers, and taxols. Particularly useful members of those classes include, for example, duocarmycin, methotrexate, methopterin, dichloromethotrexate, 5-fluorouracil DNA minor groove binders, 6-mercaptopurine, cytosine arabinoside, melphalan, leurosine, leurosideine, actinomycin, daunorubicin, doxorubicin, mitomycin C, mitomycin A, caminomycin, aminopterin, tallysomycin, podophyllotoxin and podophyllotoxin derivatives such as etoposide or etoposide phosphate, vinblastine, vincristine, vindesine, taxol, taxotere retinoic acid, butyric acid, N8-acetyl spermidine, camptothecin, calicheamicin, esperamicin, ene-diynes, and their analogues.

Exemplary drugs include the dolastatins and analogues thereof including: dolastatin A (U.S. Pat. No. 4,486,414), dolastatin B (U.S. Pat. No. 4,486,414), dolastatin 10 (U.S. Pat. Nos. 4,486,444, 5,410,024, 5,504,191, 5,521,284, 5,530,097, 5,599,902, 5,635,483, 5,663,149, 5,665,860, 5,780,588, 6,034,065, 6,323,315), dolastatin 13 (U.S. Pat. No. 4,986,988), dolastatin 14 (U.S. Pat. No. 5,138,036), dolastatin 15 (U.S. Pat. No. 4,879,278), dolastatin 16 (U.S. Pat. No. 6,239,104), dolastatin 17 (U.S. Pat. No. 6,239,104), and dolastatin 18 (U.S. Pat. No. 6,239,104), each patent incorporated herein by reference in their entirety.

In exemplary embodiments of the invention, the drug moiety is a mytomycin, vinca alkaloid, taxol, anthracycline, a calicheamicin, maytansinoid or an auristatin.

It will be understood that chemical modifications may also be made to the desired compound in order to make reactions of that compound more convenient for purposes of preparing conjugates of the invention. Drugs containing an amine functional group for coupling to the TCO include mitomycin-C, mitomycin-A, daunorubicin, doxorubicin, aminopterin, actinomycin, bleomycin, 9-amino camptothecin, N8-acetyl spermidine, 1-(2 chloroethyl)1,2-dimethanesulfonyl hydrazide, tallysomycin, cytarabine, dolastatins (including auristatins) and derivatives thereof.

Drugs containing a hydroxyl function group for coupling to the TCO include etoposide, camptothecin, taxol, esperamicin, 1,8-dihydroxy-bicyclo[7.3.1]trideca-4-9-diene-2,6-diyne-13-one (U.S. Pat. No. 5,198,560), podophyllotoxin, anguidine, vincristine, vinblastine, morpholine-doxorubicin, n-(5,5-diacetoxy-pentyl)doxorubicin, and derivatives thereof.

Drugs containing a sulfhydryl functional group for coupling to the TCO include esperamicin and 6-mecaptopurine, and derivatives thereof.

It will be understood that the drugs can optionally be attached to the TCO derivative through a linker $L^D$ or a self-immolative linker $L^D$, or a combination thereof, and which may consist of multiple (self-immolative, or non immolative) units.

It will further be understood that one ore more targeting agents $T^T$ or masking moieties $M^M$ may optionally be attached to the Drug $D^D$, Trigger $T^R$, or Linker $L^D$, optionally via a spacer or spacers $S^P$.

Several drugs may be replaced by an imageable label to measure drug targeting and release.

According to a further particular embodiment of the invention, the Prodrug is selected so as to target and or address a disease, such as cancer, an inflammation, an infection, a cardiovascular disease, e.g. thrombus, atherosclerotic lesion, hypoxic site, e.g. stroke, tumor, cardiovascular disorder, brain disorder, apoptosis, angiogenesis, an organ, and reporter gene/enzyme.

According to one embodiment, the Prodrug and/or the Activator can be multimeric compounds, comprising a plurality of Drugs and/or bioorthogonal reactive moieties. These multimeric compounds can be polymers, dendrimers, liposomes, polymer particles, or other polymeric constructs.

In the Prodrug, the Drug $D^D$ and the Trigger $T^R$—the TCO derivative—can be directly linked to each other. They can also be bound to each other via a linker or a self-immolative linker $L^D$. It will be understood that the invention encompasses any conceivable manner in which the dienophile Trigger is attached to the Drug. The same holds for the attachment of an optional targeting agent $T^T$ or masking moiety $M^M$ to the Prodrug. Methods of affecting conjugation to these drugs, e.g. through reactive amino acids such as lysine or cysteine in the case of proteins, are known to the skilled person.

It will be understood that the drug moiety is linked to the TCO in such a way that the drug is eventually capable of being released after formation of the retro Diels-Alder adduct. Generally, this means that the bond between the drug and the TCO, or in the event of a linker $L^D$, the bond between the TCO and the linker $L^D$, or in the event of a self-immolative linker, the bond between the linker and the TCO and between the drug and the linker, should be cleavable. Predominantly, the drug and the optional linker is linked via a hetero-atom, preferably via O, N, NH, or S. The cleavable bond is preferably selected from the group consisting of carbamate, thiocarbamate, carbonate, ether, ester, amine, amide, thioether, thioester, sulfoxide, and sulfonamide bonds.

Figure 7:
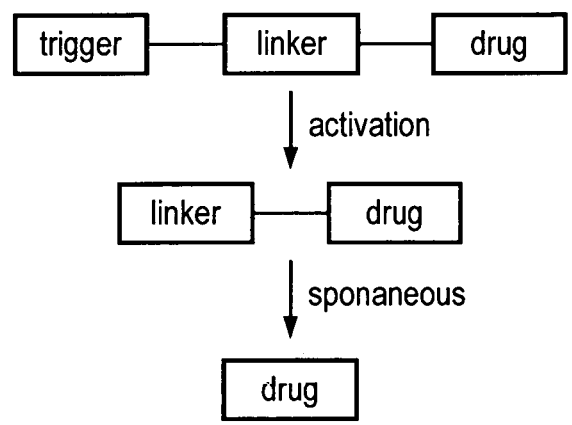
FIG. 7 illustrates the general concept of the linker modulation of the prodrug.

Thus, in the invention, linker concepts can be applied analogously to those known to the skilled person. Most reported prodrugs consist of three components: a trigger, a linker, and a parent drug, optionally a targeting molecule is attached to either the linker or the trigger. The trigger, which can e.g. be a substrate for a site-specific enzyme, or pH labile group, is often connected to the parent drug via a self-elimination linker. This linker is incorporated to facilitate enzymatic cleavage of the trigger, increasing active site accessibility and decreasing steric hindrance from the attached drug. Also the linker facilitates the straightforward use of a broad range of prodrugs in combination with the same trigger. Furthermore, the linker modulates prodrug stability, pharmacokinetics, organ distribution, enzyme recognition, and release kinetics. After trigger activation/removal, the linker must spontaneously eliminate to release the parent drug. Depending on the attached drug the linker or parts thereof can remain on the drug without impairing its action. The general concept is depicted in Scheme 2. See FIG. 7.

Two types of self-elimination linkers can be distinguished a) the electronic cascade linker b) the cyclization linker. The most prominent example of a cascade linker is the 1,6 elimination spacer shown in Scheme 3 in a β-glucuronide prodrug of anticancer agent 9-aminocamptothecin. After unmasking of the aromatic hydroxyl function by the enzyme β-glucuronidase (present in certain necrotic tumor areas), this group becomes electron-donating and initiates an electronic cascade that leads to expulsion of the leaving group, which releases the free drug after elimination of $CO_2$. This cascade, based on a quinone-methide rearrangement, can also be initiated by the lone pair of an unmasked amine or thiol instead of the hydroxyl. The formed quinone-methide species is trapped by water to form a phenol derivative.

Scheme 3:

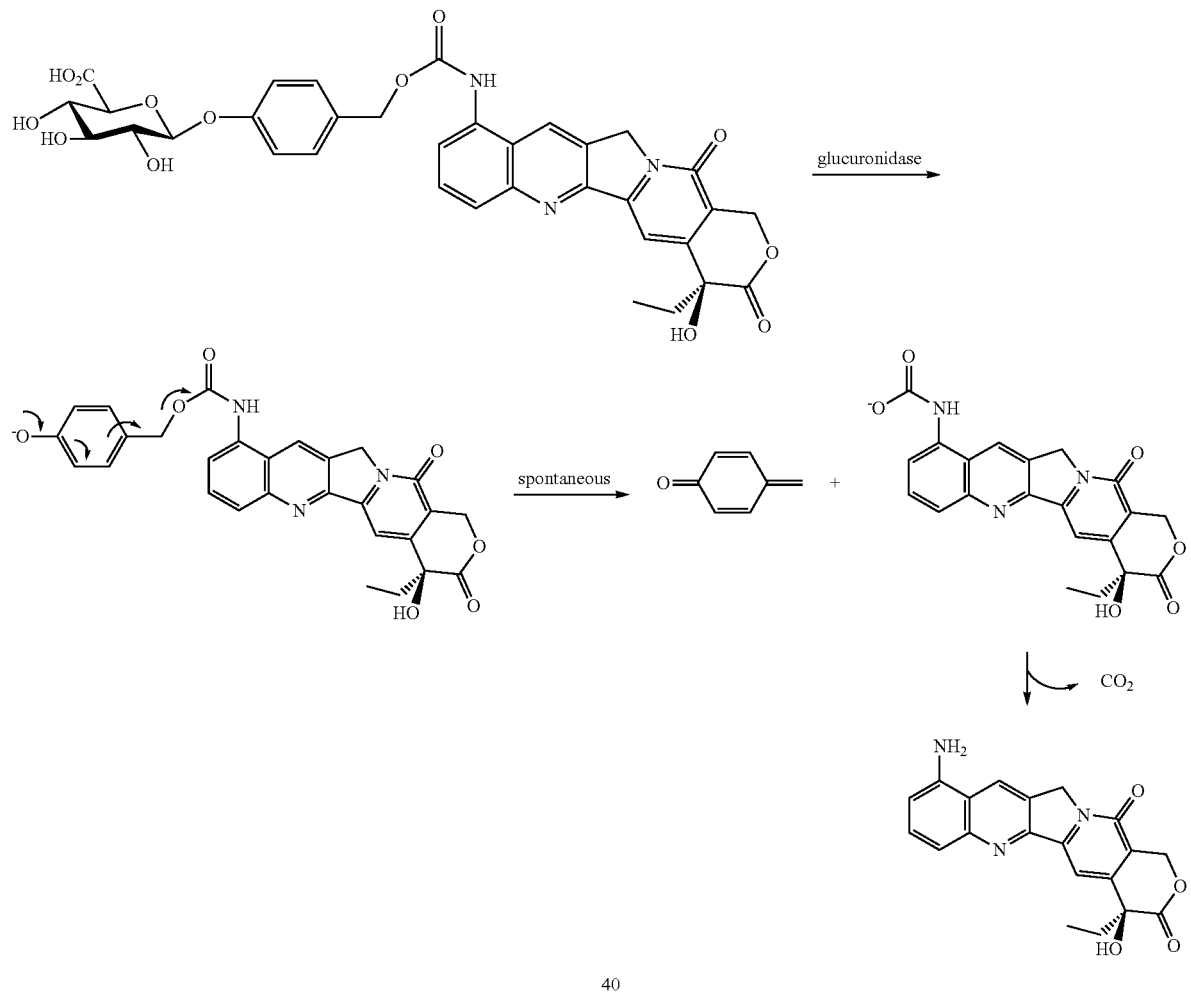

Some other trigger-linker concepts are depicted in Scheme 4. The trigger in A is activated by plasmatic esterases. Hydrolysis of the tert-butyl ester affords the free aromatic hydroxyl group, which starts the quinone-methide cascade. This construct has been targeted by conjugation to an antibody (R). In B, the hydrolysis of cephalosporins by beta-lactamase enzymes is used as a trigger. Hydrolysis of the lactam ring can to lead expulsion of the drug substituent depending on its leaving group nature. Drugs have been conjugated via an ester, amide, sulfide, amine and carbamate link. Two examples of aromatic cyclization-based linkers are C and D. In C cleavage by penicillin G-amidase leads to intramolecular attack of the amine on the carbonyl, releasing the drug. D shows a phosphatase-sensitive prodrug. Cleavage of the phosphate by human alkaline phosphatase affords a hydroxyl that reacts to a lactam by releasing the drug. In E an example is shown of a prodrug that it triggered by the reduction of a nitro group to an amine. This reduction can be performed by nitroreductase in the presence of NADPH. Furthermore, a number of heterocyclic nitro constructs are known (F) that are reduced in hypoxic (tumor) tissue and, hence, can initiate a cascade without the assistance of an enzyme. Other triggers used in prodrug therapy are sensitive to plasmin, tyrosine hydroxylase (highly expressed in neuroblastoma), tyrosinase or cathepsin B.

Scheme 4: X = O, N, S

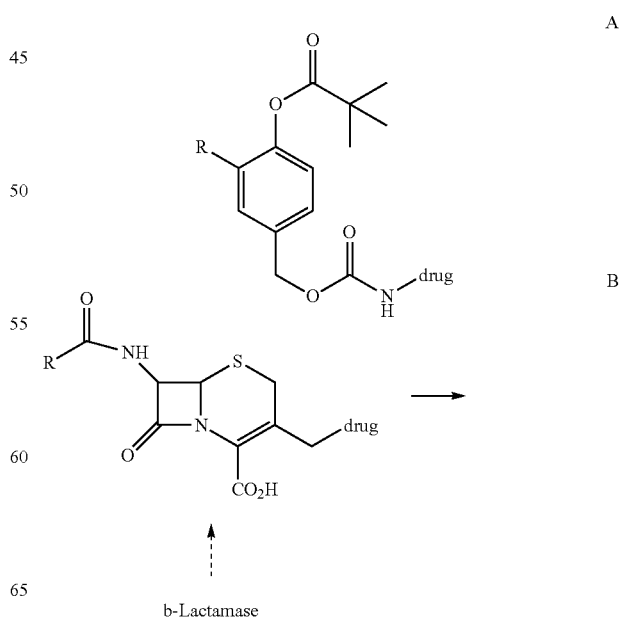

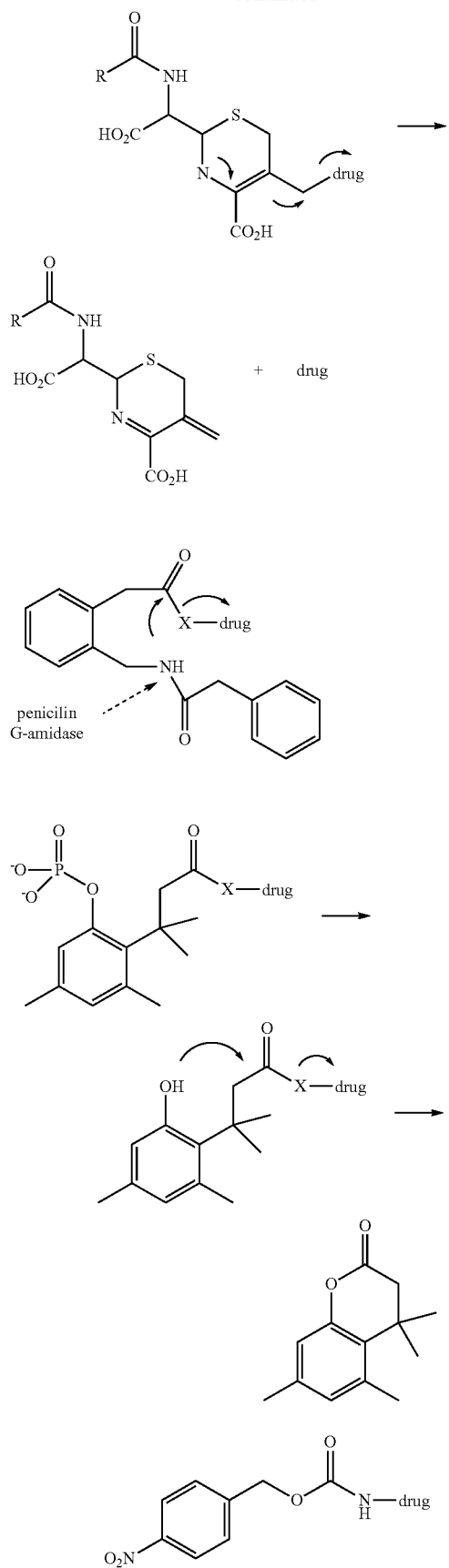

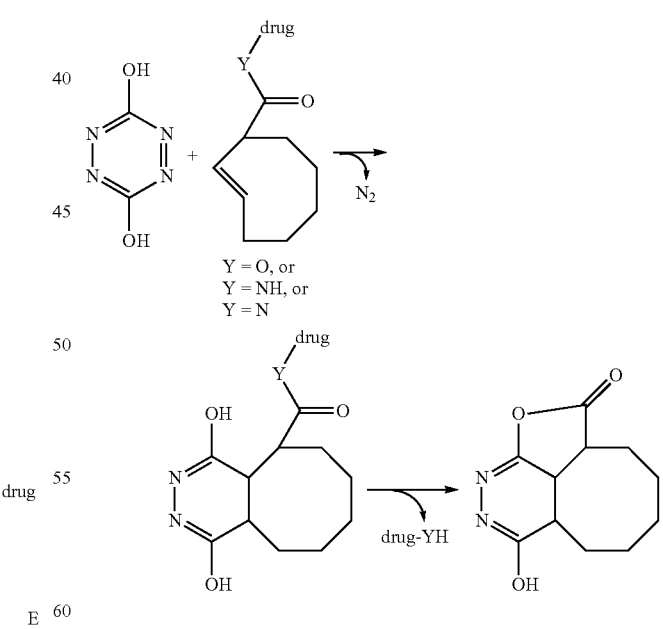

The Combination of and Reaction Between the TCO-Trigger and the Activator

The drug, whether or not via a linker, is preferably attached to a carbon atom that is adjacent to the double bond in the TCO ring.

As mentioned above, the choice of TCO as the trigger moiety, allows for a good versatility in available drug release mechanisms. Preferred mechanisms are based on a) electronic cascade-mediated release, b) intramolecular cyclization-mediated release.

The following schemes depict non-limiting examples illustrative for the various mechanism that can be made to apply on the basis of the choice for the rDA reaction for activating a prodrug. Note that in cases of release of amine functional drugs these can be e.g. primary or secondary amine, aniline, imidazole or pyrrole type of drugs, so that the drug may be varying in leaving group character. Release of drugs with other functionalities may also be possible (e.g. thiol functinalized drugs), in case corresponding hydrolytically stable TCO prodrugs are applied. The drawn fused ring products may or may not tautomerize to other more favorable tautomers.

The above examples lead to a 5-membered ring after cyclization, and the ester or amide substituted TCOs give release of an hydroxy or an amine functional drug from the retro Diels-Alder adduct. The nucleophilic sites on the tetrazine Activator are on the first (alfa) position of the 3- and 6-residues.

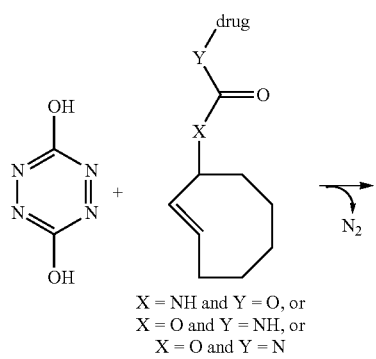

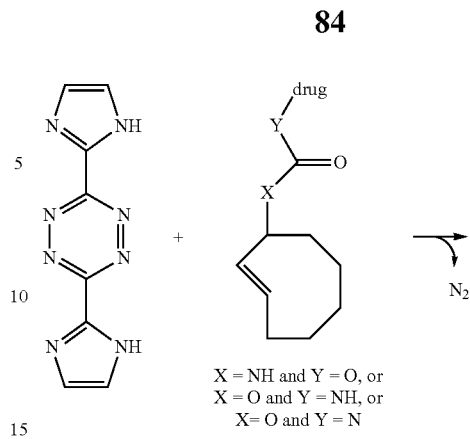

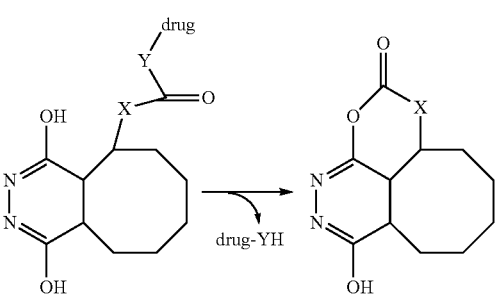

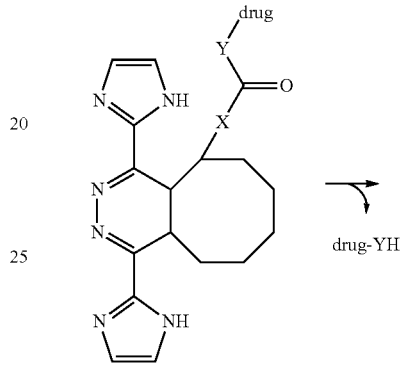

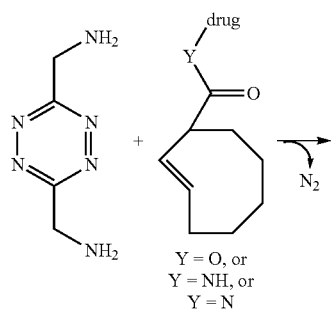

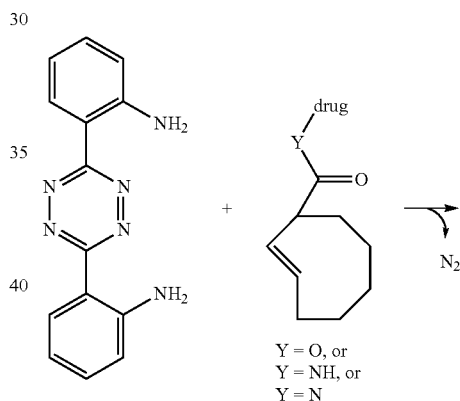

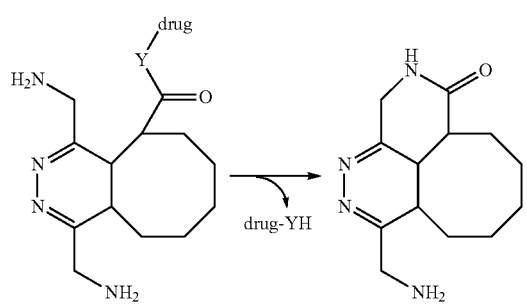

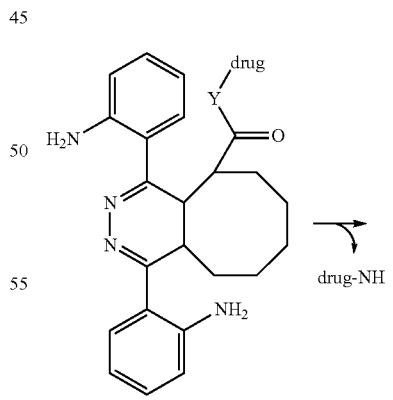

The above examples lead to a 6-membered ring after cyclization, and the urethane (or carbamate), ester or amide substituted TCOs give release of an amine or hydroxy functional drug from the retro Diels-Alder adduct. The nucleophilic sites on the tetrazine Activators are on the first (alfa) or on the second (beta) positions of the 3- and 6-residues.

The above examples lead to a 7-membered ring after cyclization, and the urethane (or carbamate), ester or amide substituted TCOs give release of an amine functional or an hydroxy functional drug. The nucleophilic sites on the tetrazine Activators are on the second (beta) or third (gamma) positions of the 3- and 6-residues.

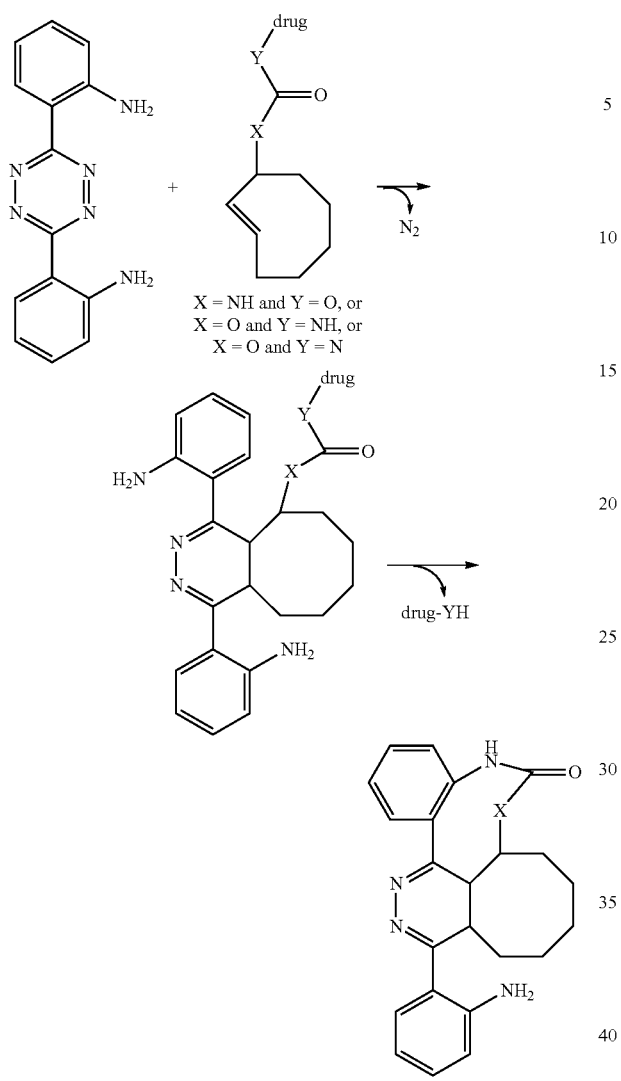

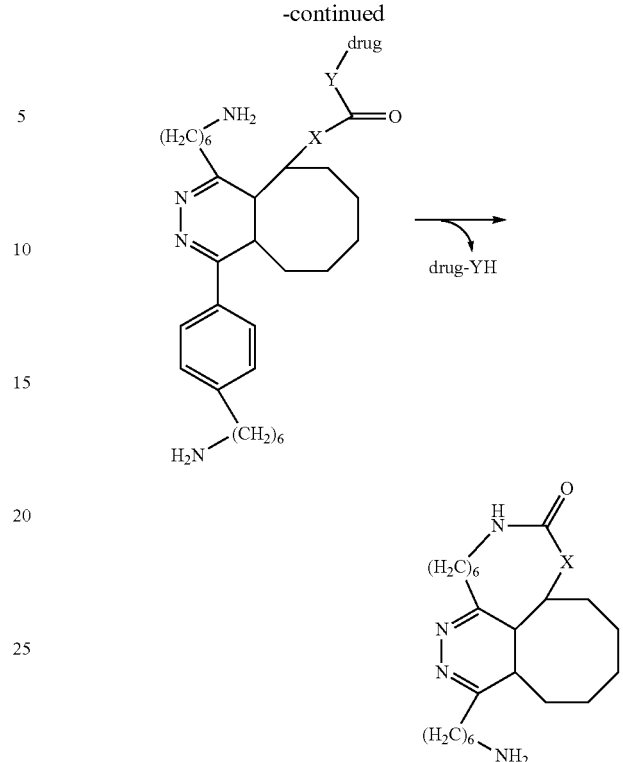

The above examples lead to an 8-membered ring after cyclization, and the urethane (or carbamate) substituted TCOs give release of an amine or hydroxy functional drug from the adduct. The nucleophilic sites on the tetrazine Activator are on the third (gamma) position of the 3- and 6-residues.

The above examples lead to a 12-membered ring after cyclization, and the urethane (or carbamate) substituted TCOs give release of an amine or hydroxy functional drug from the adduct. The nucleophilic sites on the tetrazine Activator are on the seventh position of the 3- and 6-residues.

Hereunder, some nonlimiting combinations of TCO Prodrugs and tetrazine Activators illustrate the possibilities for cascade elimination induced drug release from the retro Diels-Alder adduct. Note that in cases of release of amine functional drugs these can be e.g. primary or secondary amine, aniline, imidazole or pyrrole type of drugs, so that the drug may be varying in leaving group character. Release of drugs with other functionalities may also be possible (e.g. thiol functinalized drugs), in case corresponding hydrolytically stable TCO Prodrugs are applied. The drawn fused ring products may or may not tautomerize to other more favorable tautomers.

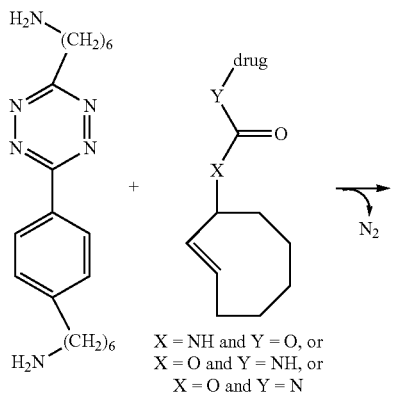

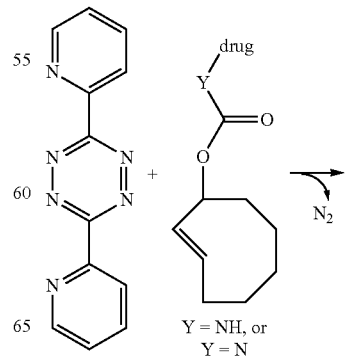

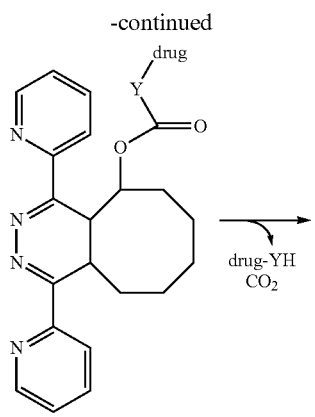

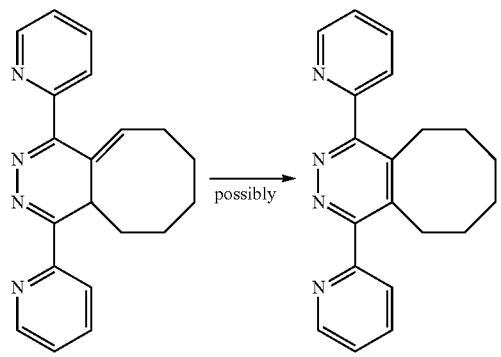

The above example of urethane (or carbamate) substituted TCOs gives release of an amine functional drug from the adduct. The tetrazine Activator is symmetric and electron deficient.

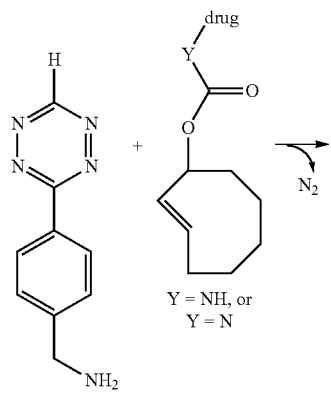

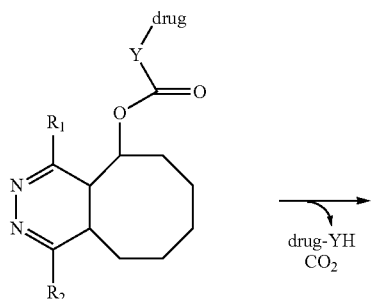

Y = NH, R$_1$ = H, and R$_2$ = Bn—NH$_2$, or
Y = N, R$_1$ = Bn—NH$_2$ and R$_2$ = H

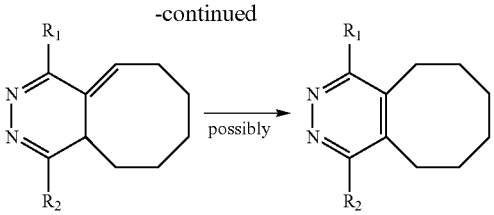

The above examples of urethane (or carbamate) substituted TCOs gives release of an amine functional drug from the adduct. The tetrazine Activator is assymetric and electron deficient. Note that use of an asymmetric tetrazine leads to formation of retro Diels-Alder adduct regiomers, apart from the stereo-isomers that are already formed when symmetric tetrazine are employed.

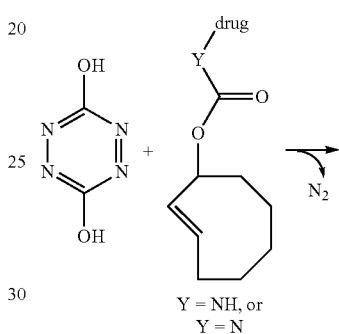

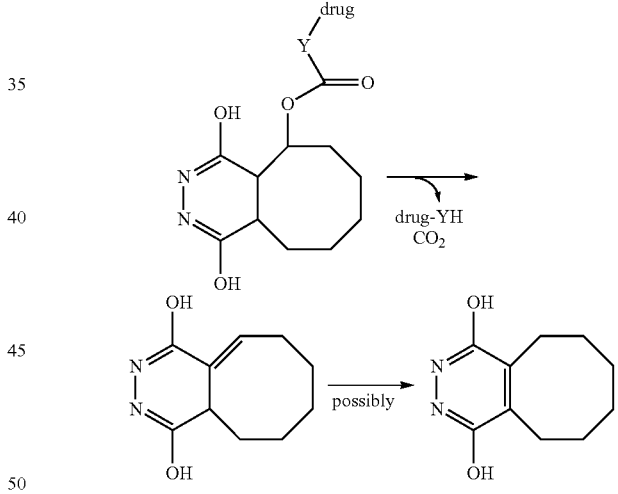

The above example of urethane (or carbamate) TCOs gives release of an amine functional drug from the adduct. The tetrazine Activator is symmetric and electron sufficient.

In a preferred embodiment, the drug is provided in the form of an antibody-toxin conjugate. The conjugate is provided with a TCO moiety as identified above, so as to enable bio-orthogonal chemically activated toxin release. In another embodiment, the drug is a bi- or trispecific antibody derivative that serves to bind to tumor cells and recruit and activate T-cells, the T-cell binding function of which is inactivated by being linked to a TCO moiety as described above. The latter, again, serving to enable bio-orthogonal chemically activated drug activation.

Targeting

The kits and method of the invention are very suitable for use in targeted delivery of drugs.

A "primary target" as used in the present invention relates to a target for a targeting agent for therapy. For example, a primary target can be any molecule, which is present in an organism, tissue or cell. Targets include cell surface targets, e.g. receptors, glycoproteins; structural proteins, e.g. amyloid plaques; abundant extracullular targets such as stroma, extracellular matrix targets such as growth factors, and proteases; intracellular targets, e.g. surfaces of Golgi bodies, surfaces of mitochondria, RNA, DNA, enzymes, components of cell signaling pathways; and/or foreign bodies, e.g. pathogens such as viruses, bacteria, fungi, yeast or parts thereof. Examples of primary targets include compounds such as proteins of which the presence or expression level is correlated with a certain tissue or cell type or of which the expression level is up regulated or down-regulated in a certain disorder. According to a particular embodiment of the present invention, the primary target is a protein such as a (internalizing or non-internalizing) receptor.

According to the present invention, the primary target can be selected from any suitable targets within the human or animal body or on a pathogen or parasite, e.g. a group comprising cells such as cell membranes and cell walls, receptors such as cell membrane receptors, intracellular structures such as Golgi bodies or mitochondria, enzymes, receptors, DNA, RNA, viruses or viral particles, antibodies, proteins, carbohydrates, monosacharides, polysaccharides, cytokines, hormones, steroids, somatostatin receptor, monoamine oxidase, muscarinic receptors, myocardial sympatic nerve system, leukotriene receptors, e.g. on leukocytes, urokinase plasminogen activator receptor (uPAR), folate receptor, apoptosis marker, (anti-)angiogenesis marker, gastrin receptor, dopaminergic system, serotonergic system, GABAergic system, adrenergic system, cholinergic system, opoid receptors, GPIIb/IIIa receptor and other thrombus related receptors, fibrin, calcitonin receptor, tufitsin receptor, integrin receptor, fibronectin, VEGF/EGF and VEGF/EGF receptors, TAG72, CEA, CD19, CD20, CD22, CD40, CD45, CD74, CD79, CD105, CD138, CD 174, CD227, CD326, CD340, MUC1, MUC16, GPNMB, PSMA, Cripto, Tenascin C, Melanocortin-1 receptor, CD44v6, G250, HLA DR, ED-B, TMEFF2, EphB2, EphA2, FAP, Mesothelin, GD2, CAIX, 5T4, matrix metalloproteinase (MMP), P/E/L-selectin receptor, LDL receptor, P-glycoprotein, neurotensin receptors, neuropeptide receptors, substance P receptors, NK receptor, CCK receptors, sigma receptors, interleukin receptors, herpes simplex virus tyrosine kinase, human tyrosine kinase. In order to allow specific targeting of the above-listed primary targets, the targeting agent $T^T$ can comprise compounds including but not limited to antibodies, antibody fragments, e.g. Fab2, Fab, scFV, diabodies, triabodies, VHH, antibody (fragment) fusions (eg bi-specific and trispecific mAb fragments), proteins, peptides, e.g. octreotide and derivatives, VIP, MSH, LHRH, chemotactic peptides, bombesin, elastin, peptide mimetics, carbohydrates, monosaccharides, polysaccharides, viruses, whole cells, drugs, polymers, liposomes, chemotherapeutic agents, receptor agonists and antagonists, cytokines, hormones, steroids. Examples of organic compounds envisaged within the context of the present invention are, or are derived from, estrogens, e.g. estradiol, androgens, progestins, corticosteroids, methotrexate, folic acid, and cholesterol. In a preferred embodiment, the targeting agent $T^T$ is an antibody. According to a particular embodiment of the present invention, the primary target is a receptor and a targeting agent is employed, which is capable of specific binding to the primary target. Suitable targeting agents include but are not limited to, the ligand of such a receptor or a part thereof which still binds to the receptor, e.g. a receptor binding peptide in the case of receptor binding protein ligands. Other examples of targeting agents of protein nature include interferons, e.g. alpha, beta, and gamma interferon, interleukins, and protein growth factor, such as tumor growth factor, e.g. alpha, beta tumor growth factor, platelet-derived growth factor (PDGF), uPAR targeting protein, apolipoprotein, LDL, annexin V, endostatin, and angio statin. Alternative examples of targeting agents include DNA, RNA, PNA and LNA which are e.g. complementary to the primary target.

According to a further particular embodiment of the invention, the primary target and targeting agent are selected so as to result in the specific or increased targeting of a tissue or disease, such as cancer, an inflammation, an infection, a cardiovascular disease, e.g. thrombus, atherosclerotic lesion, hypoxic site, e.g. stroke, tumor, cardiovascular disorder, brain disorder, apoptosis, angiogenesis, an organ, and reporter gene/enzyme. This can be achieved by selecting primary targets with tissue-, cell- or disease-specific expression. For example, membrane folic acid receptors mediate intracellular accumulation of folate and its analogs, such as methotrexate. Expression is limited in normal tissues, but receptors are overexpressed in various tumor cell types.

Masking Moieties

Masking moieties $M^M$ can be a protein, peptide, polymer, polyethylene glycol, carbohydrate, organic construct, that further shield the bound drug $D^D$ or Prodrug. This shielding can be based on eg steric hindrance, but it can also be based on a non covalent interaction with the drug $D^D$. Such masking moiety may also be used to affect the in vivo properties (eg blood clearance, recognition by the immune-system) of the drug $D^D$ or Prodrug.

Spacers

Spacers $S^P$ include but are not limited to polyethylene glycol (PEG) chains varying from 2 to 200, particularly 3 to 113 and preferably 5-50 repeating units. Other examples are biopolymer fragments, such as oligo- or polypeptides or polylactides. Further preferred examples are shown in Example 15.

Administration

In the context of the invention, the Prodrug is usually administered first, and it will take a certain time period before the Prodrug has reached the Primary Target. This time period may differ from one application to the other and may be minutes, days or weeks. After the time period of choice has elapsed, the Activator is administered, will find and react with the Prodrug and will thus activate Drug release at the Primary Target.

The compositions of the invention can be administered via different routes including intravenous injection, intraperatonial, oral administration, rectal administration and inhalation. Formulations suitable for these different types of administrations are known to the skilled person. Prodrugs or Activators according to the invention can be administered together with a pharmaceutically acceptable carrier. A suitable pharmaceutical carrier as used herein relates to a carrier suitable for medical or veterinary purposes, not being toxic or otherwise unacceptable. Such carriers are well known in the art and include saline, buffered saline, dextrose, water, glycerol, ethanol, and combinations thereof. The formulation should suit the mode of administration.

It will be understood that the chemical entities administered, viz, the prodrug and the activator, can be in a modified form that does not alter the chemical functionality of said chemical entity, such as salts, hydrates, or solvates thereof.

After administration of the Prodrug, and before the administration of the Activator, it is preferred to remove excess Prodrug by means of a Clearing Agent in cases when prodrug activation in circulation is undesired and when natural prodrug clearance is insufficient. A Clearing Agent is an agent, compound, or moiety that is administered to a subject for the purpose of binding to, or complexing with, an administered agent (in this case the Prodrug) of which excess is to be removed from circulation. The Clearing Agent is capable of being directed to removal from circulation. The latter is generally achieved through liver receptor-based mechanisms, although other ways of secretion from circulation exist, as are known to the skilled person. In the invention, the Clearing Agent for removing circulating Prodrug, preferably comprises a diene moiety, e.g. as discussed above, capable of reacting to the TCO moiety of the Prodrug.

EXAMPLES

The following examples demonstrate the invention or aspects of the invention, and do not serve to define or limit the scope of the invention or its claims.

Methods. $^1$H-NMR and $^{13}$C-NMR spectra were recorded on a Varian Mercury (400 MHz for $^1$H-NMR and 100 MHz for $^{13}$C-NMR) spectrometer at 298 K. Chemical shifts are reported in ppm downfield from TMS at room temperature. Abbreviations used for splitting patterns are s=singlet, t=triplet, q=quartet, m=multiplet and br=broad. IR spectra were recorded on a Perkin Elmer 1600 FT-IR (UATR). LC-MS was performed using a Shimadzu LC-10 AD VP series HPLC coupled to a diode array detector (Finnigan Surveyor PDA Plus detector, Thermo Electron Corporation) and an Ion-Trap (LCQ Fleet, Thermo Scientific). Analyses were performed using a Alltech Alltima HP $C_{18}$ 3 µp column using an injection volume of 1-4 µL, a flow rate of 0.2 mL min$^{-1}$ and typically a gradient (5% to 100% in 10 min, held at 100% for a further 3 min) of $CH_3CN$ in $H_2O$ (both containing 0.1% formic acid) at 25° C. Preparative RP-HPLC ($CH_3CN/H_2O$ with 0.1% formic acid) was performed using a Shimadzu SCL-10A VP coupled to two Shimadzu LC-8A pumps and a Shimadzu SPD-10AV VP UV-vis detector on a Phenomenex Gemini 5µ $C_{18}$ 110A column. Size exclusion (SEC) HPLC was carried out on an Agilent 1200 system equipped with a Gabi radioactive detector. The samples were loaded on a Superdex-200 10/300 GL column (GE Healthcare Life Sciences) and eluted with 10 mM phosphate buffer, pH 7.4, at 0.35-0.5 mL/min. The UV wavelength was preset at 260 and 280 nm. The concentration of antibody solutions was determined with a NanoDrop 1000 spectrophotometer (Thermo Fisher Scientific) from the absorbance at 322 nm and 280 nm, respectively.

Materials. All reagents, chemicals, materials and solvents were obtained from commercial sources, and were used as received: Biosolve, Merck and Cambridge Isotope Laboratories for (deuterated) solvents; and Aldrich, Acros, ABCR, Merck and Fluka for chemicals, materials and reagents. All solvents were of AR quality, 4-(t-Butyldimethylsilyloxymethyl)-2,6-dimethylphenol was synthesized according to a literature procedure (Y. H. Choe, C. D. Conover, D. Wu, M. Royzen, Y. Gervacio, V. Borowski, M. Mehlig, R. B. Greenwald, *J. Controlled Release* 2002, 79, 55-70). Doxorubicine hydrochloride was obtained from Avachem Scientific.

Example 1

Synthesis of Tetrazine Activators
General Procedures

Apart from the tetrazines described in detail below, a series of other tetrazines have been prepared. Pinner-type reactions have been used, where the appropriate nitriles have been reacted with hydrazine to make the dihydro 1,2,4,5-tetrazine intermediates. Instead of nitriles, amidines have also been used as reactants, as is known in the art. The use of sulfur in this reaction is also known, as in some cases this aids the formation of the dihydro 1,2,4,5-tetrazine. Oxidation of this intermediate results in the tetrazine diene Activators. The below reactions describe some of the prepared tetrazines, and illustrate some of the possibilities (e.g. use of solvent, concentrations, temperature, equivalents of reactants, options for oxidation, etc.) to make and isolate tetrazines. Other methods known in the art may also be used to prepare tetrazines or other Activators.

Synthesis of 3,6-bis(2-pyridyl)-1,2,4,5-tetrazine (2)

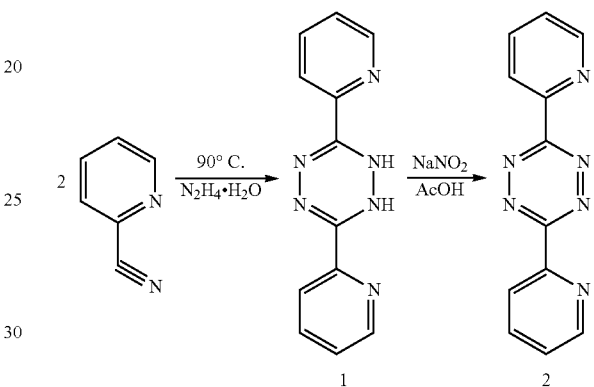

2-Cyanopyridine (10.00 g, 96.0 mmol) and hydrazine hydrate (15.1 g; 300 mmol) were stirred overnight at 90° C. in an inert atmosphere. The turbid mixture was cooled to room temperature, filtered, and the residue was subsequently washed with water (20 mL) and ethanol (20 mL), and dried in vacuo to yield the crude dihydrotetrazine 1 as an orange solid (7.35 g; 65%).

The dihydrotetrazine (1, 100 mg; 0.419 mmol) was suspended in acetic acid (3 mL), and sodium nitrite (87 mg; 1.26 mmol) was added. An immediate color change from orange to dark red was observed, and the oxidized product was isolated by filtration. The residue was washed with water (10 mL) and dried in vacuo to yield the title compound as a purple solid (2, 92 mg; 93%).

$^1$H NMR (CDCl$_3$): δ=9.00 (d, 2H), 8.76 (d, 2H), 8.02 (t, 2H), 7.60 (dd, 2H) ppm. $^{13}$C NMR (CDCl$_3$): δ=163.9, 151.1, 150.1, 137.5, 126.6, 124.5 ppm. HPLC-MS/PDA: one peak in chromatogram, m/z=237.00 (M+H$^+$), λ$_{max}$=296 and 528 nm.

Synthesis of 3-(5-acetamido-2-pyridyl)-6-(2-pyridyl)-1,2,4,5-tetrazine (5)

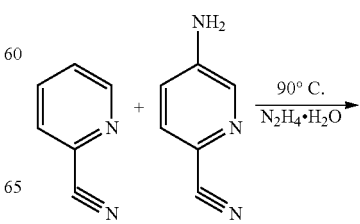

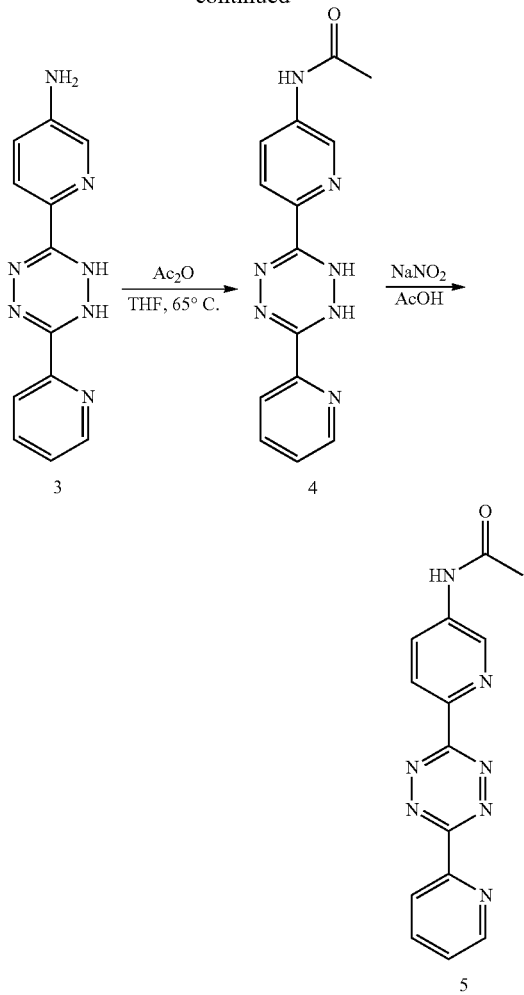

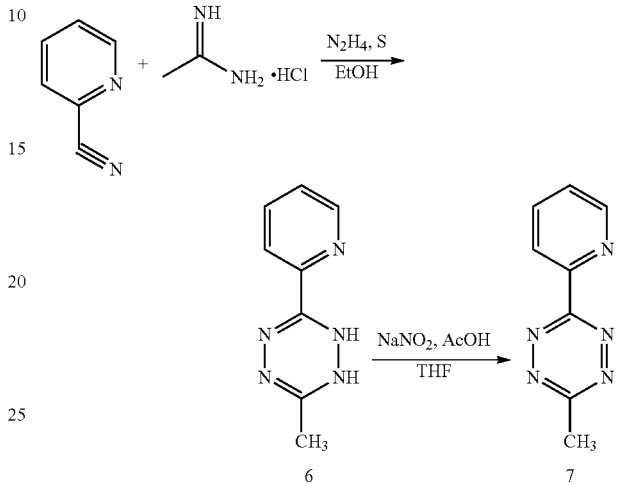

2-Cyanopyridine (5.00 g, 48.0 mmol), 5-amino-2-cyanopyridine (5.72 g; 48.0 mmol) and hydrazine hydrate (15.1 g; 300 mmol) were stirred overnight at 90° C. in an inert atmosphere. The turbid mixture was cooled to room temperature, filtered, and the residue was subsequently washed with water (20 mL) and ethanol (20 mL), and dried in vacuo. The orange solid was suspended in acetone (200 mL), impregnated onto silica gel (20 gram), and chromatographed using a gradient (0% to 70%) of acetone and heptane, to yield dihydrotetrazine 3 as an orange solid (1.46 g; 12% yield).

The dihydrotetrazine (3, 90 mg; 0.355 mmol) was dissolved in THF (1 mL), and acetic anhydride (54.4 mg; 0.533 mmol) was added. The solution was heated to reflux in an inert atmosphere for 18 hr. The orange precipitate was isolated by filtration, and washed with THF (3 mL) to give the acetamide of the dihydrotetrazine (4, 90 mg; 86% yield).

Acetamide 4 (50 mg, 0.169 mmol) was suspended in acetic acid (1 mL), and sodium nitrite (35 mg; 0.508 mmol) was added. An immediate color change from orange to dark red was observed, and the oxidized product was isolated by filtration. The residue was washed with water (5 mL) and dried in vacuo to yield the title compound as a purple solid (5, 42 mg; 84%).

$^1$H NMR (DMSO-$d_6$): δ=9.03 (d, 1H), 8.93 (d, 1H), 8.61 (dd, 2H), 8.42 (dd, 1H), 8.16 (dt, 1H), 7.73 (dd, 1H), 2.17 (s, 3H) ppm. $^{13}$C NMR (DMSO-$d_6$): δ=169.5, 163.0, 162.8, 150.6, 150.2, 143.8, 141.2, 138.5, 137.8, 126.6, 126.1, 124.9, 124.2, 24.1 ppm. HPLC-MS/PDA: one peak in chromatogram, m/z=293.9 (M+H$^+$), $\lambda_{max}$=323 and 529 nm.

Synthesis of
3-(2-pyridyl)-6-methyl-1,2,4,5-tetrazine (7)

2-Cyanopyridine (500 mg, 4.8 mmol), acetamidine hydrochloride (2.00 g, 21.2 mmol) and sulfur (155 mg, 4.8 mmol) were stirred in ethanol (5 mL) under an inert atmosphere of argon. Hydrazine hydrate (2.76 g; 55.2 mmol) was added and the mixture was stirred overnight at 20° C. The turbid mixture was filtered and the filtrate was evaporated to dryness, to yield 2.9 g of orange colored crude product 6.

Subsequently, 6 (800 mg) was suspended in a mixture of THF (3 mL) and acetic acid (4 mL). A solution of NaNO$_2$ (2.0 g; 29.0 mmol) in water (3 mL) was added at 0° C. Instantaneous coloration to a red/purple suspension was observed. After 5 minutes of stirring at 0° C., chloroform and water were added. The purple chloroform layer was washed twice with water and then concentrated. The solid residue was stirred in a 1:1 mixture of chloroform and hexane, and then filtered. The filtrate was concentrated and the crude product was purified by silica column chromatography applying chloroform/acetone mixtures as eluent, yielding pure product (7, 48 mg, 21% yield overall, as calculated from 2-cyanopyridine).

$^1$H NMR (CDCl$_3$): δ=8.96 (d, 1H), 8.65 (d, 1H), 7.99 (t, 1H), 7.56 (dd, 1H), 3.17 (s, 3H) ppm. $^{13}$C NMR (CDCl$_3$): δ=168.1, 163.6, 150.9, 150.3, 137.4, 126.3, 123.9, 21.4 ppm. HPLC-MS/PDA: one peak in chromatogram, m/z=174.3 (M+H$^+$), $\lambda_{max}$=274 and 524 nm.

Synthesis of
3,6-bis(2-aminophenyl)-1,2,4,5-tetrazine (9)

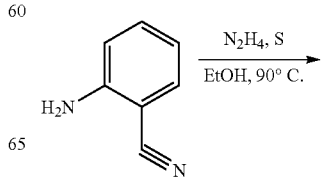

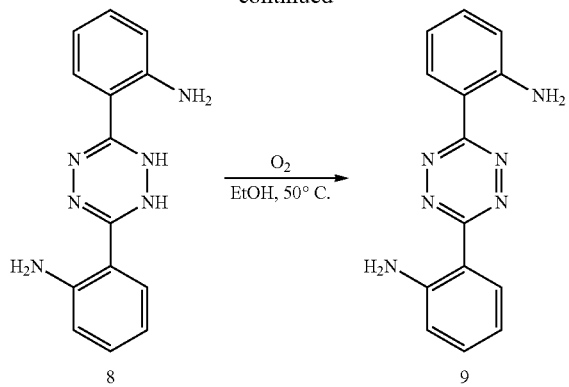

2-Aminobenzonitrile (1.00 g; 8.46 mmol) was dissolved in ethanol (3 mL) and hydrazine hydrate (2.06 g; 41.2 mmol) was added. The mixture was cooled to 0° C. and sulfur (0.17 g; 5.30 mmol) was added. Stirring was continued for 15 min, and subsequently the mixture was heated at 90° C. After 3 hr, the yellow precipitate was isolated by filtration, washed with ethanol (10 mL), and subsequently triturated twice with chloroform (2 times 10 mL), to yield the yellow intermediate 8 (343 mg, 30%).

Intermediate 8 (105 mg; 0.394 mmol) was dissolved in ethanol (15 mL), and oxygen was bubbled through this solution at 50° C. Within minutes, the color changed from yellow to dark orange/red, and a precipitate was formed. After 2 hr, the precipitate was filtered, washed with ethanol and dried to give the product 9 as dark red crystals (89 mg, 86%).

$^1$H NMR (DMSO-$d_6$): δ=8.39 (d, 2H), 7.32 (t, 2H), 7.04 (s, 4H), 6.93 (d, 2H), 6.75 (t, 2H) ppm. $^{13}$C NMR (DMSO-$d_6$): δ=162.7, 149.6, 133.0, 129.0, 117.1, 115.8, 111.6 ppm. HPLC-MS/PDA: one peak in chromatogram, m/z=265.4 (M+H$^+$), $\lambda_{max}$=237, 293, 403 and 535 nm.

Synthesis of 3,6-bis(4-hydroxyphenyl)-1,2,4,5-tetrazine (11)

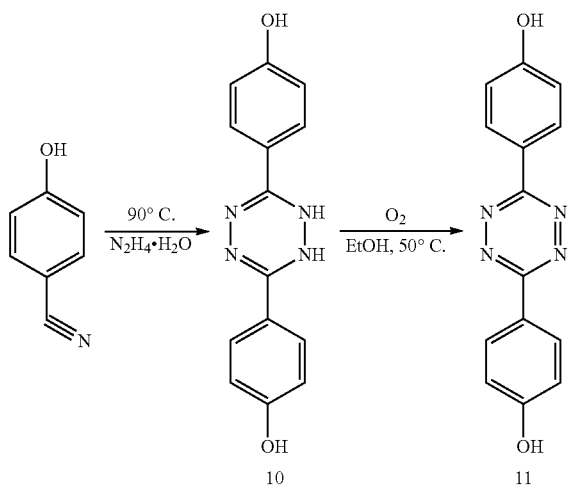

4-Hydroxybenzonitrile (1.06 g; 8.90 mmol) was dissolved in hydrazine hydrate (3.09 g; 61.7 mmol), and the mixture was heated to 90° C. for 16 hr. The yellow precipitate was filtered and washed with water (25 mL) and ethanol (10 mL), to yield crude intermediate 10 as a yellow powder (870 mg; 62%).

The intermediate (10, 173 mg; 0.645 mmol) was suspended in ethanol (10 mL), and oxygen was bubbled through this mixture at 50° C. Within minutes, the color changed from yellow to dark orange/red. After 6 hr. the precipitate was filtered, washed with ethanol and dried, to give the product 11 as dark red crystals (136 mg, 80%).

$^1$H NMR (DMSO-$d_6$): δ=10.35 (br. s, 2H), 8.36 (d, 4H), 7.02 (d, 4H) ppm. $^{13}$C NMR (DMSO-$d_6$): δ=162.6, 161.5, 129.2, 122.6, 116.3 ppm. HPLC-MS/PDA: one peak in chromatogram, m/z=267.1 (M+H$^+$), $\lambda_{max}$=235, 330 and 535 nm.

Synthesis of 3,6-bis(4-aminophenyl)-1,2,4,5-tetrazine (13)

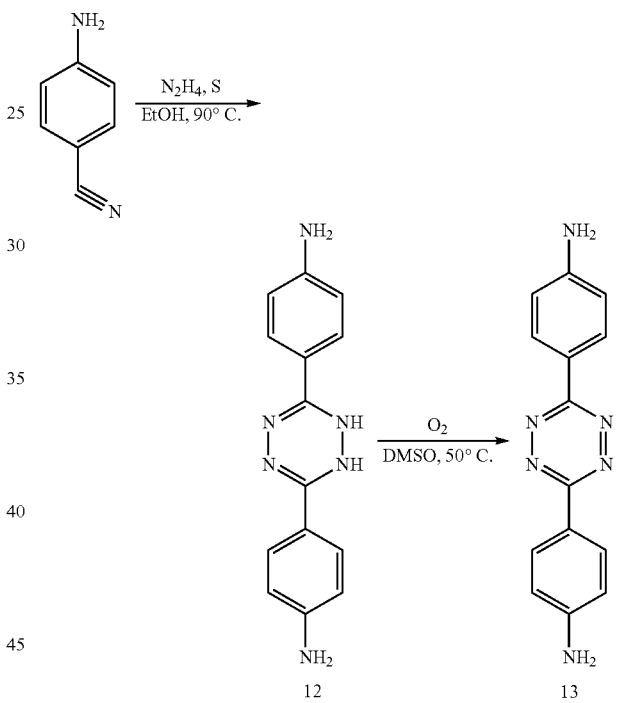

4-Aminobenzonitrile (1.00 g; 8.46 mmol) was dissolved in ethanol (3 mL), and subsequently hydrazine hydrate (2.12 g; 42.2 mmol) and sulfur (0.176 g; 5.5 mmol) were added. The mixture was heated at 90° C. for 90 min, and the yellow precipitate was isolated by filtration, washed with ethanol (10 mL), and subsequently triturated with acetone (12 mL) to yield the yellow intermediate 12 (190 mg, 17%).

Intermediate 12 (50 mg; 0.188 mmol) was dissolved in DMSO (1 mL), and oxygen was bubbled through this solution at 20° C. After 5 hr, the reaction mixture was poured in brine (13 mL), and the red precipitate was filtered off, washed with water (10 mL), and dried in vacuo. The red powder was further purified by trituration with acetone (15 mL), to yield product 13 as a red solid (13.7 mg, 27%).

$^1$H NMR (DMSO-$d_6$): δ=8.17 (d, 2H), 7.75 (d, 2H), 6.02 (s, 4H) ppm. $^{13}$C NMR (DMSO-$d_6$): δ=162.3, 152.8, 128.5, 118.3, 113.8 ppm. HPLC-MS/PDA: one peak in chromatogram, m/z=265.2 (M+H$^+$), $\lambda_{max}$=241, 370 and 530 nm.

Synthesis of 3,6-bis(3-aminophenyl)-1,2,4,5-tetrazine (15)

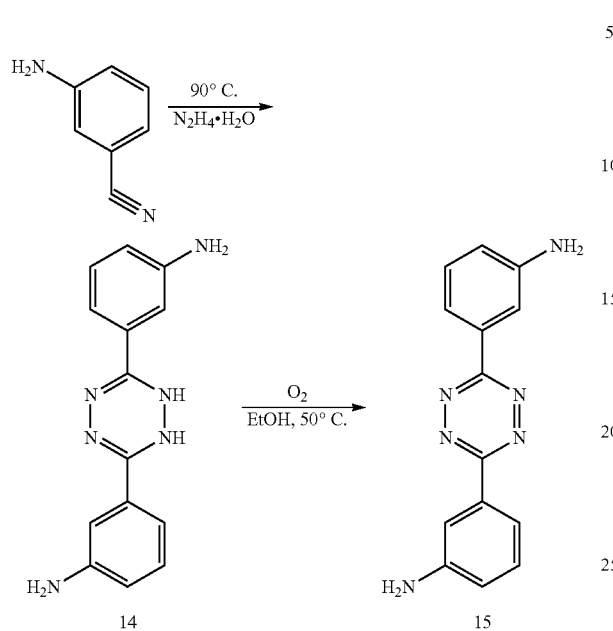

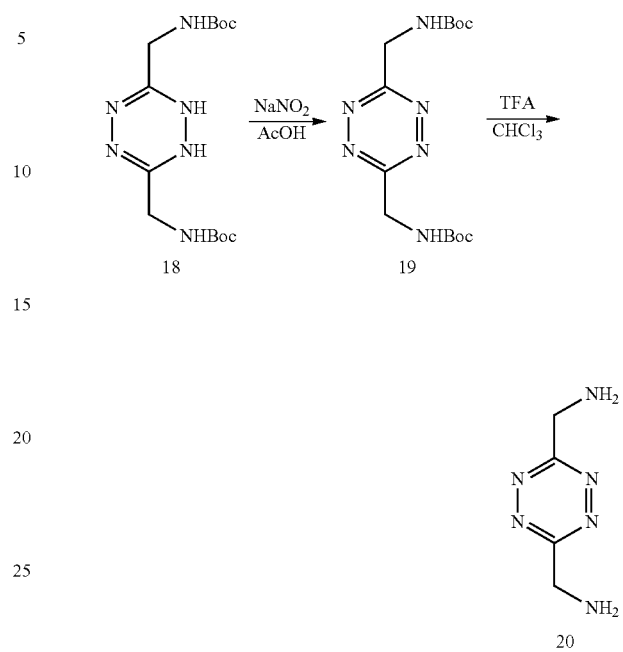

3-Aminobenzonitrile (1.00 g; 8.460 mmol) was dissolved in hydrazine hydrate (2.50 mL; 51.4 mmol), and the mixture was heated to 90° C. for 3 days. Water (5 mL) was added, and the yellow precipitate was filtered off and washed with water (15 mL) and ethanol (10 mL), to yield the crude intermediate 14 as a orange powder (910 mg; 81%).

Intermediate 14 (50 mg; 0.188 mmol) was suspended in ethanol (4 mL), and oxygen was bubbled through this mixture at 50° C. Within minutes, the color changed from yellow to red. After 16 hr, the precipitate was filtered off, and washed with ethanol, to give the product 15 as a red powder (31 mg, 62%).

$^1$H NMR (DMSO-$d_6$): δ=7.77 (s, 2H), 7.66 (d, 2H), 7.30 (t, 2H), 6.85 (d, 2H), 5.53 (s, 4H) ppm. HPLC-MS/PDA: one peak in chromatogram, m/z=265.2 (M+H$^+$), $\lambda_{max}$=240, 296 and 527 nm.

Synthesis of 3,6-bis(aminomethyl)-1,2,4,5-tetrazine (20)

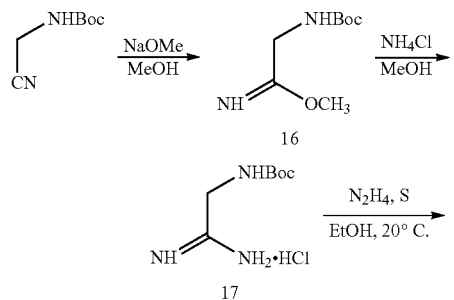

Boc-amino acetonitrile (1.00 g; 6.40 mmol) was dissolved in methanol (10 mL) and sodium methoxide (0.145 mL 25% in MeOH; 0.64 mmol) was added. The mixture was stirred at 20° C. for 18 hr. and subsequently ammonium chloride (0.34 g; 6.40 mmol) was added, and the mixture was stirred at 20° C. for 3 days. The solution was precipitated in diethyl ether (40 mL), and the precipitate was collected by filtration, washed, and dried to yield the amidine hydrochloride 17.

The amidine hydrochloride (17, 241 mg; 1.15 mmol) was dissolved in hydrazine hydrate (3 mL; 61.9 mmol), and the solution was stirred at 20° C. for 16 hr. Then it was diluted with water (10 mL), and the precipitate was collected by centrifugation, and dried. The colorless solid was dissolved in acetic acid (1.5 mL) and sodium nitrite (28 mg; 0.41 mmol) was added. The pink mixture was stirred for 15 min and subsequently chloroform (15 mL) and saturated sodium bicarbonate (30 mL) were added. The organic layer was isolated and washed with water (15 mL), dried over sodium sulfate, and evaporated to dryness, to yield the Boc-protected tetrazine as a pink solid (19, 70 mg; 35%). This compound (12 mg; 0.035 mmol) was dissolved in chloroform (1 mL), and TFA (1 mL) was added. The mixture was stirred for 15 min, and the precipitated in diethyl ether (15 mL). The pink precipitate was filtered off, washed, and dried to give the title compound as its TFA salt (20, 10 mg, 78%).

$^1$H NMR (D$_2$O): δ=5.06 (s, 4H) ppm. $^{13}$C NMR (D$_2$O): δ=164.5, 41.1 ppm. HPLC-MS/PDA: one peak in chromatogram, m/z=141 (M+H$^+$), $\lambda_{max}$=267 and 517 nm.

Synthesis of 2,2',2"-(10-(2-oxo-2-(6-oxo-6-(6-(6-(pyridin-2-yl)-1,2,4,5-tetrazin-3-yl)pyridin-3-ylamino)hexylamino)ethyl)-1,4,7,10-tetraazacyclododecane-1,4,7-triyl)triacetic acid (27) and 2,2',2"-(10-(2-oxo-2-(11-oxo-11-(6-(6-(pyridin-2-yl)-1,2,4,5-tetrazin-3-yl)pyridin-3-ylamino)undecylamino)ethyl)-1,7,10-tetraazacyclododecane-1,4,7-triyl)triacetic acid (28)
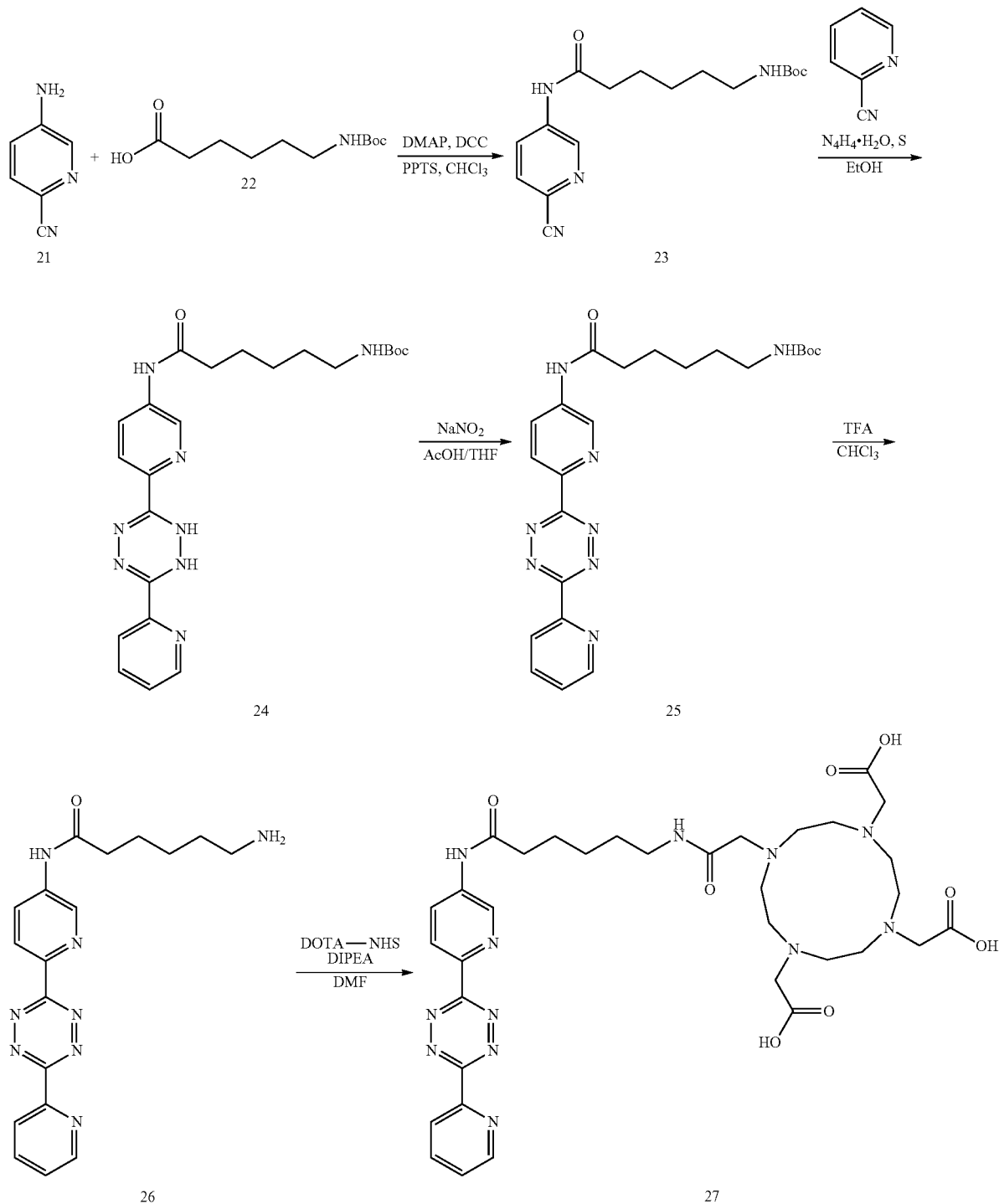

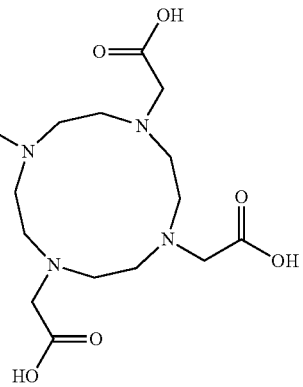

28

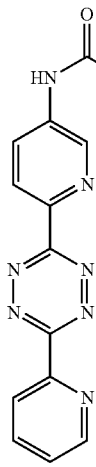

5-Amino-2-cyanopyridine 21 (1.02 g; 8.60 mmol), N-Boc-6-amino-hexanoic acid 22 (0.99 g; 4.30 mmol), DCC (1.77 g; 8.60 mmol), DMAP (1.05 g; 8.60 mmol), and PPTS (0.37 g; 1.47 mmol) were suspended in chloroform (15 mL). The mixture was stirred at room temperature for 18 hr, and then evaporated to dryness, and stirred in acetonitrile (20 mL). The precipitate was removed by filtration, and the filtrate was evaporated to dryness, dissolved in chloroform (20 mL), and washed with respectively aqueous citric acid (15 mL 0.5 M), aqueous potassium hydrogencarbonate (15 mL, 1 M), and water (15 mL). The organic phase was dried over sodium sulfate and evaporated to dryness. The crude product was purified by column chromatography (silica, hexane/ethylacetate=1:1) to yield the product 23 as a white solid (0.95 g; 61%).

MS (ESI, m/z): Calcd for $C_{17}H_{25}N_4O_3^+$([M+H]$^+$): 333.19. Found: 333.17.

Tert-butyl 6-(6-cyanopyridin-3-ylamino)-6-oxohexylcarbamate 23 (0.70 g; 2.1 mmol), 2-cyanopyridine (0.87 g; 8.4 mmol), hydrazine hydrate (1.25 g; 20 mmol) were dissolved in ethanol (2 mL), and sulfur (0.22 g; 7 mmol) was added. The mixture was stirred at 70° C. under an inert atmosphere of argon for 2 hr, and then at 50° C. for 16 hr. The orange suspension was diluted with chloroform (10 mL), and the resulting solution was washed with water (2 times 15 mL). The organic phase was dried over sodium sulfate and evaporated to dryness. The crude product was purified by column chromatography (silica, chloroform/acetone=4:1) to yield the product 24 as an orange solid (0.65 g; 66%). MS (ESI, m/z): Calcd for $C_{23}H_{31}N_8O_3^+$ ([M+H]$^+$): 467.25. Found: 467.33.

Tert-butyl 6-oxo-6-(6-(6-(pyridin-2-yl)-1,2-dihydro-1,2,4,5-tetrazin-3-yl)pyridin-3-ylamino)hexylcarbamate 24 (0.30 g; 0.64 mmol) was dissolved in THF (1.5 mL), and acetic acid (2 mL) was added. Sodium nitrite (0.25 g; 3.62 mmol) was dissolved in water (1 mL) and added dropwise. The red solution was poured in aqueous potassium hydrogencarbonate (50 mL; 1M), and the product was extracted with chloroform (50 mL). The organic layer was washed with water (50 mL), and dried over sodium sulfate and evaporated to dryness, to yield the product 25 as a purple solid (0.25 g; 83%).

MS (ESI, m/z): Calcd for $C_{23}H_{29}N_8O_3^-$ ([M+H]$^+$): 465.23. Found: 465.42.

tert-Butyl 6-oxo-6-(6-(6-(pyridin-2-yl)-1,2,4,5-tetrazin-3-yl)pyridin-3-ylamino) hexylcarbamate 25 (66 mg; 0.14 mmol) was dissolved in chloroform (6 mL), and TFA (6 mL) was added. The solution was stirred at room temperature for 2 hr, and subsequently evaporated to dryness, to yield the product 26 as its TFA salt (52 mg; 100%).

MS (ESI, m/z): Calcd for $C_{18}H_{21}N_8O^+$ ([M+H]$^+$): 365.19. Found: 365.33.

6-Amino-N-(6-(6-(pyridin-2-yl)-1,2,4,5-tetrazin-3-yl) pyridin-3-yl)hexanamide 26 (52 mg; 0.14 mmol) was dissolved in DMF (2.5 mL), and DIPEA was added (320 mg; 2.0 mmol). N-Hydroxysuccinimide activated DOTA (161 mg; 0.2 mmol) was added, and the mixture was stirred at room temperature for 5 hr. The solution was evaporated to dryness, and the crude product was dissolved in a mixture of acetonitrile and water, and purified by preparative RP-HPLC. After lyophilisation the pure product 27 was obtained as a pink fluffy solid (80 mg, 76% yield).

$^1$H-NMR (30% acetonitrile-d$_3$ in D$_2$O): δ=8.90 (m, 2H, ArH), 8.68 (d, 1H, ArH), 8.60 (dd, 1H, ArH), 8.31 (m, 1H, ArH), 8.24 (t, 1H, ArH), 7.82 (t, 1H, ArH), 3.80 (br s, 6H, NCH$_2$COOH), 3.72 (br s, 2H, NCH$_2$CONH), 3.34-3.23 (br m, 18H, NCH$_2$CH$_2$N, CH$_2$NHCO), 2.49 (t, 2H, NHCOCH$_2$), 1.70 (m, 2H, NHCOCH$_2$CH$_2$), 1.59 (m, 2H. CH$_2$CH$_2$NHCO), 1.41 (m, 2H, CH$_2$CH$_2$CH$_2$NHCO) ppm. $^{13}$C-NMR (30% acetonitrile-d$_3$ in D$_2$O): δ=175.5, 171.5 (br), 162.6, 162.5, 150.1, 148.1, 142.9, 141.6, 139.6, 138.4, 128.0, 127.9, 125.4, 124.8, 55.4, 54.3 (br), 49.4 (br), 39.4, 36.5, 28.2, 25.9, 24.6 ppm. ESI-MS: m/z for $C_{34}H_{47}N_{12}O_8^+$ ([M+H]+): 751.37; Obs. [M+H]$^+$ 751.58, [M+Na]$^+$ 773.50, [M+2H]$^{2+}$ 376.42, [M+3H]$^+$ 251.33. FT-IR (ATR): v=3263, 3094, 2941, 2862, 1667, 1637, 1582, 1540, 1460, 1431, 1395, 1324, 1296, 1272, 1251, 1226, 1198, 1128, 1087, 1060, 1020, 992, 977, 920, 860, 831, 798, 782, 742, 718, 679, 663 cm$^{-1}$.

For 28, a procedure was used comparable to the described synthesis of 2,2',2''-(10-(2-oxo-2-(6-oxo-6-(6-(6-(pyridin-2-yl)-1,2,4,5-tetrazin-3-yl)pyridin-3-ylamino) hexylamino) ethyl)-1,4,7,10-tetraazacyclododecane-1,4,7-triyl)triacetic acid (27).

After lyophilisation the pure product 28 was obtained as a pink fluffy solid (90 mg, 78% yield).

$^1$H-NMR (DMSO-d$_6$): δ=10.65 (s, 1H, NH), 9.06 (d, 1H, ArH), 8.93 (d, 1H, ArH), 8.61 (t, 2H, ArH), 8.44 (dd, 1H, ArH), 8.16 (t, 2H, ArH, NH), 7.73 (dd, 1H, ArH), 3.51 (br s, 6H, NCH$_2$COOH), 3.28 (br s, 2H, NCH$_2$CONH), 3.06 (q, 2H, CH$_2$NHCO), 3.34-3.23 (br m, 16H, NCH$_2$CH$_2$N), 2.43 (t, 2H, NHCOCH$_2$), 1.64 (m, 2H, NHCOCH$_2$CH$_2$), 1.42 (m, 2H, CH$_2$CH$_2$NHCO), 1.38-1.22 (m, 12H, CH$_2$) ppm. $^{13}$C-NMR (DMSO-d$_6$): δ=173.0, 171.0 (br), 169.1 (br), 163.5, 163.2, 151.0, 150.6, 144.2, 141.7, 139.1, 138.2, 127.0, 126.5, 125.3, 124.6, 57.3 (br), 55.2 (br), 50.7, 39.0, 36.8, 29.5, 29.4, 29.3, 29.19, 29.17, 29.1, 26.9, 25.3 ppm. ESI-MS: m/z Calcd for C$_{39}$H$_{57}$N$_{12}$O$_8$$^+$ ([M+H]$^+$): 821.44; Obs. [M+Na]$^+$ 843.58, [M+H]$^+$ 821.58, [M+2H]$^{2+}$ 411.42, [M+3H]$^{3+}$ 274.67. FT-IR (ATR): ν=3261, 3067, 2925, 2851, 1633, 1583, 1541, 1458, 1433, 1394, 1324, 1298, 1270, 1249, 1228, 1200, 1165, 1128, 1088, 1059, 1016, 991, 920, 885, 860, 832, 798, 782, 764, 742, 719, 687, 661 cm$^{-1}$.

DOTA-Tetrazine Activator 29

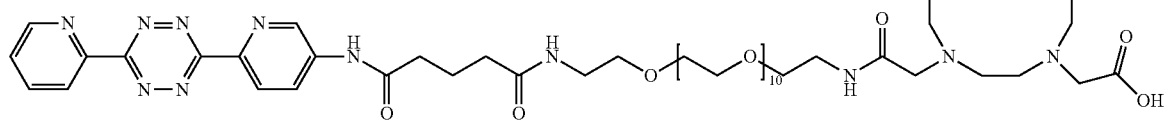

The tetrazine 29 above has been described in detail in Robillard et al., Angew. Chem., 2010, 122, 3447-3450. It also serves as an example a structure that can be used as an Activator according to this invention. The amide function on one of the 2-pyridyl groups of the 1,2,4,5-tetrazine moiety is an electron donating group, while both pyridine groups can be viewed as electron withdrawing. The tetrazine can therefore be seen as slightly electron deficient.

Activator 29 displays suitable and favorable pharmacological properties: 29 is rather stable in PBS solution with little degradation within 2 hr and most of the material still intact after overnight incubation; it has a 10 min blood clearance half-life in mice; its partial volume of distribution (V$_d$) in mice corresponds to the total extracellular water compartment, as it does not significantly enter cells. Activator 29 contains a DOTA ligand, and such ligands are instrumental in a variety of imaging modalities (e.g. MRI, SPECT). Consequently, Activator 29 is not only suitable for drug release, but it can simultaneously be used for imaging purposes. In fact, Activator 29 has been employed as a SPECT/CT imaging probe after complexation with $^{111}$In$^{3+}$. See Robillard et al., Angew. Chem., 2010, 122, 3447-3450 for further details.

Note that the amino-1,2,4,5-tetrazine moieties comprised in activators 27-29 can be used for conjugation to a range additional functional groups such as sugars, PEG, polymers, peptides (such as RGD or c-RGD), proteins, fluorescent molecules or dye molecules.

Example 2

Synthesis of (E)-cyclooctene model prodrugs and prodrugs

Synthesis of (E)-cyclooct-2-enol (31), (E)-cyclooct-2-en-1-yl benzylcarbamate (32), and (E)-cyclooct-2-en-1-yl (3,5-dimethylphenyl)carbamate (33)

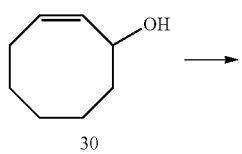

30

-continued

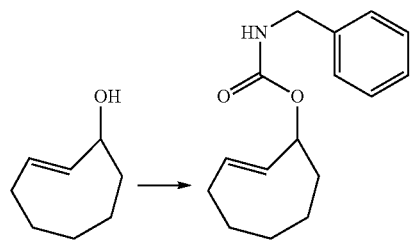

31      32

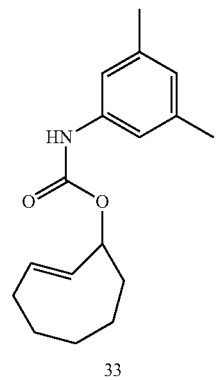

33

Synthesis of (E)-cyclooct-2-enol (31)

A solution of (Z)-cyclooct-2-enol 30 (2.36 g, 14.0 mmol) and methyl benzoate (1.8 mL, 1.94 g, 14.3 mmol, 1.0 eq) in diethyl ether/heptanes 1:2 (500 mL) was irradiated for 32 hr, while it was continuously lead through a column filled with silica/silver nitrate 10:1 (41 g), silica (0.5 cm) and sand (0.5 cm). The column was placed in the dark during the irradiation. The column was eluted with dichloromethane (250 mL) to give unreacted starting material. The silica was stirred with dichloromethane/12.5% aqueous ammonia 1:1 (3×100 mL). The combined organic layers were dried over sodium sulfate, filtered and evaporated in vacuo to give crude product 31 as a grey oil. The oil was purified by column chromatography (silica, eluents pentane/diethyl ether 10% to 50%) to give (E)-cyclooct-2-enol 31 (major isomer, second fraction, 440 mg, 3.49 mmol, 24.9%) as a colorless oil and (E)-cyclooct-2-enol 31 (minor isomer, first fraction, 325 mg, 2.58 mmol, 18.4%) as a colorless oil. The major diastereoisomer is identical to the (1RS,2RS)-trans-cyclooct-2-en-1-ol prepared via a different route by G. H. Whitham, M. Wright, J. Chem. Soc. (C) 1971, 883. The minor diastereoisomer is identical to the (1SR,2RS)-trans-cyclooct-2-en-1-ol prepared via a different route by G. H. Whitham, M. Wright, J. Chem. Soc. (C) 1971, 886. Minor isomer: $^1$H-NMR (CDCl$_3$, 300 MHz) δ=0.71-0.82 (m, 1H), 1.05-1.17 (m, 1H), 1.43-1.72 (m, 4H), 1.80-2.09 (m, 4H), 2.45-2.52 (m, 1H), 4.61 (s, 1H), 5.54-5.61 (m, 1H), 5.90-6.00 (m, 1H) ppm. $^{13}$C-NMR (CDCl$_3$, 75 MHz) δ=23.35, 29.42, 36.08, 36.27, 43.40, 71.40, 130.78, 135.39 ppm. Major isomer: $^1$H-NMR (CDCl$_3$, 300 MHz) δ=0.64-0.90 (m, 2H), 1.31-1.51 (m, 2H), 1.66-1.95 (m, 4H), 2.06-2.14 (m, 1H), 2.22-2.37 (m, 1H), 2.78 (br, 1H), 4.15-4.23 (m, 1H), 5.45-5.65 (m, 2H) ppm. $^{13}$C-NMR (CDCl$_3$, 75 MHz) δ=27.83, 29.28, 30.52, 35.58, 36.05, 44.48, 131.86, 136.00 ppm.

Note: Reference is made to Whitham et al J. Chem. Soc. (C), 1971, 883-896, describing the synthesis and characterization of the equatorial and axial isomers of trans-cyclooct-2-en-ol, identified as (1RS, 2RS) and (1SR, 2RS), respectively. In these isomers the OH substituent is either in the equatorial or axial position. The above mentioned major and minor isomer refer respectively to the equatorial and axial isomer. Throughout the following examples major/equatorial and minor/axial are used interchangeably for trans-cyclo-oct-2-en-ol derivatives, and this characterization is based on the aforementioned characterization of the parent compound trans-cyclo-oct-2-en-ol.

Synthesis of (E)-cyclooct-2-en-1-yl benzylcarbamate (major isomer) (32)

To a solution of (E)-cyclooct-2-enol 31 (major isomer 100) mg, 0.792 mmol) in dichloromethane (6 mL) were added benzyl isocyanate (101 µL, 110 mg, 0.826 mmol, 1.04 eq) and a drop of triethylamine. The flask was covered with aluminum foil and the solution was stirred under a nitrogen atmosphere at room temperature overnight. Evaporation of the reaction mixture gave mainly starting material. Benzyl isocyanate (200 µL, 220 mg, 1.65 mmol, 2.08 eq) and a drop of triethylamine in dichloromethane (6 mL) were added and the solution was stirred overnight at room temperature, at 50° C. for 1 hr and at 25-30° C. over the weekend. The volatiles were removed by bulb-to-bulb distillation (50° C., 2 hr). The residue was purified by column chromatography to give carbamate 32 (101 mg, 0.389 mmol, 49.2%) as a white solid.

$^1$H-NMR (CDCl$_3$, 300 MHz) δ=0.81-0.86 (m, 2H), 1.35-1.55 (m, 2H), 1.82-1.99 (m, 4H), 2.21-2.30 (m, 1H), 2.38-2.47 (m, 1H), 4.36 (d, 5.8 Hz, 2H), 4.96 (br, 1H), 5.08-5.20 (m, 1H), 5.48-5.57 (m, 1H), 5.71-5.82 (m, 1H), 7.26-7.36 (M, 5H) ppm. $^{13}$C-NMR (CDCl$_3$, 75 MHz) δ=27.69, 29.25, 35.68, 35.76, 35.83, 41.32, 44.53, 78.33, 100.02, 127.65, 127.78, 128.86, 132.03, 133.31, 138.88 ppm.

Synthesis of (E)-cyclooct-2-en-1-yl benzylcarbamate (minor isomer) (32)

To a solution of (E)-cyclooct-2-enol 31 (minor isomer 100 mg, 0.792 mmol) in dichloromethane (6 mL) were added benzyl isocyanate (101 , 110 mg, 0.826 mmol, 1.04 eq) and a drop of triethylamine. The flask was covered with aluminum foil and the solution was stirred under a nitrogen atmosphere at room temperature overnight. Evaporation of the reaction mixture gave mainly starting material. Benzyl isocyanate (200 µL, 220 mg, 1.65 mmol, 2.08 eq) and a drop of triethylamine in dichloromethane (6 mL) were added and the solution was stirred overnight at room temperature, at 50° C. for 1 hr and at 25-30° C. over the weekend. The volatiles were removed by bulb-to-bulb distillation (50° C., 2 hr). The residue was purified by column chromatography to give carbamate 32 (43 mg, 0.166 mmol, 20.9%) as a white solid.

$^1$H-NMR (CDCl$_3$, 300 MHz) δ=0.74-0.93 (m, 2H), 1.01-1.14 (m, 1H), 1.41-1.57 (m, 1H), 1.62-1.76, 2H), 1.84-2.12 (m, 3H), 2.46-2.49 (m, 1H), 4.40 (d. J=6.0 Hz, 2H), 5.05 (br, 1H), 5.40 (s, 1H), 5.52-5.59 (m, 1H), 5.79-5.89 (m, 1H), 7.31-7.36 (m, 5H) ppm. $^{13}$C-NMR (CDCl$_3$, 75 MHz) δ=24.34, 29.33, 36.13, 36.20, 40.97, 45.30, 74.33, 127.67, 127.85, 128.87, 131.72, 131.99, 138.87, 156.11 ppm.

Synthesis of (E)-cyclooct-2-en-1-yl (3,5-dimethylphenyl)carbamate (major isomer) (33)

To a solution of (E)-cyclooct-2-enol 31 (major isomer 260 mg, 2.06 mmol) in dichloromethane (12 mL) were added 3,5-dimethylphenyl isocyanate (305 µL, 318 mg, 2.16 mmol, 1.05 eq) in dichloromethane (3 mL) and a few drops of triethylamine. The flask was covered with aluminum foil and the solution was stirred under a nitrogen atmosphere at 29° C. for 4 nights. Evaporation of the reaction mixture gave 0.57 g off-white solid. The residue was purified by column chromatography (silica, 30 mL eluents ethyl acetate/heptanes 5 to 10%) to give partially purified carbamate 33 (94 mg). The product was further purified by column chromatography (silica, 30 mL eluents ethyl acetate/heptanes 5%) to give carbamate 33 (72 mg, 0.263 mmol, 12.8% yield, contains ca 10% Z-isomer) as a white solid.

$^1$H-NMR (CDCl$_3$, 300 MHz) δ=0.79-0.98 (m, 2H), 1.28-2.02 (m, 4H), 1.80-2.07 (m, 3H), 2.30 (s, 6H), 2.42-2.50 (m, 1H), 5.13-5.22 (m, 1H), 5.55-5.87 (m, 2H), 6.49 (br, 1H), 6.71 (s, 1H), 7.04 (s, 2H) ppm. $^{13}$C-NMR (CDCl$_3$, 75 MHz) δ=21.61, 27.67, 29.24, 35.70, 35.84, 41.21, 79.34, 116.59, 125.22, 131.83, 133.51, 138.11, 138.50, 153.43 ppm.

Synthesis of (E)-cyclooct-2-en-1-y (3,5-dimethylphenyl)carbamate (minor isomer) (33)

To a solution of (E)-cyclooct-2-enol 31 (minor isomer, contains also Z isomer, 260 mg, 2.06 mmol) in dichloromethane (12 mL) were added 3,5-dimethylphenyl isocyanate (305 µL, 318 mg, 2.16 mmol, 1.05 eq) in dichloromethane (3 mL) and a few drops of triethylamine. The flask was covered with aluminum foil and the solution was stirred under a nitrogen atmosphere at 30° C. for 2 nights and at 50° C. overnight. Evaporation of the reaction mixture gave 0.54 g yellow solid. The residue was purified by column chromatography (silica, 40 mL eluents ethyl acetate/heptanes 5%) to give partially purified carbamate 33 (20 mg). The product was further purified in vacuo (0.08 mbar) at 40° C. for 3 hr and at room temperature overnight to give carbamate 33 (11 mg, 0.040 mmol, 2.0%) as a light yellow semi-solid.

$^1$H-NMR (CDCl$_3$, 300 MHz) δ=0.78-0.90 (m, 1H), 1.07-2.18 (m, 8H), 2.30 (s, 6H), 2.45-2.53 (m, 1H), 5.42 (s, 1H), 5.56-5.62 (m, 1H), 5.83-5.94 (m, 1H), 6.60 (s, 1H), 6.71 (s, 1H), 7.03 (s, 2H) ppm. $^{13}$C-NMR (CDCl$_3$, 75 MHz) δ=21.64, 24.42, 29.43, 36.77, 40.19, 74.46, 116.47, 118.77, 125.35, 131.34, 132.31, 138.00, 138.91 ppm.

Synthesis of (E)-cyclooct-2-en-1-yl (4-nitrophenyl) carbonate (34)

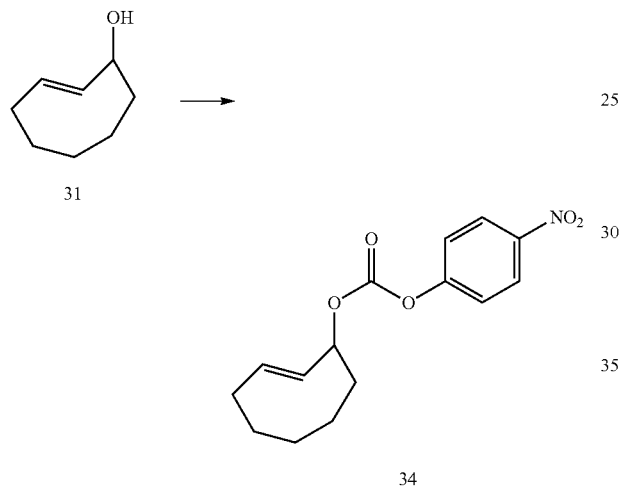

A solution of minor (E)-cyclooct-2-enol 31 (304 mg, 2.41 mmol) in 15 mL dichloromethane was cooled in ice, 4-(N,N-Dimethylamino)pyridine (1.16 g, 9.50 mmol) was added, followed by 4-nitrophenylchloroformate (0.90 g, 4.46 mmol). The solution was stirred overnight, then poured on a 20 g silica column. Elution was performed with dichloromethane, then with dichloromethane containing 5% TBME. The product fractions were combined and rotary evaporated to yield minor-34 as a solidifying oil (338 mg, 1.16 mmol, 48%).

In a similar fashion, from major (E)-cyclooct-2-enol 31 (259 mg, 2.06 mmol) in 10 mL dichloromethane, with 4-(N,N-dimethylamino)pyridine (1.11 g, 9.09 mmol) and 4-nitrophenylchloroformate (0.85 g, 4.22 mmol), the major-34 was obtained as a solidifying oil (234 mg, 0.80 mmol, 39%).

$^1$H-NMR of minor 34(CDCl$_3$): δ=0.9 (m, 1H), 1.25 (m, 1H), 1.5-2.2 (m, 6H), 2.25 (dd, 1H), 2.6 (m, 1H), 5.45 (s, 1H), 5.6 (dd, 1H), 6.0 (m, 1H), 7.4 (d, 2H), 8.3 (d, 2H) ppm. $^{13}$C-NMR (CDCl$_3$): δ=24.0, 29.0, 36.0, 36.0, 40.6 (all CH$_2$), 79.0, 122.0, 125.8, 129.8, 133.2 (all CH), 145.4, 151.8, 156.0 (C and C=O) ppm.

$^1$H-NMR of major 34 (CDCl$_3$): δ=0.8-1.0 (m, 2H), 1.4-2.1 (m, 6H), 2.35 (m, 1H), 2.45 (m, 1H), 5.2 (m, 1H), 5.65 (m, 1H), 5.85 (m, 1H), 7.4 (d, 2H), 8.3 (d 2H) ppm. $^{13}$C-NMR (CDCl$_3$): δ=27.8, 29.0, 35.8, 36.0, 40.4 (all CH$_2$), 83.0, 121.8, 125.0, 130.4, 134.4 (all CH), 145.8, 152.0, 156.0 (C and C=O) ppm.

Synthesis of (E)-cyclooct-2-en-1-yl (4-(hydroxymethyl)phenyl)carbamate (35)

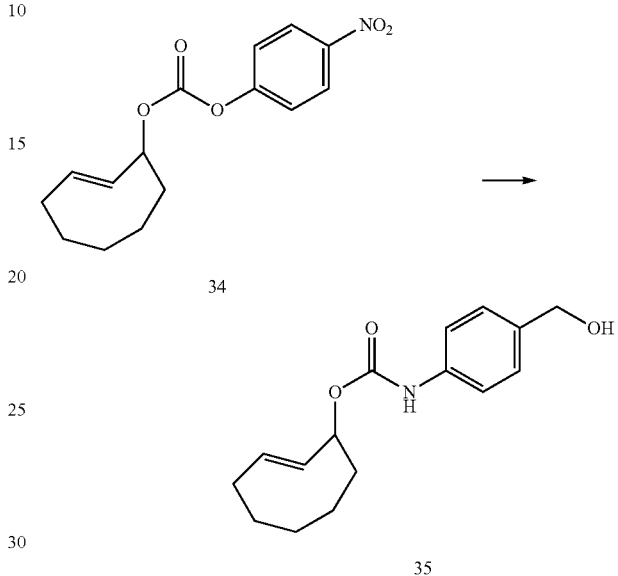

The PNP-derivative 34 derived from the minor alcohol 31 (136 mg, 0.467 mmol) was dissolved in 7.5 g THF. Diisopropylethylamine (182 mg, 1.41 mmol) was added, followed by 1-hydroxybenzotriazole (24 mg, 0.178 mmol) and 4-aminobenzylalcohol (94 mg, 0.76 mmol). The mixture was stirred in the dark at ca. 30° C. for 6 days. The solvent was removed by rotary evaporation and the residue was chromatographed on 20 g silica, using dichloromethane with gradually increasing amounts of TBME as the eluent. The product eluted with ca. 5% TBME. Rotary evaporation of the product fractions left the product minor-35 as a viscous oil (112 mg, 0.407 mmol, 87%).

In a similar fashion, the PNP-derivative 34 derived from the major alcohol 31 (145 mg, 0.498 mmol) in 6.0 g THF, was reacted with diisopropylethylamine (210 mg, 1.63 mmol), 1-hydroxybenzotriazole (34 mg, 0.251 mmol) and 4-aminobenzylalcohol (128 mg, 1.04 mmol) for 3 days at ca. 30° C. Rotary evaporation and chromatography yielded the product major-35 as a viscous oil (110 mg, 0.40 mmol, 80%).

$^1$H-NMR of minor-35 (CDCl$_3$): δ=0.8 (m, 1H), 1.1 (m, 1H), 1.45 (m, 1H), 1.6-2.2 (m, 6H), 2.4 (m, 1H), 4.6 (s, 2H), 5.4 (s, 1H), 5.55 (dd, 1H), 5.85 (m, 1H), 7.15 (bs, 1H), 7.2-7.4 (AB, 4H) ppm. $^{13}$C-NMR (CDCl$_3$): δ=24.2, 29.0, 36.0, 36.0, 41.0, 65.0 (all CH$_2$), 75.0, 119.0, 128.0, 131.0, 132.6 (all CH), 136.0, 138.0, 153.6 (C and C=O) ppm.

$^1$H-NMR of the major-35 (CDCl$_3$): δ=0.8-1.0 (m, 2H), 1.4-2.1 (m, 6H), 2.3 (m, 1H), 2.45 (m, 1H), 4.65 (s, 2H), 5.2 (m, 1H), 5.6 (m, 1H), 5.8 (m, 1H), 6.6 (bs, 1H), 7.45-7.65 (AB, 4H) ppm. $^{13}$C-NMR (CDCl$_3$): δ=27.4, 29.2, 35.8, 36.0, 41.2, 65.0 (all CH$_2$), 79.8, 119.0, 128.2, 132.0, 134.0 (all CH), 136.0, 137.8, 153.6 (C and C=O) ppm.

Synthesis of minor (E)-ethyl 2-(4-(((cyclooct-2-en-1-yloxy)carbonyl)amino)phenyl)-2-((((2,5-dioxopyrrolidin-1-yl)oxy)carbonyl)oxy)acetate (37)

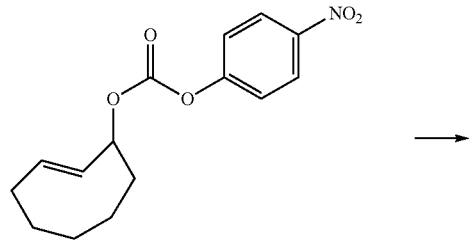

34

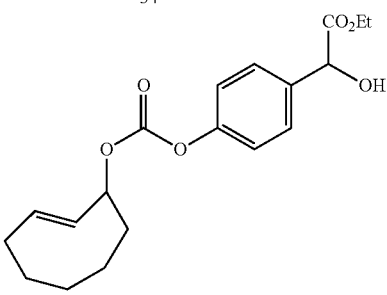

36

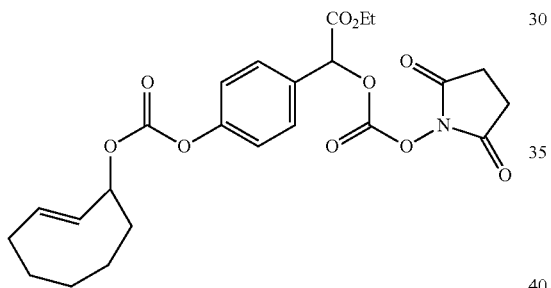

37

The PNP-derivative 34 derived from the minor alcohol 31 (300 mg, 1.03 mmol) was dissolved in 10.3 g THF. Diisopropylethylamine (362 mg, 2.80 mmol) was added, followed by 1-hydroxybenzotriazole (75 mg, 0.556 mmol) and ethyl 2-(4-aminophenyl)-2-hydroxyacetate (325 mg, 1.67 mmol, prepared as described in WO 2009109998). The mixture was stirred in the dark at ca. 30° C. for 6 days. The solvent was removed by rotary evaporation and the residue was chromatographed on 21 g silica, using dichloromethane with gradually increasing amounts of TBME as the eluent. The product eluted with ca. 5% TBME. Rotary evaporation of the product fractions afforded minor (E)-ethyl 2-(4-(((cyclooct-2-en-1-yloxy)carbonyl)amino)phenyl)-2-hydroxyacetate (36) as a viscous oil (350 mg, 1.01 mmol, 99%).

$^1$H-NMR (CDCl$_3$): δ=0.8 (m, 1H), 1.1 (m, 1H), 1.2 (t, 3H), 1.4-2.2 (m, 7H), 2.5 (m, 1H), 4.1-4.3 (2q, 2H), 5.1 (s, 1H), 5.45 (s, 1H), 5.55 (dd, 1H), 5.85 (m, 1H), 6.7 (bs, 1H), 7.3-7.45 (AB, 4H) ppm.

The product 36 obtained above (80 mg, 0.23 mmol) was dissolved in 4.1 g acetonitrile. Diisopropylethylamine (215 mg, 1.67 mmol) was added, followed by N,N'-disuccinimidyl carbonate (217 mg, 0.85 mmol). The solution was stirred for 2 days at ca. 30° C. The solvent was removed by rotary evaporation and the residue was chromatographed on 16 g silica, using dichloromethane with gradually increasing amounts of TBME as the eluent. The product eluted with ca. 20% TBME. Rotary evaporation of the product fractions afforded the product minor-(E)-ethyl 2-(4-(((cyclooct-2-en-1-yloxy)carbonyl)amino)phenyl)-2-((((2,5-dioxopyrrolidin-1-yl)oxy)carbonyl)oxy)acetate (37) as a viscous oil (60 mg, 0.123 mmol, 53%).

$^1$H-NMR (CDCl$_3$): δ=0.8 (m, 1H), 1.1 (m, 1H), 1.2 (t, 3H), 1.4-2.2 (m, 7H), 2.5 (m, 1H), 2.6 (s, 4H), 4.15-4.3 (2q, 2H), 5.4 (s, 1H), 5.55 (dd, 1H), 5.8 (s) and 5.85 (m) (2H), 6.7 (bs, 1H), 7.35-7.5 (AB, 4H) ppm.

Synthesis of (E)-cyclooctene doxorubicin prodrug (38)

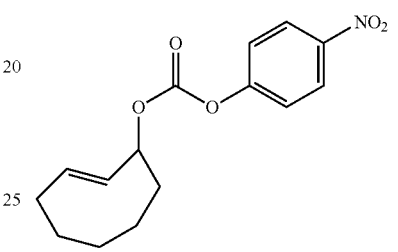

34

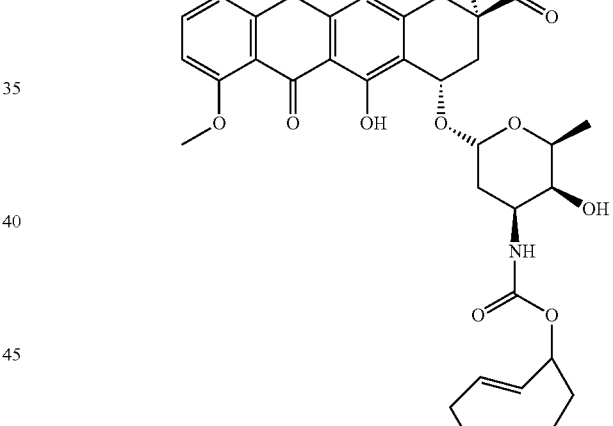

38

The PNP-derivative 34 derived from the minor alcohol 31 (20 mg, 0.0687 mmol) was dissolved in 3.0 g DMF. Diisopropylethylamine (80 mg, 0.62 mmol) was added, followed by doxorubicin hydrochloride (45 mg, 0.0776 mmol). The mixture was stirred in the dark at ca. 30° C. for 3 days. The solvent was removed under high vacuum and the residue was chromatographed on 17 g silica, using dichloromethane with gradually increasing amounts of methanol as the eluent. Rotary evaporation of the product fractions left a residue which was stirred with 5 mL TBME. After addition of 15 mL heptane and filtration minor-38 was obtained (27 mg, 0.039 mmol, 50%/). The filtrate contained an additional amount of product.

In a similar fashion, from the PNP-derivative 34 derived from the major alcohol 31 (22 mg, 0.0756 mmol) in 7.2 g DMF, after reaction with diisopropylethylamine (80 mg, 0.62 mmol) and doxorubicin hydrochloride (47.7 mg, 0.0822 mmol), followed by removal of the solvent under high vacuum, chromatography and TBME/heptane treatment major-38 was obtained (21 mg, 0.030 mmol, 30%). The filtrate contained an additional amount of product.

$^1$H-NMR of minor-38 (CDCl$_3$): δ=0.7-2.0 (m) and 1.35 (d) (18H), 2.2 (m, 2H), 2.4 (m, 2H), 3.0-3.4 (dd, 2H), 3.65 (s, 1H), 3.9 (m, 1H), 4.1 (s+m, 4H), 4.8 (s, 1H), 5.05 (m, 1H), 5.2-5.85 (m, 2H), 7.4 (d, 1H), 7.8 (t, 1H), 8.05 (d, 1H) ppm.

$^1$H-NMR of major-38 (CDCl$_3$): δ=0.7-2.0 (m) and 1.35 (d) (18H), 2.2 (m, 2H), 2.4 (m, 2H), 3.0-3.4 (dd, 2H), 3.65 (s, 1H), 3.9 (m, 1H), 4.1 (s+m, 4H), 4.8 (s, 1H), 5.0 (m, 1H), 5.3-5.8 (m, 2H), 7.4 (d, 1H), 7.8 (t, 1H), 8.05 (d, 1H) ppm. MS: 694.3 (M−1).

Synthesis of (E)-cyclooctene-doxorubicin prodrug 46

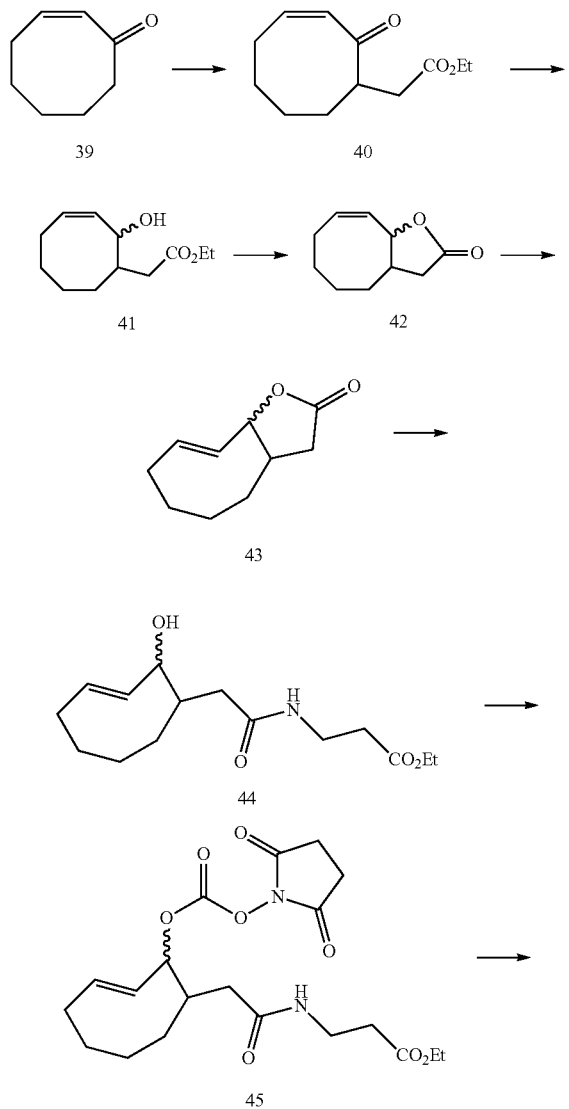

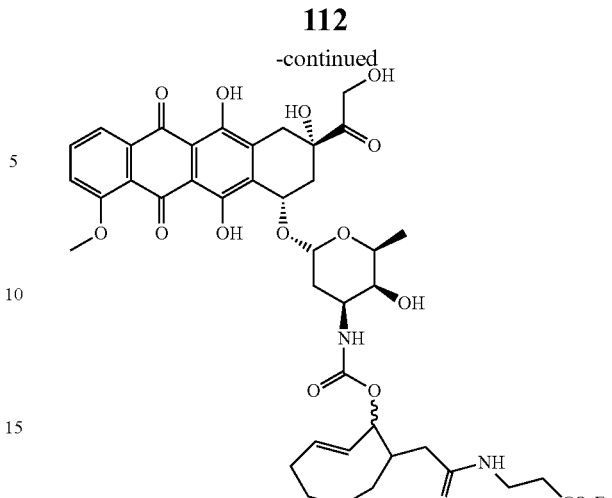

46 n-Butyllithium (97 mL, 2.5 N in hexanes, 0.242 mol) was added to diisopropylamine (23.66 g, 0.234 mol) in 100 mL THF at temperatures below −20° C. The solution was cooled and cyclooct-2-enone (39, 23.07 g, 0.185 mol), dissolved in 60 mL THF, was added over a 20 min period at −65 to −80° C. The solution was then stirred for 1 hr at −67 to −72° C. Ethyl bromoacetate (45.4 g, 0.272 mol), dissolved in 40 mL THF, was added over a 25 min period at −63 to −75° C. The resulting mixture was stirred for 3 hr at −55 to −70° C. Heptane (50 mL) was added at −60° C., followed by the addition of a solution of 40 g ammonium chloride in 100 mL water (with cooling), allowing the temperature to rise from −70° C. to −30° C. The cooling-bath was removed and the mixture was stirred for an additional 30 min, whereby the temperature raised to −15° C. The mixture was poured in 200 mL TBME and 50 mL water, the layers were separated and the organic layer was washed with 50 mL water. The successive aqueous layers were extracted with 250 mL TBME. The organic layers were dried and rotary evaporated. The excess of ethyl bromoacetate was removed under high vacuum by warming in a Kugelrohr apparatus. The residue comprising (Z)-ethyl 2-(2-oxocyclooct-3-en-1-yl)acetate (40) was used as such in the next step.

$^1$H-NMR (CDCl$_3$): δ=1.25 (t, 3H), 1.4-2.6 (m, 9H), 2.9 (2d, 1H), 3.55 (m, 1H), 4.15 (q, 2H), 6.05-6.5 (m, 2H) ppm.

A solution of the crude ester 40 in a mixture of 180 mL THF and 20 mL methanol was cooled in ice. Phosphotungstic acid (250 mg) was added, followed by the portion-wise addition of sodium borohydride (4.0 g, 0.105 mol) over a 30 min period, at temperatures below 7° C. The mixture was stirred for 90 min in ice, then 250 mL water and 250 mL toluene were added. The layers were separated and the organic layer was washed with 50 mL water. The successive aqueous layers were extracted with 250 mL toluene. The organic layers were dried and rotary evaporated. Crude 41 did not produce well-defined fractions, therefore all material was combined and hydrolyzed by refluxing for 2 hr with 25 mL 50% sodium hydroxide solution in 200 mL ethanol (another 25 mL water being added during the process). Most of the ethanol was removed by rotary evaporation. Some water was added to the residue. The mixture was extracted with 2×200 mL toluene. The organic layers were washed with 50 mL water. Toluene (200 mL) was added to the combined aqueous layers, which were acidified with concentrated hydrochloric acid. The layers were separated and the organic layer was washed with 20 mL water. The successive aqueous layers were extracted with 200 mL toluene. The 2 organic layers were dried and rotary evaporated. Kugelrohr distillation yielded the lactone 42 as a mixture of 2 isomers in a ca. 2:1 ratio (7.33 g, 44.1 mmol, 24% based on cyclooct-2-enone).

$^1$H-NMR (CDCl$_3$): δ=1.2-2.6 (m, 10H), 2.6-2.8 (m, 1H), 4.95 (m, 0.35H), 5.35 (m, 0.65H), 5.6 (m, 1H), 5.85 (m, 1H) ppm. $^{13}$C-NMR (CDCl$_3$): δ=24.1, 25.2, 27.0, 28.0, 29.2, 29.6, 34.4, 36.8 (all CH$_2$), 43.5, 47.2, 80.8, 81.9 (all CH), 126.4, 129.6, 130.2, 134.2 (all CH), 176.4 (C=O), 177.0 (C=O) ppm.

The lactone 42 obtained above (7.33 g, 44.1 mmol) was mixed with 10.0 g methyl benzoate and ca. 500 mL heptane/ether (ca. 4:1). The mixture was irradiated for 36 hr while the solution was continuously flushed through a 69 g silver nitrate impregnated silica column (containing ca. 6.9 g silver nitrate). The column material was then flushed with 250 mL portions of heptane/TBME in the ratios 3:1, 2:1, 1:1, 1:2 and then with 400 mL TBME. The first two fraction contained only methyl benzoate. The last 3 fractions were washed with 200 mL 10% ammonia, dried and rotary evaporated. After removal of most of the methyl benzoate under high vacuum, the combined residue weighed 800 mg (a mixture of the Z and E isomer, as well as methyl benzoate). The remaining column material was stirred with TBME and ammonia, then filtered and the layers were separated. The solid was treated twice more with the aqueous layer and TBME, then filtered and the layers were separated. The organic layers were dried and rotary evaporated to yield 3.70 g of 43 as a ca. 4:1 mixture of isomers, each isomer probably consisting of 2 E-isomers (22.29 mmol, 51%6).

$^1$H-NMR (CDCl$_3$): δ=0.8-2.75 (m, 10.6H), 3.0 (m, 0.4H), 4.45 (t, 0.2H), 5.0 (m, 0.8H), 5.6 (dd, 0.5H), 5.65 (m, 0.5H), 5.8 (m, 0.5H), 6.05 (m, 0.5H) ppm.

The recovered major isomer (see experiment below) has the following data:

$^1$H-NMR (CDCl$_3$): δ=0.8-2.75 (m, 10.6H), 3.0 (m, 0.4H), t, 0.2H), 4.95 (m, 1H), 5.6 (dd, 0.8H), 5.65 (m, 0.3H), 5.8 (m, 0.3H), 6.05 (m, 0.6H) ppm.

$^{13}$C-NMR (CDCl$_3$): δ=21.6, 25.8, 30.0, 30.4, 33.0, 34.8, 35.4, 36.0, 38.0 (all CH$_2$), 46.0, 47.0, 80.8, 84.0 (all CH), 128.2, 131.4, 133.0, 134.0 (all CH), 177.2 (C=O), 177.4 (C=O) ppm. The ratio of the signals indicates a ca. 2:1 isomer ratio. Diisopropylethylamine (5.91 g, 45.8 mmol) was added to a solution of the lactone 43 (865 mg, 5.21 mmol) in 15 mL dichloromethane, followed by the addition of beta-alanine ethyl ester hydrochloride (1.38 g, 8.98 mmol). The mixture was stirred for 16 days at room temperature, then rotary evaporated at 55° C. The residue was chromatographed on 50 g silica using dichloromethane as the eluent. This yielded the starting lactone 43 (the major E-isomer, which by C-NMR appeared to be a mixture of 2 isomers). Further elution with dichloromethane containing increasing amounts of methanol gave the amide 44. The product was taken up in 75 mL TBME and washed with 5 g citric acid in 25 mL water and with 2×10 mL water. The successive aqueous layers were extracted with 50 mL TBME. The combined organic layers were dried and rotary evaporated to yield amide 44 (360 mg, 1.27 mmol, 24%), consisting of a mixture of isomers.

$^1$H-NMR (CDCl$_3$): δ=0.8-2.7 (m,), 1.25 (t), 2.45 (t) (16H), 3.5 (q, 2H), 3.9 (t, 0.5H), 4.15 (q, 2H), 4.35 (m, 0.5H), 5.5-5.9 (m, 2H), 6.2-6.5 (2 bt, 1H) ppm.

$^{13}$C-NMR (CDCl$_3$) (signals of a fraction which was much enriched in 1 set of isomers): δ=14.3 (CH$_3$), 22.4, 27.8, 29.9, 33.0, 34.0, 34.1, 34.2, 34.5, 35.3, 35.3, 35.5, 35.7, 36.1, 36.2, 41.7 (all CH$_2$), 46.2 (CH), 51.6 (CH), 60.9 (CH$_2$), 77.1, 80.2, 131.2, 131.7, 134.2, 135.6 (all CH), 172.7, 173.9, 175.1 (all C=O) ppm.

The amide 44 (115 mg, 0.406 mmol, mainly 1 set of isomers) was dissolved in 4.4 g acetonitrile. Diisopropylethylamine (370 mg, 2.87 mmol) was added, followed by N,N'-disuccinimidyl carbonate (355 mg, 1.38 mmol). The solution was stirred for 2 days at ca. 30° C. The solvent was removed by rotary evaporation and the residue was chromatographed on 16 g silica, using dichloromethane with gradually increasing amounts of TBME as the eluent. The product eluted with ca. 20% TBME. Rotary evaporation of the product fractions afforded the NHS carbonate 45 as a viscous oil (150 mg, 0.353 mmol, 87%).

$^1$H-NMR (CDCl$_3$): δ=0.8-2.6 (m), 1.25 (t), 2.55 (t) (16H), 2.85 (q, 4H), 3.5 (q, 2H), 4.15 (q, 2H), 4.95 (t, 0.8H), 5.2 (dd, 0.2H), 5.55-6.0 (m, 2H), 6.4 (bt, 1H) ppm.

The NHS-carbonate 45 obtained above (150 mg, 0.353 mmol) was dissolved in 7.56 g DMF. Diisopropylethylamine (132 mg, 1.02 mmol) was added, followed by doxorubicin hydrochloride (66 mg, 0.114 mmol). The mixture was stirred in the dark at room temperature for 3 days. The solvent was removed under high vacuum and the residue was chromatographed on 13 g silica, using dichloromethane with gradually increasing amounts of methanol as the eluent. Rotary evaporation of the product fractions afforded 112 mg of prodrug 46.

$^1$H-NMR (CDCl$_3$, only relevant signals given): δ=1.25 (t), 3.2 (m), 3.5 (m), 4.05 (s), 4.15 (q), 4.8 (s), 5.2-5.8 (m), 6.15 (m), 6.25 (m), 7.4 (d), 7.8 (t), 8.0 (d) ppm.

Optionally prodrug 46 may be conjugated to an antibody by converting the ester functionality to a carboxylic acid, which may then be converted into an NHS ester for lysine conjugation.

Synthesis of minor-(E)-cyclooct-2-en-1-yl (2,5-dioxopyrrolidin-1-yl) carbonate (47)

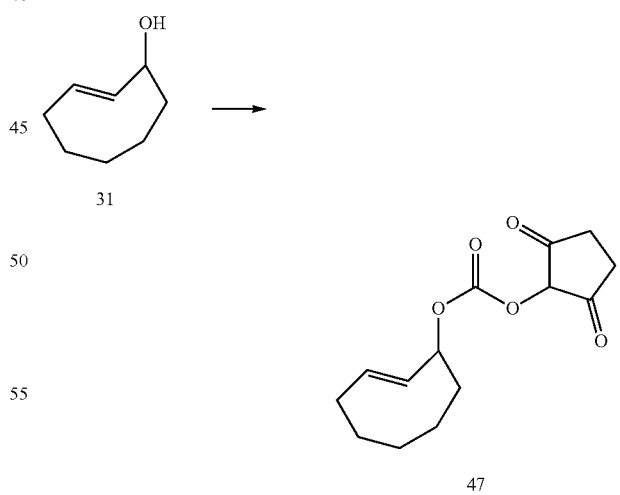

N,N'-disuccinimidyl carbonate (372 mg, 1.45 mmol) is added to a stirred mixture of minor alcohol 31 (77 mg, 0.61 mmol), 3.33 g acetonitrile and diisopropylethylamine (410 mg, 3.18 mmol). The mixture was stirred at 25° C. for 3 d, adding an additional 120 mg N,N'-disuccinimidyl carbonate after 2 days. The solution was chromatographed on 15 g silica using dichloromethane and then dichloromethane containing a small amount TBME as the eluent. The product fractions were rotary evaporated to yield the product 47 as a solid (62 mg, 0.23 mmol, 38%).

¹H-NMR (CDCl₃): δ=0.8 (m, 1H), 1.15 (m, 1H), 1.45-2.15 (m, 6H), 2.2 (dd, 1H), 2.55 (m, 1H), 2.8 (s, 4H), 5.4 (s, 1H), 5.5 (d, 1H), 6.0 (m, 1H) ppm.

Example 3

Stability and Reactivity of Tetrazine Activators
Hydrolytic Stability Tests of Tetrazines 10 µL of a solution of the specific tetrazine in DMSO (25 mM) was diluted with PBS buffer (3 mL) (or a mixture of PBS and acetonitrile in case the aqueous solubility was too low). This solution was filtered and, the decrease of the absorption band at 525 nm was monitored using UV spectroscopy. The rate of hydrolysis and half-life time was determined from these data.

Reactivity of Tetrazines Towards trans-cyclooct-4-ene-1-ol (Axial Isomer)

A competition experiment was performed to determine the reactivity ratio of a specific tetrazine and 3-(5-acetamido-2-pyridyl)-6-(2-pyridyl)-1,2,4,5-tetrazine (5) (that was chosen as the reference tetrazine), in the inverse-electron demand Diels-Alder reaction with trans-cyclooct-4-ene-1-ol ("minor" isomer with OH in axial position, see: Whitham et al. *J. Chem. Soc.* (C), 1971, 883-896)).

To acetonitrile (0.100 mL) was added 5 µL of a solution of the specific tetrazine in DMSO (25 mM) and 5 µL of a solution of the reference tetrazine in DMSO (25 mM). This mixture was diluted with water (0.9 mL), and the absolute amounts of both tetrazines was determined by HPLC-MS/PDA analysis. Subsequently, a solution of trans-cyclooct-4-ene-1-ol (axial isomer) in DMSO (25 µL 2.5 mM) was slowly added, and the mixture was stirred for 5 min. Again, the absolute amounts of both tetrazines was determined by HPLC-MS/PDA analysis, and conversions for both tetrazines was calculated. From these conversions, the reactivity ratio ($R=k_{2,TCO}/k_{2,Ref}$) of both tetrazines was calculated using the mathematical procedure from Ingold and Shaw (*J. Chem. Soc.*, 1927, 2918-2926).

The table below demonstrates how the reactivity and stability profile of tetrazines can be tailored to certain specifications by varying the substituents.

| tetrazine | stability in PBS at 20° C. $t_{1/2}$ (hr) | Reactivity ratio ($R = k_{2,TZ}/k_{2,Ref}$) |
|---|---|---|
|  2 | 44 | 1.17 |
| 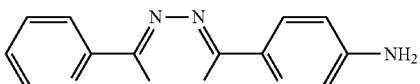 | 340 | 0.4 |
| 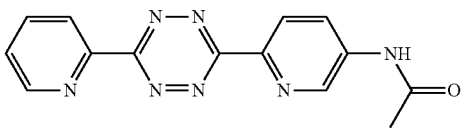 5 | 80 | 1 |
| 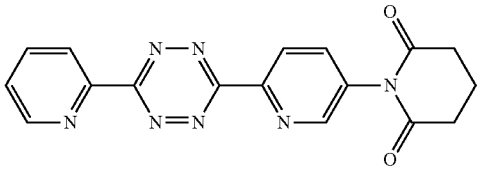 [SMILES: O=C1CCCC(=O)N1c1ccc(-c2nnc(-c3ccccn3)nn2)nc1] | 24 | 1.6 |
| 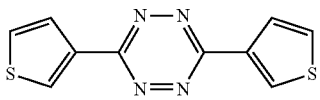 [SMILES: c1cc(-c2nnc(-c3ccsc3)nn2)cs1] | >300* | <0.01* |
| 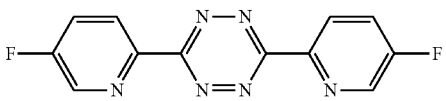 | 115 | 1.07 |
| 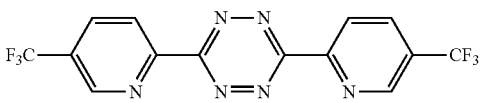 | 3.6* | 5.3* |

-continued
| tetrazine | stability in PBS at 20° C. $t_{1/2}$ (hr) | Reactivity ratio (R = $k_{2,TZ}/k_{2,Ref}$) |
|---|---|---|
| 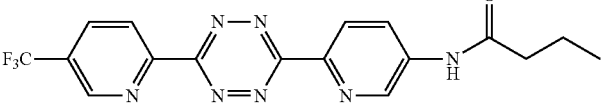 | 35* | 1.84* |
| 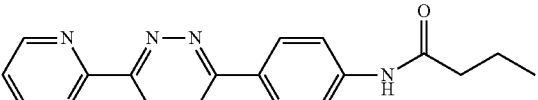 | 3.2 | 2.7 |
| 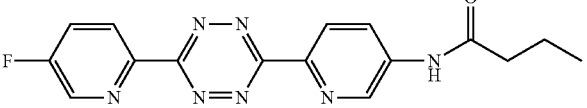 | 117 | 0.95 |
| 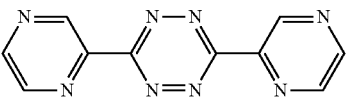 | 0.68 | 1.5 |
| 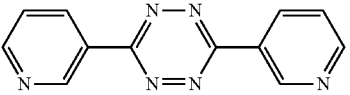 | >150 | 0.19 |
| 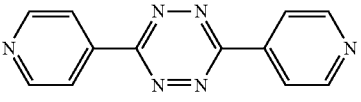 | 2.4 | 0.83 |
| 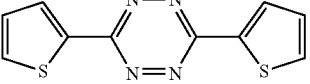 | >300* | <0.01* |
| 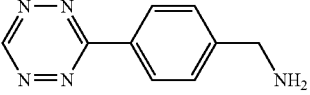 | 183 | 0.77 |
| 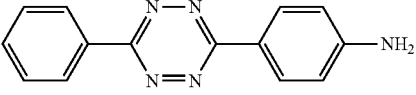 | >300* | <0.01* |
| 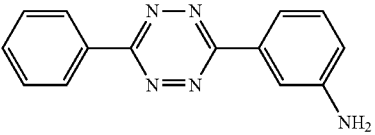 | >300* | <0.01* |
| 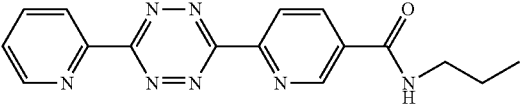 | 4 | 1.76 |
|  | >300* | <0.01* |

-continued
| tetrazine | stability in PBS at 20° C. $t_{1/2}$ (hr) | Reactivity ratio (R = $k_{2,TZ}/k_{2,Ref}$) |
|---|---|---|
| 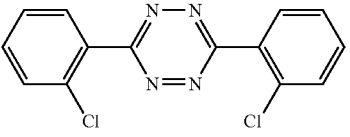 [SMILES: Clc1ccccc1-c1nnc(-c2ccccc2Cl)nn1] | >300* | <0.01* |
| 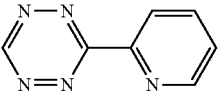 | 2.7 | 3.06 |
| 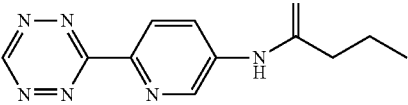 | 10.3 | 2.8 |
| 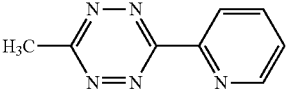 7 | 230 | 0.25 |
| 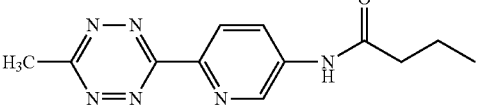 | 300 | 0.18 |
| 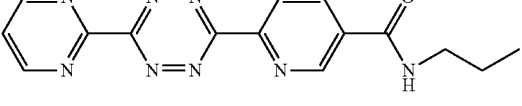 | 0.42 | 2 |
| 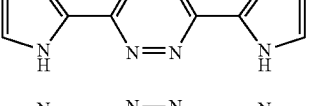 | >300* | <0.01* |
| 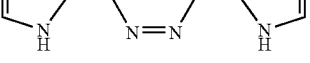 | n.d. | 1.2 |
| 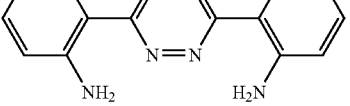 9 | >300* | <0.01* |
| 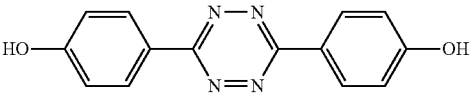 11 | >300* | <0.01* |
| 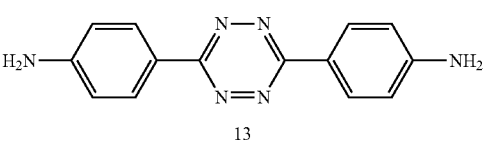 [SMILES: Nc1ccc(-c2nnc(-c3ccc(N)cc3)nn2)cc1] 13 | >300* | <0.01* |

| tetrazine | stability in PBS at 20° C. $t_{1/2}$ (hr) | Reactivity ratio (R = $k_{2,TZ}/k_{2,Ref}$) |
|---|---|---|
| 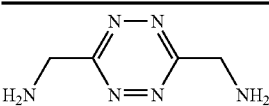 20 | 16 | n.d. |

*This value was determined in a 50:50 mixture of PBS and acetonitrile.

Example 4

Stability and Reactivity of Trans-cyclooctene Model Prodrugs and Prodrugs

Stability

10 µL of a solution of the specific trans-cyclooctene derivative in dioxane (25 mM) was diluted with PBS buffer (3 mL), and this solution was stored at 20° C. in the dark. The fate of the TCO compound was monitored by HPLC-MS analysis, and an estimation of the half-life time was made.

Reactivity of trans-cyclooctene Derivatives Towards bis(2-pyridyl)-1,2,4,5-tetrazine: Second-order Rate Constant Determination The kinetics of the inverse-electron demand Diels-Alder reaction of a trans-cyclooctene derivative with 3-(5-acetamido-2-pyridyl)-6-(2-pyridyl)-1,2,4,5-tetrazine (5), performed in acetonitrile at 20° C., was determined using UV-visible spectroscopy. A cuvette was filled with acetonitrile (3 mL) and equilibrated at 20° C. 3-(5-Acetamido-2-pyridyl)-6-(2-pyridyl)-1,2,4,5-tetrazine (5, 2.50×10$^{-7}$ mol) was added, followed by the trans-cyclooctene derivative (2.50×10$^{-7}$ mol). The decay of the absorption at λ=540 nm was monitored, and from this curve the second-order rate constant, $k_2$, was determined assuming second order rate kinetics.

Reactivity of trans-cyclooctene Derivatives Towards bis(2-pyridyl)-1,2,4,5-tetrazine: Competition Experiment A competition experiment was performed to determine the reactivity ratio of a specific trans-cyclooctene derivative and trans-cyclooct-4-ene-1-ol (axial isomer) (that was chosen as the reference trans-cyclooctene), in the inverse-electron demand Diels-Alder reaction with bis(2-pyridyl)-1,2,4,5-tetrazine (2).

To acetonitrile (0.05 mL) was added a solution of the specific trans-cyclooctene derivative in dioxane (5 µL 25 mM; 1.25×10$^{-7}$ mol) and a solution of the reference trans-cyclooctene in dioxane (5 µL 25 mM; 1.25×10$^{-7}$ mol). This mixture was diluted with water (0.45 mL). Subsequently, a solution of bis(2-pyridyl)-1,2,4,5-tetrazine (2, 6.25×10$^{-8}$ mol) in a mixture of acetonitrile (0.05 mL) and water (0.45 mL) was slowly added while stirring vigorously. After addition, the mixture was stirred for an additional 5 min. The conversion of both trans-cyclooctene derivatives was determined by HPLC-MS/PDA analysis, and from these conversions, the reactivity ratio (R=$k_{2,TCO}/k_{2,Ref}$) of the specific trans-cyclooctene derivative was calculated using the mathematical procedure from Ingold and Shaw (*J. Chem. Soc.*, 1927, 2918-2926).

| trans-cyclooctene derivative | stability in PBS at 20° C., $t_{1/2}$ | rate constant* $k_2$ (M$^{-1}$ s$^{-1}$) | reactivity ratio** (R = $k_{2,TCO}/k_{2,Ref}$) |
|---|---|---|---|
| 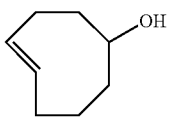 minor isomer | >3 days | 577 | 1 |
| 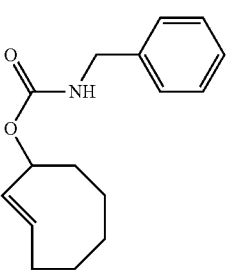 [SMILES: O=C(NCc1ccccc1)OC1/C=C/CCCCC1] 32 major isomer | >>20 days | | 0.26 |

-continued
| trans-cyclooctene derivative | stability in PBS at 20° C., $t_{1/2}$ | rate constant* $k_2$ (M$^{-1}$ s$^{-1}$) | reactivity ratio** (R = $k_{2,TCO}$/ $k_{2,Ref}$) |
|---|---|---|---|
| 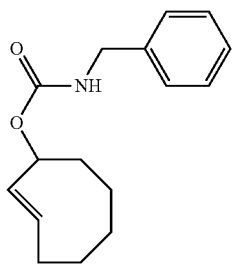 [SMILES: O=C(NCc1ccccc1)OC1/C=C/CCCCC1] 32 minor isomer | >>20 days | 40 | 0.067 |
| 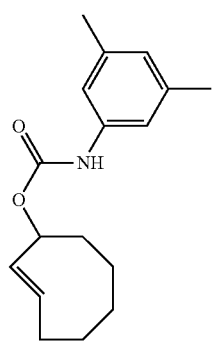 [SMILES: Cc1cc(C)cc(NC(=O)OC2/C=C/CCCCC2)c1] 33 minor isomer | >>20 days | 25.7 | |
| 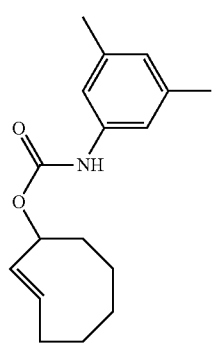 [SMILES: Cc1cc(C)cc(NC(=O)OC2/C=C/CCCCC2)c1] 33 major isomer | >>20 days | 0.15 | |

| trans-cyclooctene derivative | stability in PBS at 20° C., $t_{1/2}$ | rate constant* $k_2$ (M$^{-1}$ s$^{-1}$) | reactivity ratio** (R = $k_{2,TCO}/k_{2,Ref}$) |
|---|---|---|---|
| 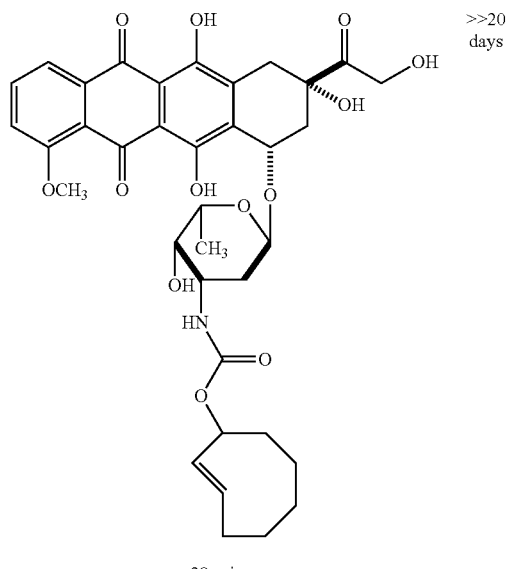   38 minor | >>20 days | | |
| 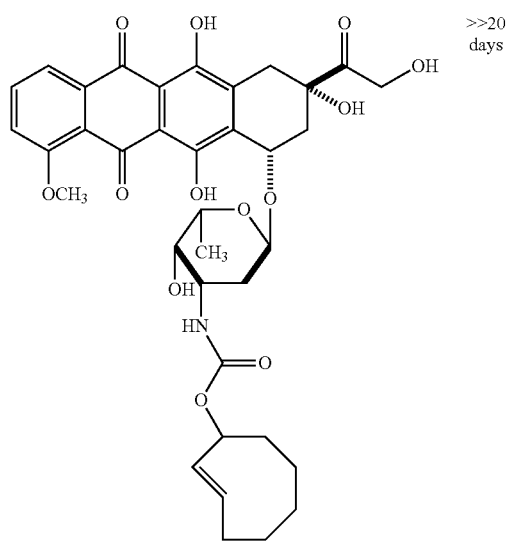   38 major | >>20 days | | |

*determined by UV-visible spectroscopy in acetonitrile at 20° C.
**determined by a competition experiment Example 5

Activation of Model Prodrugs

The example demonstrates the Inverse Electron Demand Diels-Alder reaction of 1,2,4,5-tetrazines and a model trans-cyclooctene prodrug, and subsequent elimination of the model drug (e.g. benzylamine).

General Procedure:

3,6-Bis(2-pyridinyl)-1,2,4,5-tetrazine (2) and minor-(E)-cyclooct-2-en-1-yl benzylcarbamate (32)

6-Methyl-3-(4-butanamido-2-pyridinyl)-1,2,4,5-tetrazine and minor-(E)-cyclooct-2-en-1-yl benzylcarbamate (32)

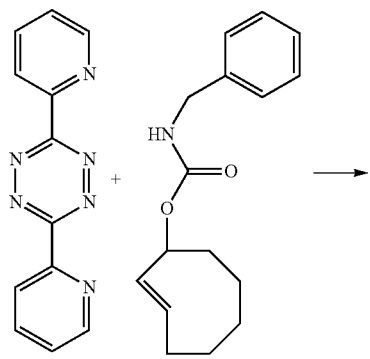

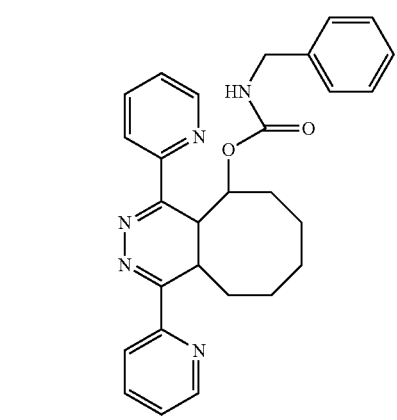

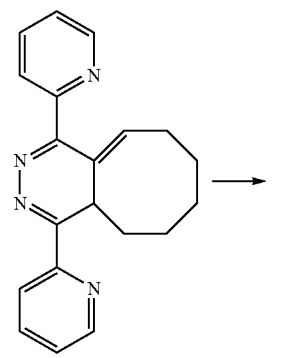

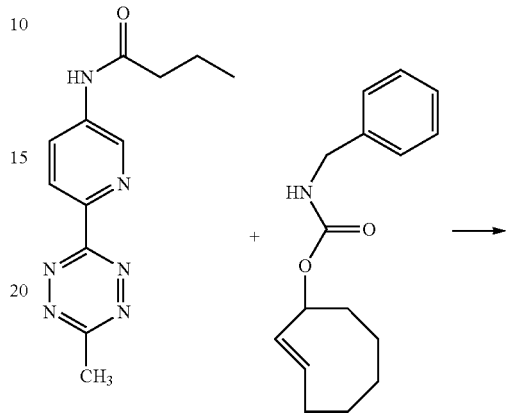

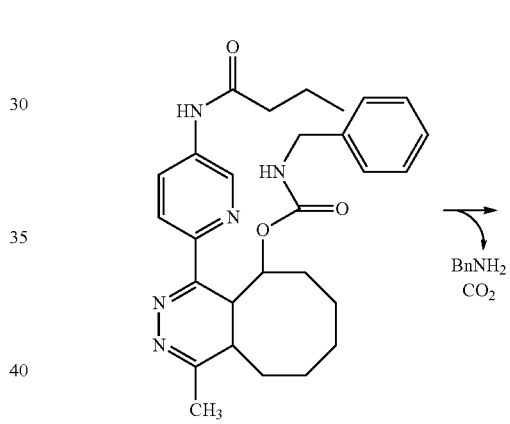

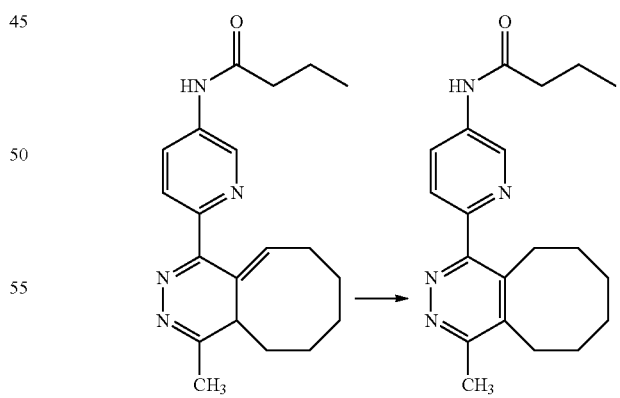

3,6-Bis(2-pyridinyl)-1,2,4,5-tetrazine (2, $5.91 \times 10^{-5}$ g; $2.5 \times 10^{-7}$ mol) was dissolved in 0.2 mL acetonitrile, and minor-(E)-cyclooct-2-en-1-yl benzylcarbamate (32, the isomer with the carbamate in the axial position; $6.48 \times 10^{-5}$ g; $2.50 \times 10^{-7}$ mol) was added. After 5 min, the reaction mixture was diluted with water (0.8 mL) and stirred at 20° C. for 24 hr. HPLC-MS analysis of the mixture proved the formation of the elimination product (the rDA adduct without the aminobenzyl carbamate) with m/z=+317 Da (M+H$^+$), and release of benzylamine (m/z=+108 Da: M+H$^+$).

According to above general procedure, both title compounds were reacted and analysis by HPLC-MS demonstrated the formation of the elimination product with m/z=+339 Da (M+H$^+$), and release of benzylamine (mz=+108 Da: M+H$^+$).

129

6-Phenyl-3-(4-aminophenyl)-1,2,4,5-tetrazine and minor-(E)-cyclooct-2-en-1-yl benzylcarbamate (32)

130

6-Phenyl-3-(3-aminophenyl)-1,2,4,5-tetrazine and minor-(E)-cyclooct-2-en-1-yl benzylcarbamate (32)

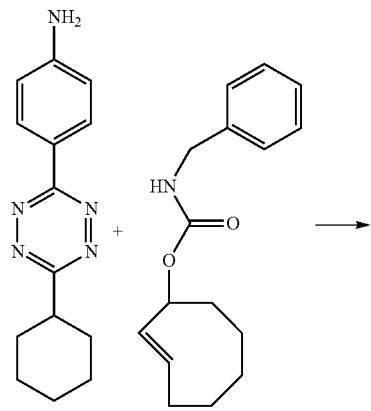

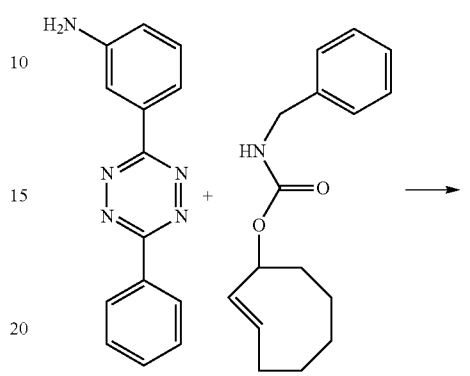

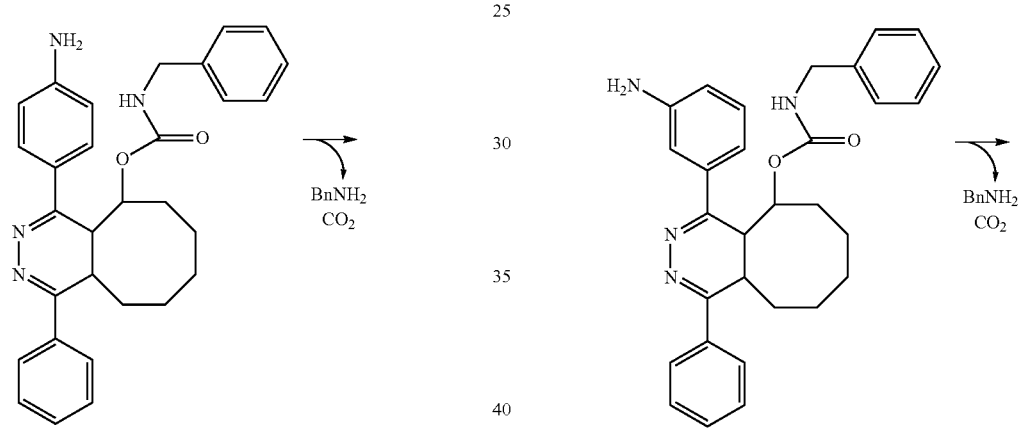

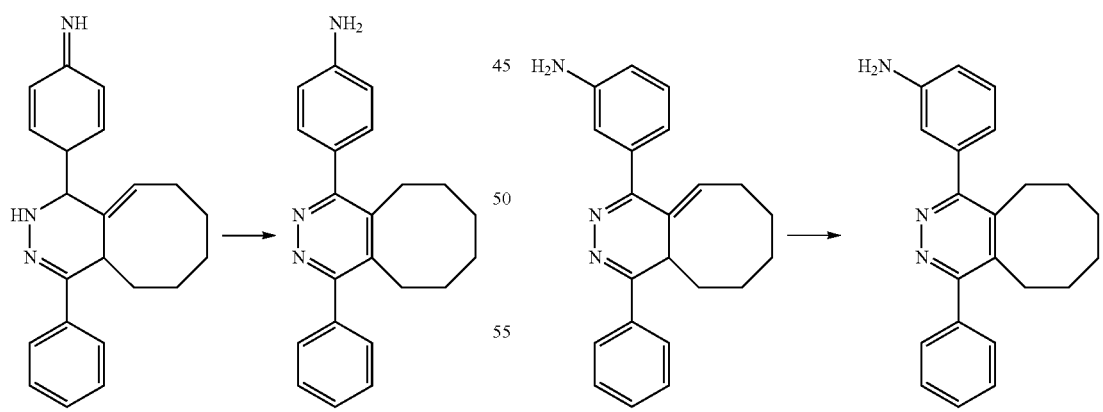

According to above general procedure, both title compounds were reacted and analysis by HPLC-MS demonstrated the formation of the elimination product with m/z=+330 Da (M+H$^+$), and release of benzylamine (m/z=+108 Da M+H+).

According to above general procedure, both title compounds were reacted and analysis by HPLC-MS demonstrated the formation of the elimination product with mz=+330 Da (M+H$^+$), and release of benzylamine (m/z=+108 Da: M+H$^+$).

131

6-H-3-(4-Aminomethylphenyl)-1,2,4,5-tetrazine and minor-(E)-cyclooct-2-en-1-yl benzylcarbamate (32)

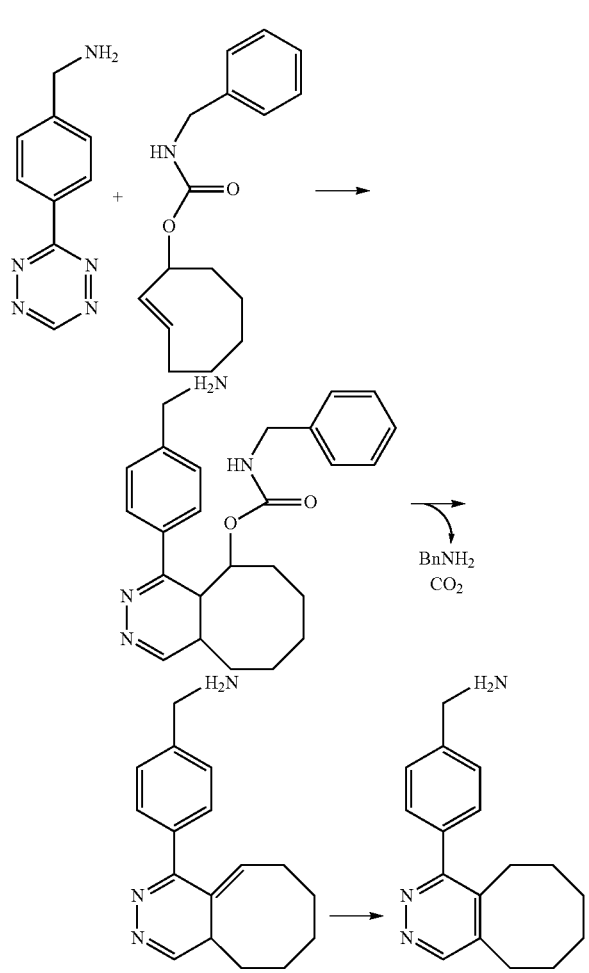

According to above general procedure, both title compounds were reacted and analysis by HPLC-MS demonstrated the formation of the elimination product with m/z=+ 268 Da (M+H$^+$), and release of benzylamine (m/z=+108 Da: M+H$^+$).

3,6-Diphenyl-1,2,4,5-tetrazine and minor-(E)-cyclooct-2-en-1-yl benzylcarbamate (32)

132

-continued

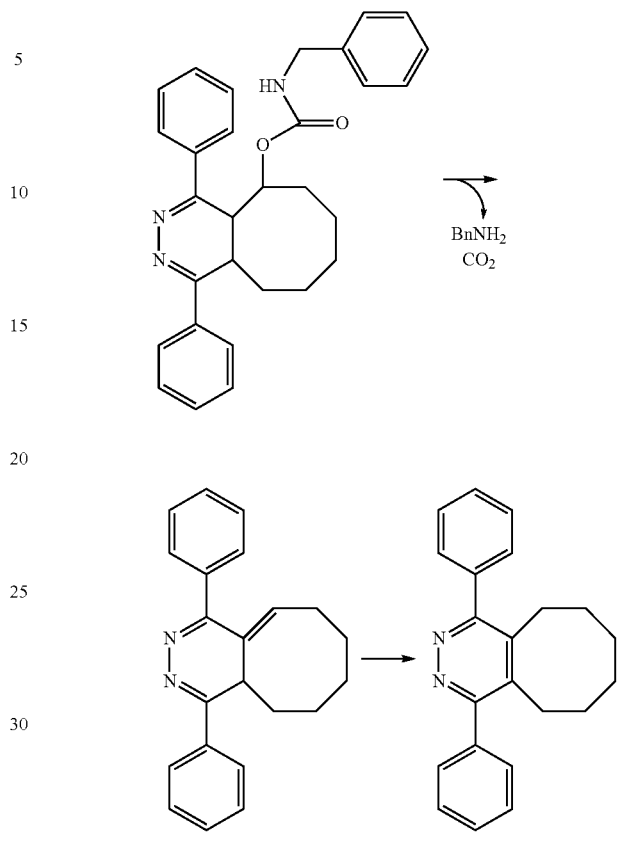

According to above general procedure, both title compounds were reacted and analysis by HPLC-MS demonstrated the formation of the elimination product with m:z=+ 315 Da (M+H$^+$), and release of benzylamine (m/z=+108 Da: M+H$^+$).

3,6-Bis(2-aminophenyl)-1,2,4,5-tetrazine (9) and minor-(E)-cyclooct-2-en-1l-yl benzylcarbamate (32)

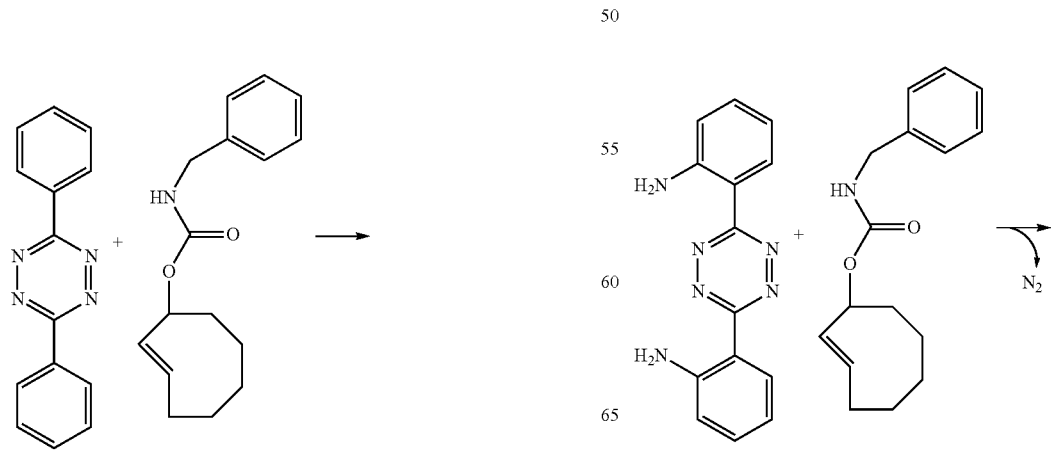

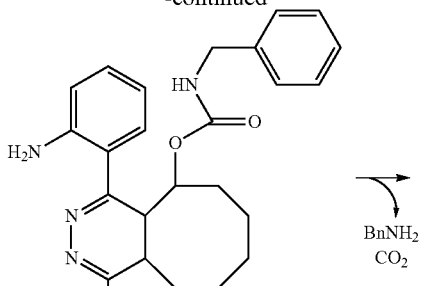

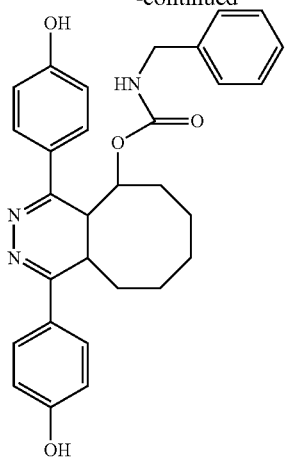

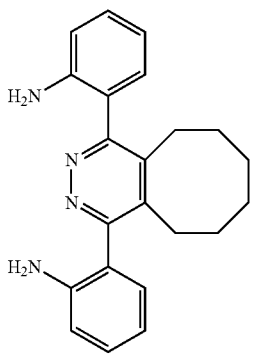

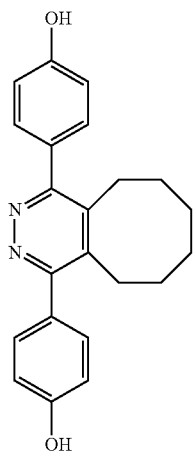

3,6-Bis(2-aminophenyl)-1,2,4,5-tetrazine (3.34 mg; $1.26 \times 10^{-5}$ mol) was dissolved in 0.5 mL DMSO-$d_6$, and minor-(E)-cyclooct-2-en-1-yl benzylcarbamate (32; 3.28 mg; $1.26 \times 10^{-5}$ mol) was added. After 5 min, the reaction mixture was diluted with $D_2O$ (0.2 mL) and stirred at 20° C. for 24 hr. $^1$H-NMR of the reaction mixture indicated the formation of benzylamine: $\delta$=3.86 ppm (s, 2H, PhCH$_2$NH$_2$). HPLC-MS analysis of this mixture demonstrated the formation of the elimination product ($t_r$=5.45 min: m/z=+345 Da (M+H$^+$)), and release of benzylamine: ($t_r$=0.88 min: m/z=+108 Da: (M+H$^+$)).

3,6-Bis(4-hydroxyphenyl)-1,2,4,5-tetrazine (11, 6.65× $10^{-5}$ g; $2.50 \times 10^{-7}$ mol) was dissolved in 0.5 mL acetonitrile, and minor-(E)-cyclooct-2-en-1-yl benzylcarbamate (32; $6.48 \times 10^{-5}$ g; $2.50 \times 10^{-7}$ mol) was added. After 2 min, the reaction mixture was diluted with water (0.5 mL) and stirred at 20° C. for 5 hr. HPLC-MS analysis of the mixture demonstrated the formation of the elimination product with m/z=+347 Da (M+H$^+$), and release of benzylamine: m/z=+108 Da (M+H$^+$).

3,6-Bis(4-hydroxyphenyl)-1,2,4,5-tetrazine (11) and minor-(E)-cyclooct-2-en-1-yl benzylcarbamate (32)

3,6-Bis(2-aminophenyl)-1,2,4,5-tetrazine (9) and minor-(E)-cyclooct-2-en-1-yl (3,5-dimethylphenyl) carbamate (33)

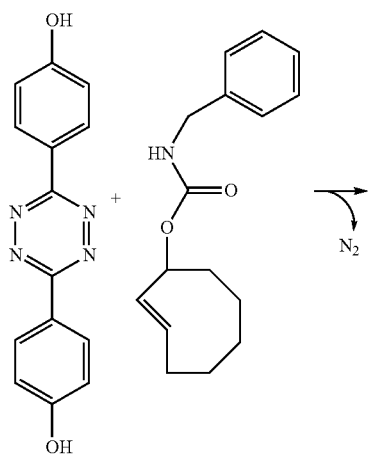

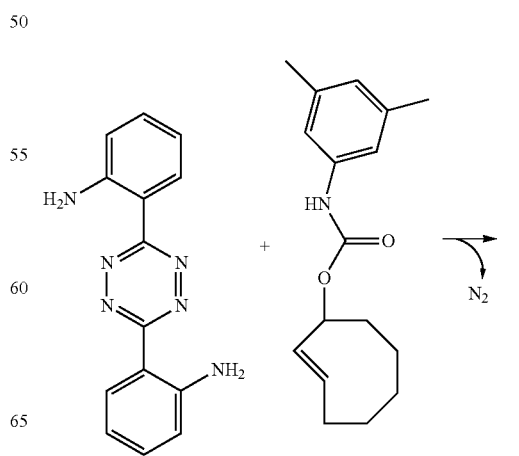

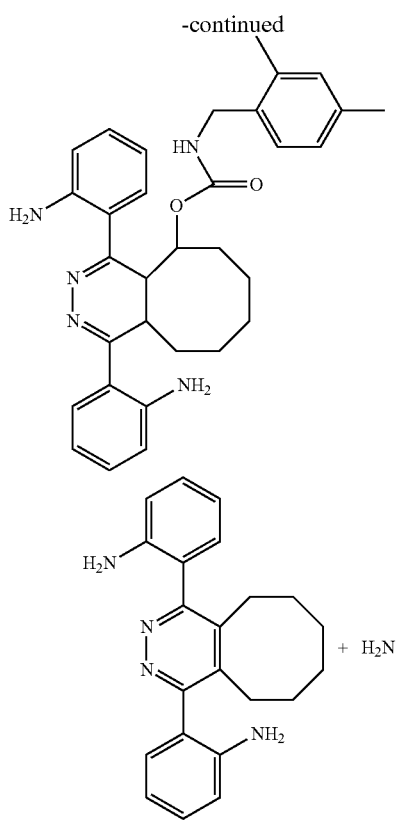

3,6-Bis(2-aminophenyl)-1,2,4,5-tetrazine (9, 6.60×10$^{-5}$ g; 2.50×10$^{-7}$ mol) was dissolved in acetonitrile (0.3 mL) and this mixture was diluted with PBS buffer (0.7 mL). Next, minor-(E)-cyclooct-2-en-1-yl (3,5-dimethylphenyl)carbamate (33, the isomer with the carbamate in the axial position; 6.84×10$^{-5}$ g; 2.50×10$^{-7}$ mol) was added. The solution was stirred at 20° C. for 20 hr. HPLC-MS analysis of the mixture demonstrated the formation of the elimination product with m/z=+345 Da (M+H$^+$), and release of 3,5-dimethylaniline: m/z=+122 Da (M+H$^+$).

3,6-Bis(4-hydroxyphenyl)-1,2,4,5-tetrazine (11) and minor-(E)-cyclooct-2-en-1-yl (3,5-dimethylphenyl) carbamate (33)

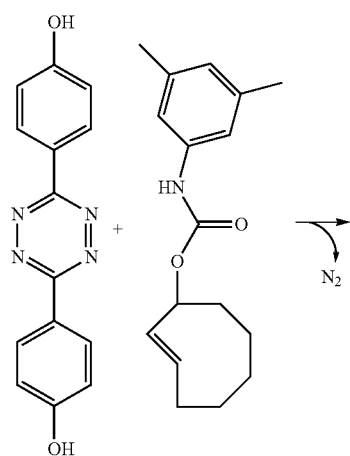

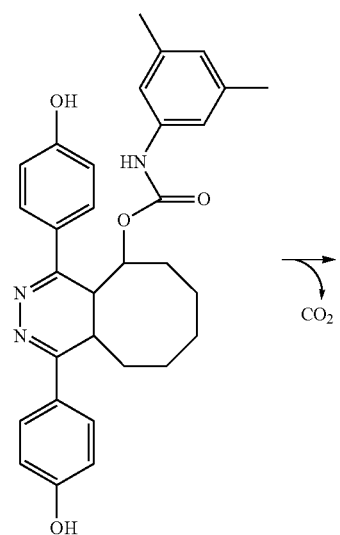

3,6-Bis(4-hydroxyphenyl)-1,2,4,5-tetrazine (11, 6.65×10$^{-5}$ g; 2.50×10 mol) was dissolved in acetonitrile (0.2 mL) and this mixture was diluted with PBS buffer (0.8 mL). Next, minor-(E)-cyclooct-2-en-1-yl (3,5-dimethylphenyl) carbamate (33; 6.84×10$^{-5}$ g; 2.50×10$^{-7}$ mol) was added. The solution was stirred at 20° C. for 20 hr. HPLC-MS analysis of the mixture demonstrated the formation of the elimination product with m/z=+347 Da (M+H$^+$), and release of 3,5-dimethylaniline: m/z=+122 Da (M+H$^+$).

3,6-Diphenyl-1,2,4,5-tetrazine and minor-(E)-cyclooct-2-en-1-yl (3,5-dimethylphenyl) carbamate (33)

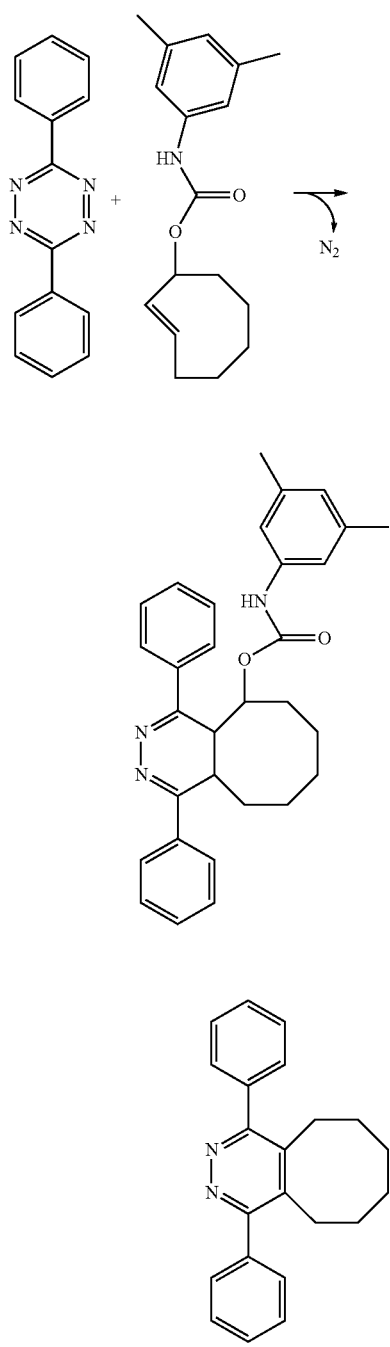

3,6-Diphenyl-1,2,4,5-tetrazine (5.85×10−5 g; 2.50×10−7 mol) was dissolved in acetonitrile (0.3 mL) and this mixture was diluted with PBS buffer (0.7 mL). Next, minor-(E)-cyclooct-2-en-1-yl (3,5-dimethylphenyl)carbamate (33; 6.84×10−5 g; 2.50×10−7 mol) was added. The solution was stirred at 20° C. for 20 hr. HPLC-MS analysis of the mixture proved the formation of the elimination product with m/z=+315 Da (M+H$^+$), and release of 3,5-dimethylaniline: m/z=+122 Da (M+H$^+$).

3-(2-pyridyl)-6-methyl-1,2,4,5-tetrazine (7) and minor-(E)-cyclooct-2-en-1-yl (3,5-dimethylphenyl) carbamate (33)

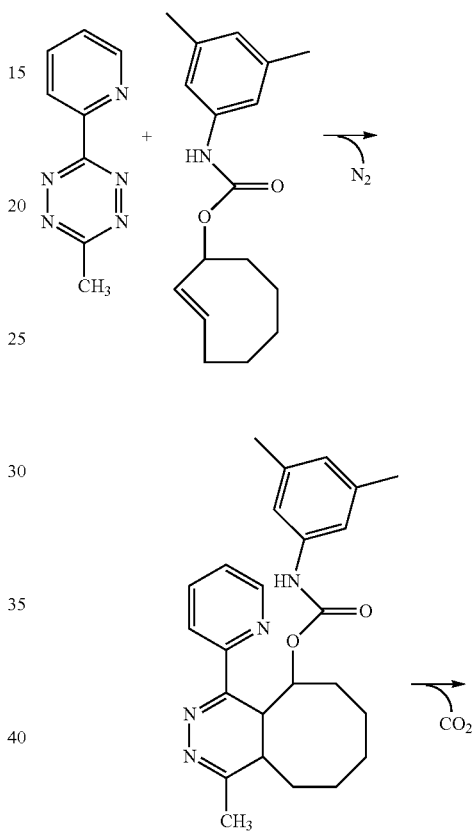

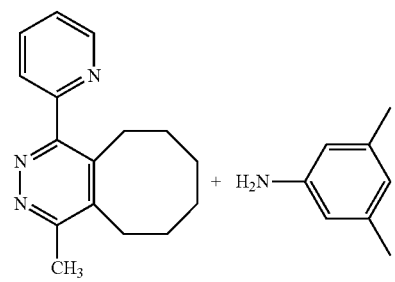

3-(2-Pyridyl)-6-methyl-1,2,4,5-tetrazine (7, 4.33×10−5 g; 2.50×10−7 mol) was dissolved in PBS buffer (1 mL). Next, minor-(E)-cyclooct-2-en-1-yl (3,5-dimethylphenyl)carbamate (33; 6.84×10−5 g: 2.50×10−7 mol) was added. The solution was stirred at 20° C. for 20 hr. HPLC-MS analysis of the mixture demonstrated the formation of the elimination product with m/z=+254 Da (M+H$^+$), and release of 3,5-dimethylaniline: m/z=+122 Da (M+H$^+$).

Example 6

Activation of Doxorubicin Prodrugs 3-(2-Pyridyl)-6-methyl-1,2,4,5-tetrazine (7) and minor-(E)-cyclooct-2-en-1-yl doxorubicin carbamate (38)

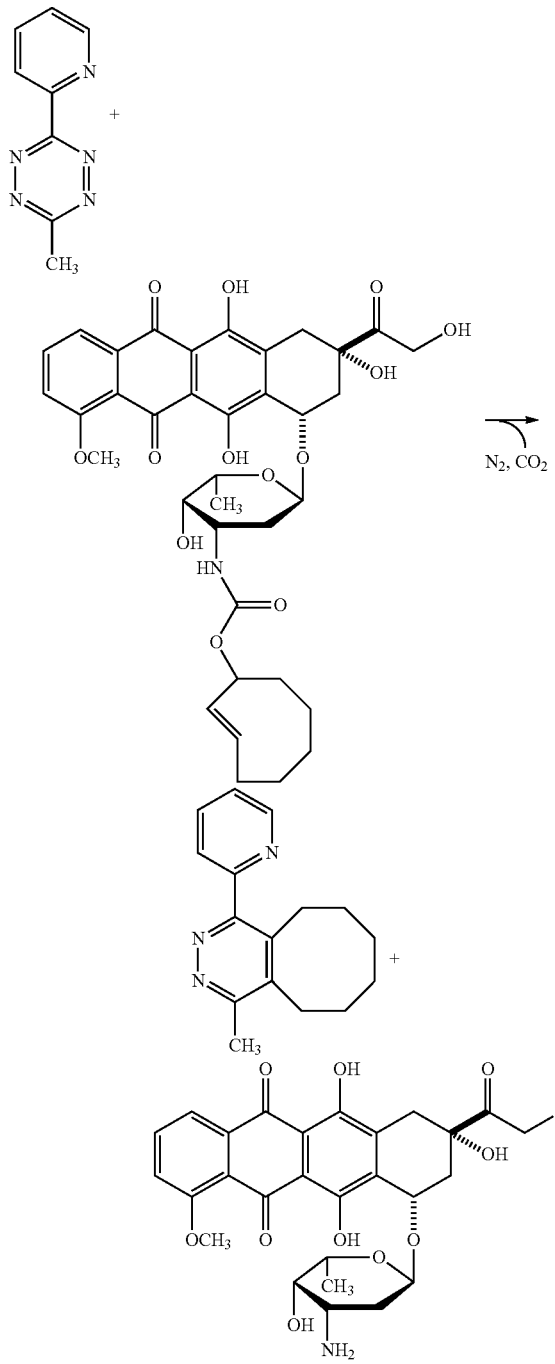

3-(2-Pyridyl)-6-methyl-1,2,4,5-tetrazine (7, 4.33×10$^{-6}$ g; 2.50×10$^{-8}$ mol) was dissolved in PBS buffer (1 mL) (c=25 µM). Next, minor-(E)-cyclooct-2-en-1-yl doxorubicin carbamate (38, the isomer with the carbamate in the axial position; 1.74×10$^{-5}$ g: 2.50×10$^{-8}$ mol) was added. The solution was stirred at 20° C. for 4 hr. HPLC-MS analysis of the mixture demonstrated the formation of the elimination product with m/z=+254 Da (M+H), and release of doxorubicin (69% yield): m/z=+544 Da (M+H$^+$) and $\lambda_{max}$=478 nm. Comparable results were obtained at concentrations of 2.5 and 1.0 µM.

3-(2-Pyridyl)-6-methyl-1,2,4,5-tetrazine (7) and major-(E)-cyclooct-2-en-1-yl doxorubicin carbamate (38)

3-(2-Pyridyl)-6-methyl-1,2,4,5-tetrazine (7, 4.33×10 g; 2.50×10$^{-6}$ mol) was dissolved in PBS buffer (1 mL) (c=25 µM). Next, major-(E)-cyclooct-2-en-1-yl doxorubicin carbamate (38, the isomer with the carbamate in the equatorial position: 1.74×10$^{-5}$ g; 2.50×10$^{-8}$ mol) was added. The solution was stirred at 20° C. for 16 hr. HPLC-MS analysis of the mixture showed a conversion of the DA-reaction of 40%, and demonstrated the formation of the elimination product with m/z=+254 Da (M+H$^+$), and release of doxorubicin (20% yield): m/z=+544 Da (M+H$^+$) and $\lambda_{max}$=478 nm.

3,6-Bis(2-aminophenyl)-1,2,4,5-tetrazine (9) and minor-(E)-cyclooct-2-en-1-yl doxorubicin carbamate (38)

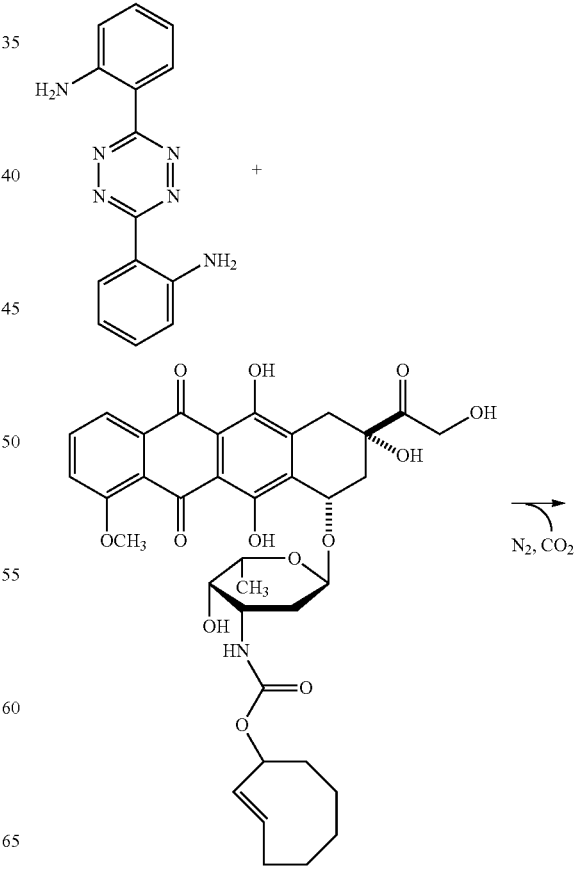

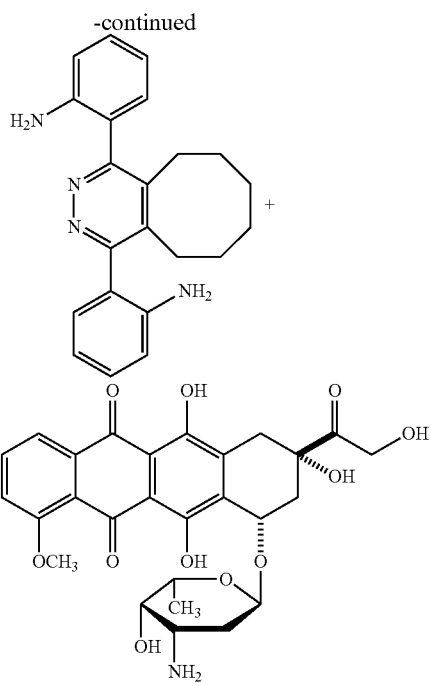

3,6-Bis(2-aminophenyl)-1,2,4,5-tetrazine (9, 2.64×10$^{-6}$ g; 1.00×10$^{-8}$ mol) was dissolved in acetonitrile (0.1 mL). This mixture was diluted with PBS buffer (0.9 mL). Next, minor-(E)-cyclooct-2-en-1-yl doxorubicin carbamate (38; 6.96×10$^{-6}$ g: 1.00×10$^{-8}$ mol) was added. The solution was stirred at 20° C. for 18 hr. HPLC-MS analysis of the mixture demonstrated the formation of the elimination product with m/z=+345 Da (M+H$^+$), and release of doxorubicin (90% yield): m/z=+544 Da (M+H$^+$) and $\lambda_{max}$=478 nm.

Example 7

Cell Proliferation Assay with Doxorubicin Prodrug Minor-38 and Tetrazine 7

Figure 1:
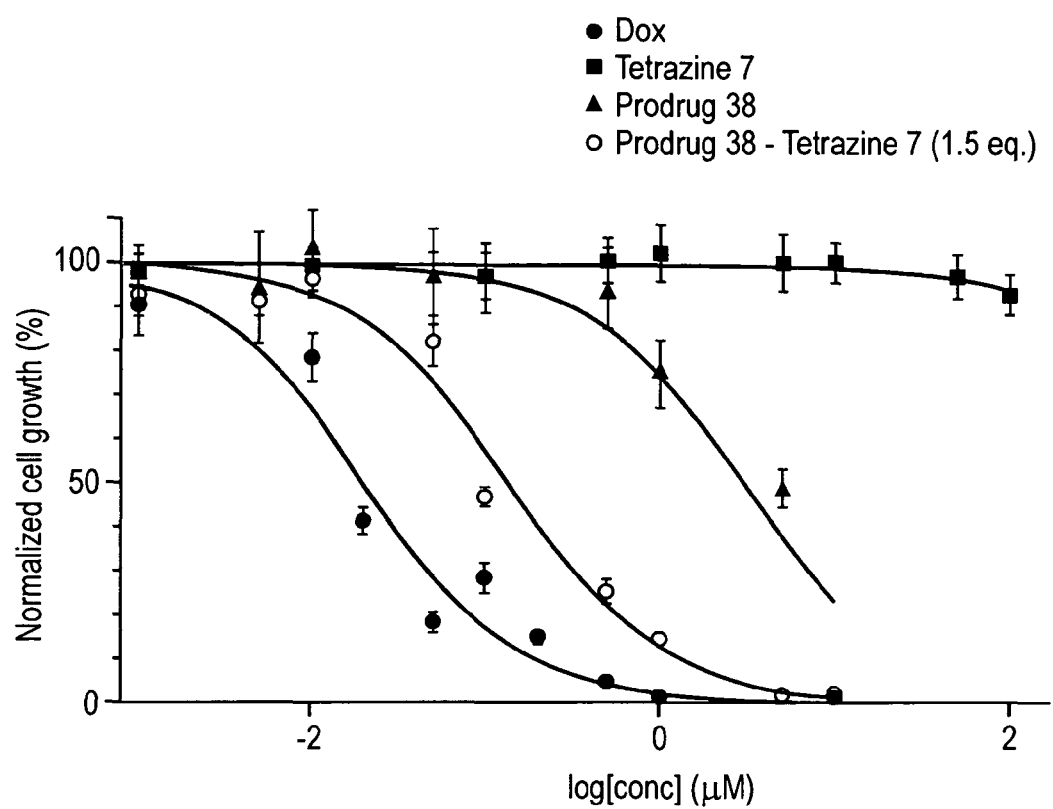
FIG. 1 shows cell a proliferation assay performed on A431 tumor cells in the presence of doxorubicin (Dox) prodrug 38, with and without activation by tetrazine 7, and tetrazine 7 alone.

A431 squamous carcinoma cells were maintained in a humidified CO$_2$ (5%) incubator at 37° C. in DMEM (Invitrogen) supplemented with 10% heat-inactivated fetal bovine serum and 0.05% glutamax (Invitrogen) in the presence of penicillin and streptomycin. The cells were plated in 96-well plates (Nunc) at a 2500 cells/well density 24 hr prior to the experiment. Doxorubicin (Dox) and the prodrug minor-38 (1 mM in DMSO) and the tetrazine 7 (10 mM in PBS) were serially diluted in pre-warmed culture medium immediately before the experiment and added to the wells (200 μl final volume per well). The prodrug was either added alone or in combination with 10 μM or 1.5 mol eq. tetrazine 7 (with respect to the prodrug). After 72 hr incubation at 37° C., cell proliferation was assessed by an MTT assay. Briefly, methylthiazolyldiphenyltetrazolium bromide (MTT) was dissolved in PBS at 5 mg/ml, filtered through 0.22 μm and 25 μl was added to each well. After 120 min incubation at 37° C., the medium was gently aspirated. The formed formazan crystals were dissolved in 100 μl DMSO and the absorbance was measured with a plate reader (BMG Labtech) at 560 nm. IC$_{50}$ values (±standard error; see Table) were derived from the normalized cell growth curves (see FIG. 1) generated with GraphPad Prism (version 5.01). The cell proliferation assay shows that, while tetrazine 7 is non-toxic (IC$_{50}$>100 μM) and the prodrug 38 is slightly toxic (IC$_{50}$=3.017±0.486 μM), the combination of these two components results in higher toxicity on A431 cells (0.137±0.012 μM and 0.278±0.022 μM IC$_{50}$ when using serial dilutions or a constant amount of tetrazine 7, respectively). This confirms that doxorubicin is released following the retro Diels-Alder reaction between the trans-cyclooctene of the prodrug and the tetrazine.

IC$_{50}$ Values for Doxorubicin (Dox), Prodrug 38 with and without Activation by Tetrazine 7, and Tetrazine 7 Alone, Determined in A431 Cell Line

| Compound | IC$_{50}$ (μM) |
| --- | --- |
| Dox | 0.020 ± 0.002 |
| Prodrug 38 | 3.017 ± 0.486 |
| Prodrug 38 + tetrazine 7 (1.5 eq.) | 0.137 ± 0.012 |
| Prodrug 38 + tetrazine 7 (10 μM) | 0.278 ± 0.022 |
| Tetrazine 7 | >100 |

Cell Proliferation Assay Performed on A431 Tumor Cells in the Presence of Doxorubicin (Dox). Prodrug 38 with and without Activation by Tetrazine 7, and Tetrazine 7 Alone.

Example 8

Antibody Masking by Modification with (E)-cyclooct-2-en-1-yl NHS Carbonate 47, and Subsequent Antibody Activation by Reaction with Tetrazine Activator
Antibody Conjugation with Minor-(E)-cyclooct-2-en-1-yl NHS Carbonate 47

A solution of CC49 (8 mg/mL, 62.5 μL) in PBS was added with 6.2 μL DMF and the pH was adjusted to 9 with 1 M sodium carbonate buffer. Subsequently, minor-(E)-cyclooct-2-en-1-yl NHS carbonate 47 freshly dissolved in dry DMF was added (5 μg/μL, 40 mol eq. with respect to CC49) and the resulting solution was incubated for 3 hr at room temperature, under gentle shaking and in the dark. After incubation the reaction mixture was diluted to 500 pIL with PBS and unreacted 47 was eliminated by means of a Zeba desalting spin column (40 kDa MW cut-off, Pierce) pre-equilibrated with PBS. The concentration of the obtained mAb solution was measured by UV-Vis (Nanodrop) and the purity and integrity of the product were assessed by SDS-PAGE. The conjugation yield was determined with a tetrazine titration. The DOTA-tetrazine derivative 29 was radiolabeled with carrier-added $^{177}$Lu as previously described (Rossin et al., Angew Chem Int Ed. 2010, 49, 3375-3378). The TCO-modified mAb (25 μg) was reacted with a known excess of $^{177}$Lu-DOTA-tetrazine in PBS (50 μL). After 10 min incubation at 37° C., the reaction mix was added with non-reducing sample buffer and analyzed by SDS-PAGE. After gel electrophoresis, the radioactivity distribution in each lane was assessed with phosphor imager. The reaction yields between $^{177}$Lu-DOTA-tetrazine and the CC49-TCO construct was estimated from the intensity of the radioactive mAb band with respect to the total radioactivity in the lane. With this procedure an average of 20 TCO moieties per CC49 molecule was found (50% conjugation yield).

CC49 and CC49-TCO (47) Radiolabeling

The unmodified CC49 was radiolabeled with $^{125}$I with the Bolton-Hunter procedure according to the manufacturer instruction. Briefly, ca. 40 MBq sodium [[125]]iodide was diluted with 50 μL PBS and added with 1 μL Bolton-Hunter reagent (SHPP, Pierce) solution in DMSO (0.1 μg/μL) and 25 μL chloramine-T (Sigma-Aldrich) solution in PBS (4 mg/mL). The solution was mixed for 10-20 sec, then 5 μL DMF and 100 μL toluene were added. After vortexing, the organic phase containing $^{125}$I-SHPP was transferred into a glass vial and dried at room temperature under a gentle stream of $N_2$. 30 μg CC49 in PBS (50 μL) were then added to the $^{125}$I-SHPP coated glass vial and the pH was adjusted to 9 with 1M sodium carbonate buffer pH 9.6. The vial was incubated at room temperature under gentle agitation for ca. 60 min then the $^{125}$I-mAb labeling yield was evaluated with radio-ITLC (47%). The crude $^{125}$I-mAb was purified through Zeba Desalting spin columns (40 kDa MW cut-off, Pierce) pre-equilibrated with saline solution and the radio-chemical purity of the obtained $^{125}$I-labeled CC49 was greater than 98%, as determined by radio-ITLC and radio-HPLC.

The CC49 carrying 20 TCO(47) moieties per molecules was reacted with DOTA-tetrazine 29 (1 mol eq. with respect to mAb) which was previously radiolabeled with non-carrier-added $^{177}$Lu as described (Rossin et al., *Angew Chem Int Ed*, 2010, 49, 3375-3378). After 10 min incubation 91% radiochemical purity for the $^{177}$Lu-labeled CC49-TCO(47) by radio-HPLC and the reaction mixture was used without further purification.

Antibody Activation Experiments

In this example we show that by over-modifying CC49 with TCO 47 we can significantly reduce the ability of the mAb to bind its target and that by reacting the over-modified CC49-TCO construct with tetrazine 7 the target binding capability is restored. The mAb re-activation upon reaction with the tetrazine indicates TCO release following the electronic cascade mediated elimination mechanism.

Figure 2:
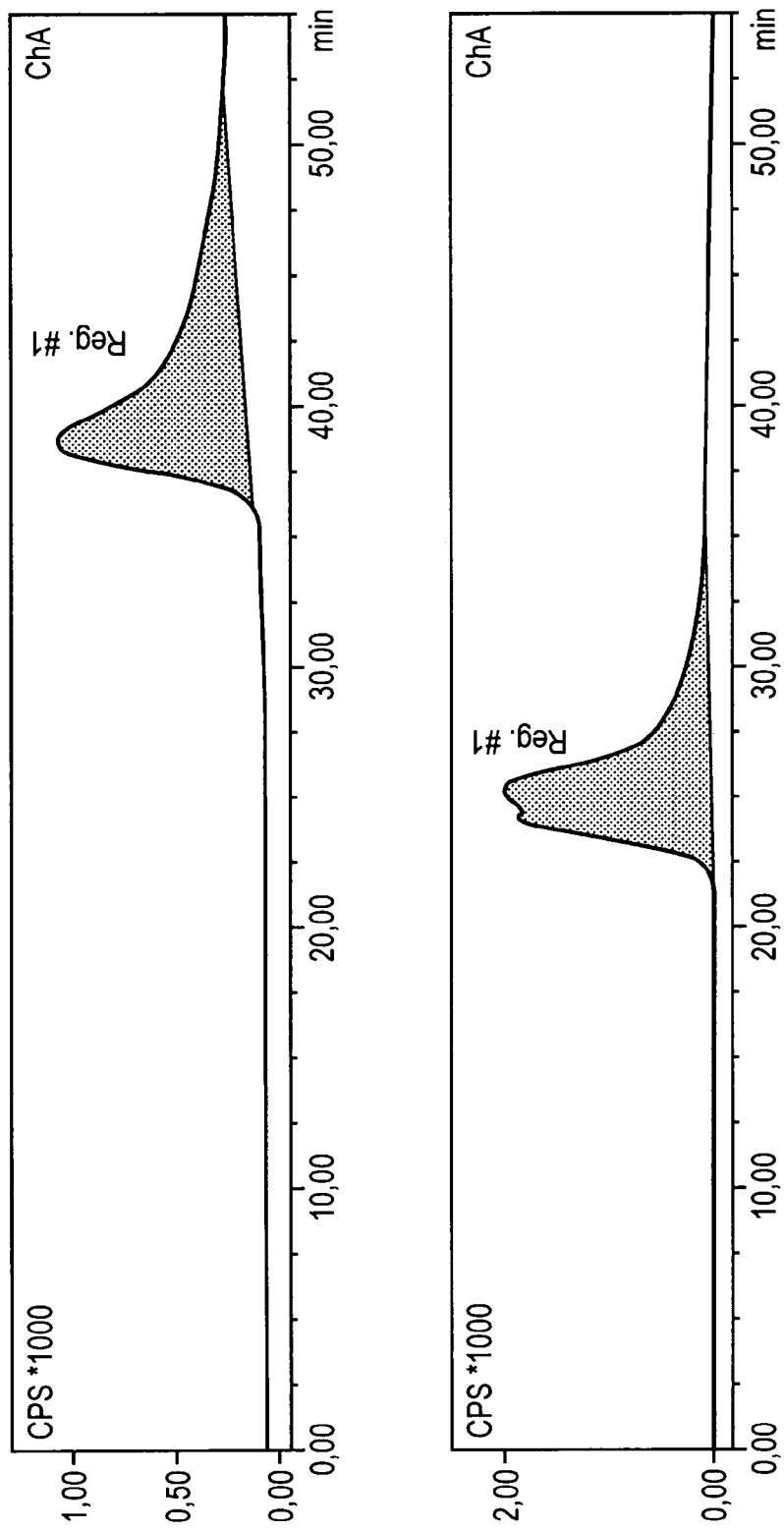
FIG. 2 shows size exclusion radio-chromatograms of $^{125}$I-CC49 (FIG. 2, top) and $^{125}$I-CC49 (FIG. 2, bottom) bound to bovine submaxillary mucin type I-S (BSM). These results show the capability of CC49 constructs to bind their target in an immunoreactivity assay.

The capability of CC49 constructs to bind their target was evaluated by using an immunoreactivity assay modified from a previously described method (Lewis et al., Bioconjug Chem. 2006, 17, 485-492). Briefly, the radiolabeled mAb constructs (1 μg) were reacted with a 20-fold molar excess of bovine submaxillary mucin type I-S (BSM: Sigma-Aldrich) in 1% BSA solution (100 μL). After 10 min incubation at 37° C. the mixtures were analyzed by radio-HPLC using a Superdex-200 column (GE Healthcare Biosciences) eluted with PBS at 0.35 mL/min. In these conditions non-TCO-modified $^{125}$I-CC49 eluted from the column in a broad peak with a 39 min retention time (FIG. 2, top). As expected, after incubation with BSM the $^{125}$I activity eluted from the column in a peak corresponding to a higher MW species (25 min retention time), confirming the binding of $^{125}$I-CC49 to BSM (100% immunoreactivity; FIG. 2, bottom).

Figure 3:
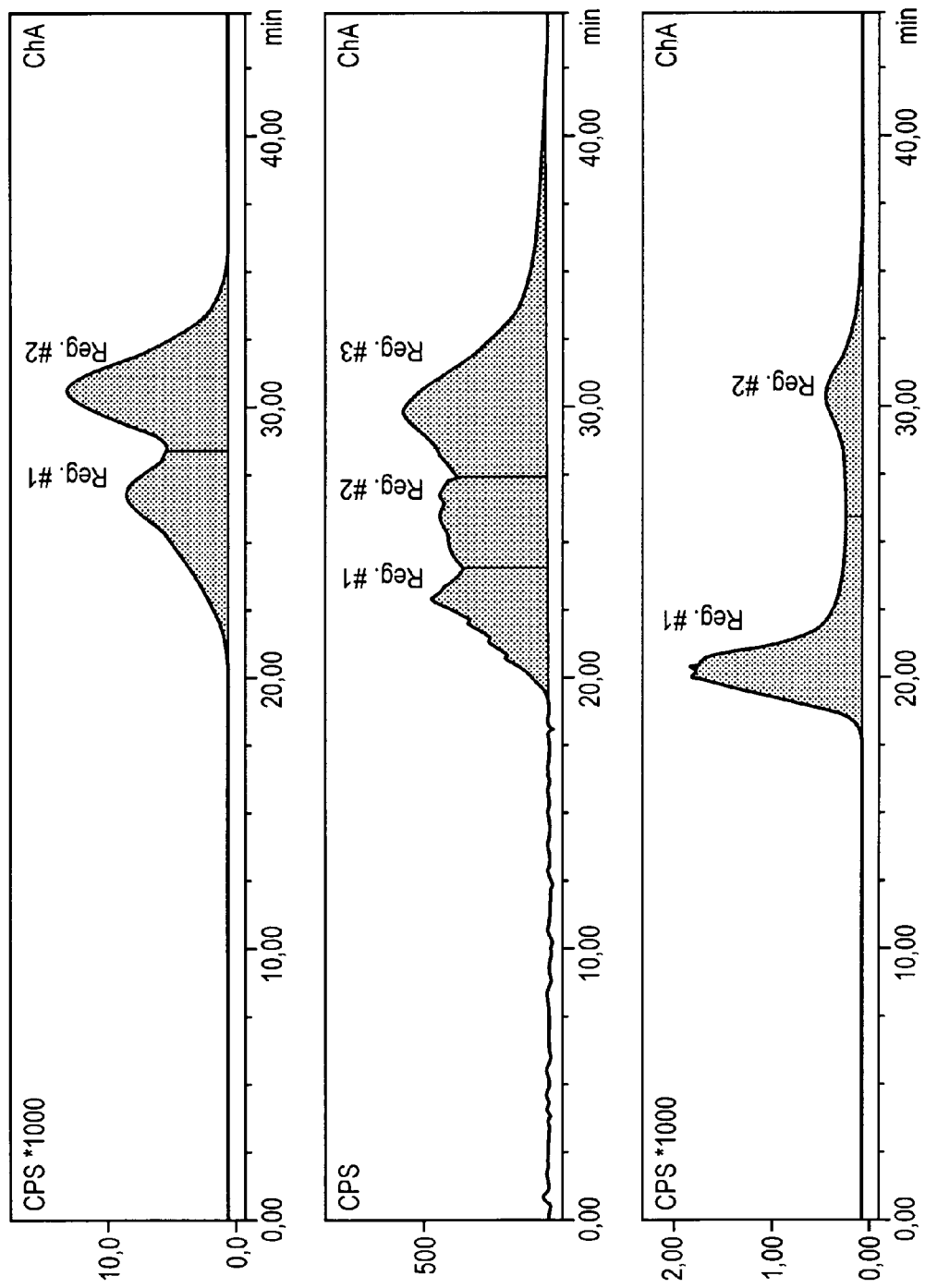
FIG. 3 shows size exclusion radio-chromatograms of $^{177}$Lu-CC49-TCO (FIG. 3, top) and $^{177}$Lu-CC49-TCO in the presence of bovine submaxillary mucin type I-S (BSM) before (FIG. 3, middle) and after (FIG. 3, bottom) 1 hr reaction with tetrazine 7.

When the $^{177}$Lu-labeled CC49 carrying 20 TCO 47 moieties per molecule was analyzed by radio-HPLC, the mAb eluted from the column in two broad unresolved peaks with 31 min and 36 min retention times, accounting for 43% and 57% of the total mAb-related activity, respectively (FIG. 3, top). This behavior suggests over-modification of CC49 with TCO groups. In fact, the change of MW after conjugation is relatively small and not likely to cause a 3 min change in retention time (from 39 to 36 min) between CC49 and CC49-TCO. Therefore, the shorter retention in the column is more likely due to conformational changes caused by the 20 TCO moieties attached to the mAb. Also, the broad peak eluting from the column at 31 min is a sign of mAb aggregation. As a consequence, after incubating the $^{177}$Lu-labeled CC49-TCO with BSM, only a small amount (ca. 20% of the total) of $^{177}$Lu activity was associated with a high MW species in the radio-chromatogram (FIG. 3, middle). The ca. 20% residual immunoreactivity confirms that the over-modified CC49-TCO(47) has lost its target binding capability.

Subsequently, the $^{177}$Lu-labeled CC49-TCO(47) was reacted with a large excess of tetrazine 7 (500-fold molar excess with respect to TCO) in PBS at 37° C. At various time points (1 hr, 4 hr and 24 hr) an aliquot of the reaction mixture (containing 1 μg mAb) was withdrawn, incubated with BSM and analyzed by radio-HPLC. As short as 1 hr after addition of tetrazine 7, the radio-chromatogram showed the disappearance of the radioactive peak attributed to CC49-TCO aggregates, a significant reduction of the peak at 36 min and the formation of an intense peak due to the formation of a $^{177}$Lu-CC49-TCO-BSM adduct ($R_t$=24 min; 72% of the total mAb-related activity; FIG. 3, bottom).

A further slight increase in peak area was observed with time (76% after 24 hr incubation of CC49-TCO with tetrazine 7). The rapid increase in CC49 immunoreactivity following retro Diels-Alder cycloaddition between TCO 47 and tetrazine 7 is indicative of TCO release as a result of the electronic cascade mediated elimination mechanism.

Example 9

Triggers that Effect Drug Release Through Intramolecular Reaction Between a Nucleophile and an Electrophile that are Both Present on the Dienophile Trans-Cyclooctene The feature that enables the selective activation of these alternative prodrug systems (with respect to the aforementioned cyclization and cascade elimination mechanisms) is the change in nature of the eight membered ring of the TCO in the dienophile reactant as compared to that of the eight membered ring in the rDA adduct. The eight membered ring in the rDA adduct has significantly more conformational freedom and has a significantly different conformation as compared to the eight membered ring in the highly strained TCO prior to rDA reaction. The nucleophilic site in the dienophile prior to rDA reaction is locked within the specific conformation of the dienophile and is therefore not properly positioned to react intramolecularly and to thereby release the drug species. In contrast, and due to the changed nature of the eight membered ring, this nucleophilic site is properly positioned within the rDA adduct and will react intramolecularly, thereby releasing the drug.

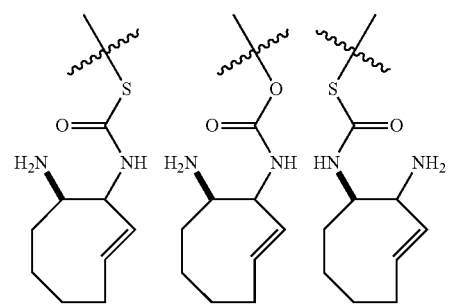

145
-continued

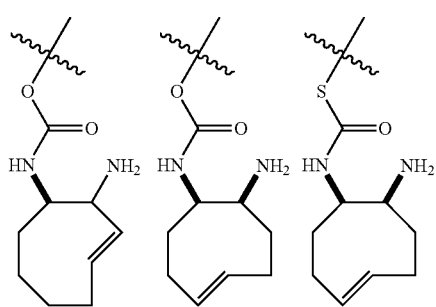

⌇⌇⌇ = rest of attached $D^D$, $L^D$—$D^D$, optionally comprising $T^T$ or $S^P$—$T^T$ or $M^M$ or $S^P$—$M^M$ Example 10

Activation of Alternative Model Prodrugs 3,6-Bis(2-pyridinyl)-1,2,4,5-tetrazine (2) and phenyl ((E)-8-aminocyclooct-4-en-1-yl)carbamate (48)

146
-continued

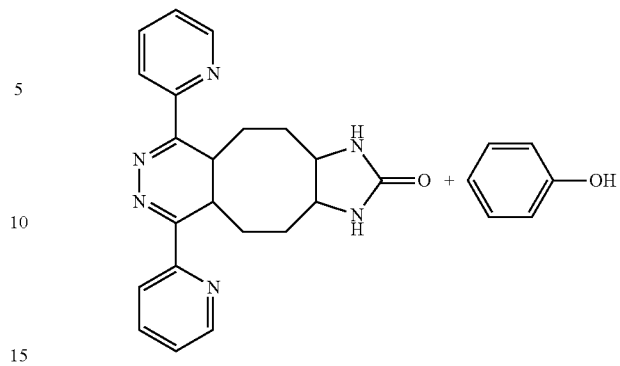

3,6-Bis(2-pyridinyl)-1,2,4,5-tetrazine (2, 2.50×10⁻⁷ mol) was dissolved in PBS buffer (1 mL). Next, phenyl ((E)-8-aminocyclooct-4-en-1-yl)carbamate (48, 2.50×10⁻⁷ mol) was added. The solution was stirred at 20° C., and the reaction progress was monitored by HPLC-MS analysis, demonstrating nearly instantaneous formation of the rDA-adduct, followed by the formation of the cyclic urea with m/z=+375 Da (M+H⁺), and release of phenol: $\lambda_{max}$=270 nm. The half-life time of this release was 40 min.

3,6-Bis(2-pyridinyl)-1,2,4, 5-tetrazine (2) and phenyl ((E)-2-aminocyclooct-3-en-1-yl)carbamate (49)

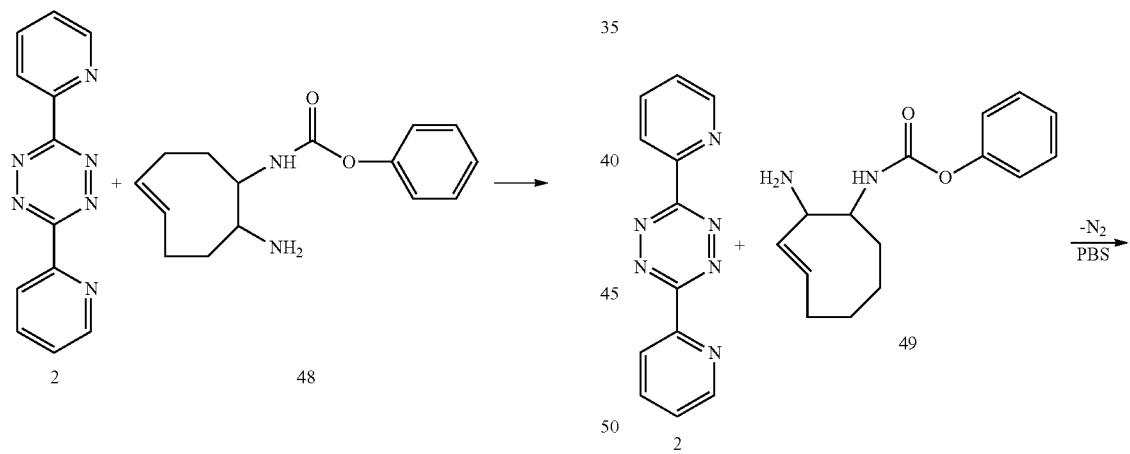

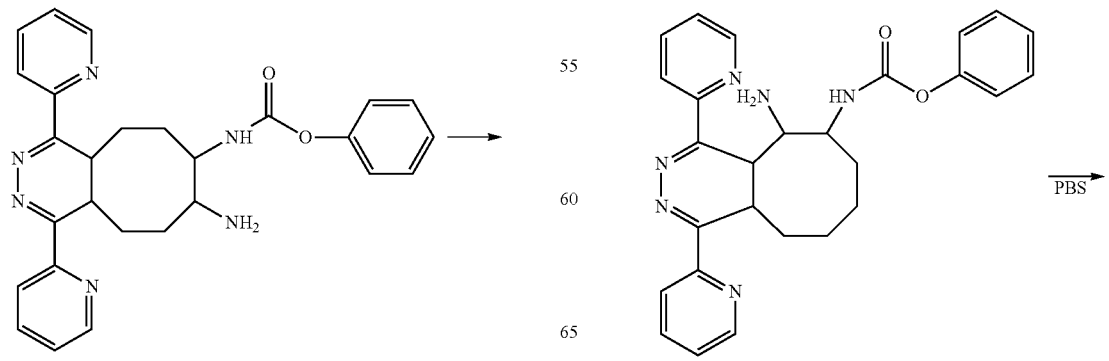

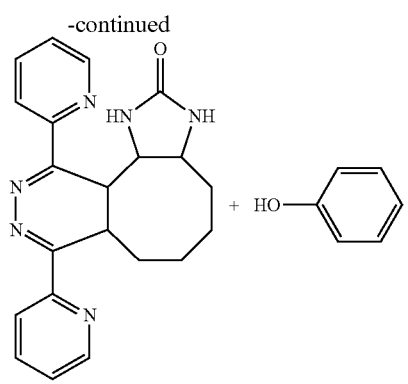

3,6-Bis(2-pyridinyl)-1,2,4,5-tetrazine (2, 2.50×10⁻⁷ mol) was dissolved in PBS buffer (1 mL). Next, phenyl ((E)-2- aminocyclooct-3-en-1-yl)carbamate (49, 2.50×10⁻⁷ mol) was added. The solution was stirred at 20° C., and the reaction progress was monitored by HPLC-MS analysis, proving almost instantaneous formation of the rDA-adduct, followed by the formation of the cyclic urea with m/z=+375 Da (M+H⁺), and release of phenol: $\lambda_{max}$=270 nm. The half-life time of this release was 40 min.

Example 11

Activation of Doxorubicin Prodrugs 3,6-Bis(2-pyridinyl)-1,2,4,5-tetrazine (2) and (E)-cyclooctene-doxorubicin conjugate (50)

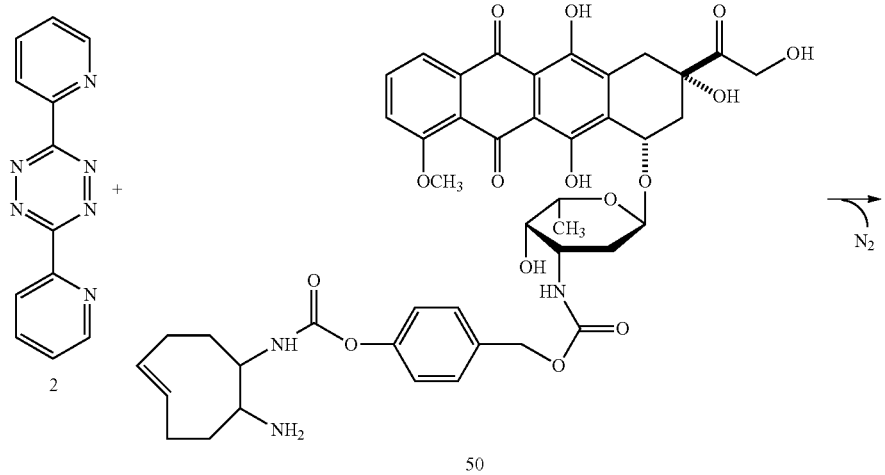

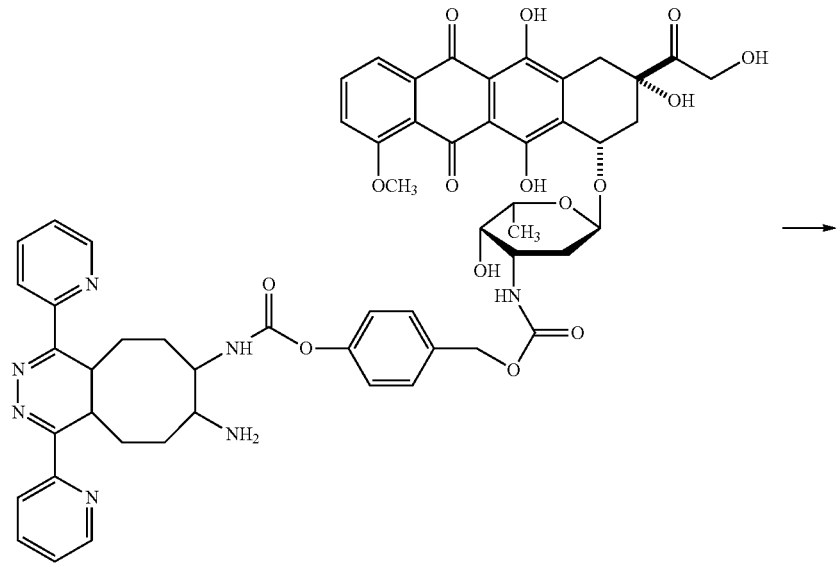

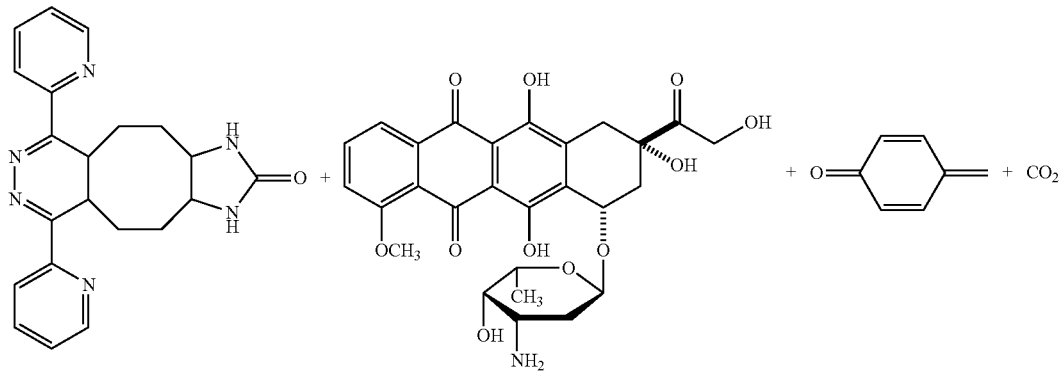

3,6-Bis(2-pyridinyl)-1,2,4,5-tetrazine (2, 1.18×10$^{-5}$ g; 5.00×10$^{-8}$ mol) was dissolved in PBS buffer (1 mL). Next, cis-(E)-cyclooctene-doxorubicin conjugate (50, 2.67×10$^{-5}$ g; 2.50×10$^{-8}$ mol) was added. The solution was stirred at 20° C., and the reaction progress was monitored by HPLC-MS analysis, proving the formation of the cyclic urea with m/z=+375 Da (M+H$^+$), and release of doxorubicin: m/z=+544 Da (M+H$^+$) and $\lambda_{max}$=478 nm. The half-life time of this release was 2 hrs.

Performing this reaction at 37° C. yielded a doxorubicin release half-life time of 40 min.

3-(5-Acetamido-2-pyridyl)-6-(2-pyridyl)-1,2,4,5-tetrazine (5) and (E)-cyclooctene-doxorubicin conjugate (50)

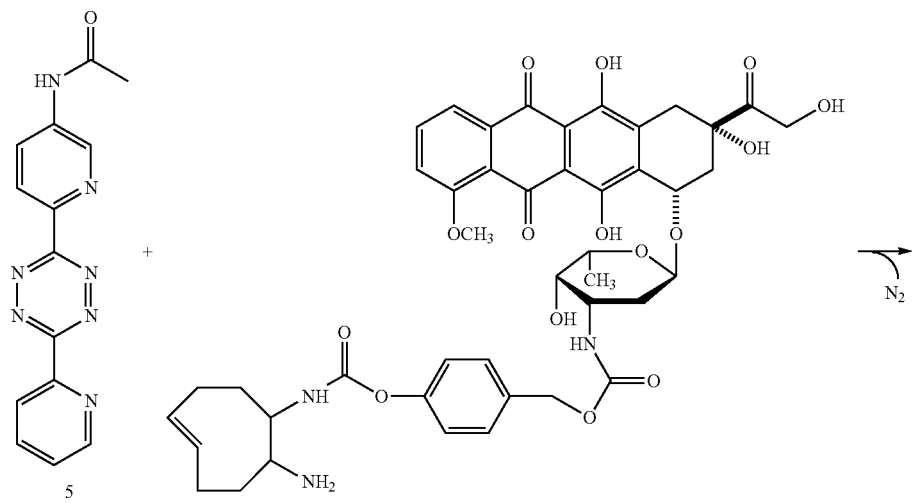

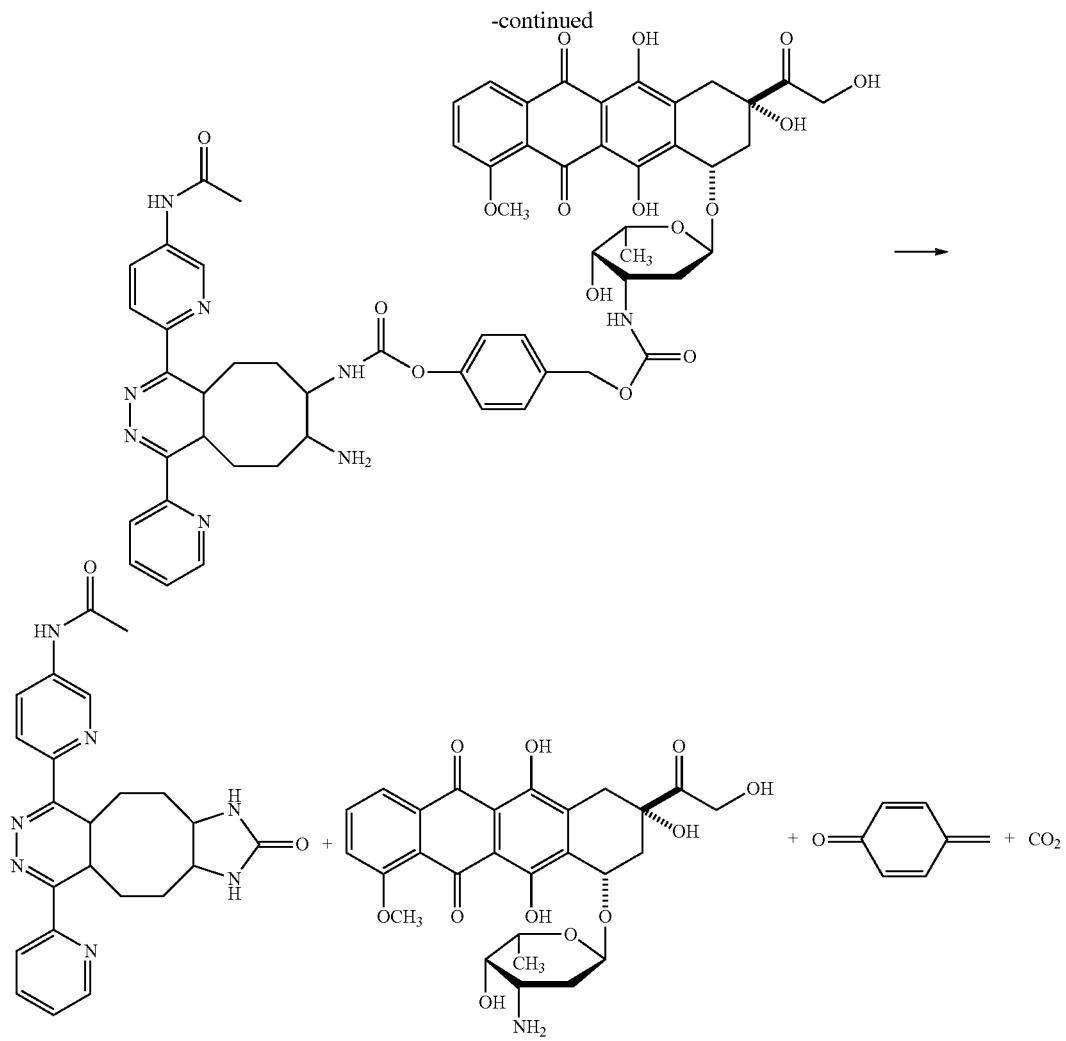
Same procedure as previous reaction.
After 1 hr at 20° C., 30% doxorubicin was released.
3-(5-Butyramido-2-pyridyl)-6-(2-pyrimidyl)-1,2,4,5-tetrazine and (E)-cyclooctene-doxorubicin conjugate (50)
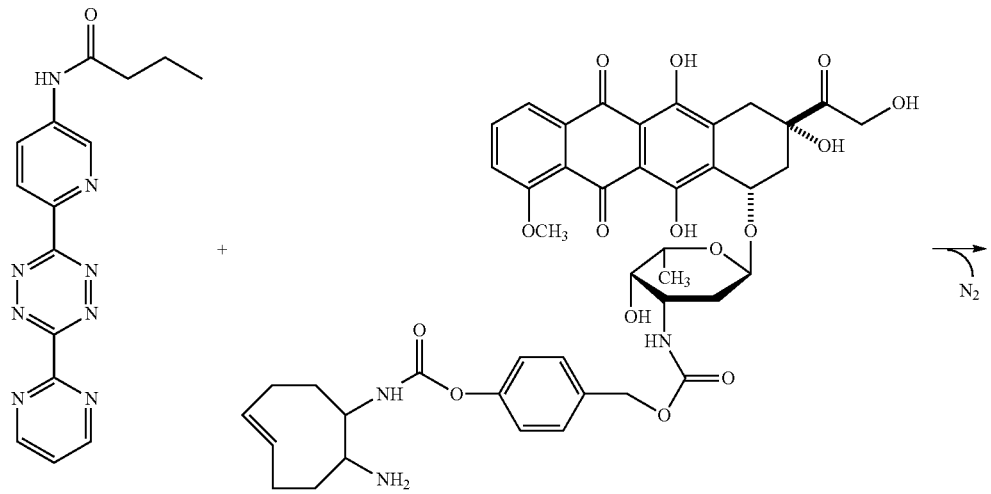

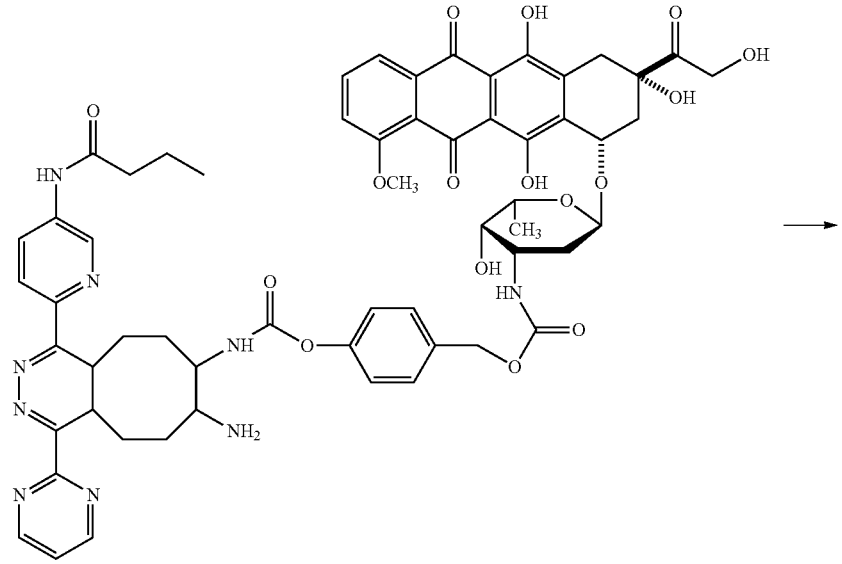
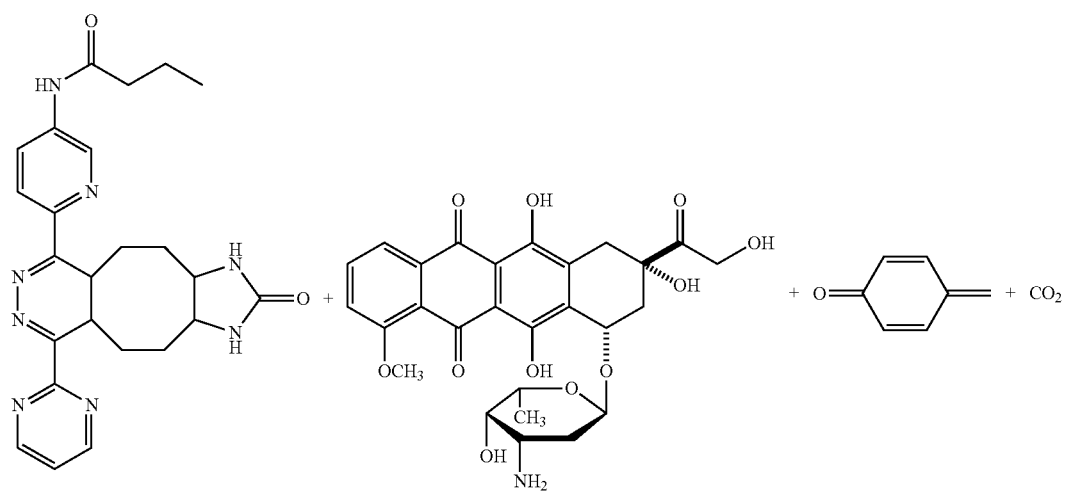

Same procedure as previous reaction.
After 1 hr at 20° C., 20% doxorubicin was released.
4-(1,2,4,5-Tetrazin-3-yl)phenylmethanamine and (E)-cyclooctene-doxorubicin conjugate (50)
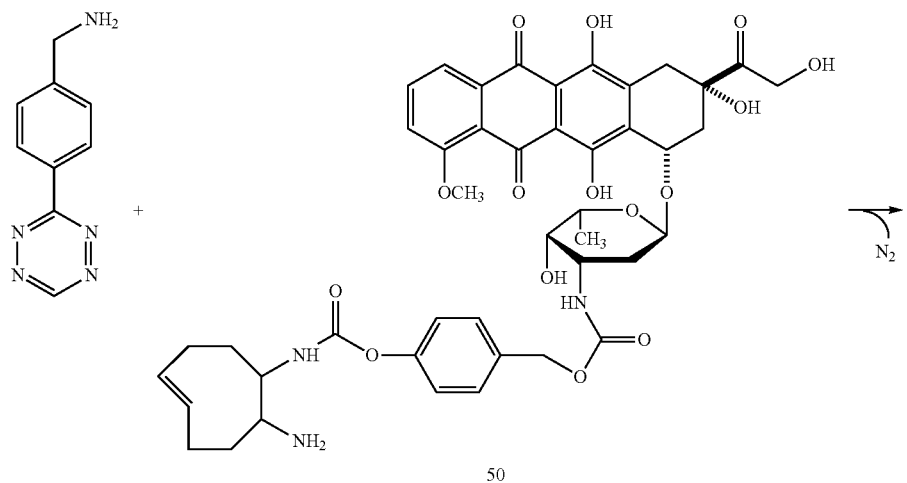
50
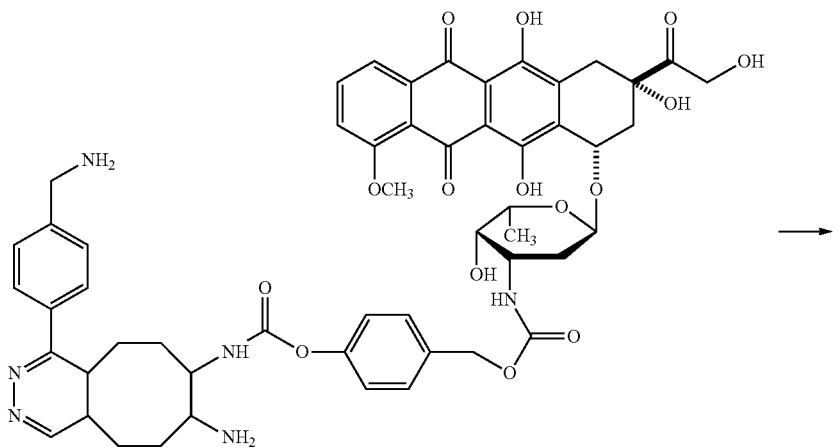
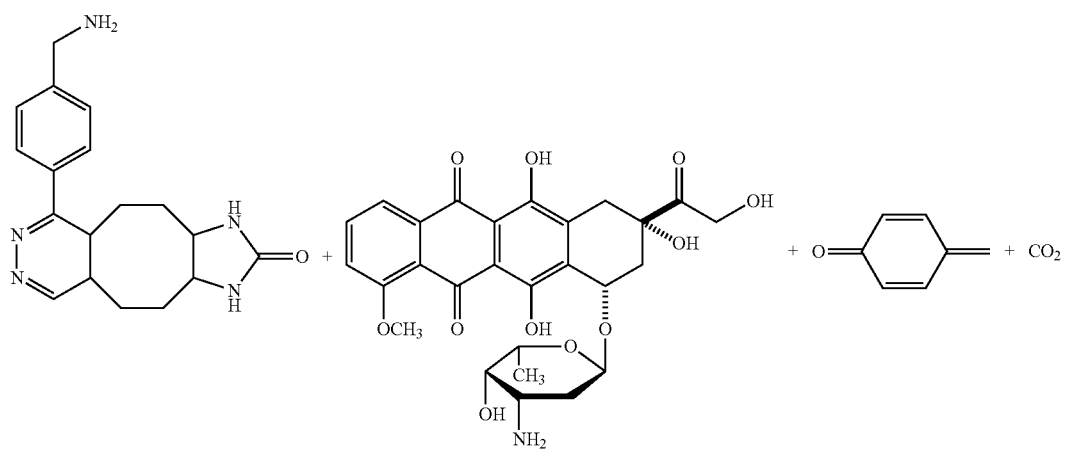

Same procedure as previous reaction.
After 1 hr at 20° C., 50% doxorubicin was released.
3-Methyl-6-(2-pyridyl)-1,2,4,5-tetrazine (7) and
(E)-cyclooctene-doxorubicin conjugate (50)
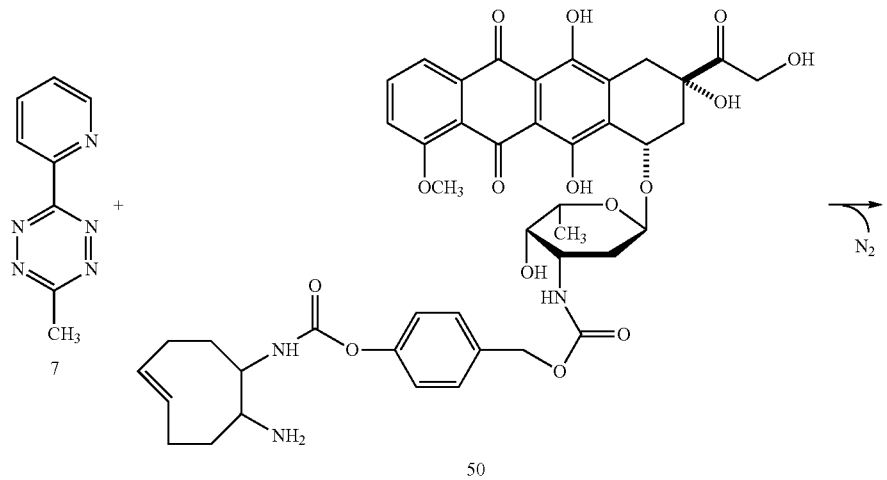
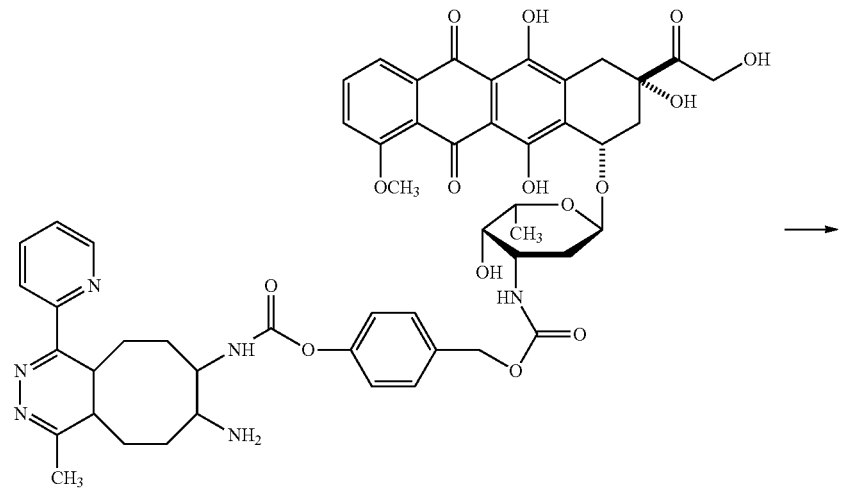
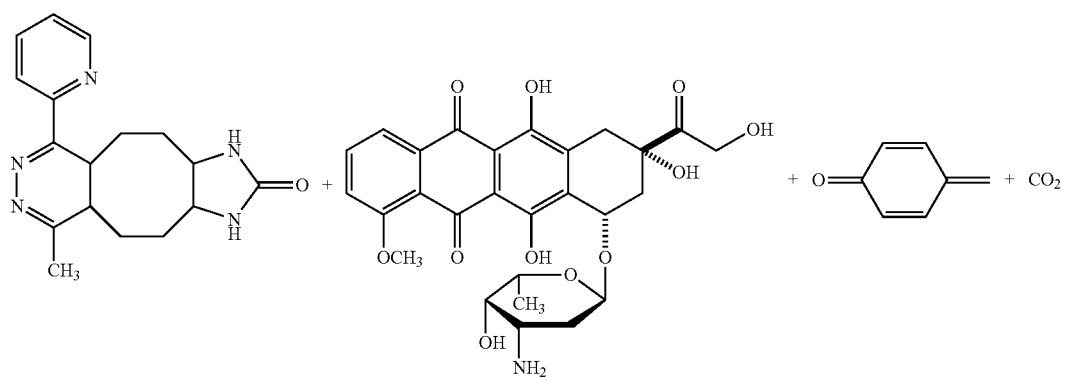

Same procedure as previous reaction.
After 1 hr at 20° C., 52% doxorubicin was released.
3,6-Diphenyl-1,2,4,5-tetrazine and
(E)-cyclooctene-doxorubicin conjugate (50)
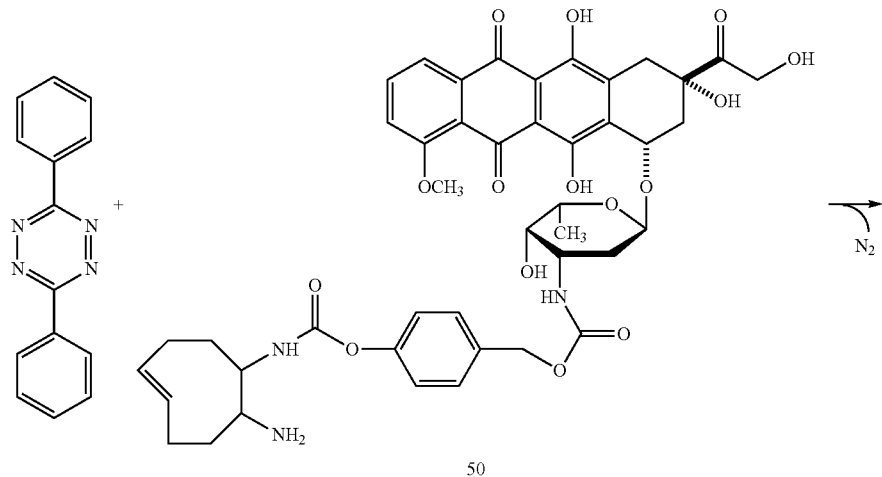
50
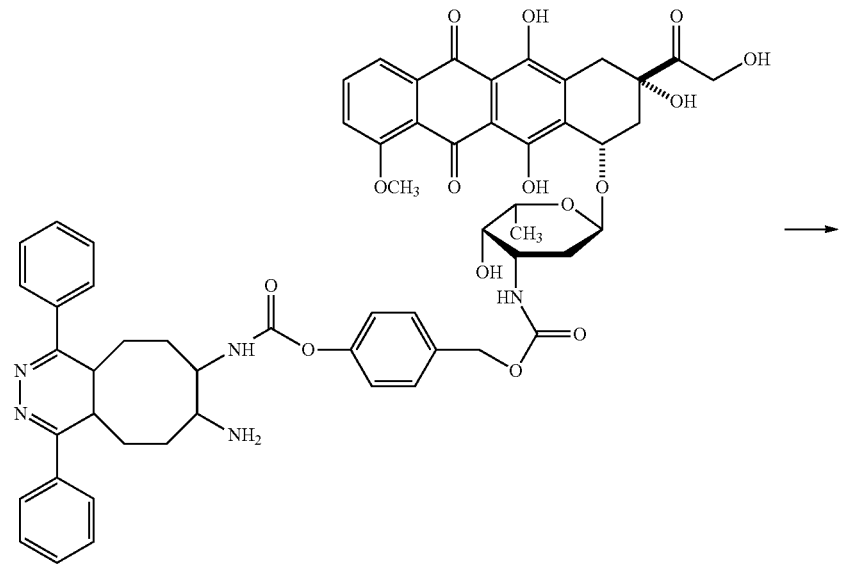
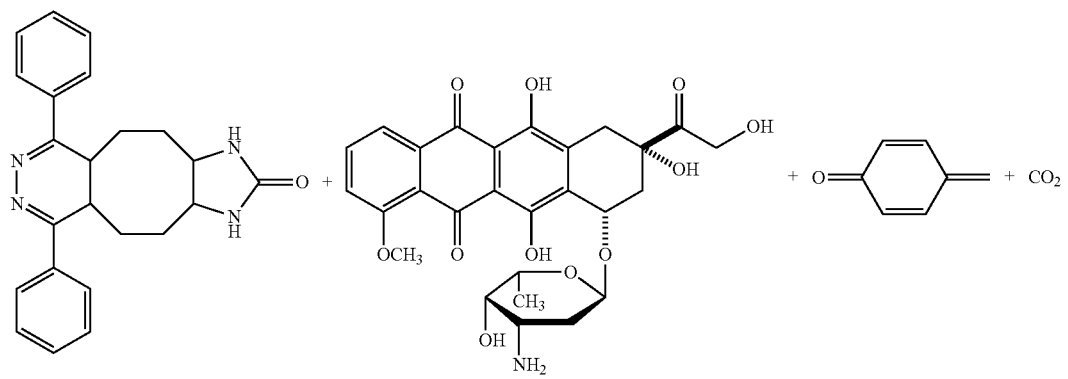

Same procedure as previous reaction.
After 1 hr at 20° C., 48% doxorubicin was released.

3,6-Bis(2-pyridinyl)-1,2,4,5-tetrazine (2) and (E)-cyclooctene-doxorubicin conjugate (51)

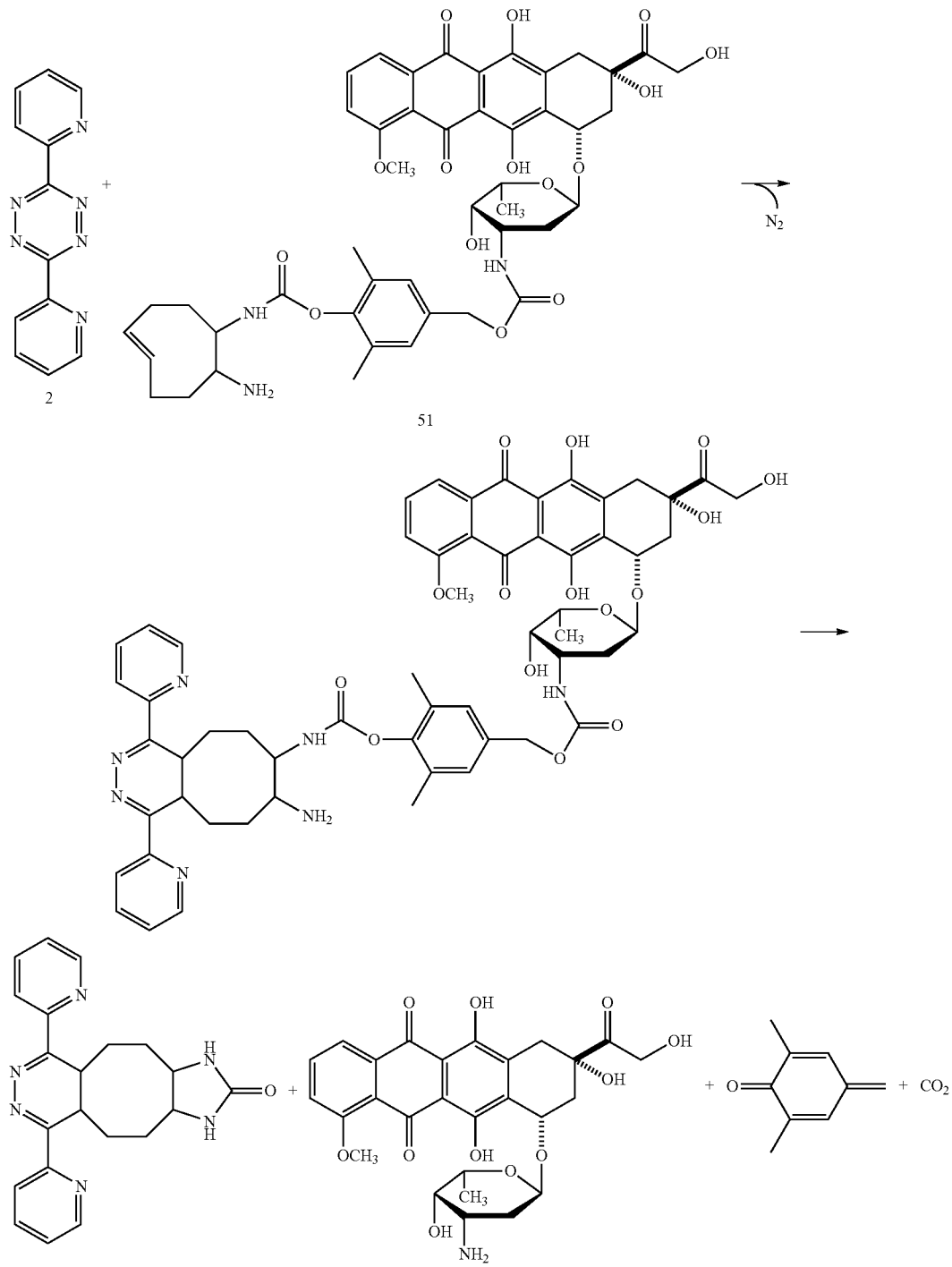

3,6-Bis(2-pyridinyl)-1,2,4,5-tetrazine (2, $1.18 \times 10^{-5}$ g; $5.00 \times 10^{-8}$ mol) was dissolved in PBS buffer (1 mL). Next, (E)-cyclooctene-doxorubicin conjugate (51, $2.67 \times 10^{-5}$ g; $2.50 \times 10^{-8}$ mol) was added. The solution was stirred at 20° C., and the reaction progress was monitored by HPLC-MS analysis, proving the formation of the cyclic urea with m/z=+375 Da (M+H$^+$), and release of doxorubicin: m/z=+544 Da (M+H$^+$) and $\lambda_{max}$=478 nm. The half-life time of this release was 4 days.

Example 12

Cell Proliferation Assay with Doxorubicin Prodrug 50 and Tetrazine 29

Figure 4:
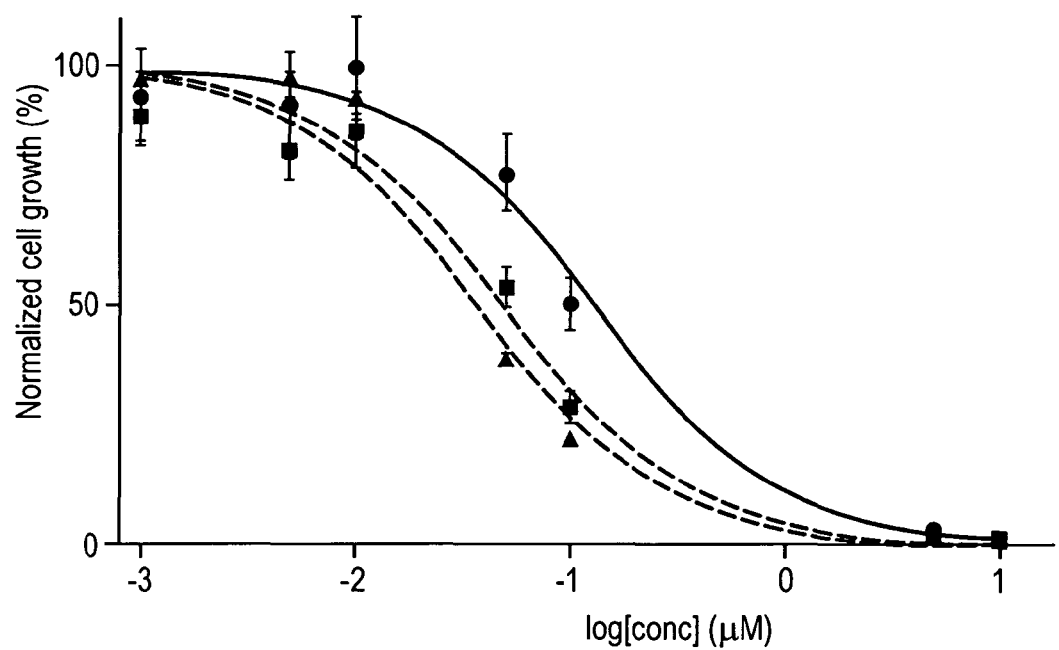
FIG. 4 shows cell a proliferation assay performed on A431 tumor cells incubated in the presence of doxorubicin (Dox) (triangle markers), prodrug 50 (circle markers), and prodrug 50 with activation by tetrazine 29 at 10 μM (square markers).

As shown in FIG. 4, a proliferation assay was performed on A431 tumor cells incubated in the presence of doxorubicin (Dox) (triangle markers), prodrug 50 (circle markers), and prodrug 50 with activation by tetrazine 29 at 10 μM (square markers).

A431 squamous carcinoma cells were maintained in a humidified $CO_2$ (5%) incubator at 37° C. in DMEM (Invitrogen) supplemented with 10% heat-inactivated fetal bovine serum and 0.05% glutamax (Invitrogen) in the presence of penicillin and streptomycin. The cells were plated in 96-well plates (Nunc) at a 2000 cells/well density 24 hrs prior to the experiment. Doxorubicin (Dox) and the prodrug 50 (1 mM in DMSO) were serially diluted in pre-warmed culture medium immediately before the experiment and added to the wells (200 μL final volume; t=0). The prodrug was either added alone or in combination with 10 μM tetrazine 29. After 6 hrs incubation at 37° C. the medium was gently aspirated, 200 μL fresh culture medium was added to each well and the cells were incubated for 66 hrs more. In a parallel experiment, a solution of tetrazine 29 (2 mM in PBS) was serially diluted (from 1 mM to 1 nM) in pre-warmed culture medium and added to A431 cells in a 96-well plate, which was incubated at 37° C. for 72 hrs. At the end of each experiment, the cell proliferation was assessed by an MTT assay. Briefly, methylthiazolyldiphenyltetrazolium bromide (MTT) was dissolved in PBS at 5 mg/ml, filtered through 0.22 μm and 25 μl was added to each well. After 120 min incubation at 37° C., the medium was gently aspirated. The formed formazan crystals were dissolved in 100 μl DMSO and the absorbance was measured with a plate reader (BMG Labtech) at 560 nm. $IC_{50}$ values (±standard error; see table) were derived from the normalized cell growth curves (see FIG. 4) generated with GraphPad Prism (version 5.01). The cell proliferation assays shows a significant toxicity increase when A431 cells are exposed to a combination of the prodrug 50 and tetrazine 29 ($IC_{50}$=49±4 nM) compared to the prodrug alone ($IC_{50}$=128±17 nM) or the tetrazine alone ($IC_{50}$>100 μM). This confirms that doxorubicin is released following the retro Diels-Alder reaction between the trans-cyclooctene of the prodrug and the tetrazine Activator.

$IC_{50}$ Values for Doxorubicin (Dox) and Prodrug 50 with and without Activation by Tetrazine 29 (10 μM) Determined in A431 Cell Line.

| Compound | $IC_{50}$ (μM) |
| --- | --- |
| Dox | 0.038 ± 0.003[a] |
| Prodrug 50 | 0.128 ± 0.017[a] |
| Prodrug 50 + tetrazine 29 (10 μM) | 0.049 ± 0.004[a] |
| Tetrazine 29 | >100[b] |

[a] 6 h incubation at 37° C. followed by medium replacement;
[b] 72 h incubation at 37° C.

Example 13

Exemplary General Synthesis Routes and Key Intermediates for the Preparation of TCO Based Triggers.

The brackets around $L^D$ and $S^P$ signify that they are optional. The $T^T$ featured in this example can optionally be replaced by $M^M$.

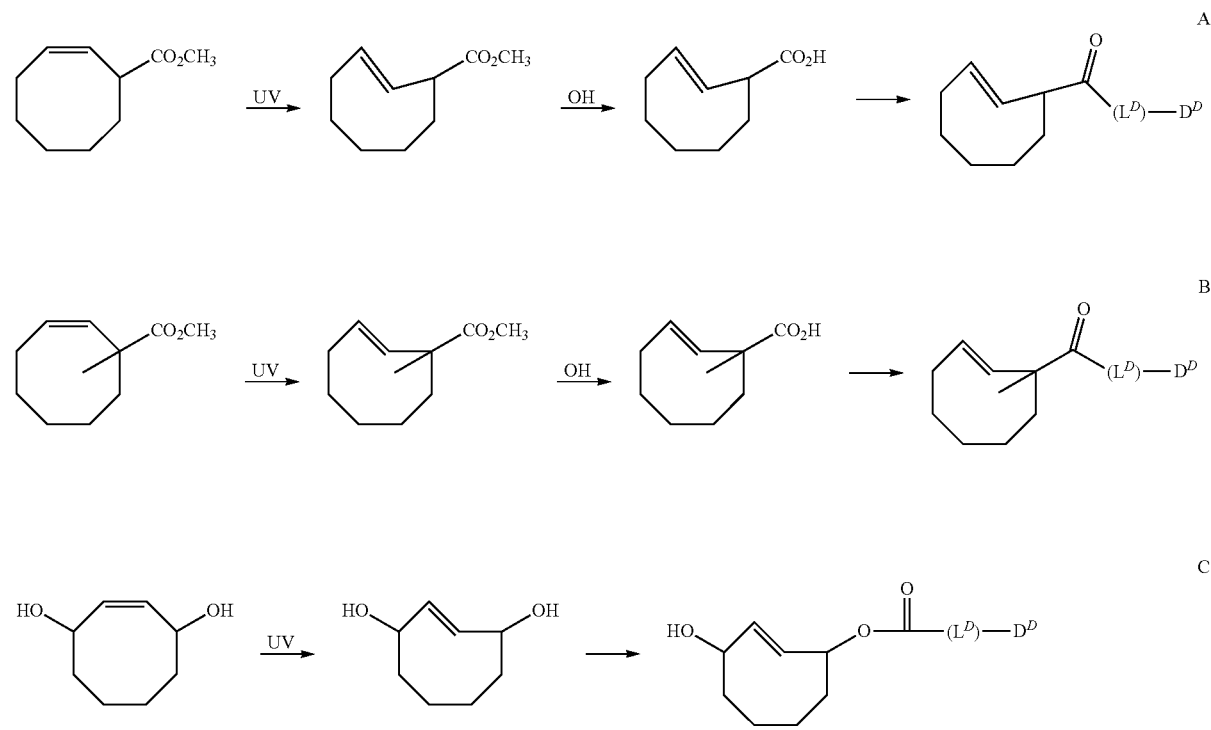

Performing this reaction at 37° C. yielded a half-life time of 16 hrs.

-continued
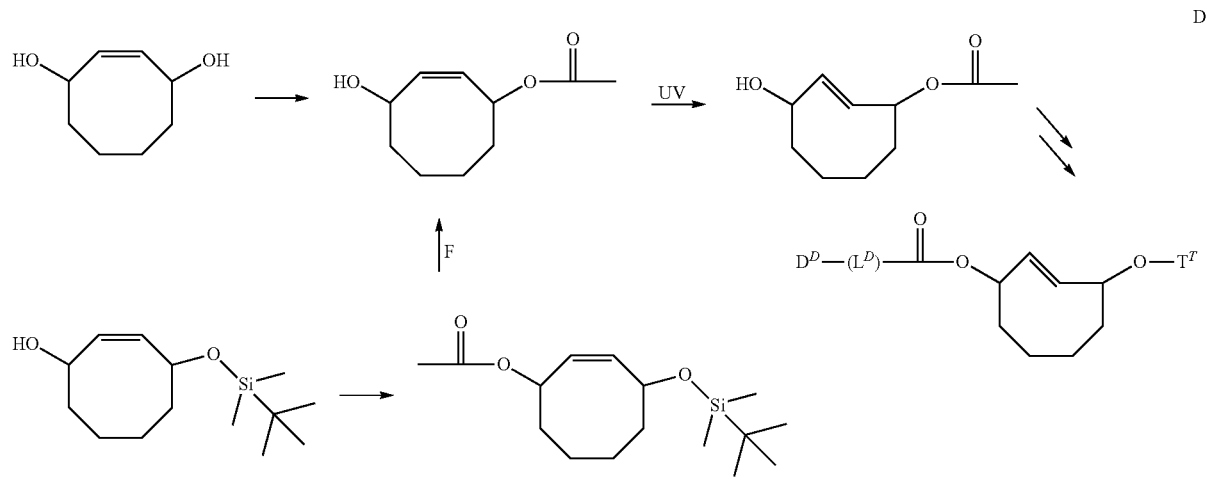
D
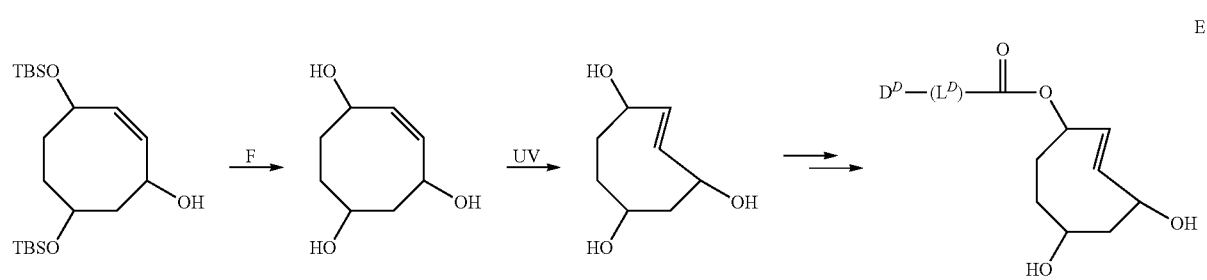
E
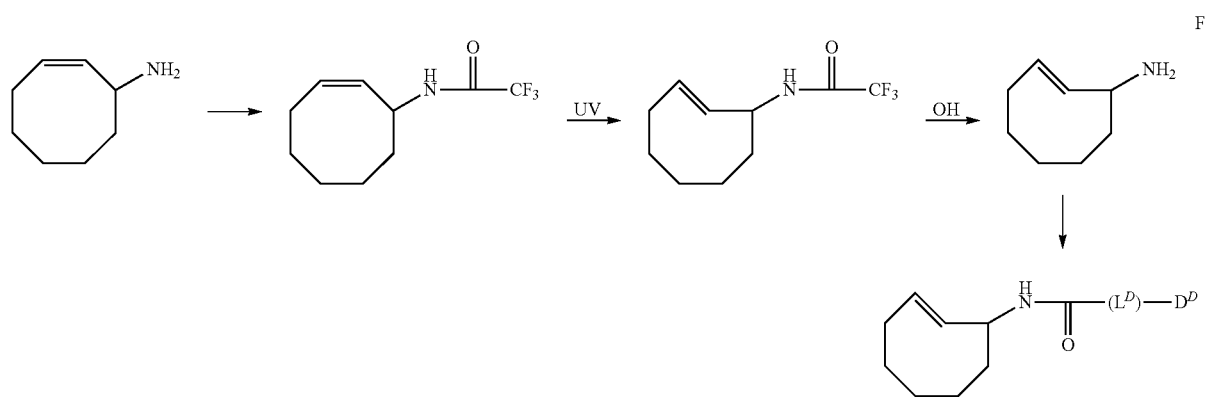
F
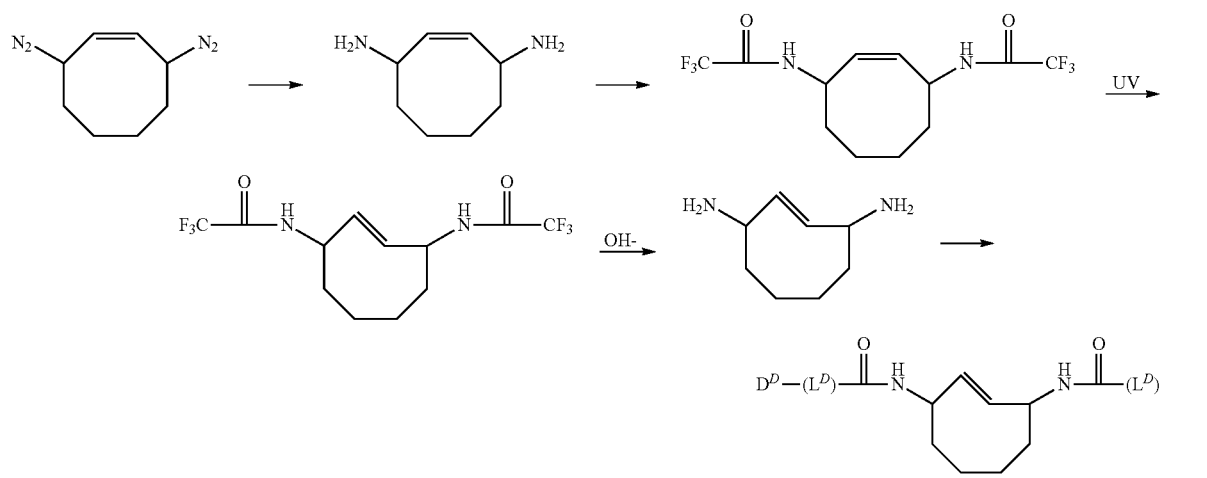
G

-continued
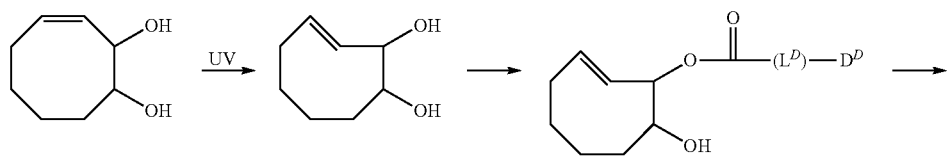
H
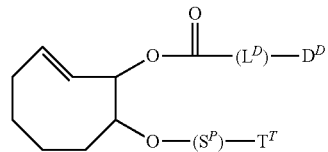
I
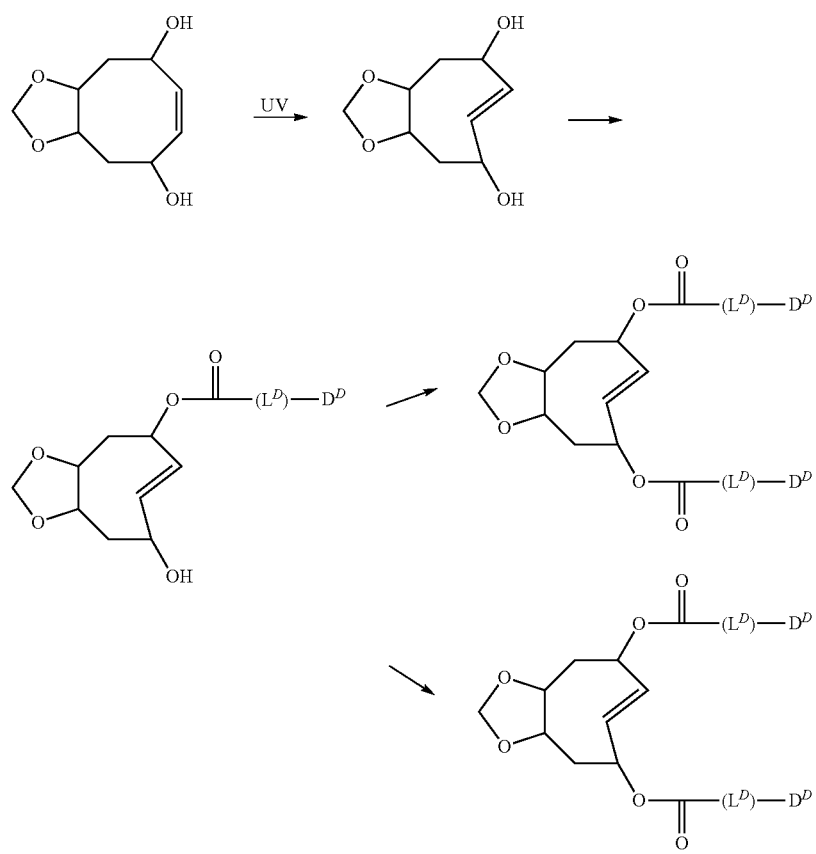
J
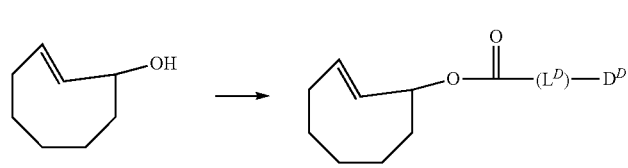
K
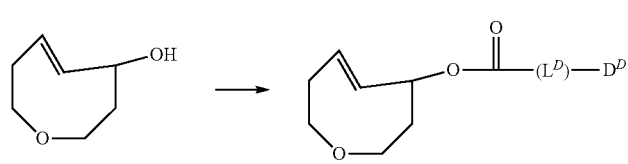

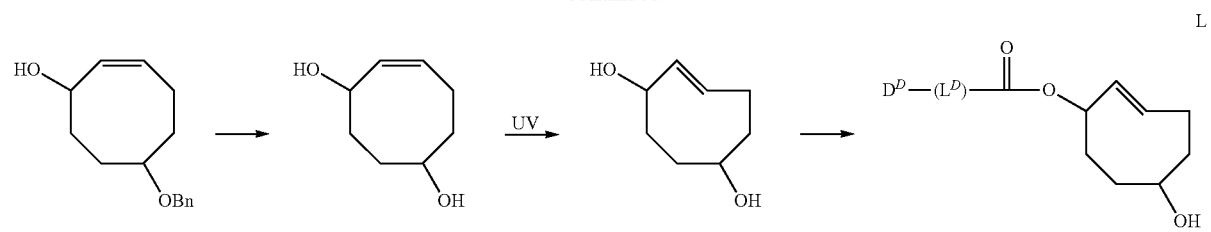
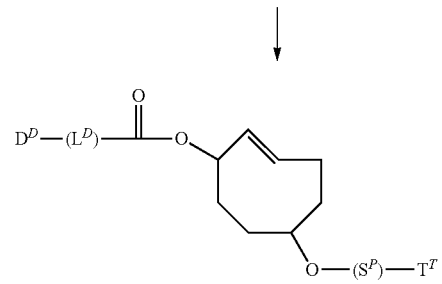
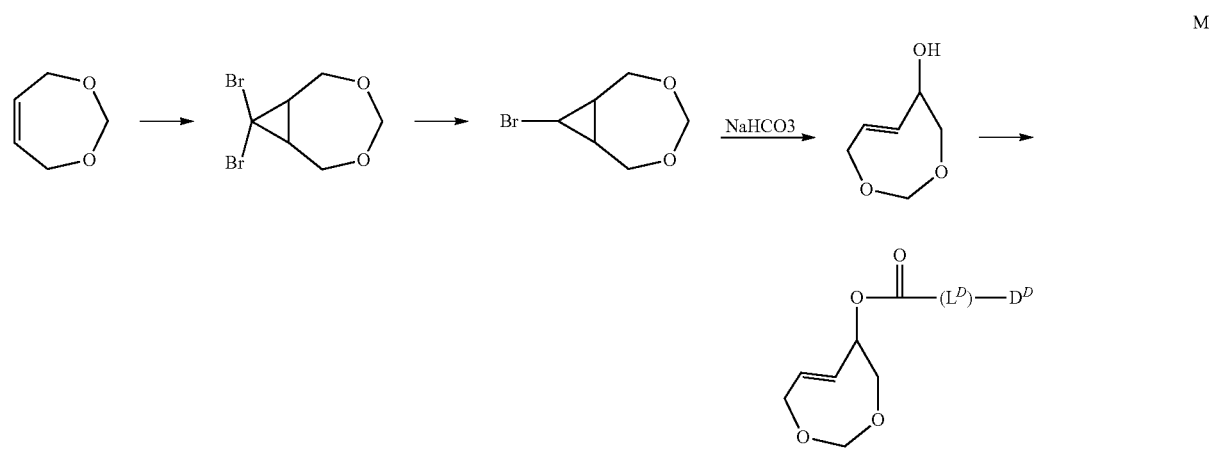
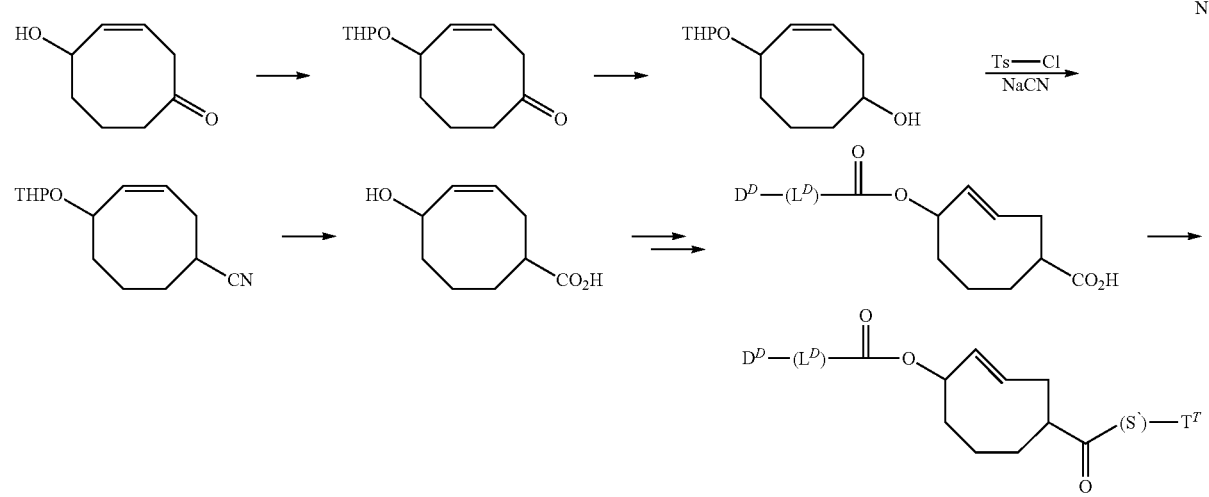

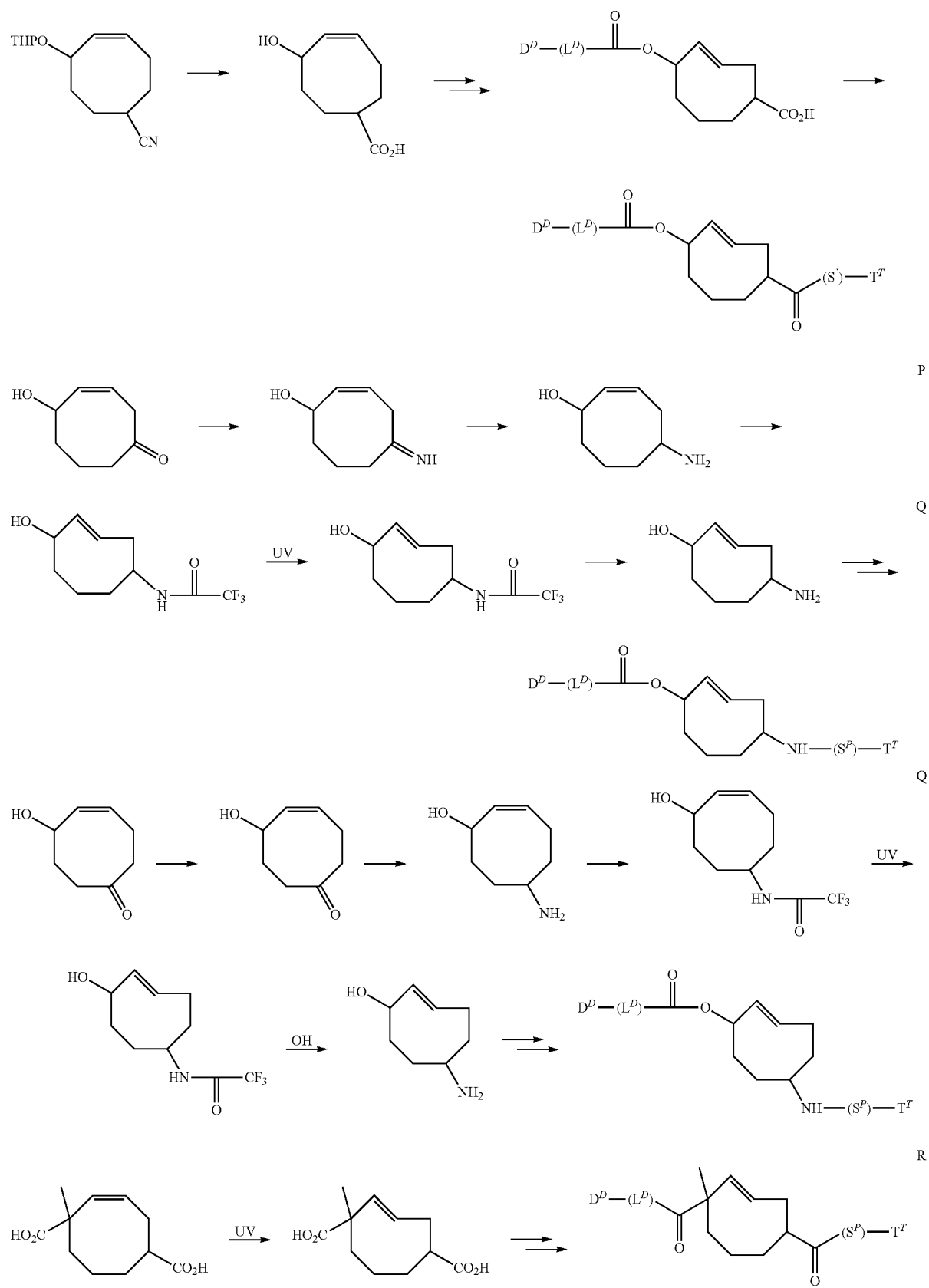

Example 14
Structures of Exemplary $L^D$ Moieties
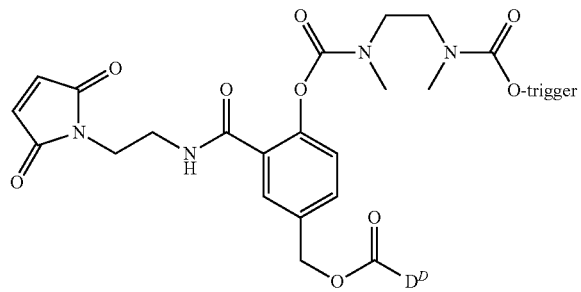
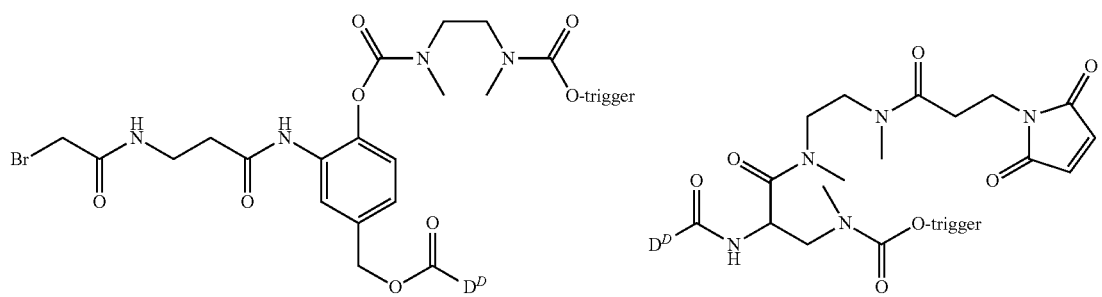
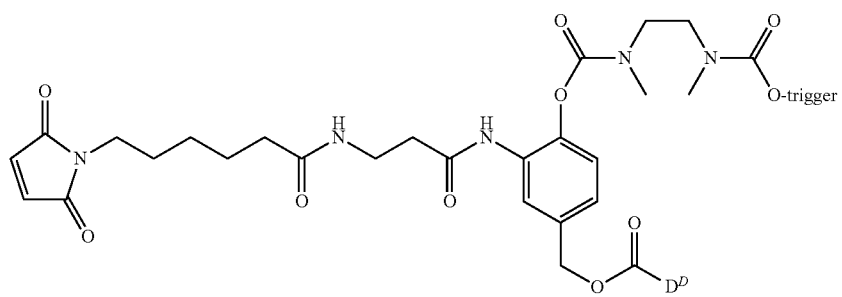
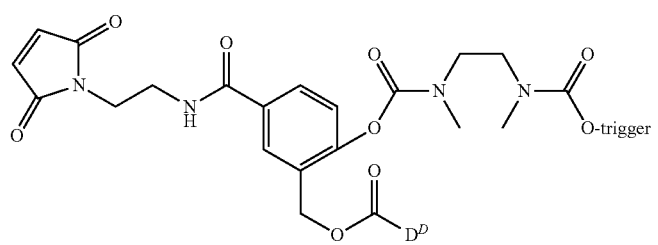
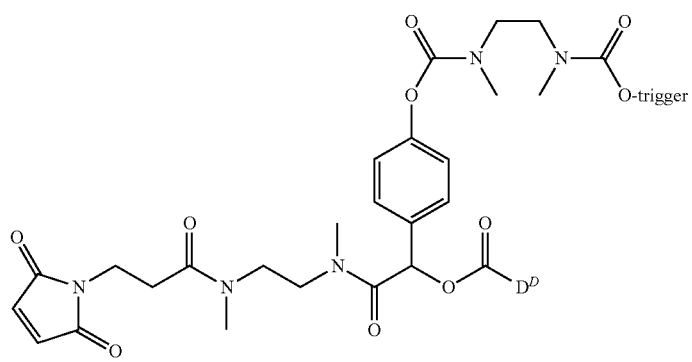

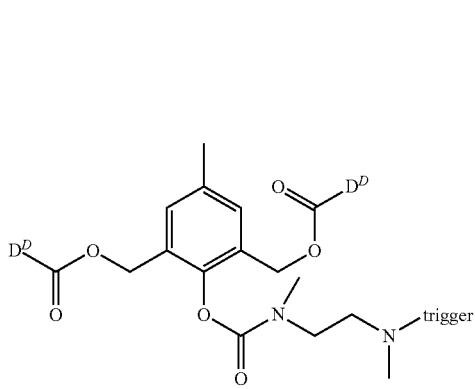
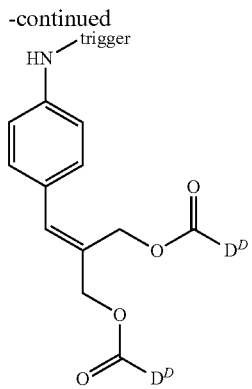

The linkers $L^D$ are so-called self-immolative linkers, meaning that upon reaction of the trigger with the activator the linker will degrade via intramolecular reactions thereby releasing the drug $D^D$. Some of the above also contain a $S^P$.

Example 15

Structures of Exemplary $S^P$ Moieties

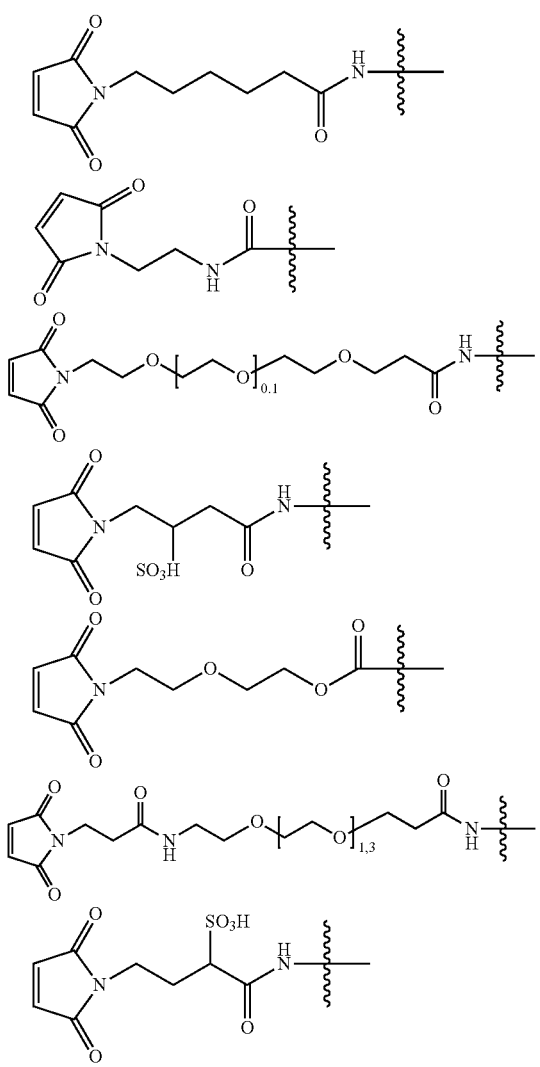

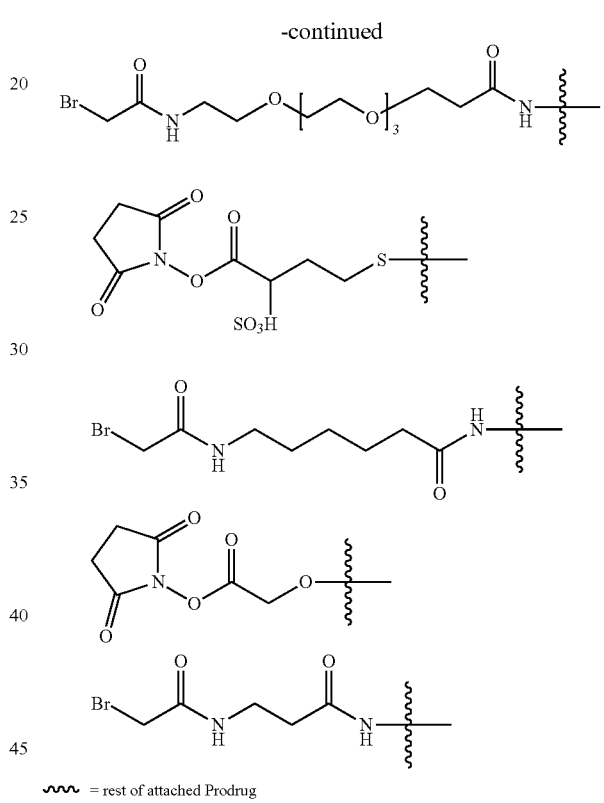

Note that the maleimide, active ester and bromo acetamide groups are active groups to which targeting moieties $T^T$ and masking moieties $M^M$, optionally via further spacers $S^P$, can be coupled. Maleimides and bromo acetamide groups typically react with thiols, while active esters are typically suitable for coupling to primary or secondary amines.

Example 16

Structures of TCO Triggers with Depicted Exemplary $L^D$ Moieties and which Function Via Cyclization Elimination The $T^T$ featured in this example can optionally be replaced by $M^M$.

177
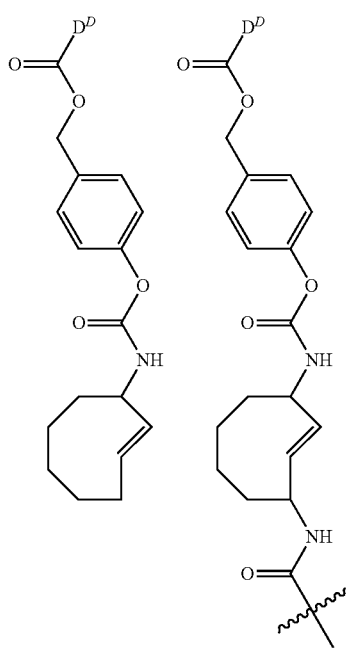
178
-continued
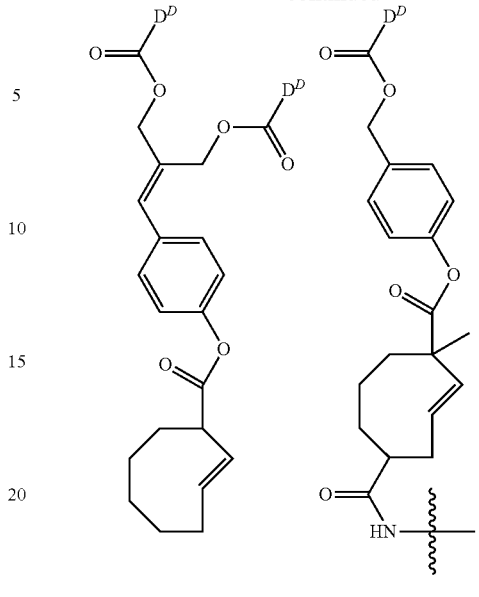
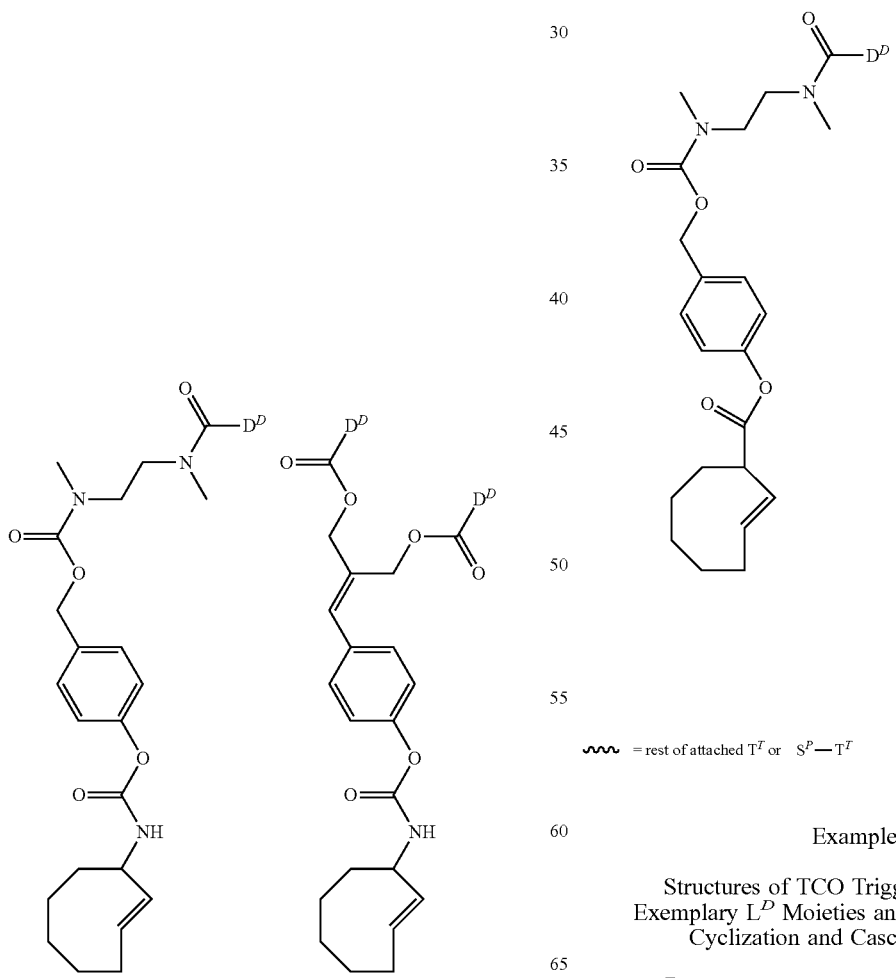
= rest of attached $T^T$ or  $S^P$—$T^T$
Example 17
Structures of TCO Triggers with Depicted Exemplary $L^D$ Moieties and which Function Via Cyclization and Cascade Elimination
The $T^T$ featured in this example can optionally be replaced by $M^M$.

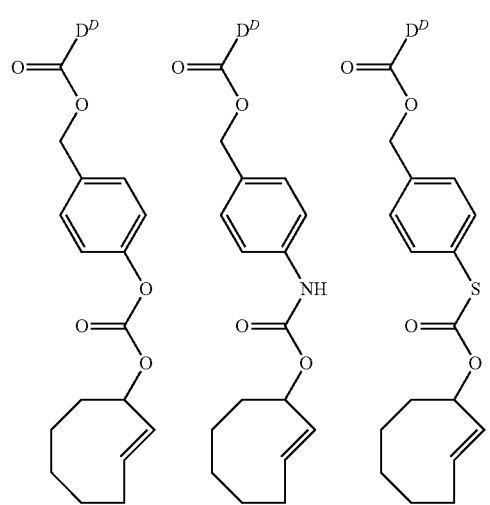
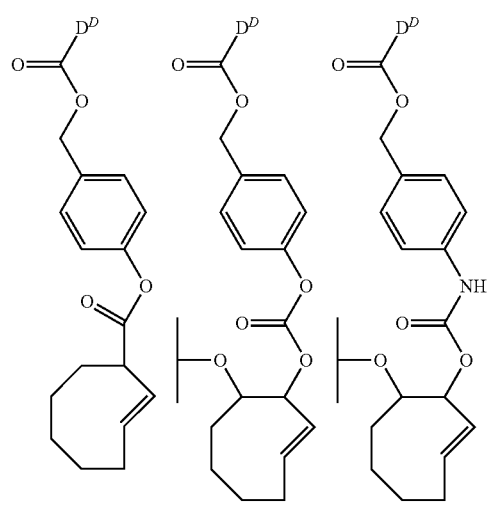
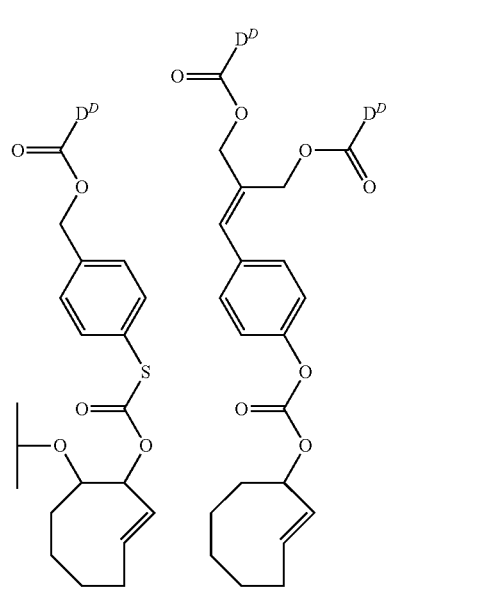
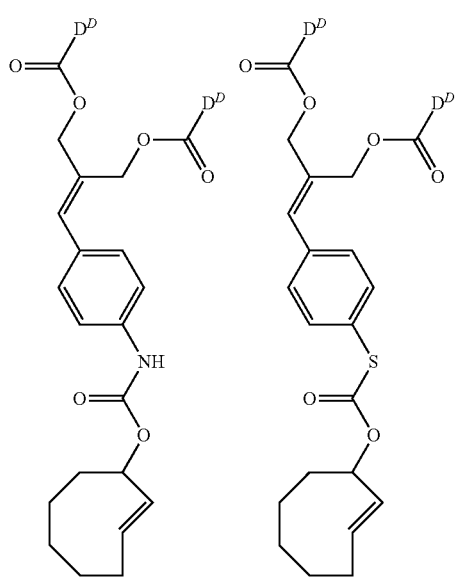
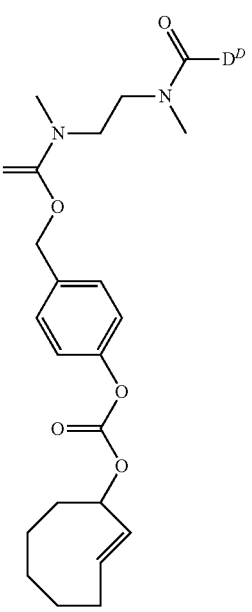

181
-continued

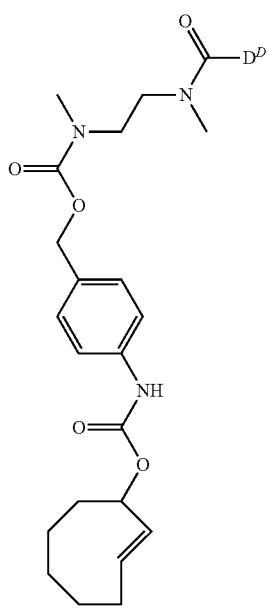

ᗯᗯ = rest of attached $T^T$ or $S^P$ — $T^T$

Example 18

Structures of TCO Triggers with Depicted Exemplary $L^D$ and/or $S^P$ Moieties and which Function Via Cyclization Elimination Trigger conjugated to $T^T$ via amine or thiol of $T^T$. The $T^T$ featured in this example can optionally be replaced by $M^M$.

182

$$T^R-L^D-D^D:\quad \overset{T^T}{\underset{|}{(S^P)}}$$

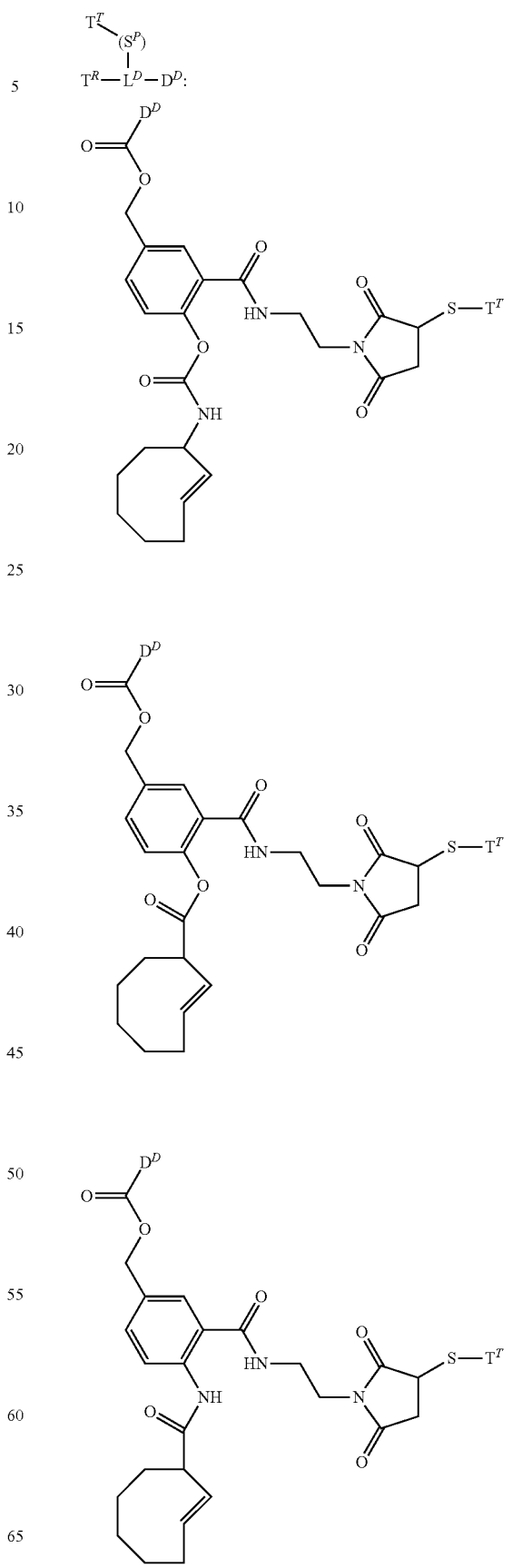

183
-continued
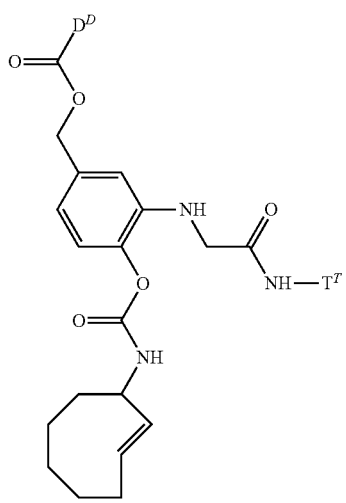
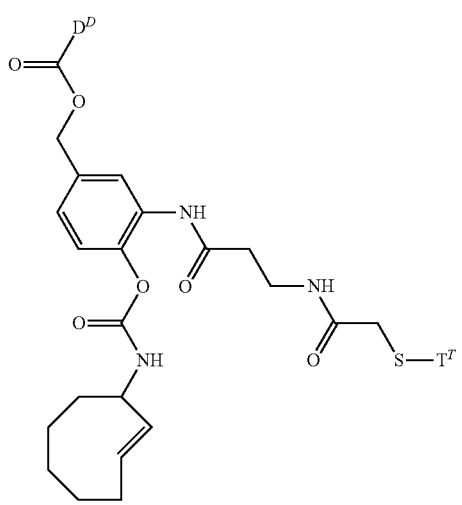
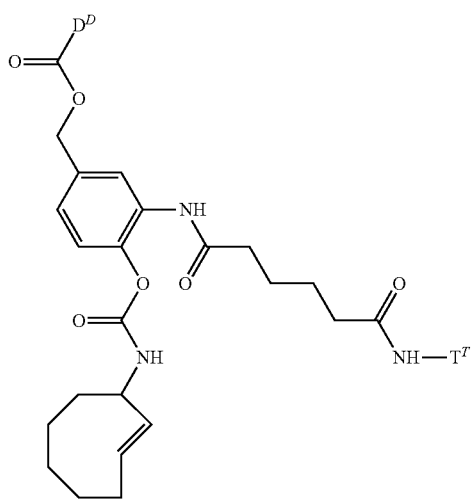
184
-continued
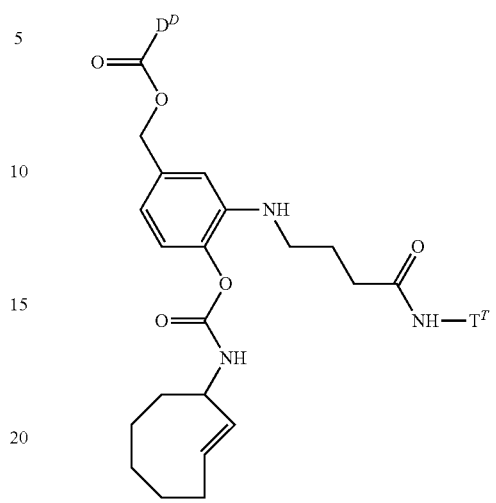
$T^T - S^P - T^R - L^D - D^D$:
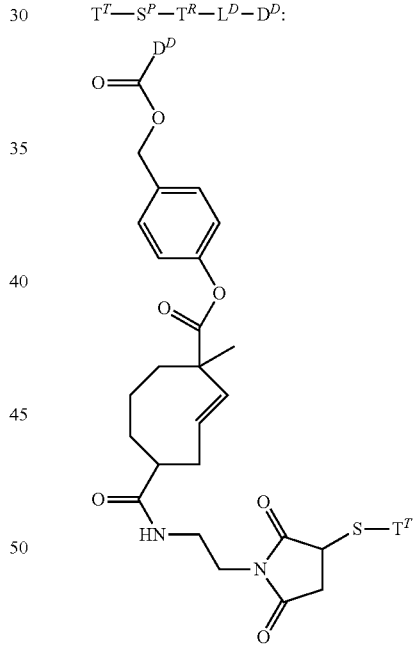
Example 19
Structures of TCO Triggers with Depicted Exemplary $L^D$ and/or $S^P$ Moieties and which Function Via Cyclization and Cascade Elimination
Trigger conjugated to $T^T$ via amine or thiol of $T^T$. The $T^T$ featured in this example can optionally be replaced by $M^M$.

185
$T^R-L^D-D^D$:
$T^T$
$(S^P)$
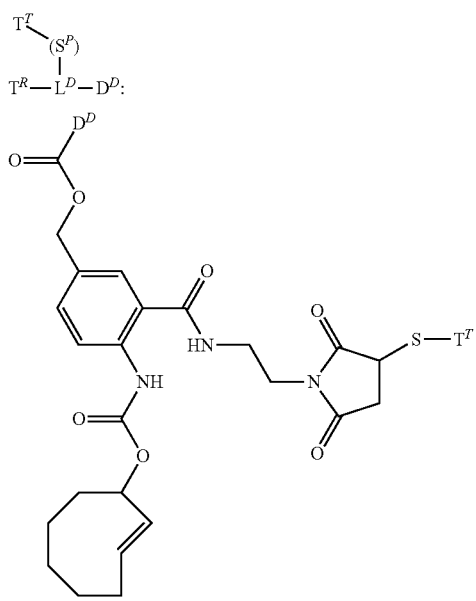
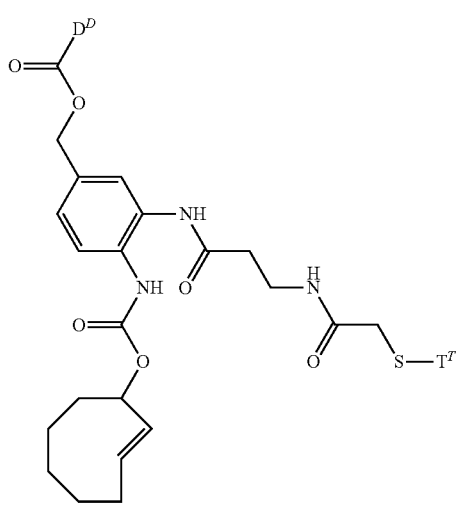
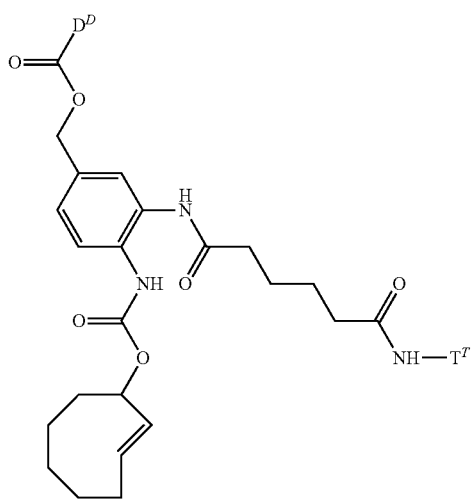
186
-continued
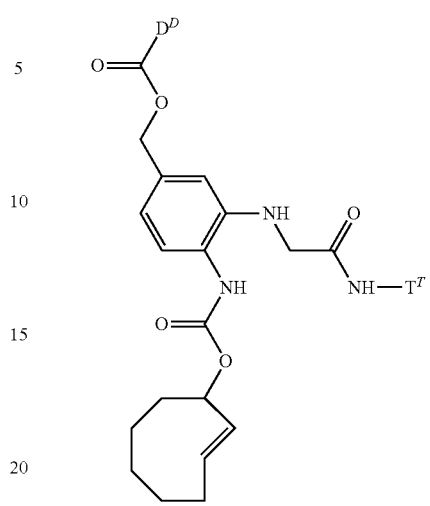
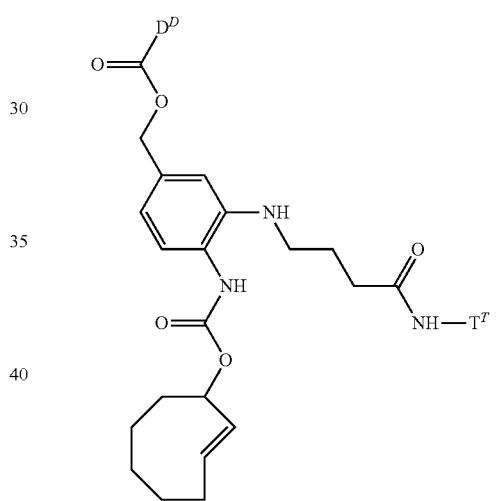
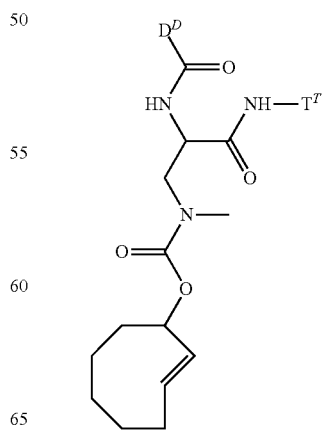

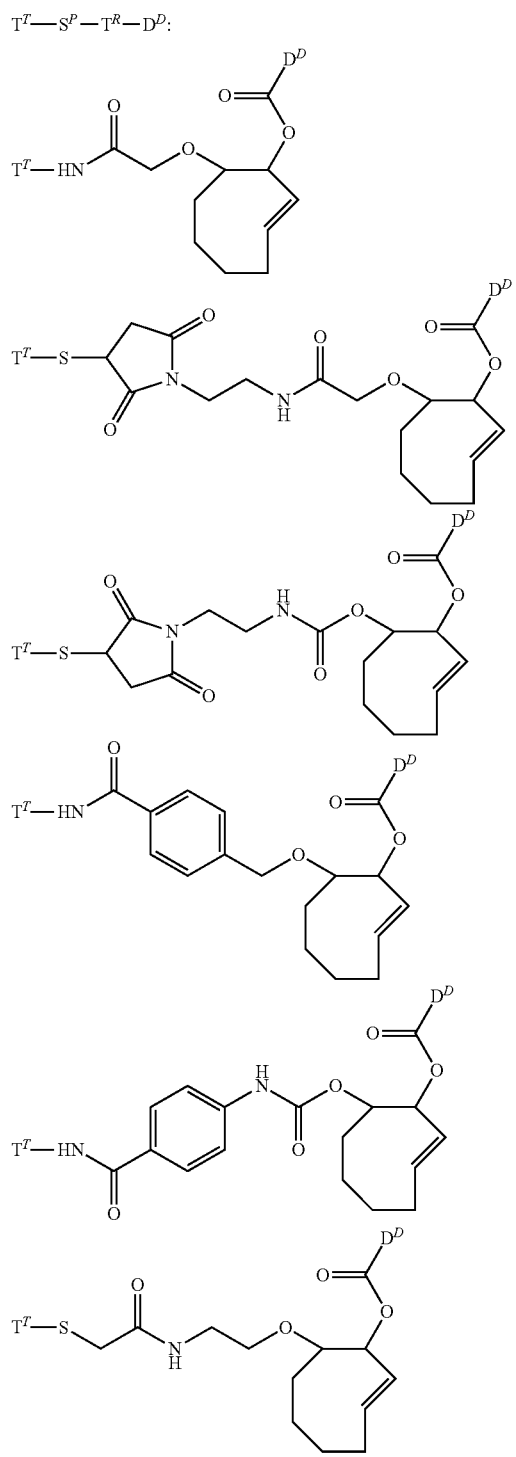
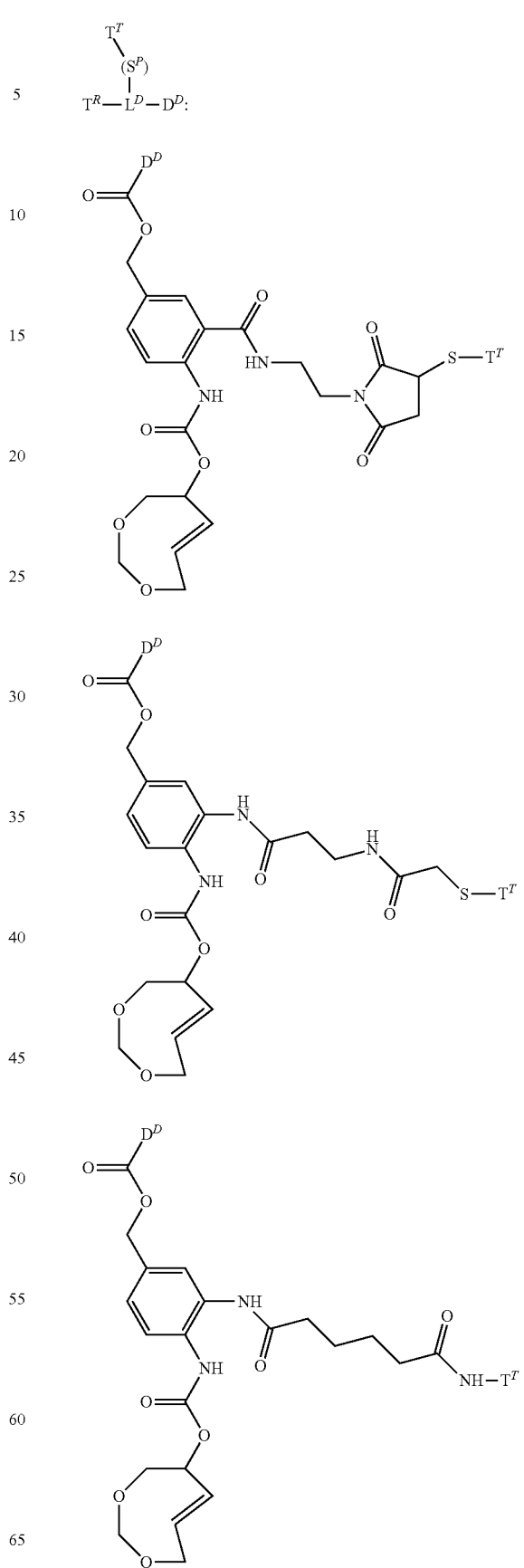
Example 20
Structures of TCO Triggers with Depicted Exemplary $L^D$ and/or $S^P$ Moieties and which Function Via Cyclization and Cascade Elimination
Trigger conjugated to $T^T$ via amine or thiol of $T^T$. The $T^T$ featured in this example can optionally be replaced by $M^M$.

189
-continued
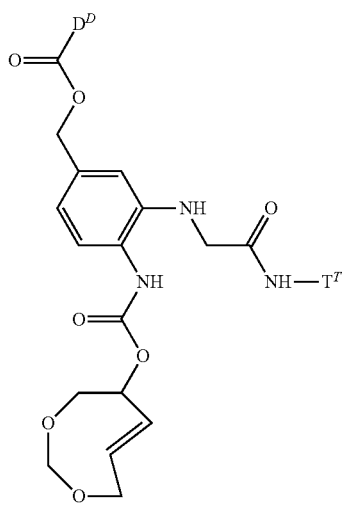
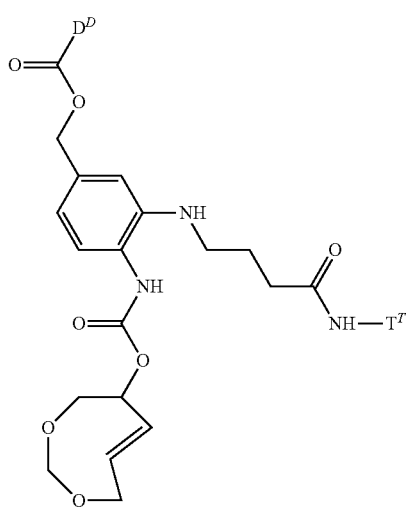
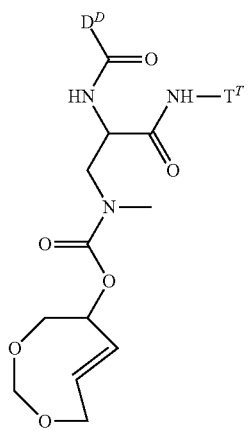
190
-continued
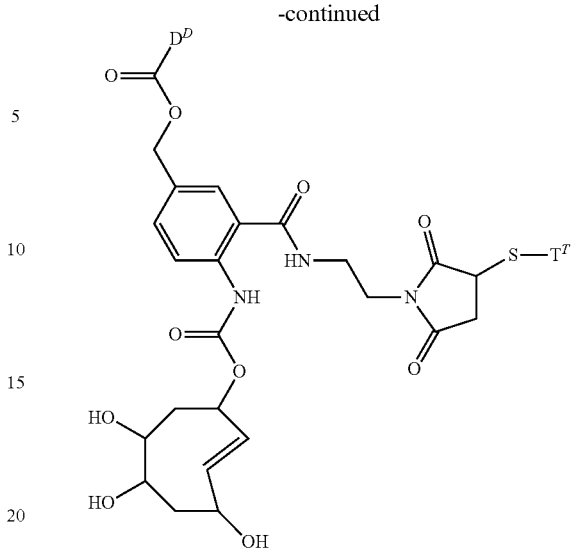
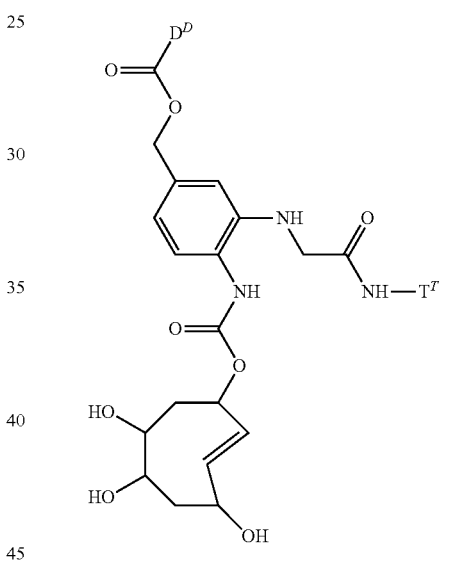
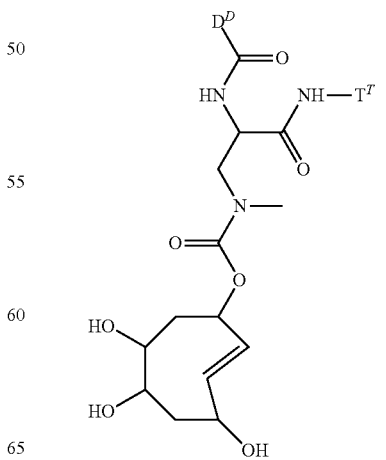

191

$T^T—S^P—T^R—D^D$:

Example 21

Structures of Antibody-Drug Conjugates, which Function Via Cyclization Elimination Auristatin E (MMAE) toxin is attached via a self immolative linker $L^D$ to a TCO trigger and via $S^P$ to a targeting antibody or fragment (conjugated through cysteine or lysine residue). Ab=antibody or antibody fragment: q=Ab modification # and is typically between 1 and 10.

193
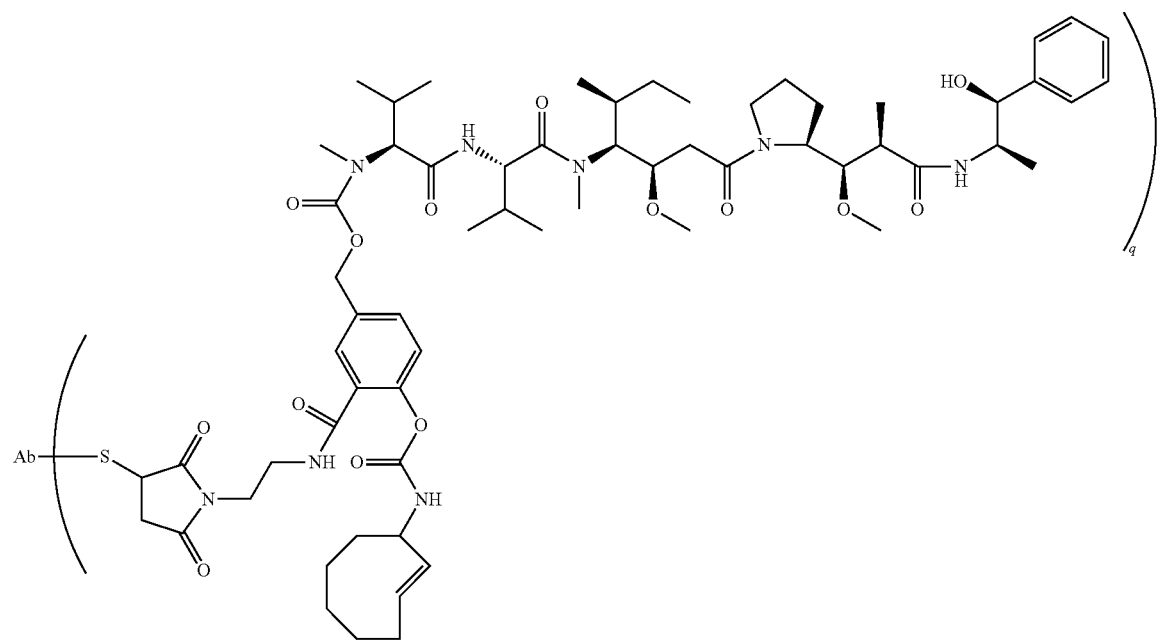
194
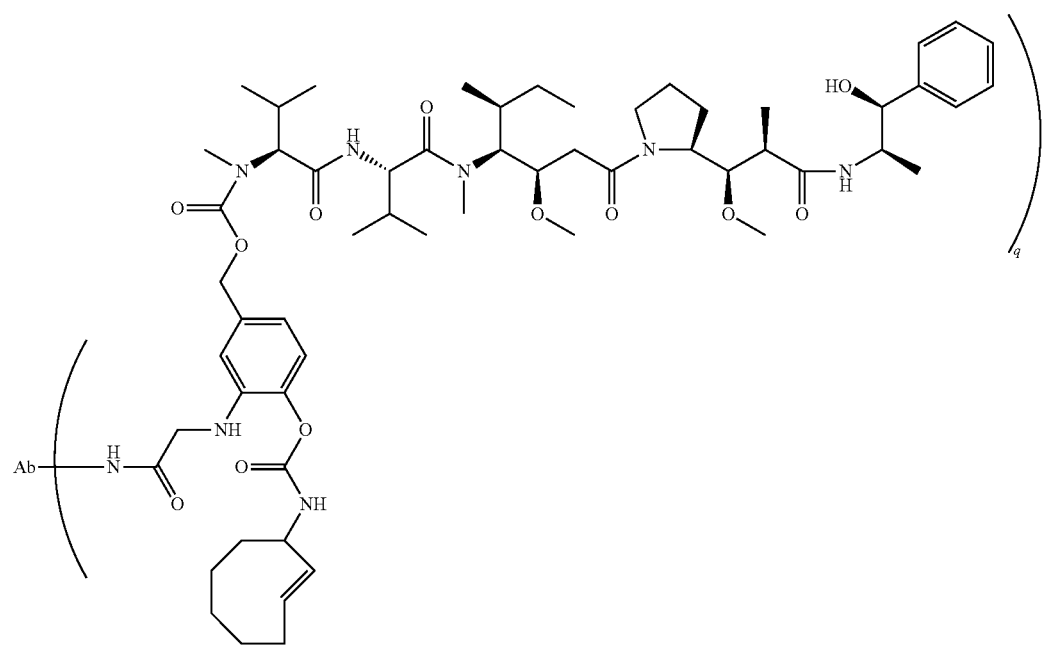

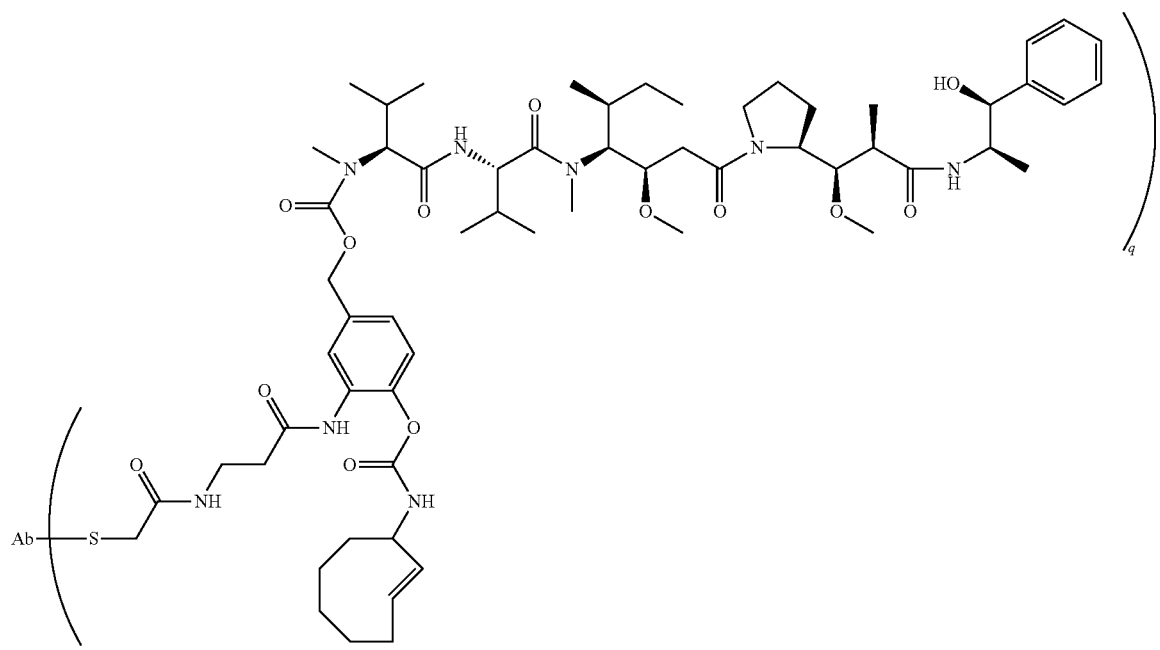
Example 22
Structures of Antibody-Drug Conjugates, which Function Via Cyclization Elimination
Maytansine toxin is attached via a self immolative linker $L^D$ to a TCO trigger and via $S^P$ to a targeting antibody or fragment (conjugated through cysteine or lysine residue). Ab=antibody or antibody fragment; q=Ab modification # and is typically between 1 and 10.
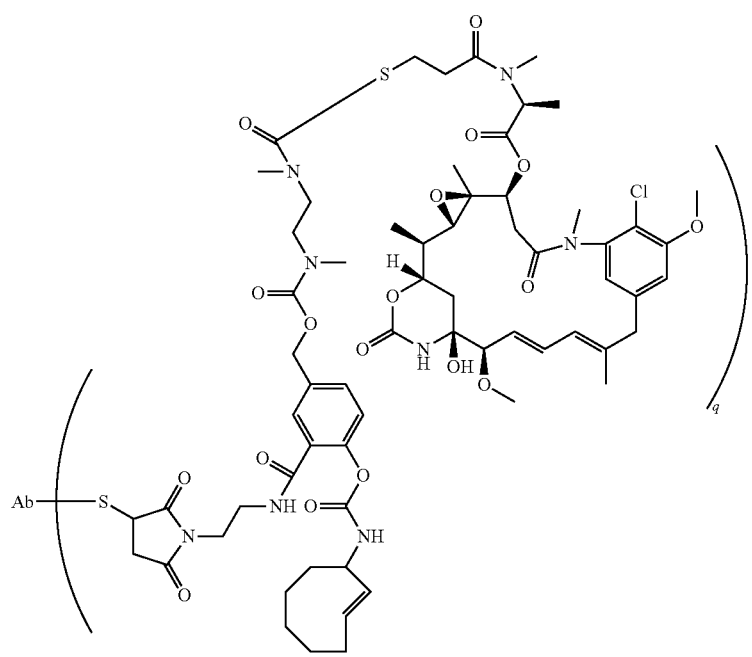

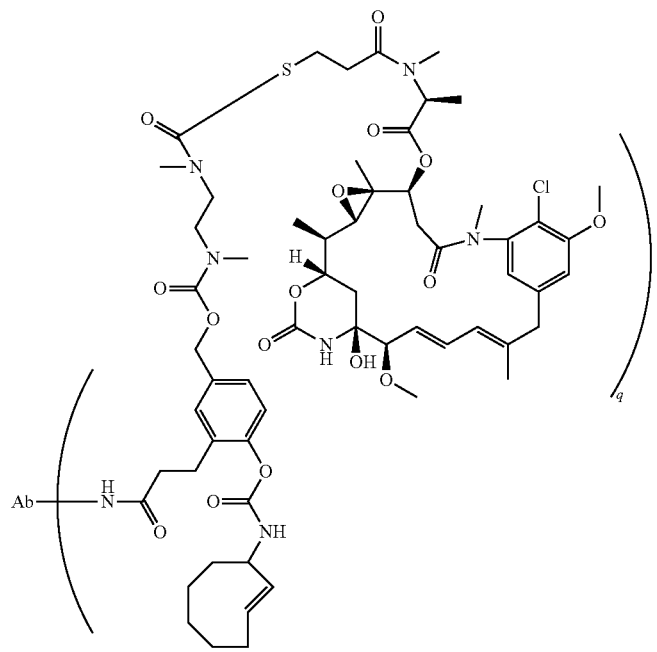
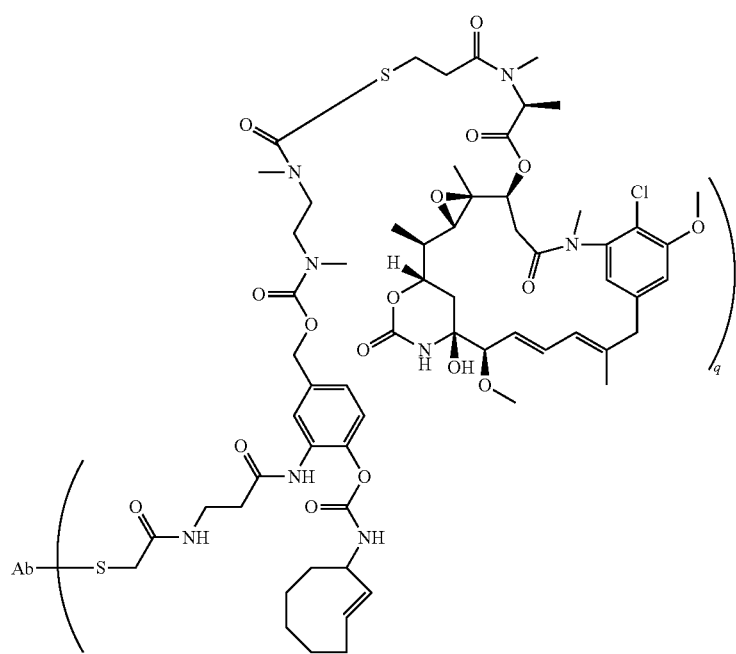

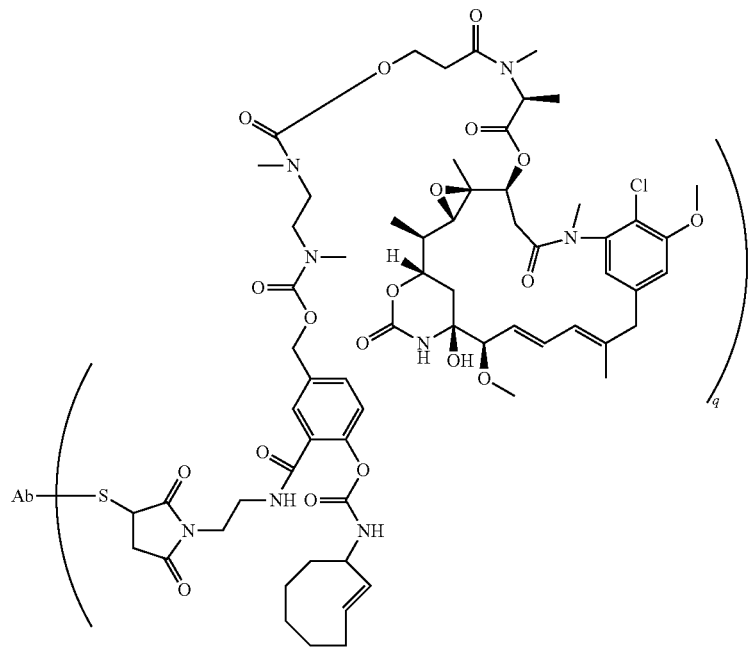
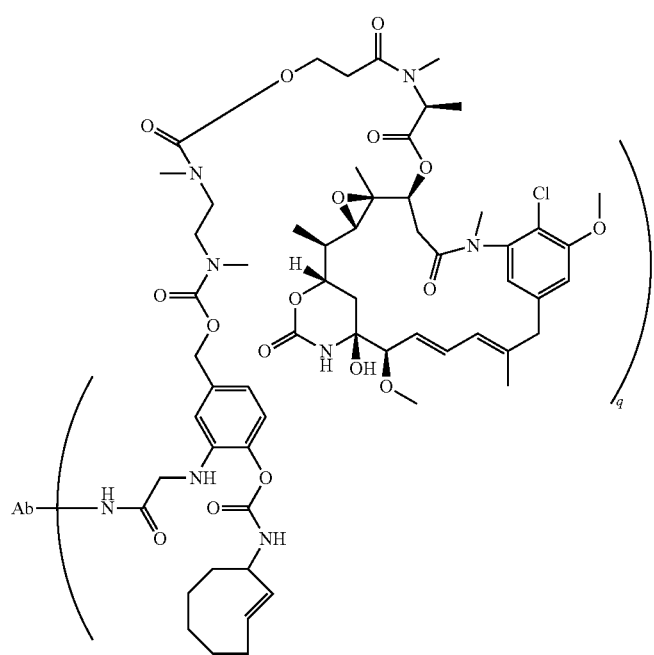

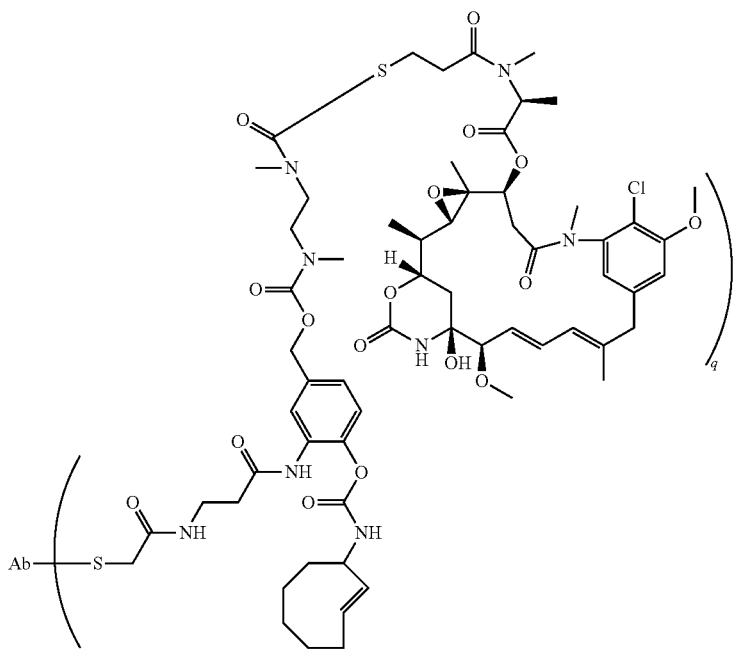

Example 23

Structures of Antibody-Drug Conjugates, which Function Via Cyclization and Cascade Elimination Auristatin E (MMAE) toxin is attached via a self immolative linker $L^D$ to a TCO trigger and, in cases via $S^P$, to a targeting antibody or fragment (conjugated through cysteine or lysine residue). Ab=antibody or antibody fragment; q=Ab modification # and is typically between 1 and 10.

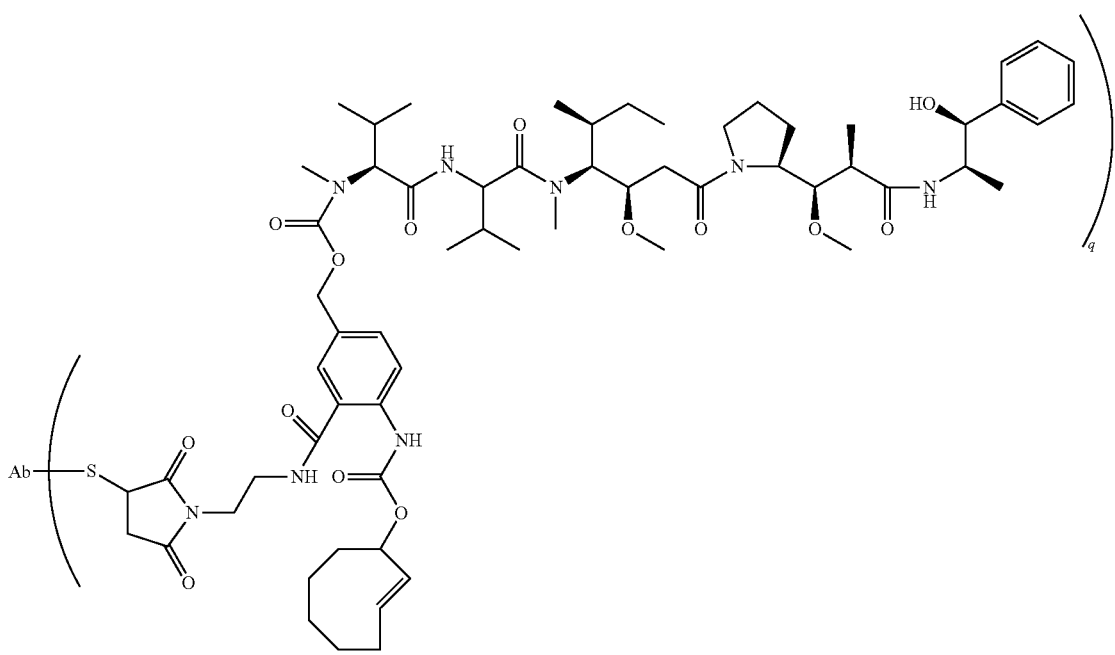

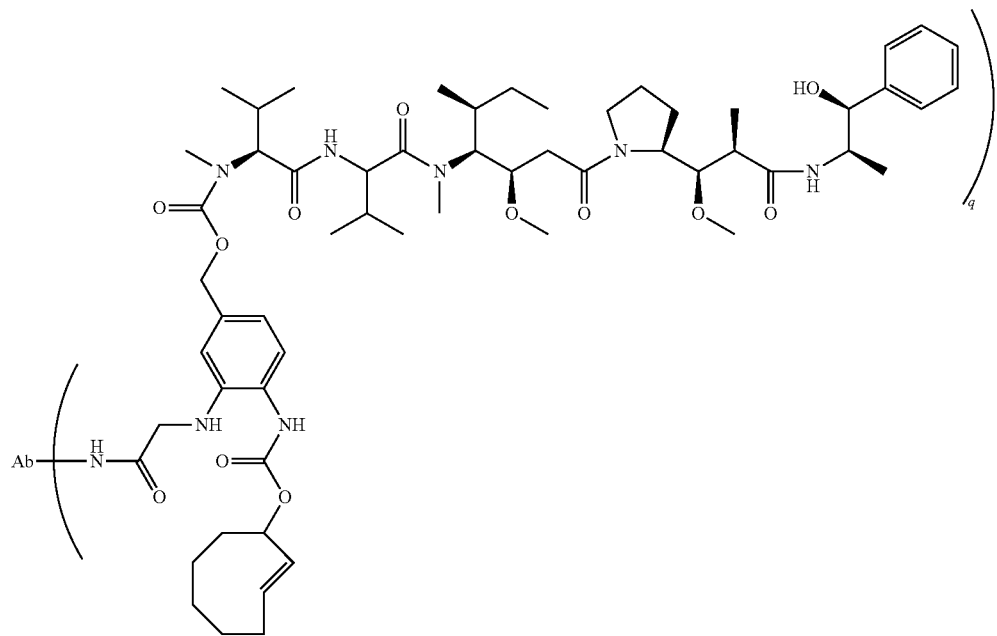
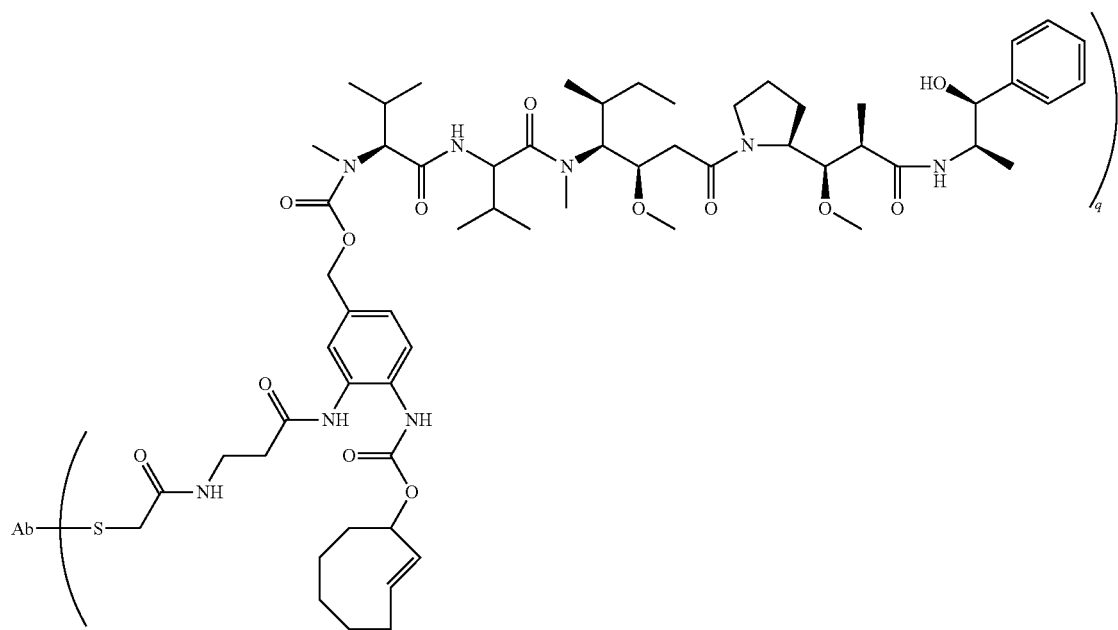

-continued
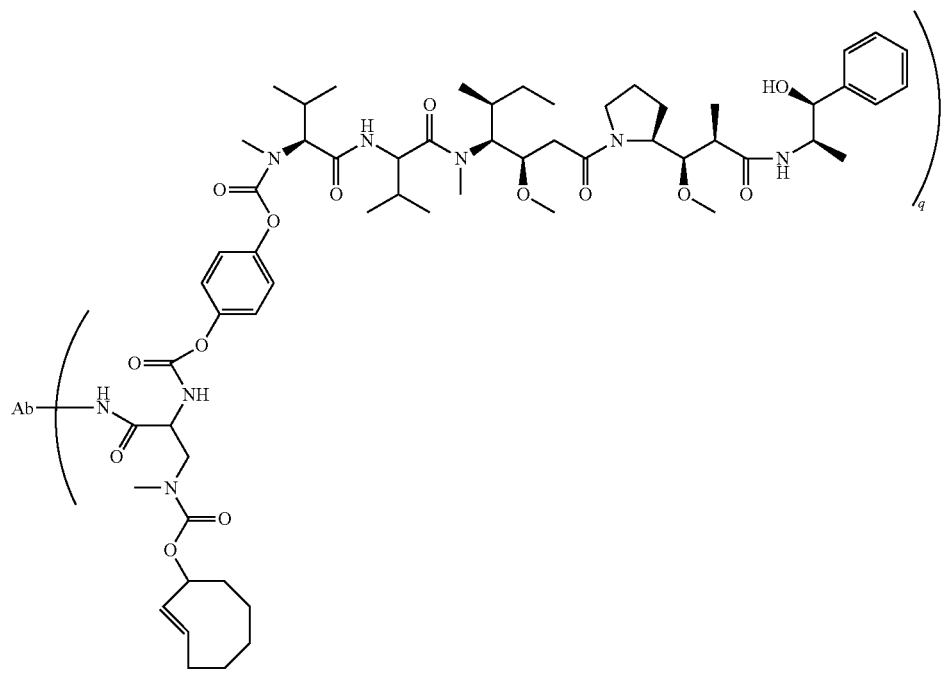
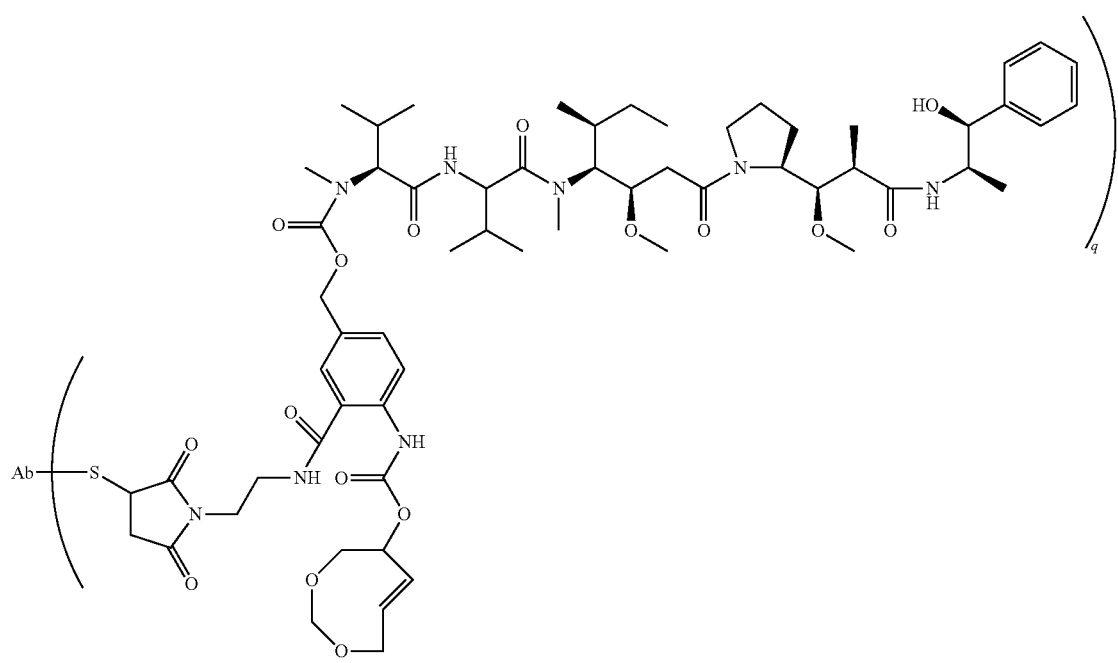

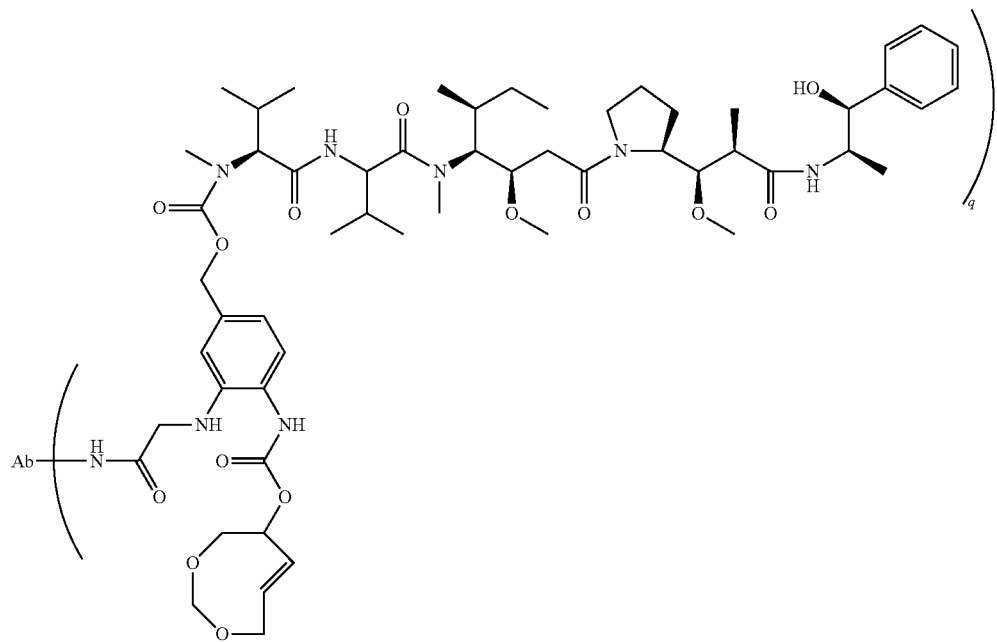
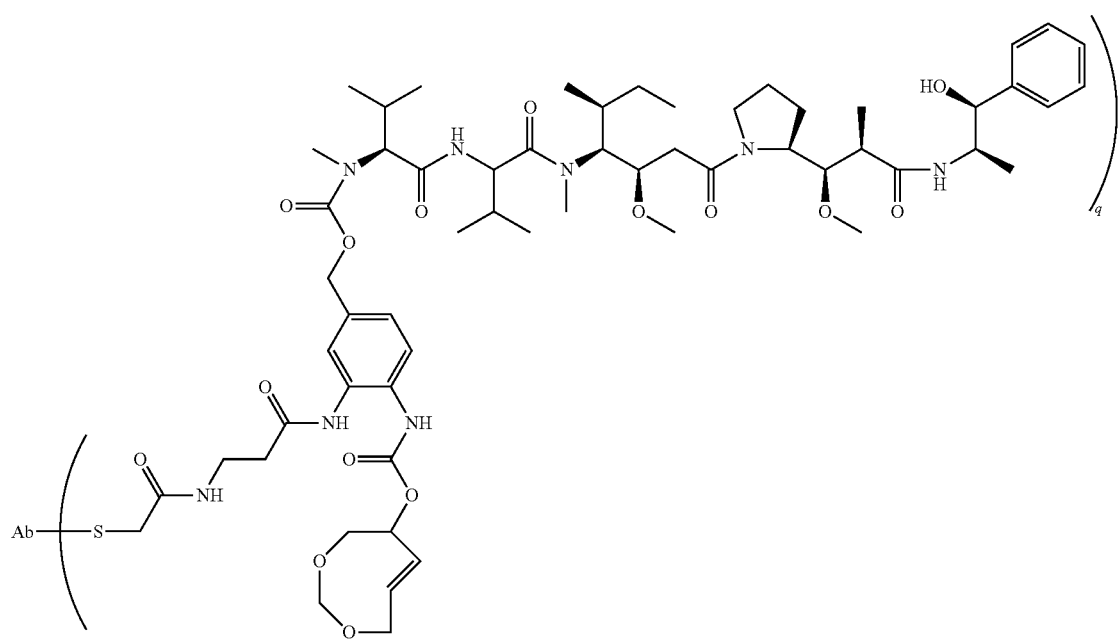

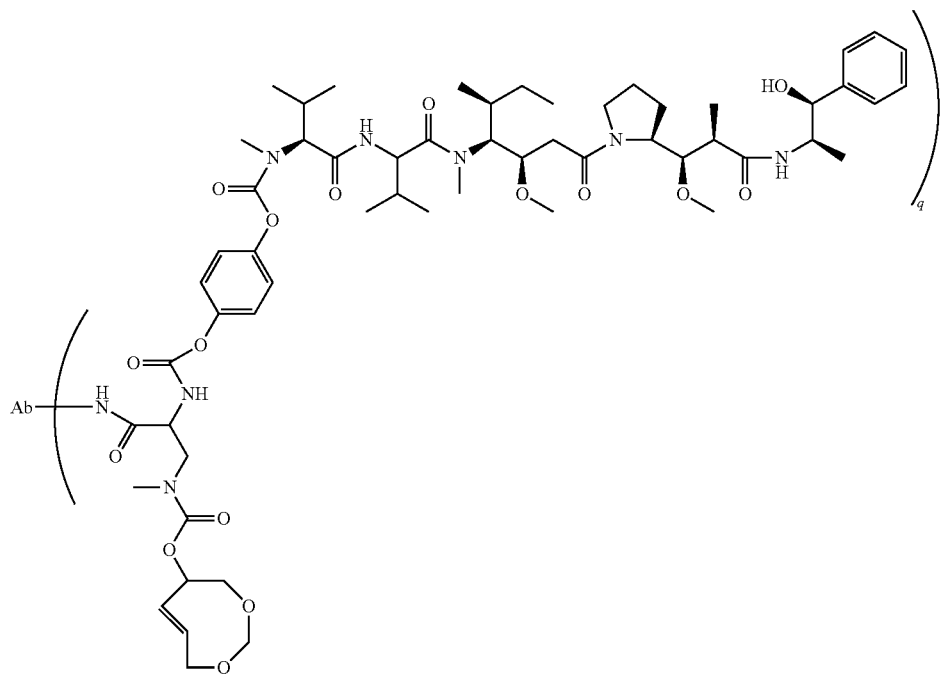
Example 24
Structures of Antibody-Drug Conjugates, which Function Via Cyclization and Cascade Elimination
Auristatin E (MMAE) toxin is attached to a TCO trigger and via $S^P$ to a targeting antibody or fragment (conjugated through cysteine or lysine residue). Ab=antibody or antibody fragment; q=Ab modification # and is typically between 1 and 10.
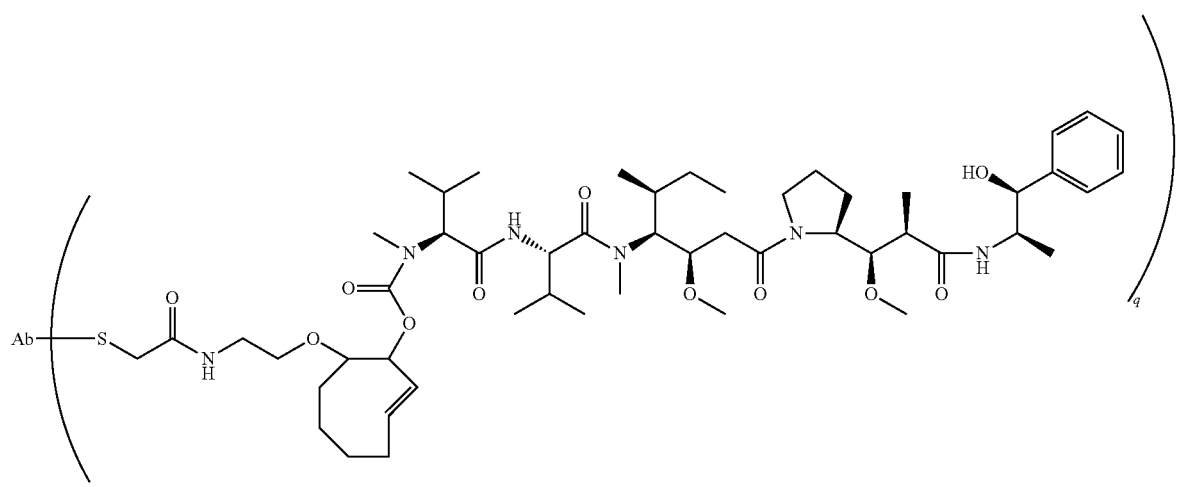

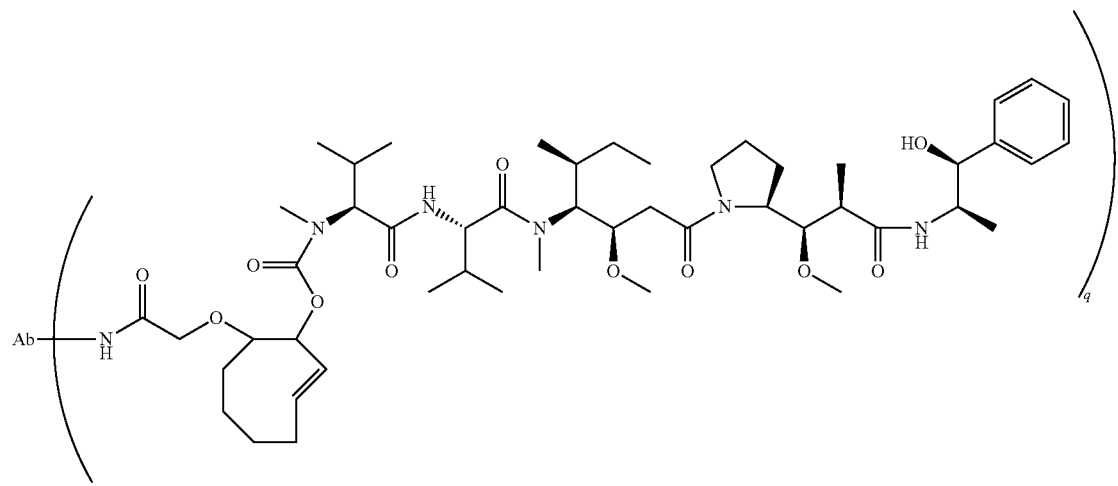
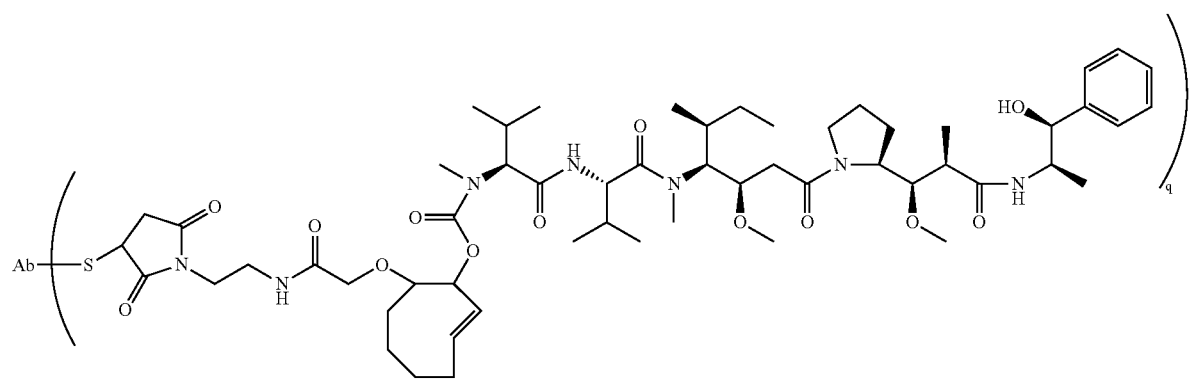
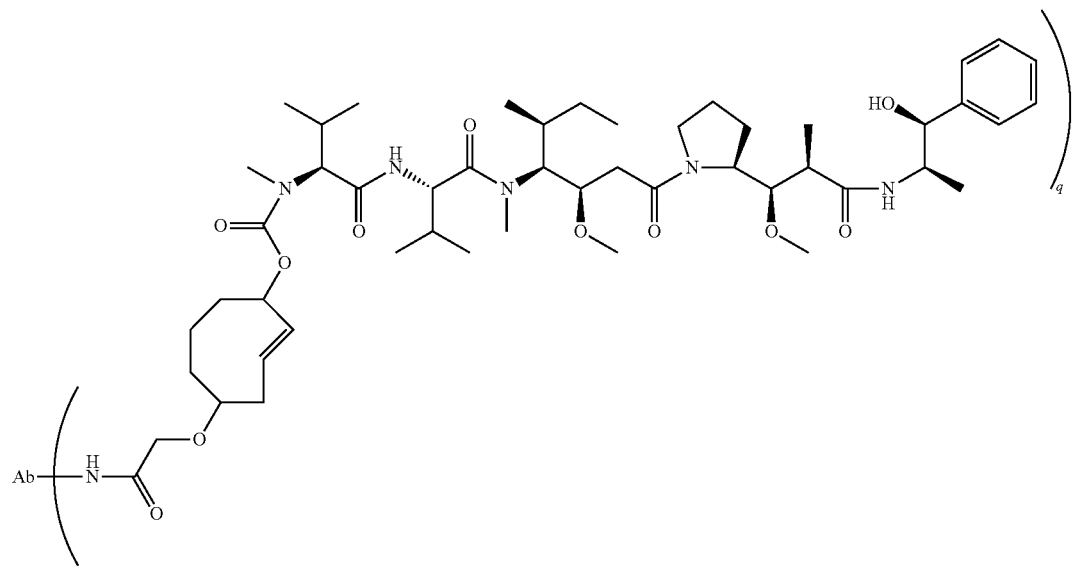

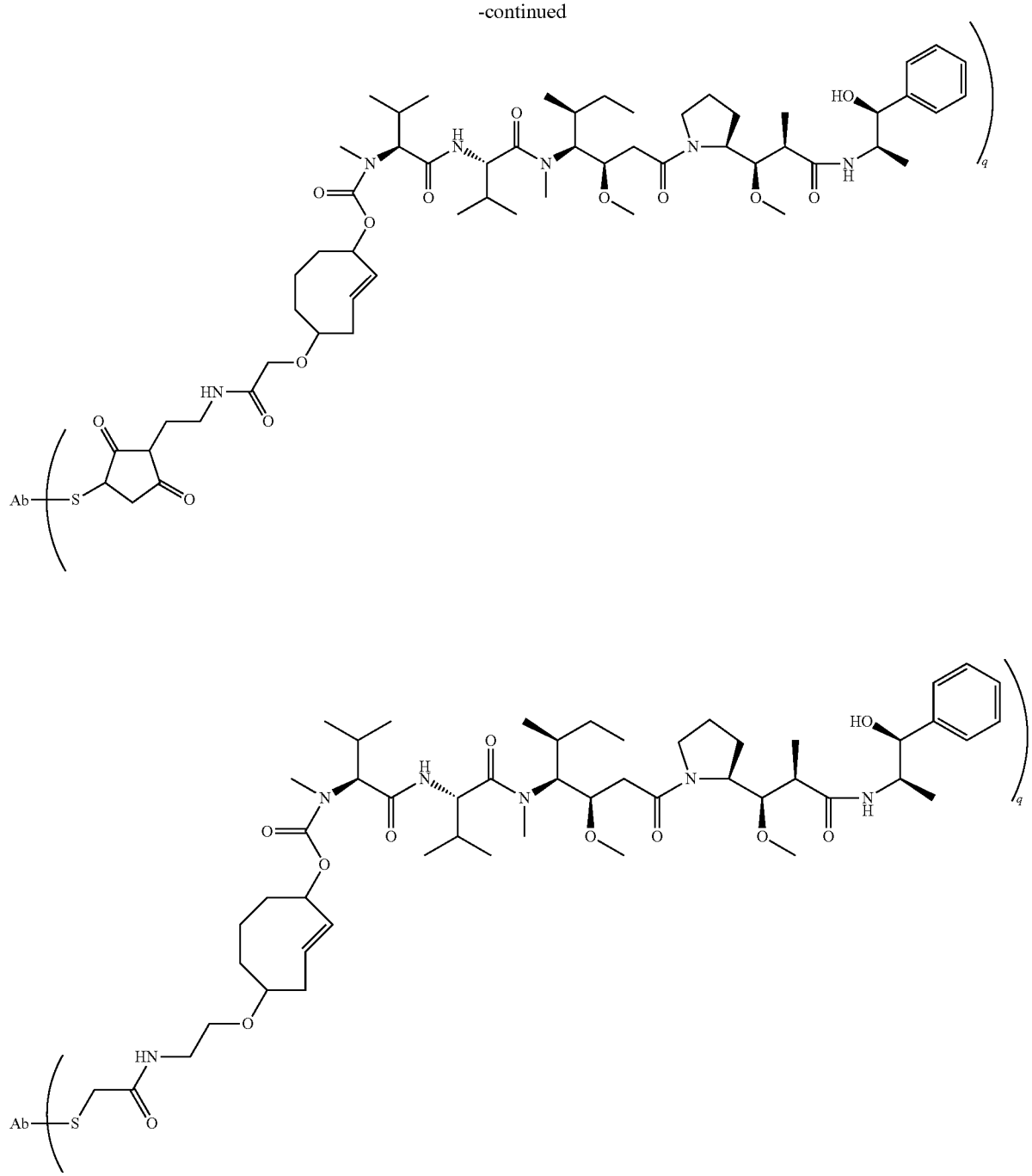

Example 25

Structures of Antibody-Drug Conjugates, which Function Via Cyclization and Cascade Elimination Maytansine toxin is attached via a self immolative linker $L^D$ to a TCO trigger and, in cases via $S^P$, to a targeting antibody or fragment (conjugated through cysteine or lysine residue). Ab=antibody or antibody fragment; q=Ab modification ratio and is typically between 1 and 10.

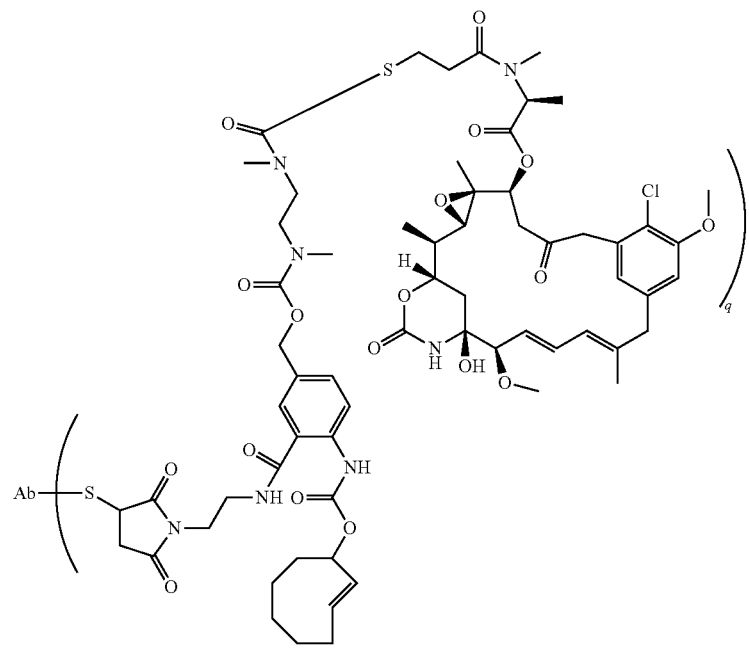
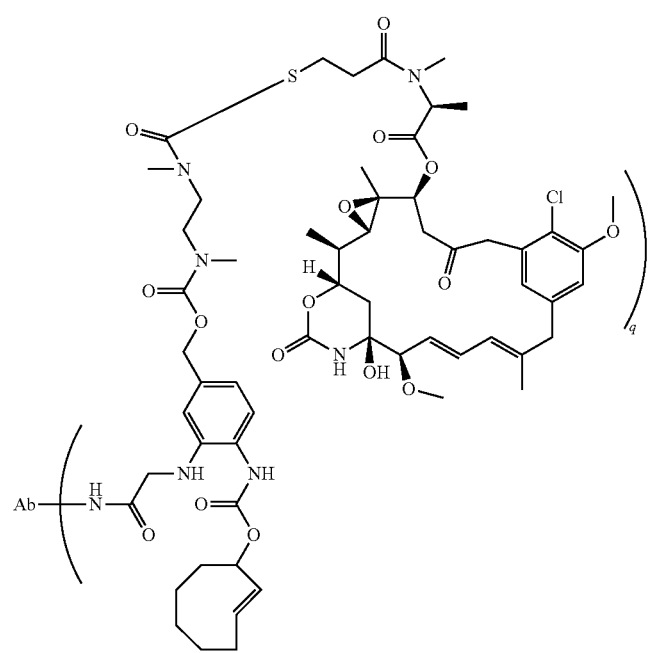

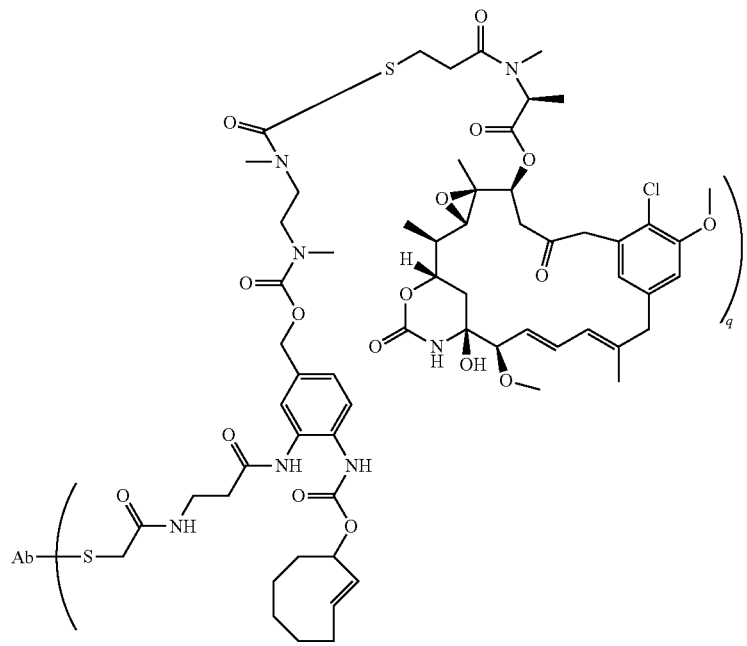
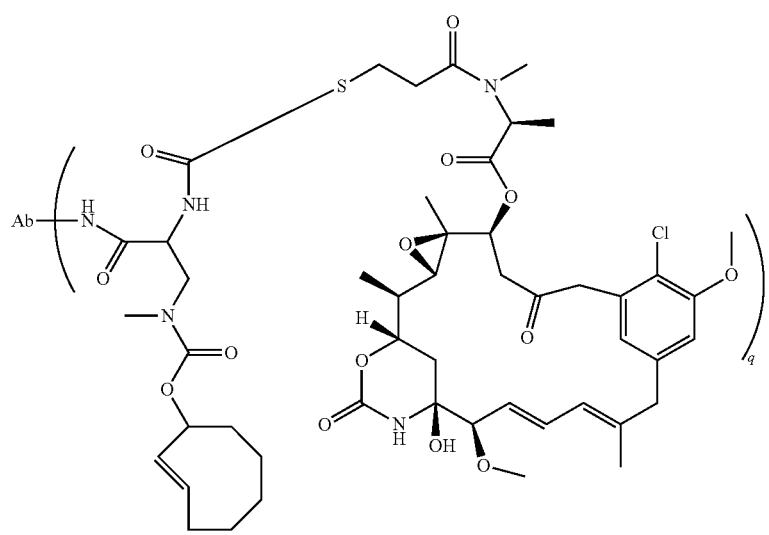

-continued
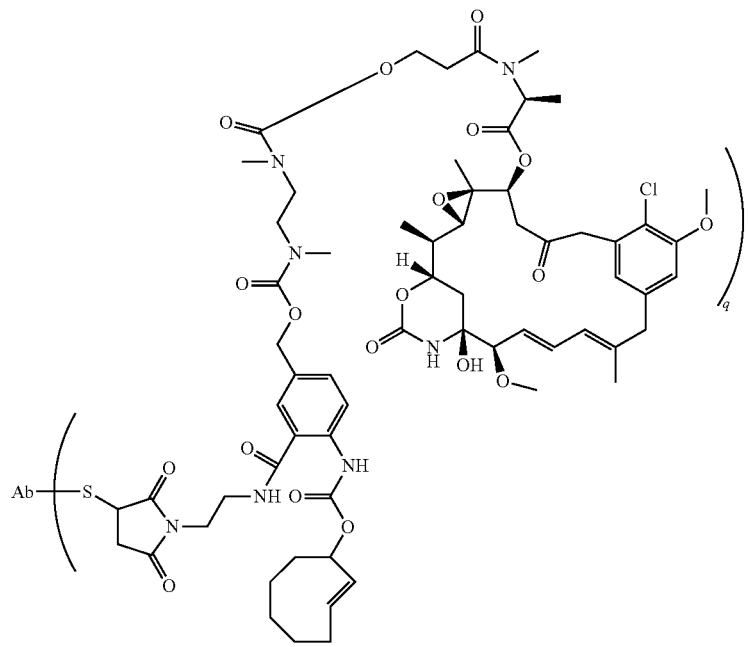
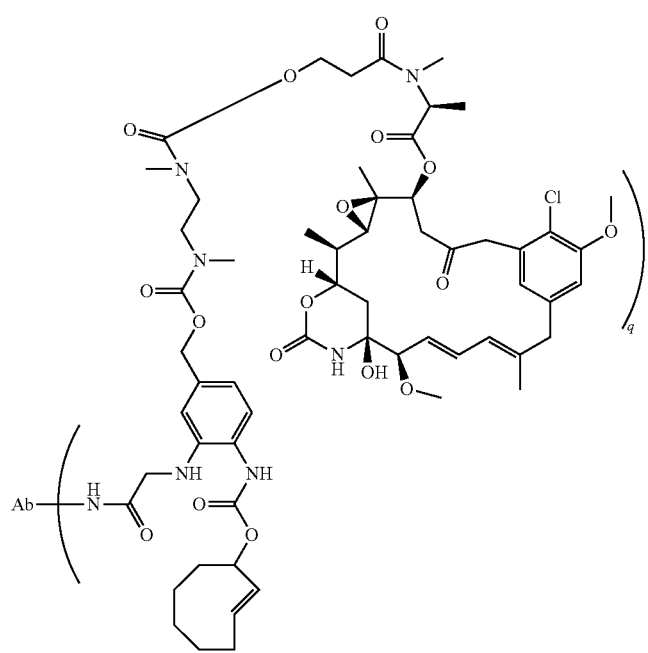

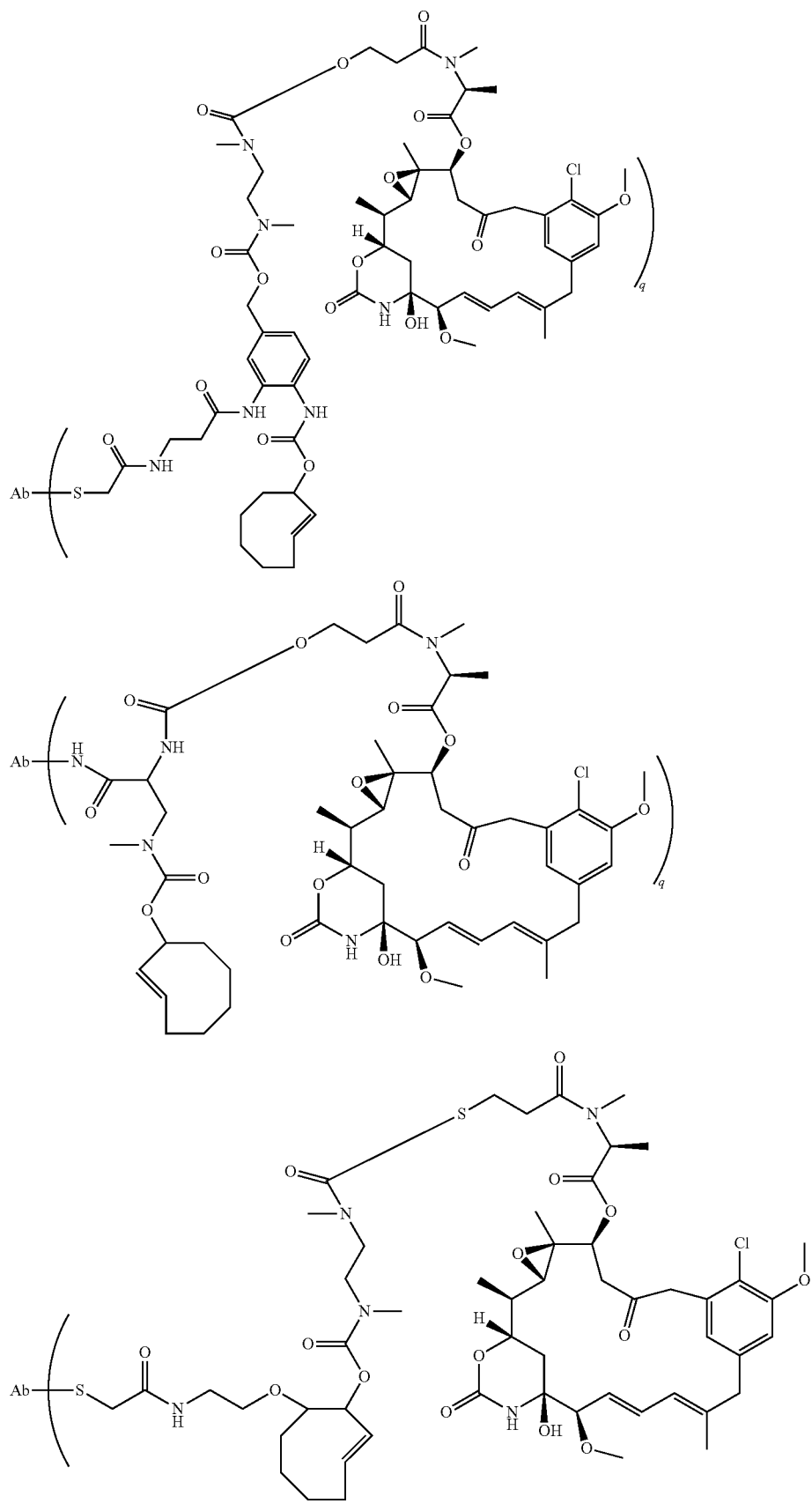

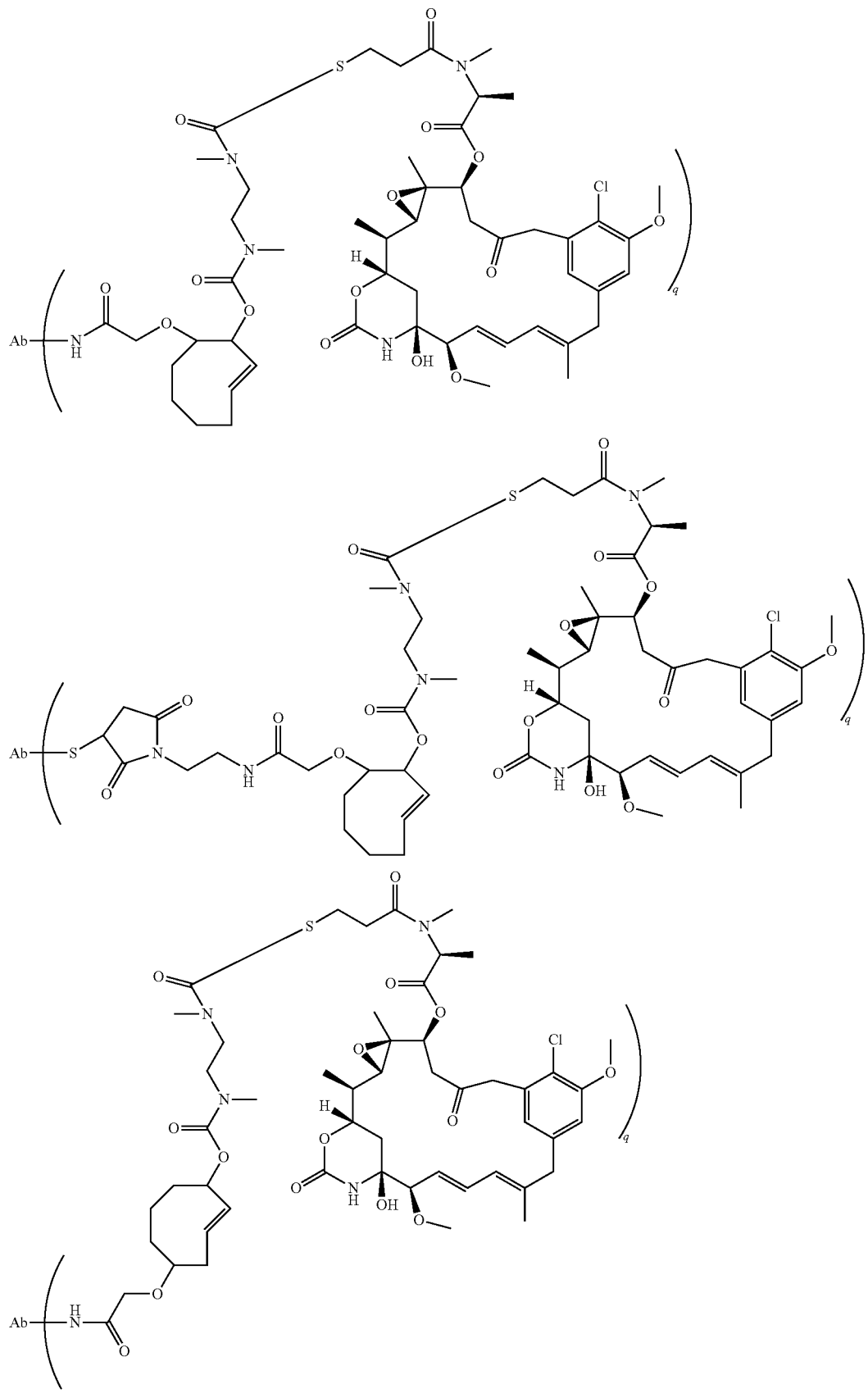

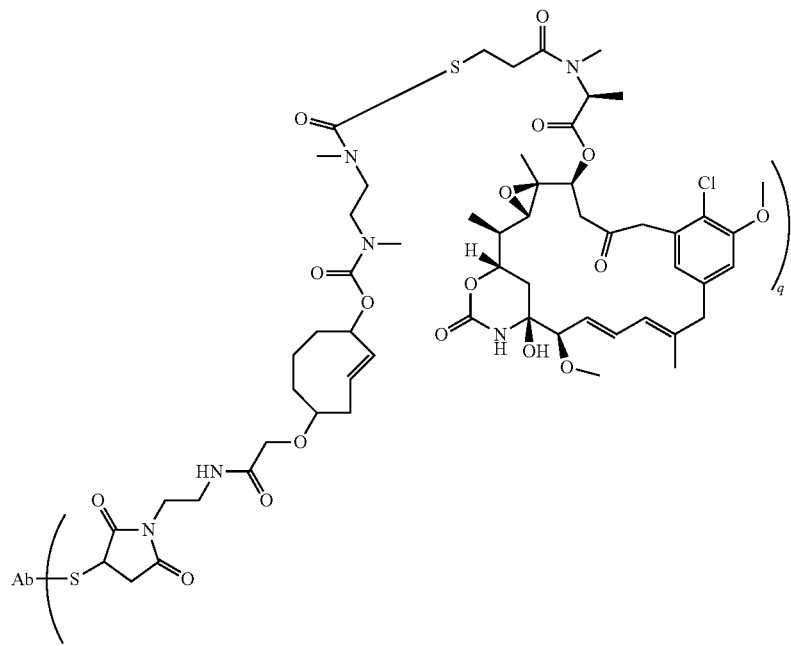
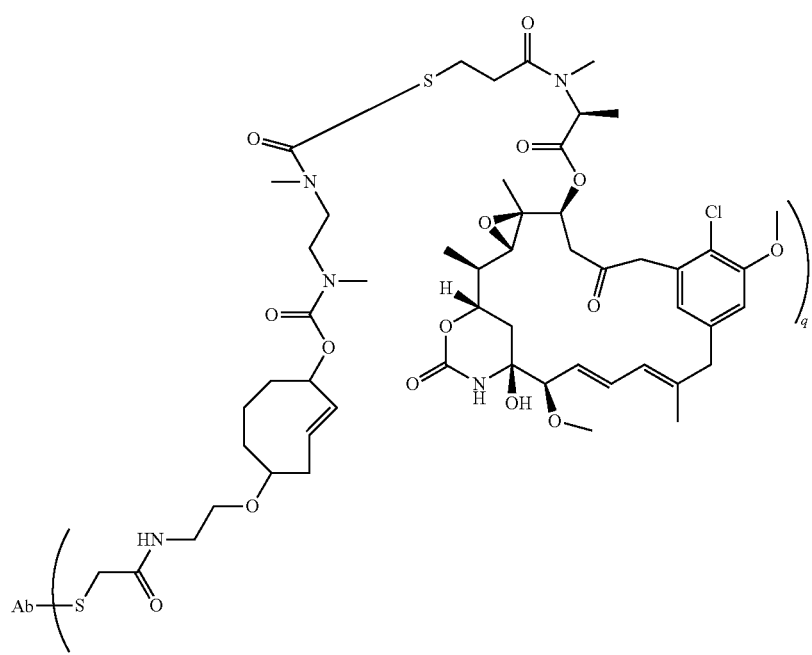

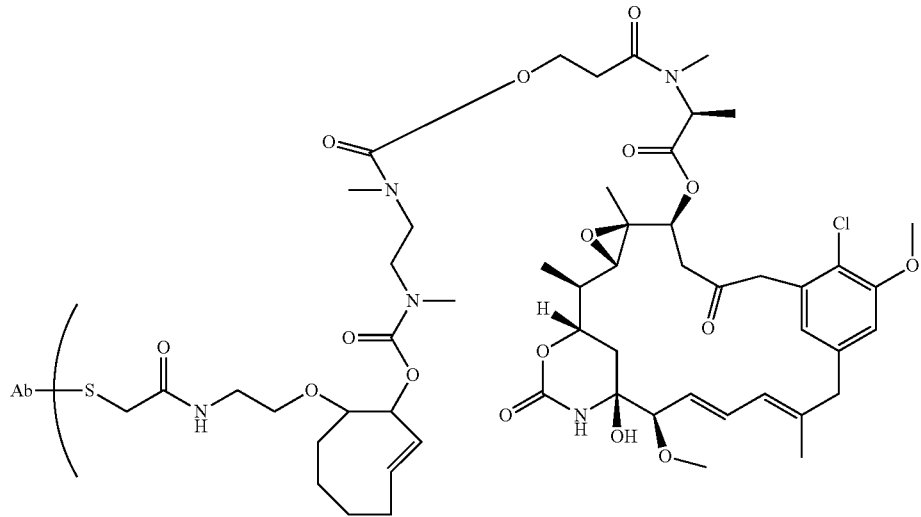
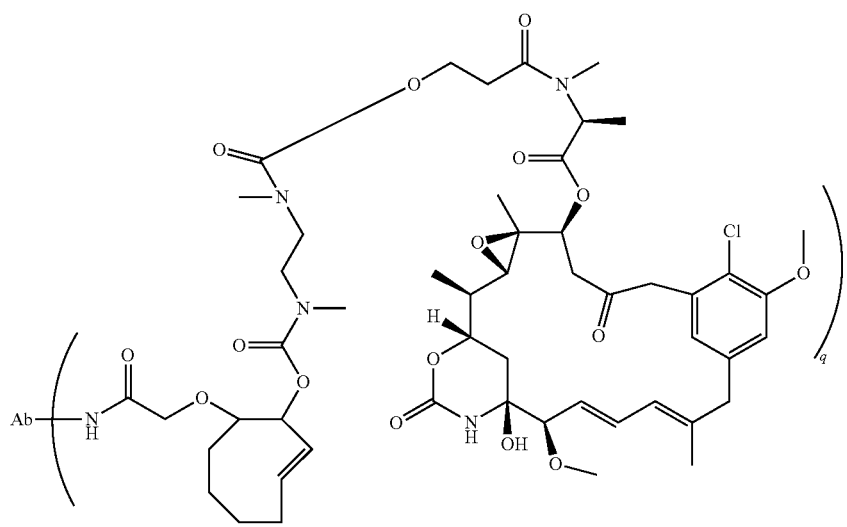
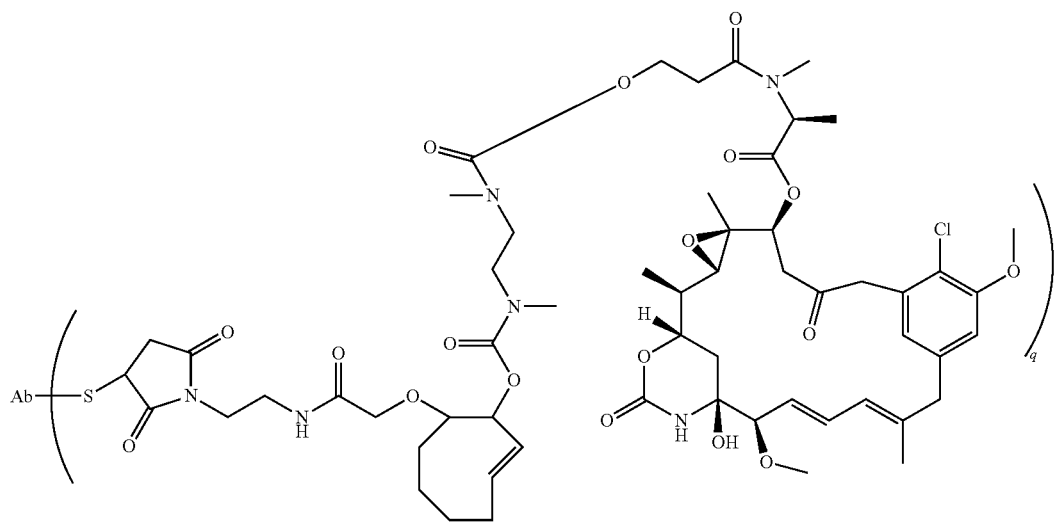

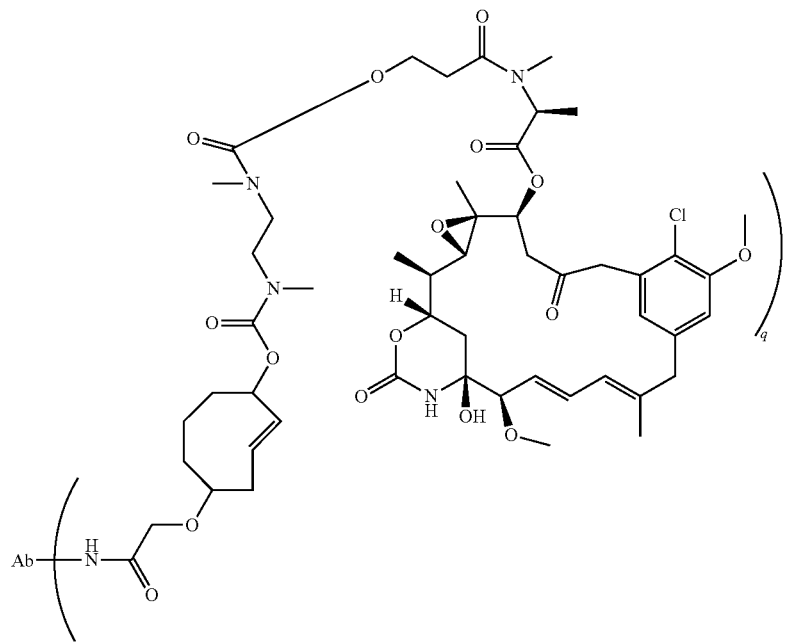
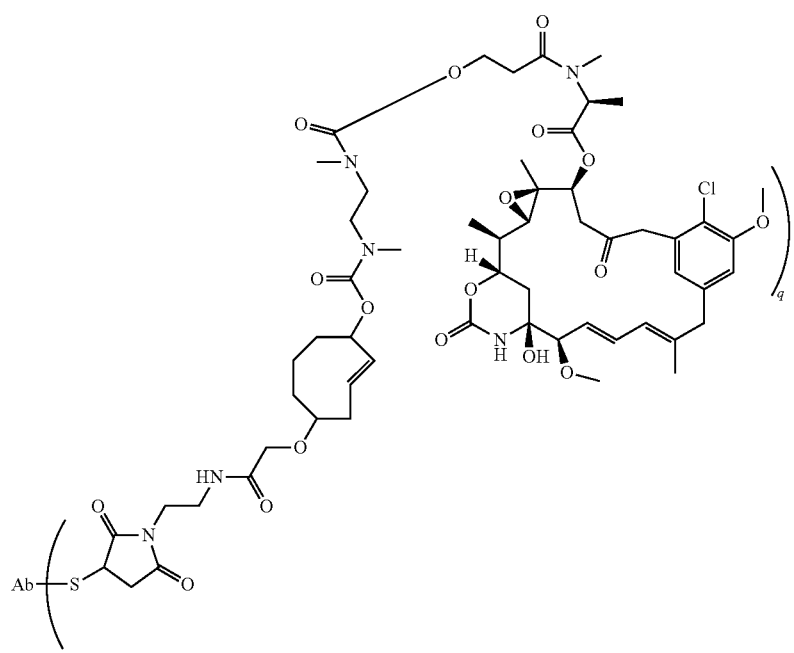

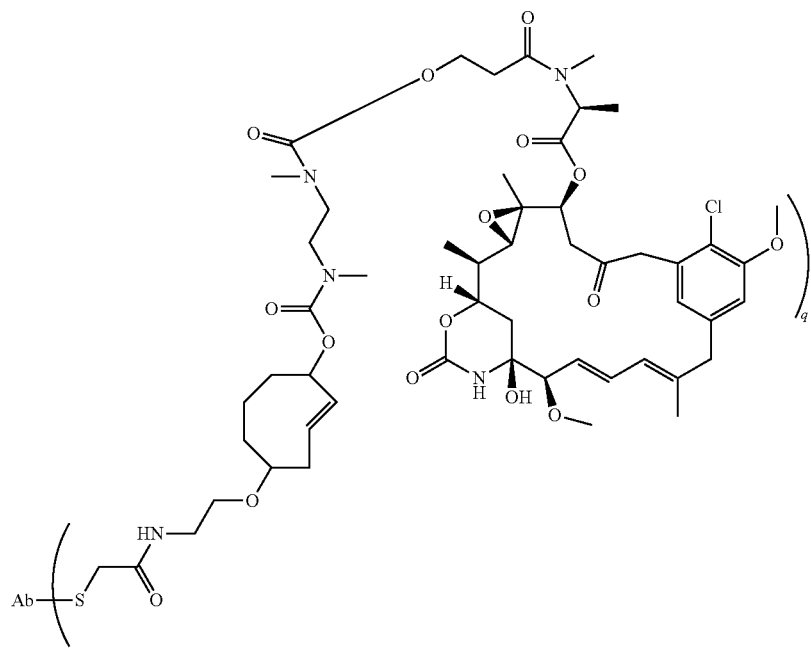
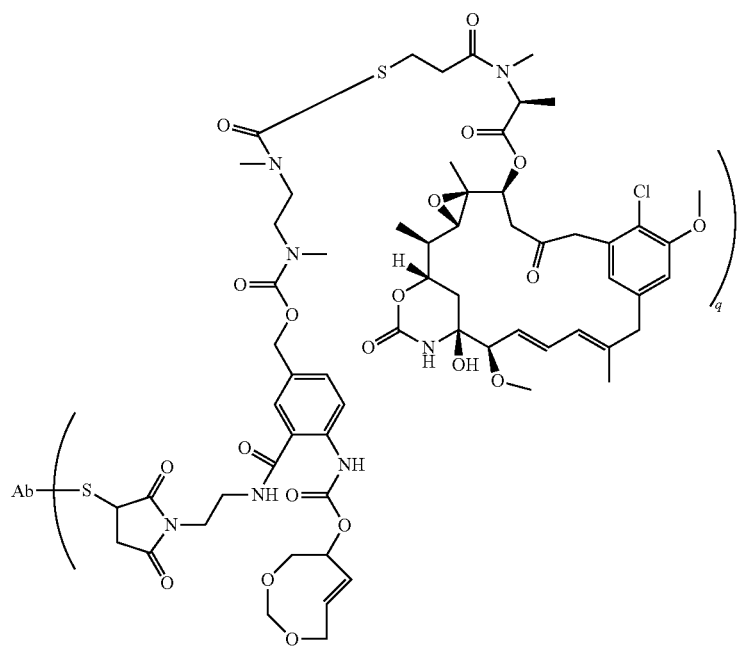

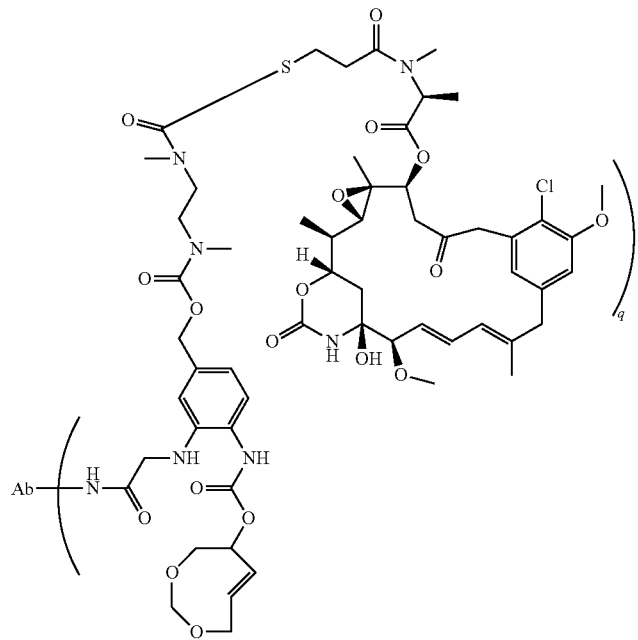
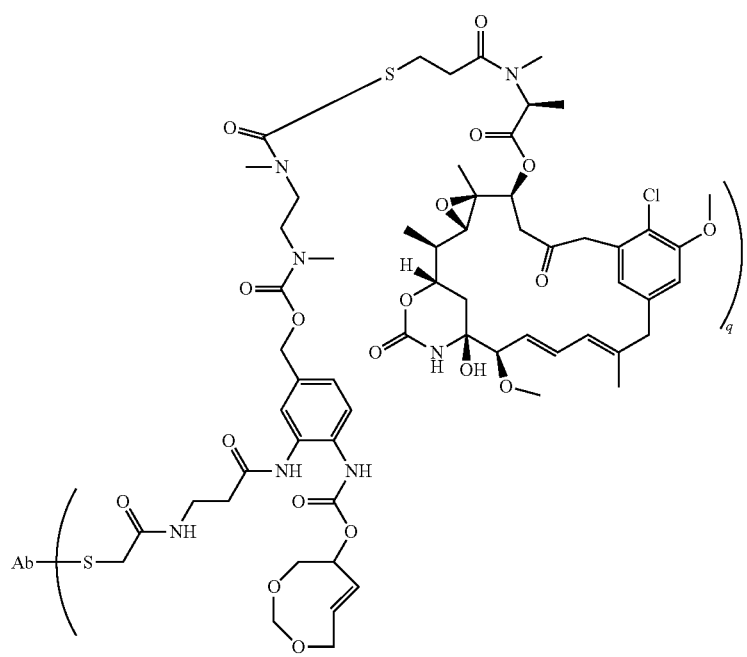

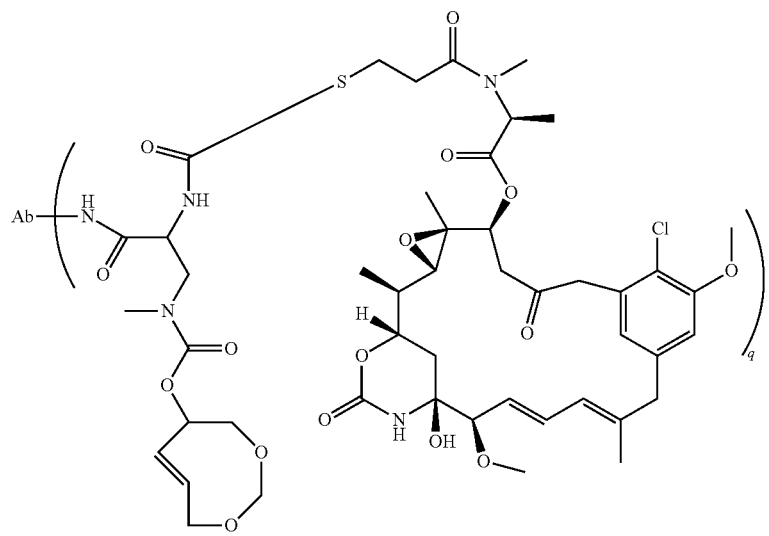
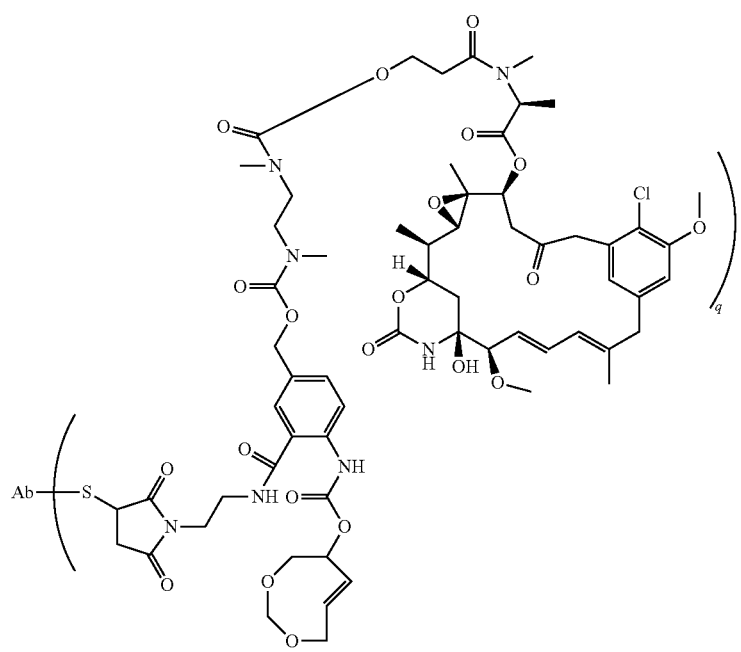

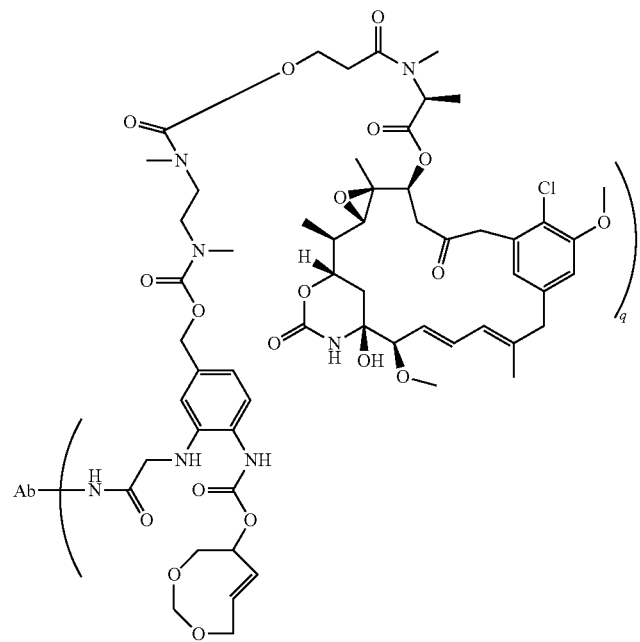
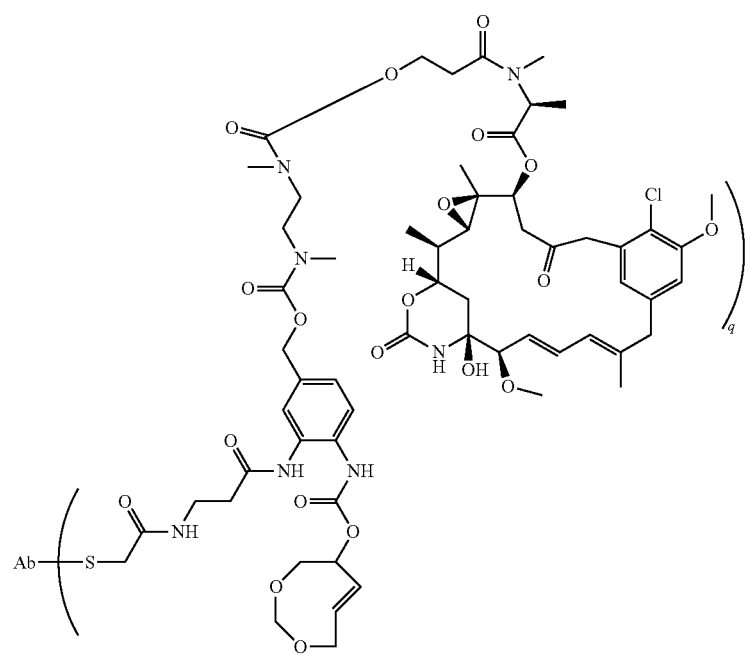

Example 26

Structures of Trigger-Drug Constructs that can be Conjugated to a Targeting Agent $T^T$ Eg Via an Amine or Thiol Moiety, and which Function Via Cyclization Elimination Auristatin E (MMAE) toxin is attached via a self immolative linker $L^D$ to a TCO trigger and via $S^P$ to a reactive moiety for $T^T$ conjugation.

Example 27

Structures of Trigger-Drug Constructs that can be Conjugated to a Targeting Agent $T^T$ Eg Via an Amine or Thiol Moiety, and which Function Via the Cyclization Elimination Maytansine toxin is attached via a self immolative linker $L^D$ to a TCO trigger and via $S^P$ to a reactive moiety for $T^T$ conjugation.

243
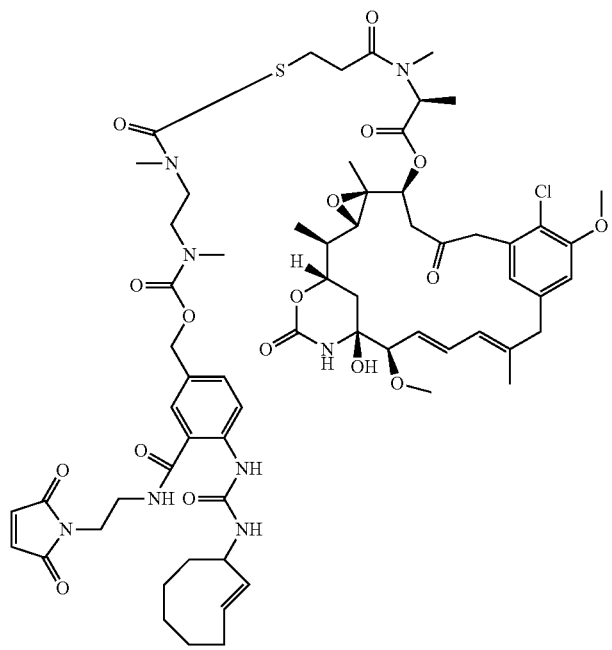
244
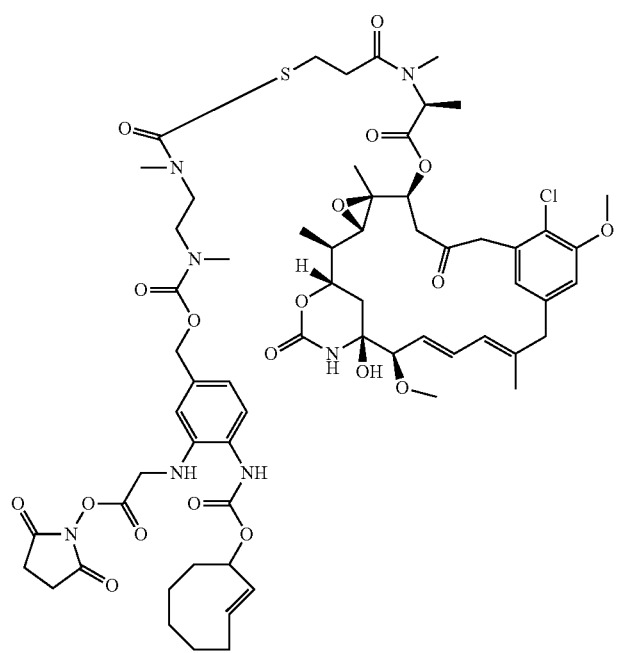

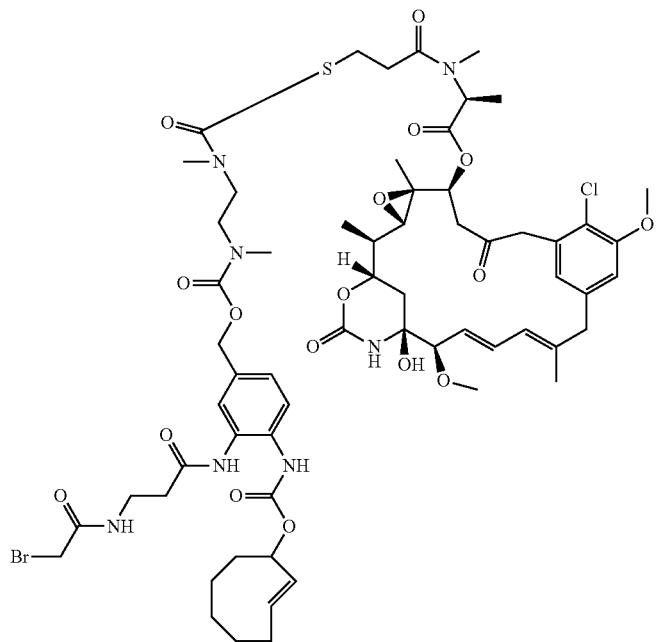
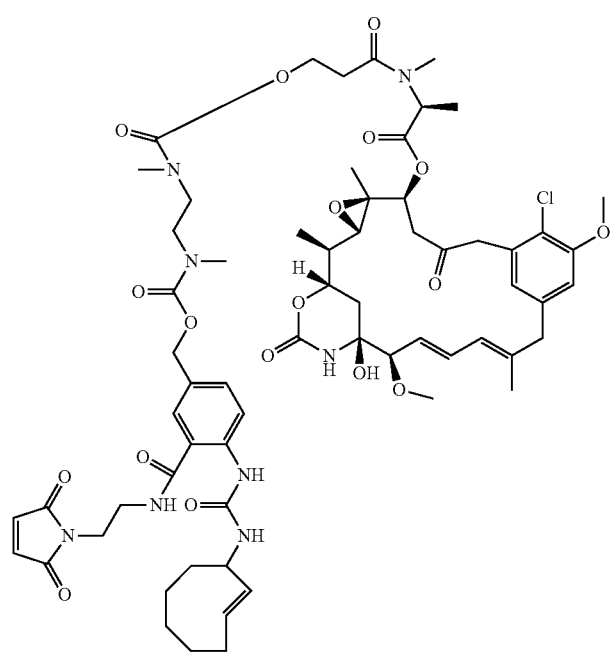

Example 28

Structures of Trigger-Drug Constructs that can be Conjugated to a Targeting Agent $T^T$ Eg Via an Amine or Thiol Moiety, and which Function Via Cyclization and Cascade Elimination Auristatin E (MMAE) toxin is attached via a self immolative linker $L^D$ to a TCO trigger and, in cases via $S^P$, to a reactive moiety for $T^T$ conjugation.

249
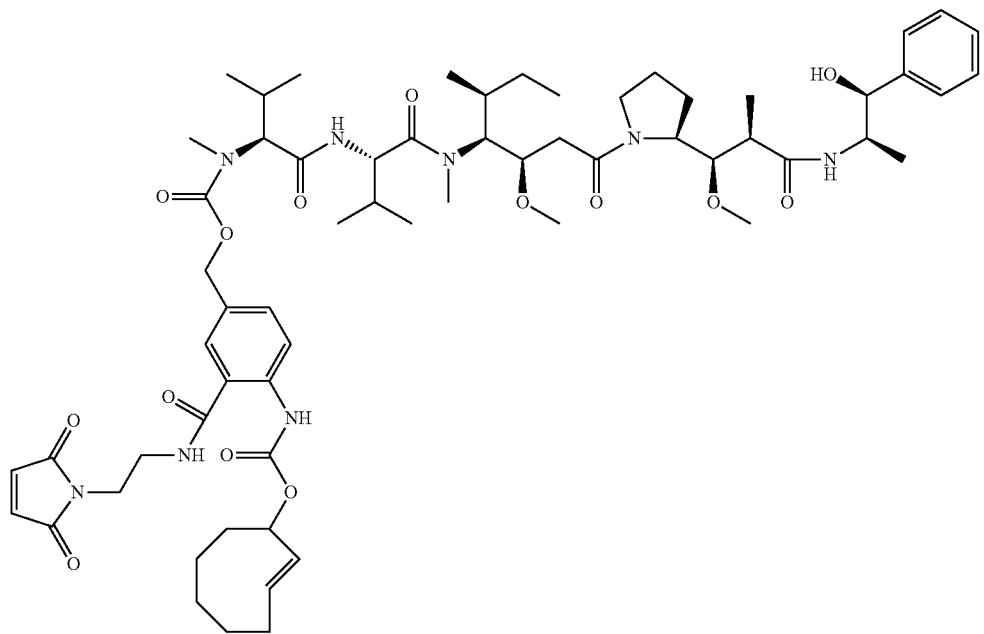
250
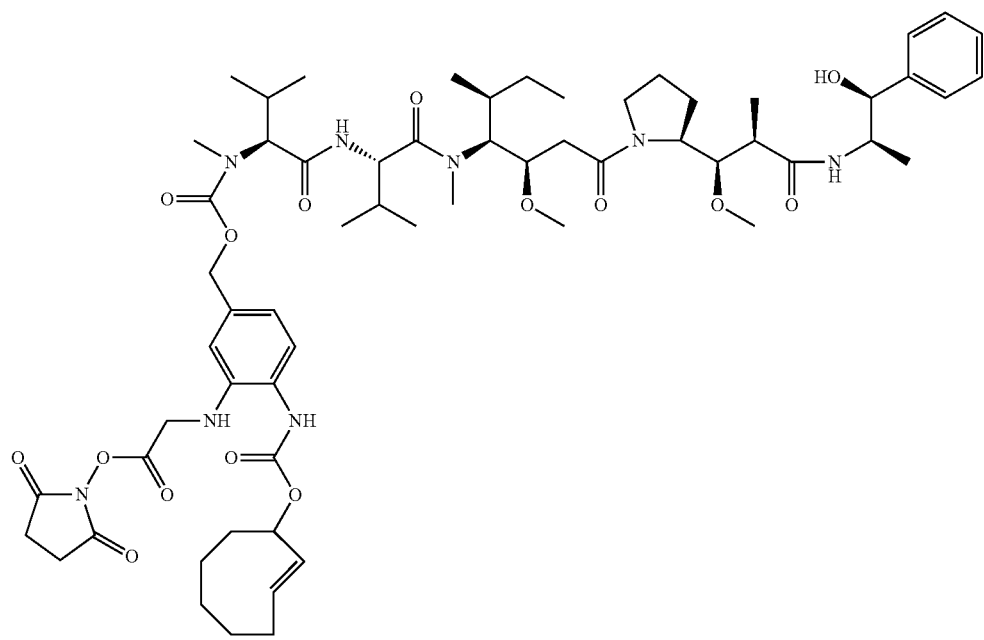

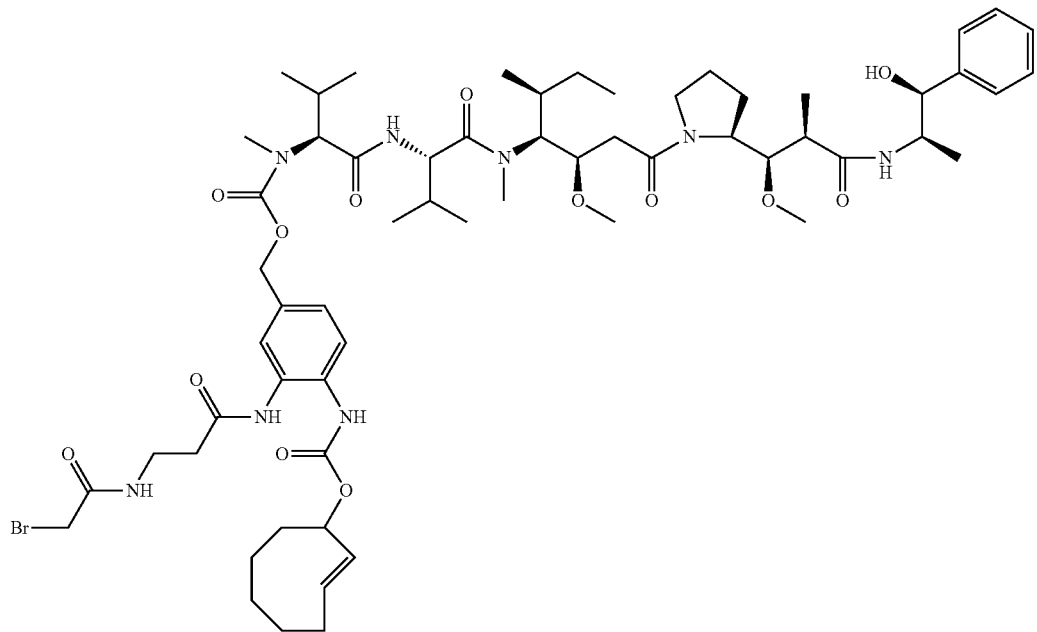 [SMILES: CC[C@H](C)[C@@H]([C@@H](CC(=O)N1CCC[C@H]1[C@H](OC)[C@@H](C)C(=O)N[C@H](C)[C@@H](O)c1ccccc1)OC)N(C)C(=O)[C@@H](NC(=O)[C@H](C(C)C)N(C)C(=O)OCc1ccc(OC(=O)NC2/C=C/CCCCC2)c(NC(=O)CCNC(=O)CBr)c1)C(C)C]
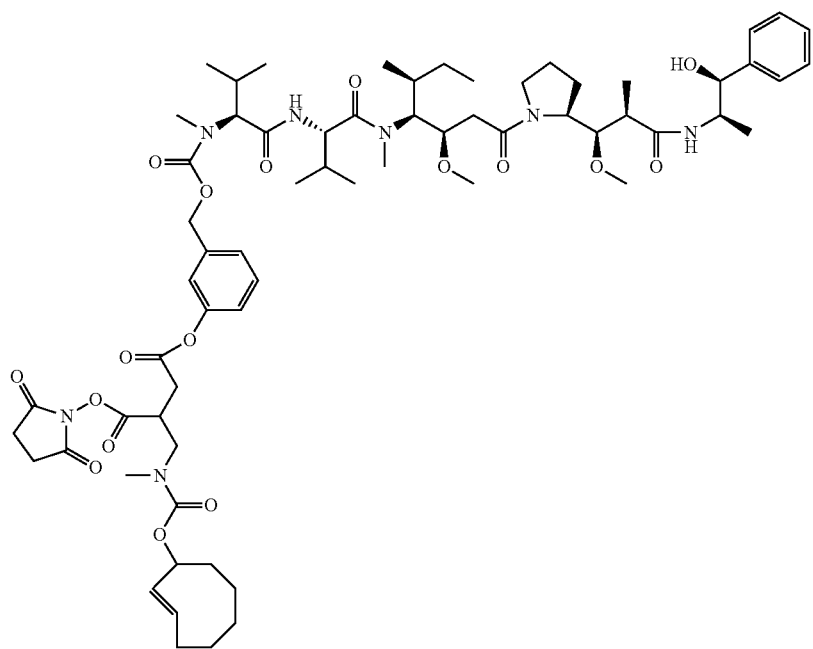

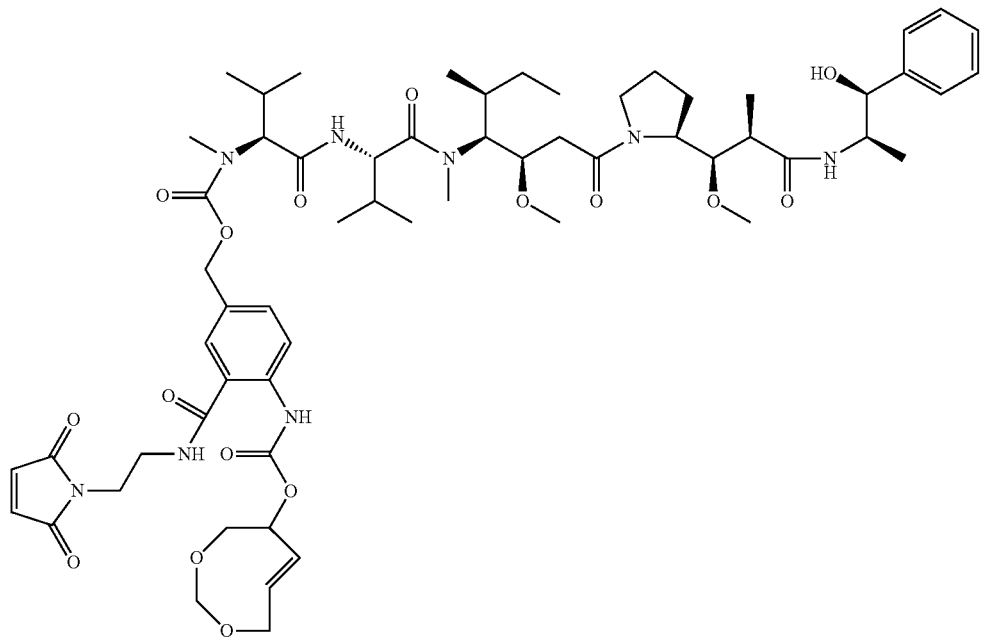
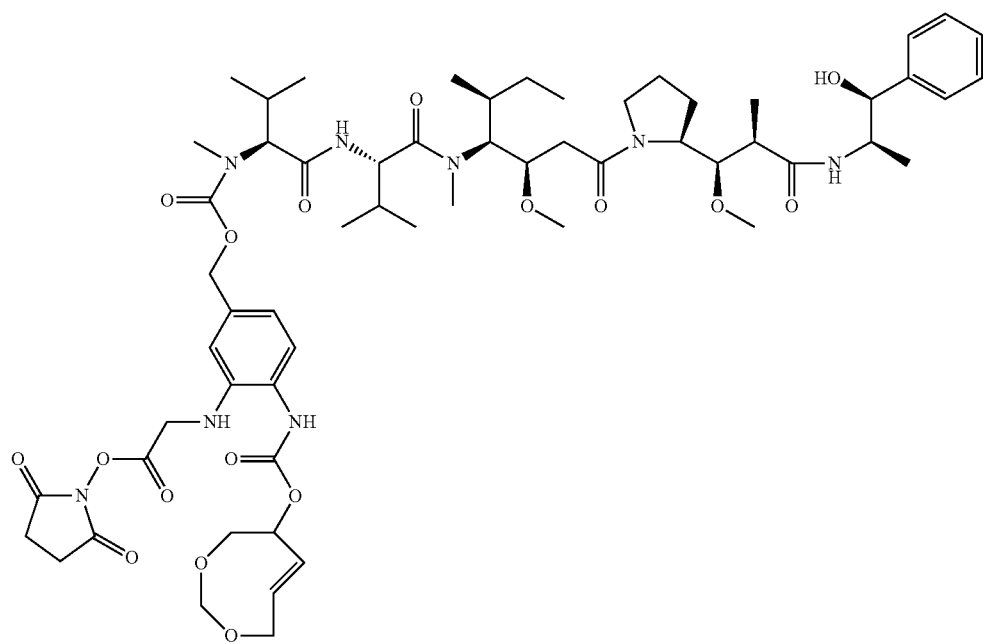

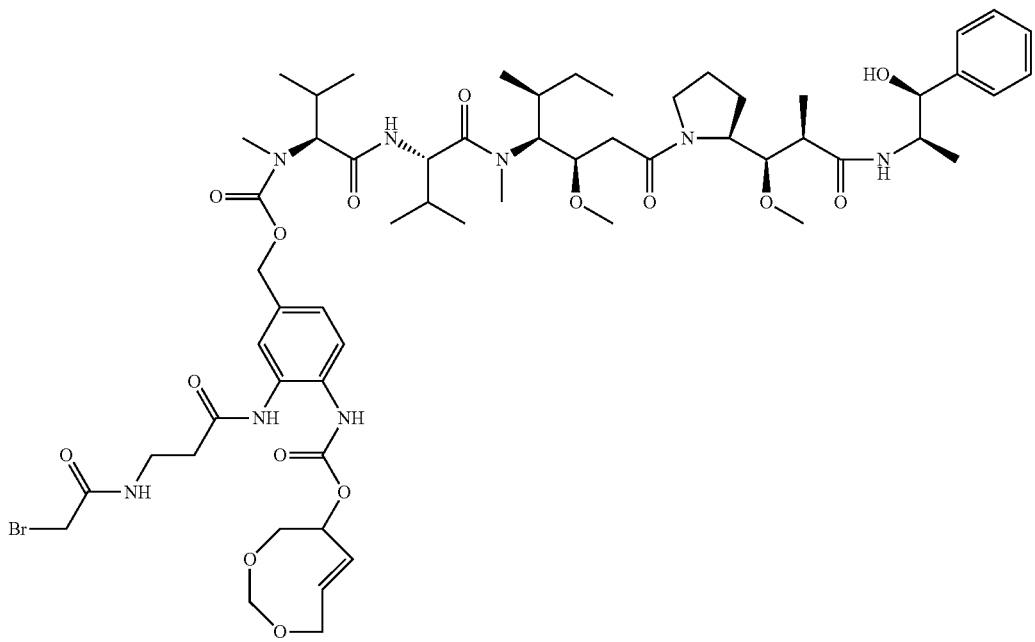
-continued
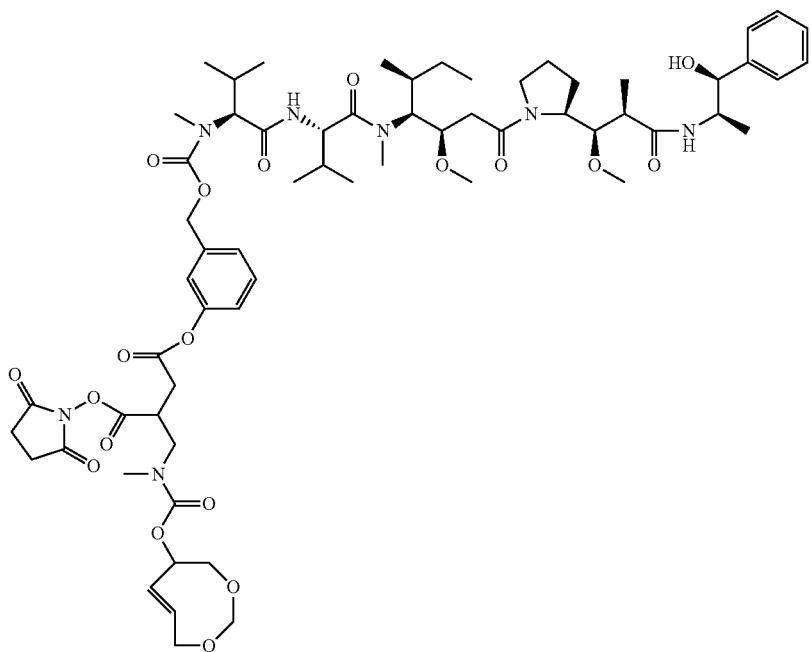
Example 29
Structures of Trigger-Drug Constructs that can be Conjugated to a Targeting Agent $T^T$ Eg Via an Amine or Thiol Moiety, and which Function Via Cyclization and Cascade Elimination
Auristatin E (MMAE) toxin is attached to a TCO trigger and via $S^P$ to a reactive moiety for $T^T$ conjugation.

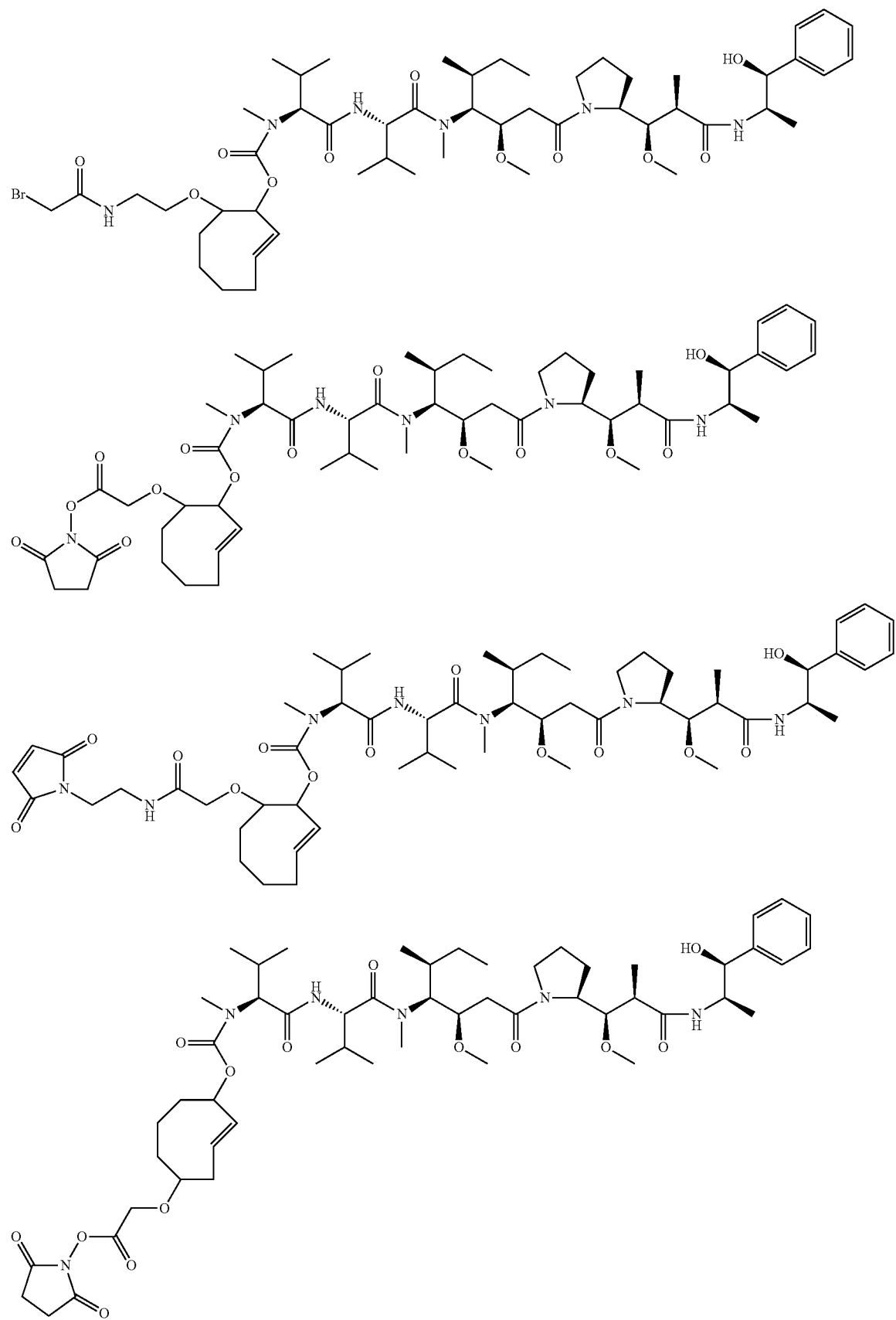

Example 30

Structures of Trigger-Drug Constructs that can be Conjugated to a Targeting Agent $T^T$ Eg Via an Amine or Thiol Moiety, and which Function Via Cyclization and Cascade Elimination Maytansine toxin is attached via a self immolative linker $L^D$ to a TCO trigger $T^R$ and, in Cases Via $S^P$, to a Reactive Moiety for $T^T$ Conjugation.

261
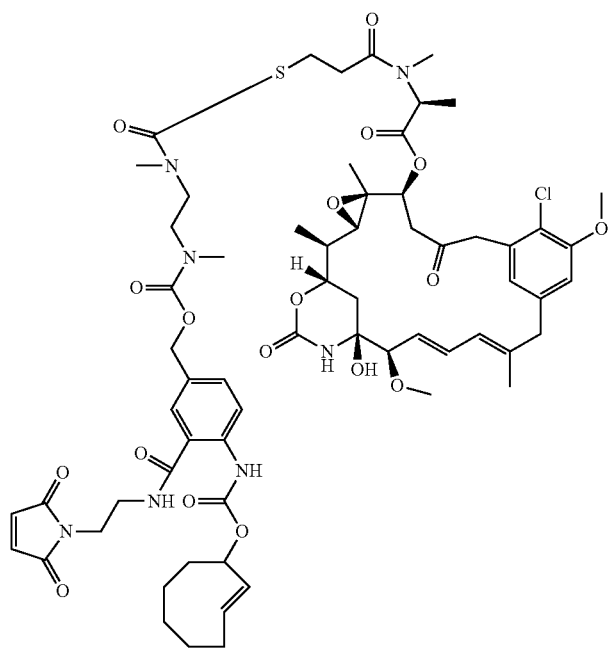
262
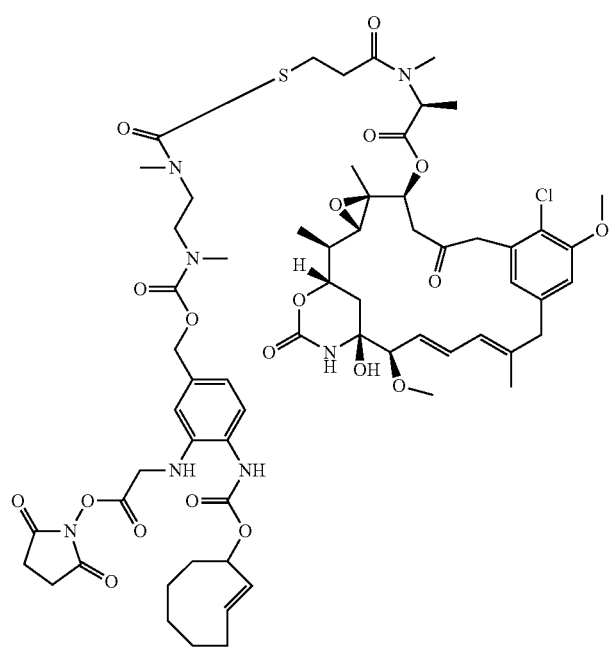

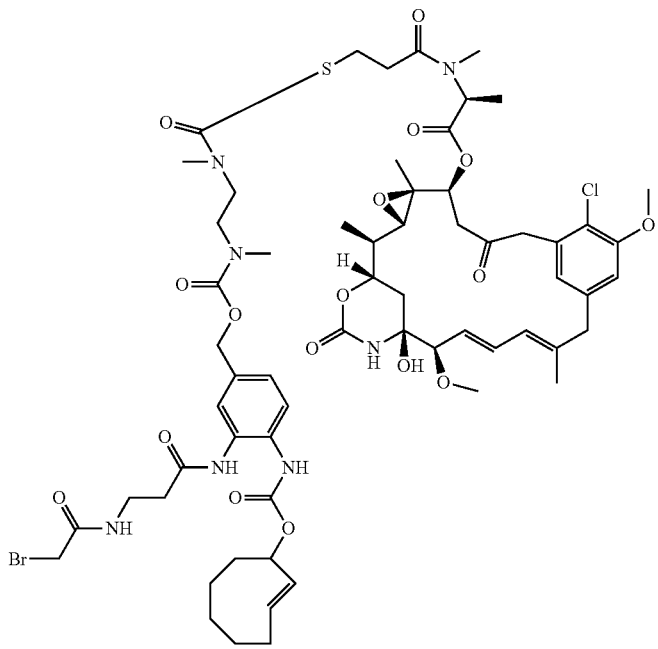
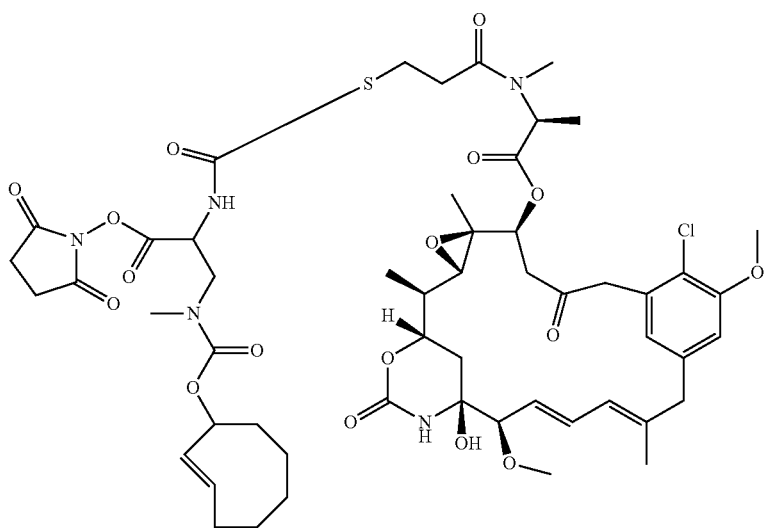

-continued
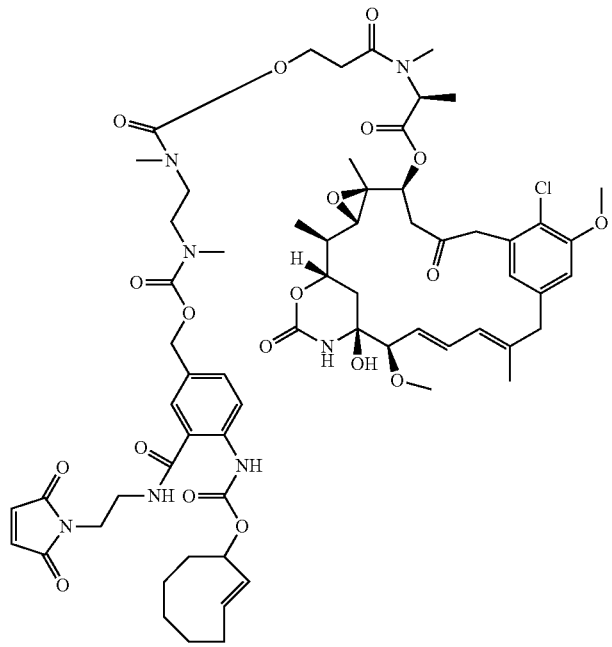
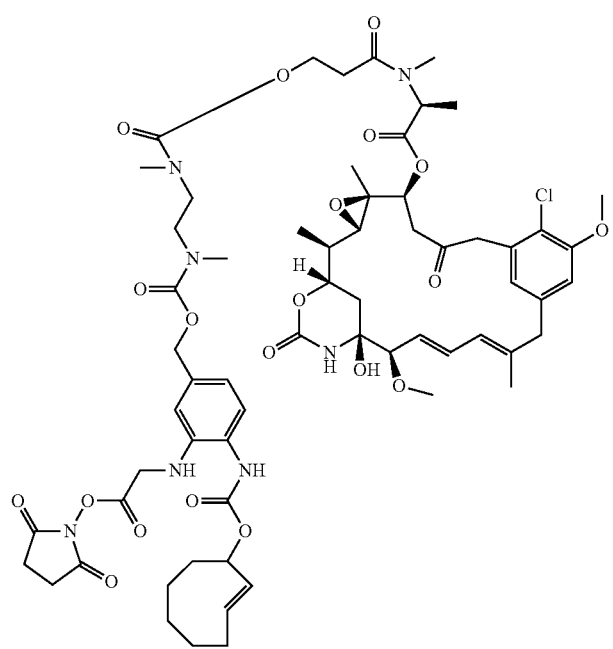

-continued
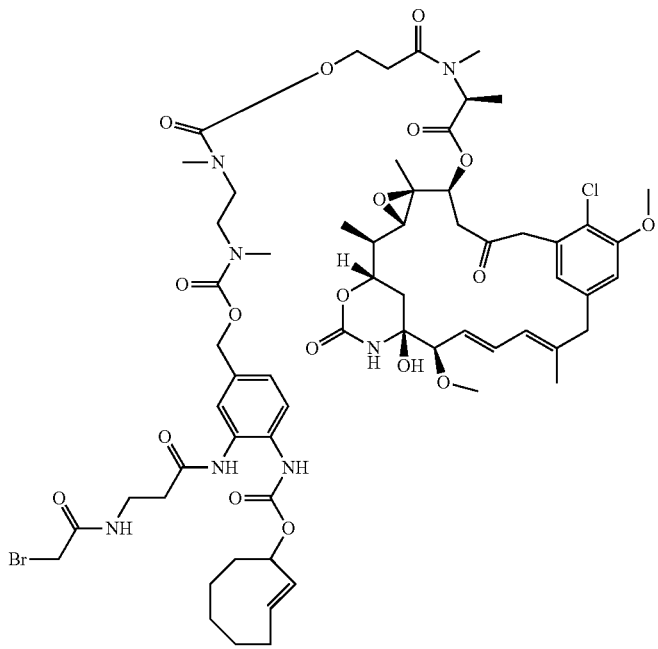
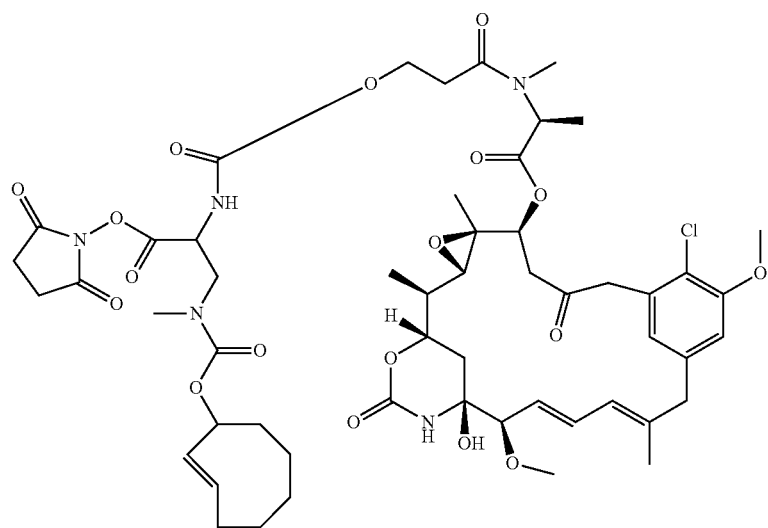

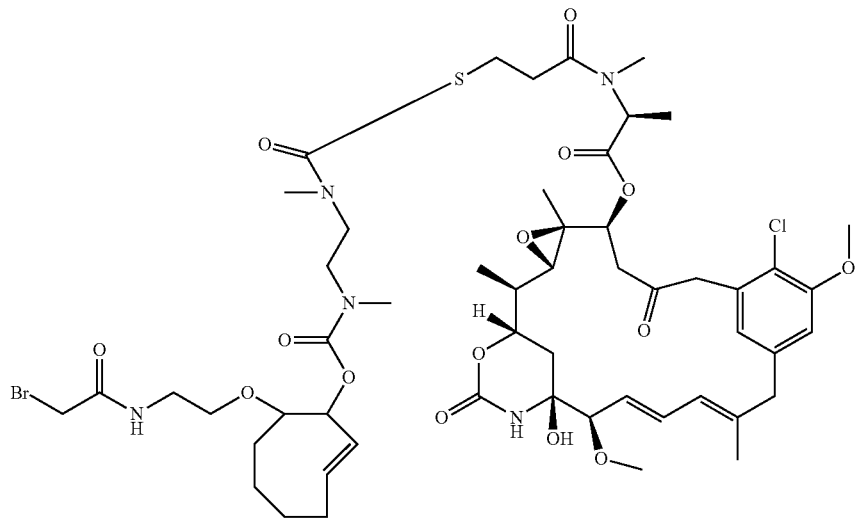
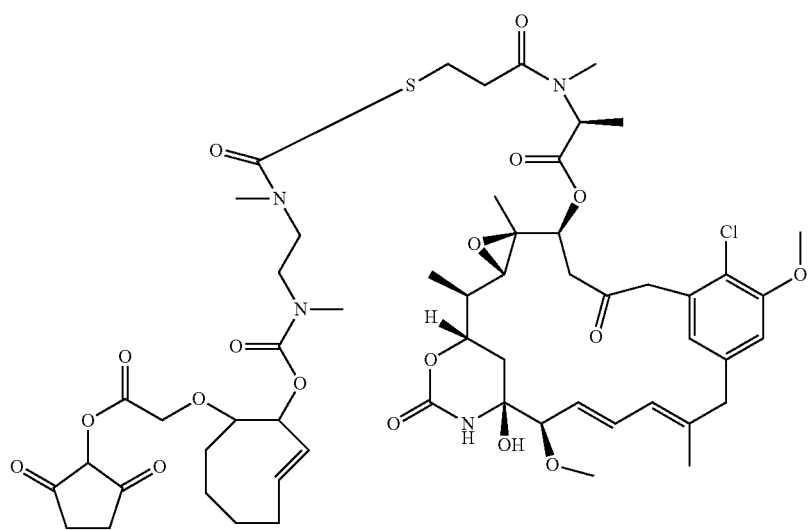

-continued
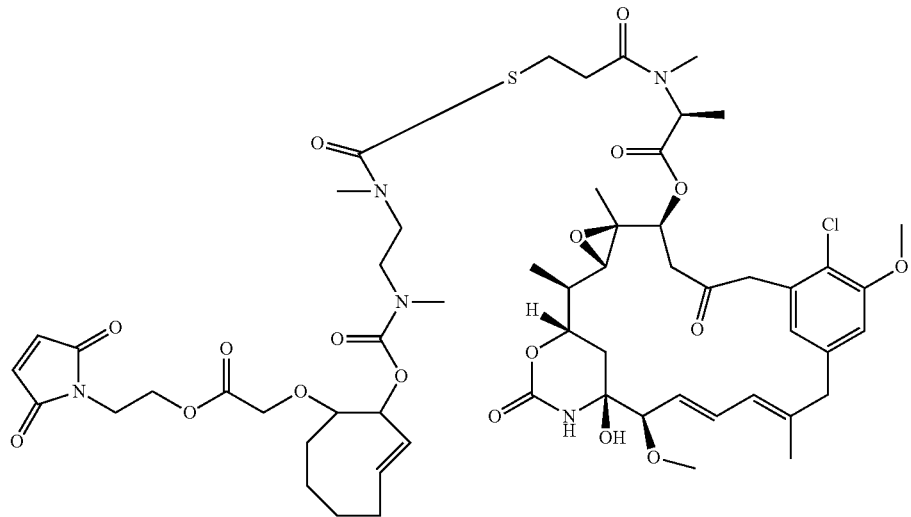
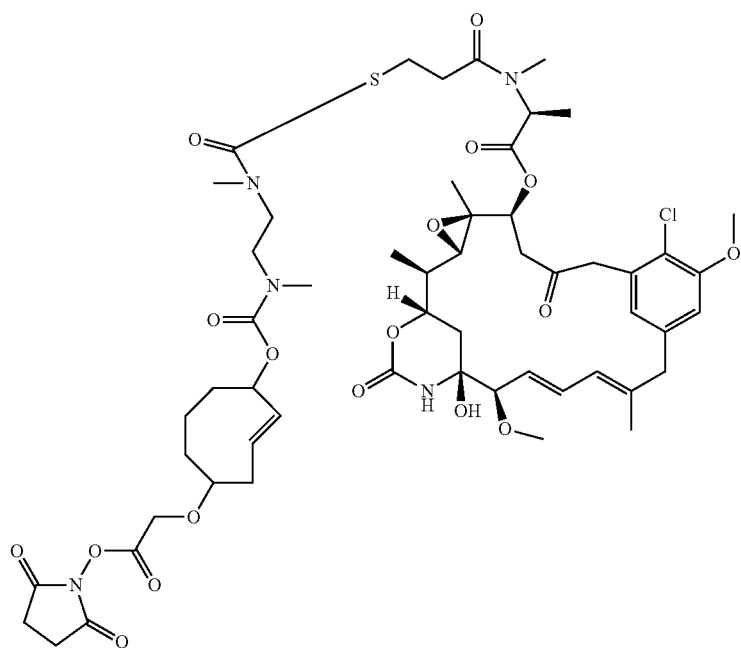

-continued
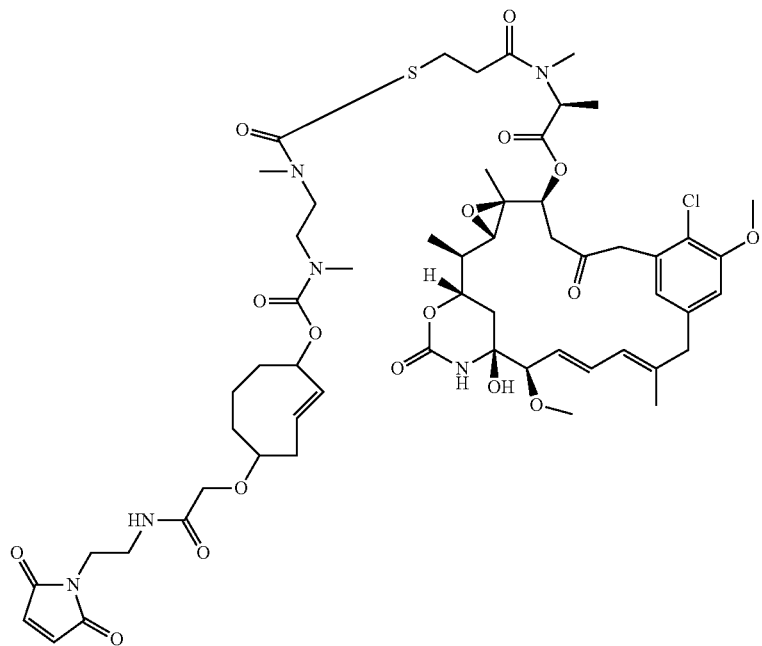
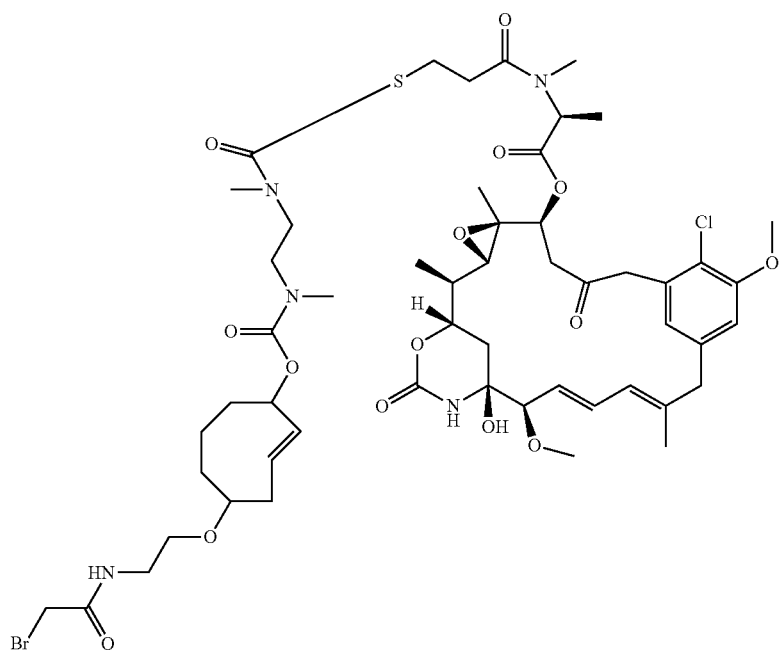

-continued
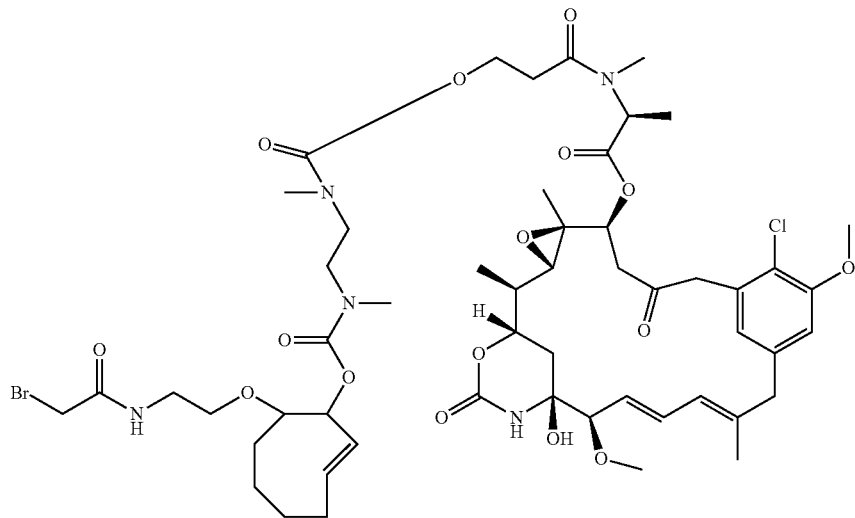
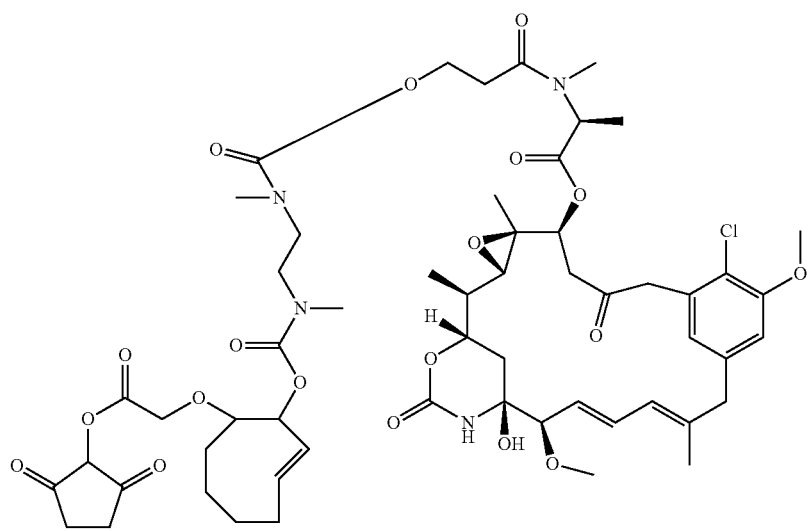

-continued
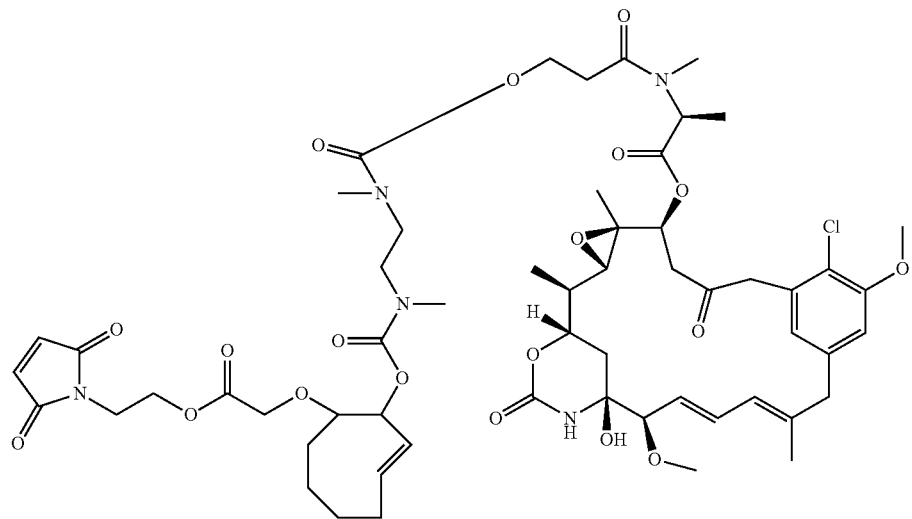
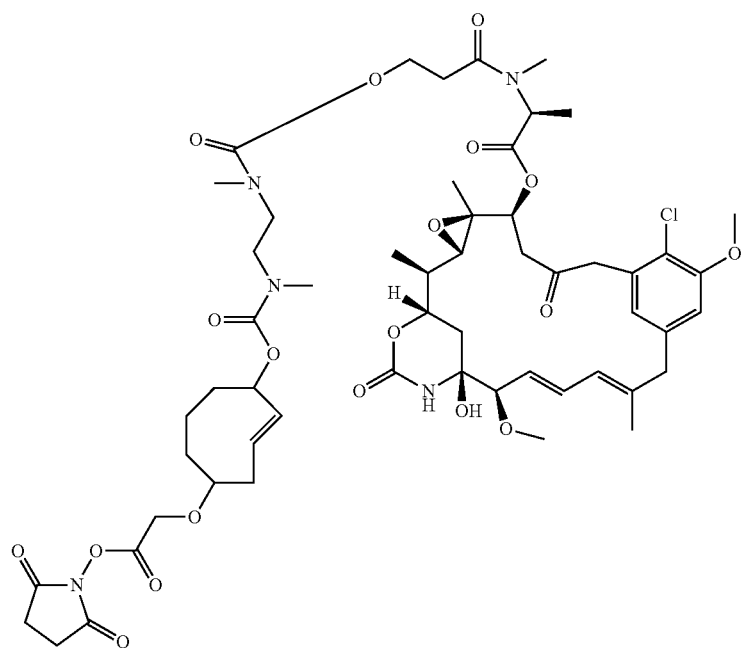

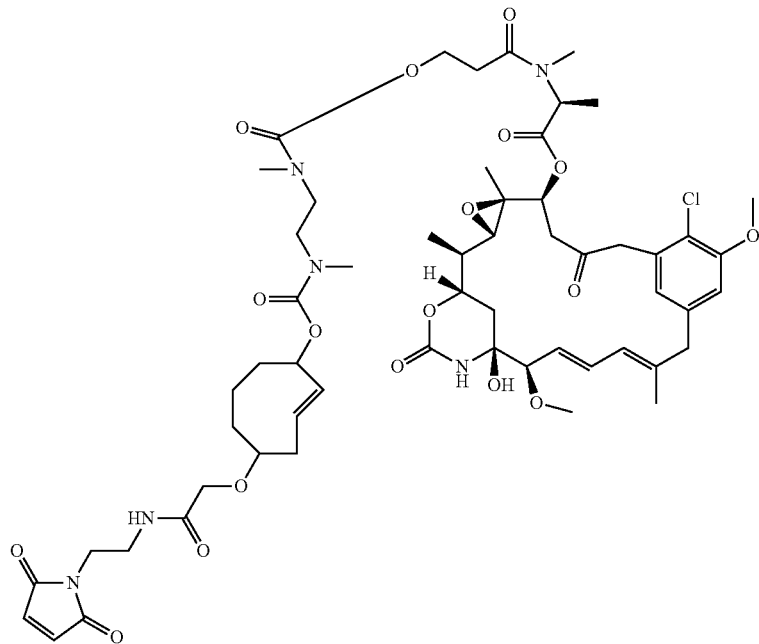
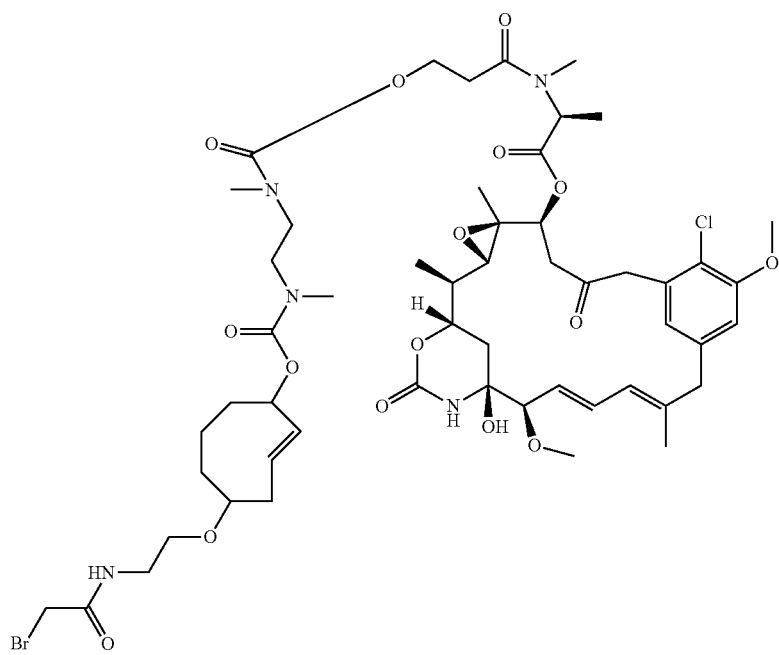

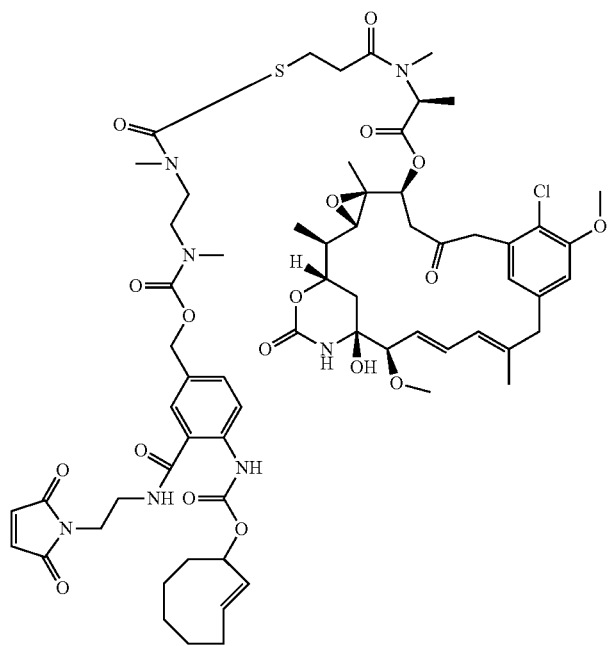
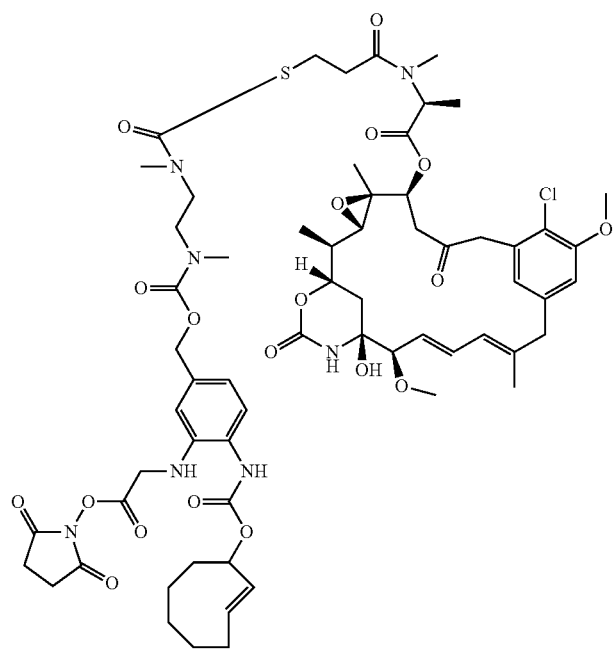

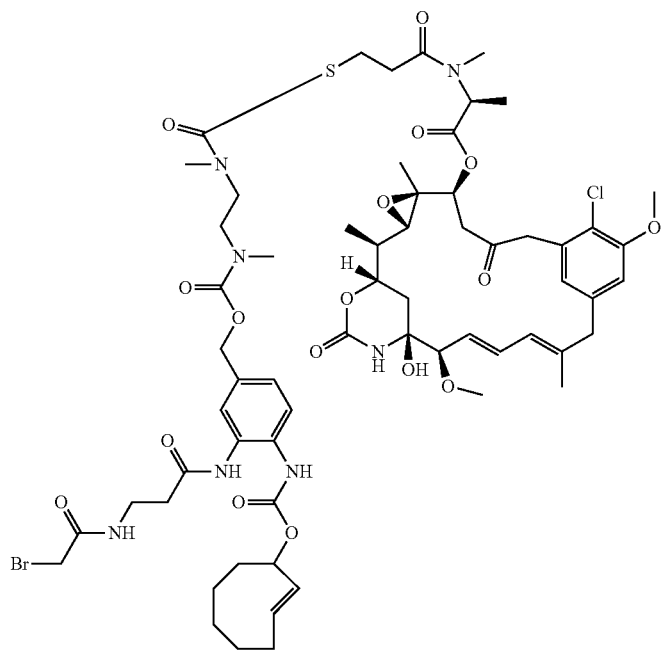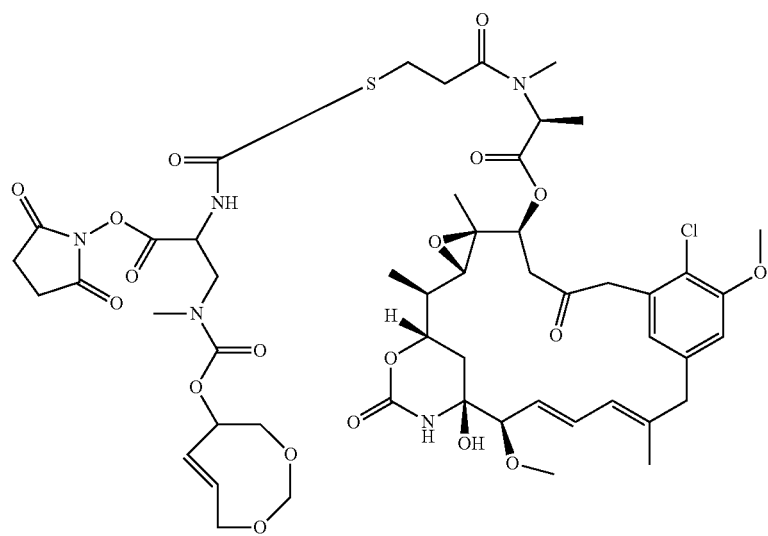

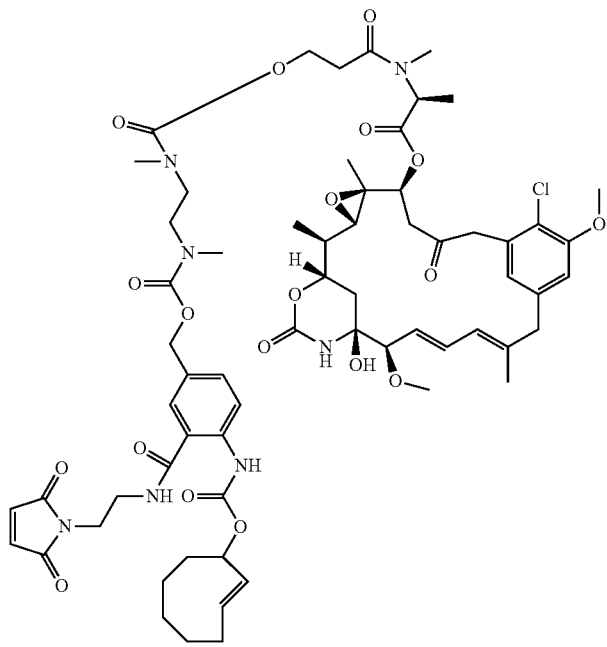
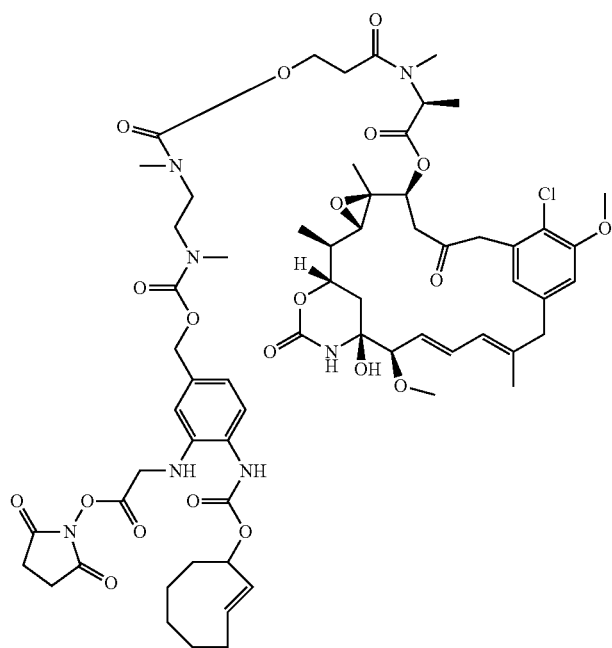

-continued

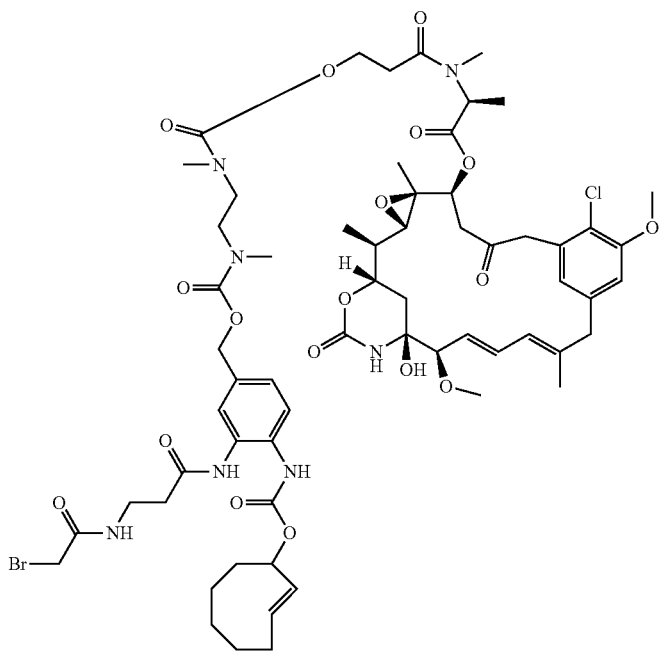

Example 31

Activation of Tumor Bound CC49-Auristatin E Conjugate

CC49 as mAb or mAb fragment binds the non-internalizing pan-solid tumor marker TAG72. After Prodrug administration, tumor binding and clearance from blood, the Activator is injected. The reaction of the Activator with the TCO trigger in the Prodrug results in release of Auristatin E from CC49 (antibody, or antibody fragment), allowing it to penetrate the cancer cell inside which it has its anticancer action.

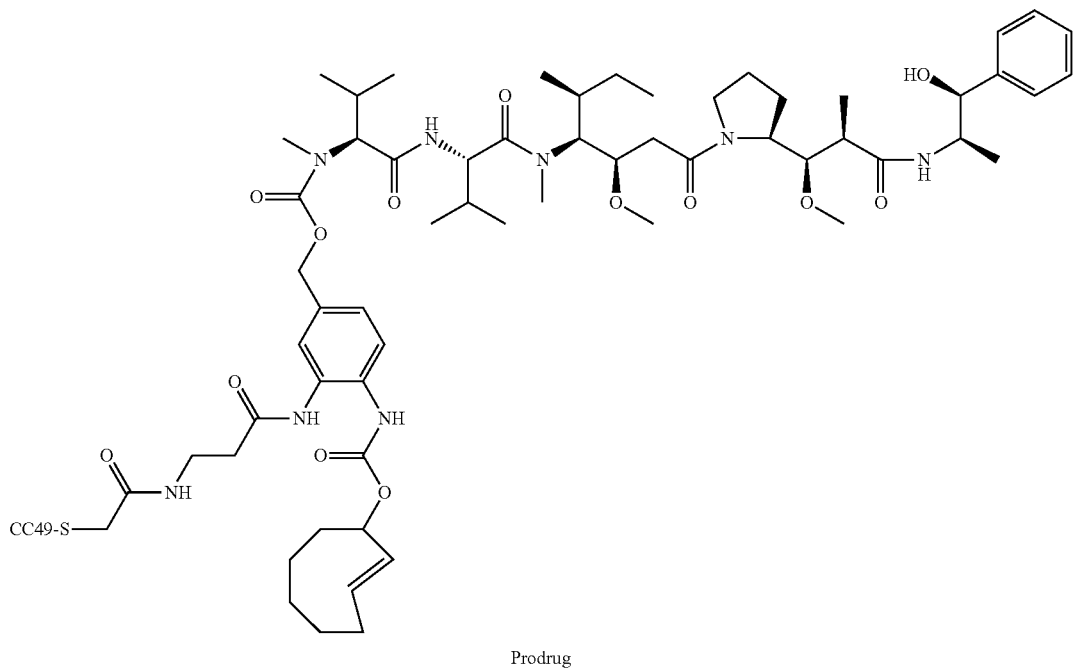
Prodrug
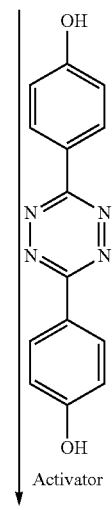
Activator

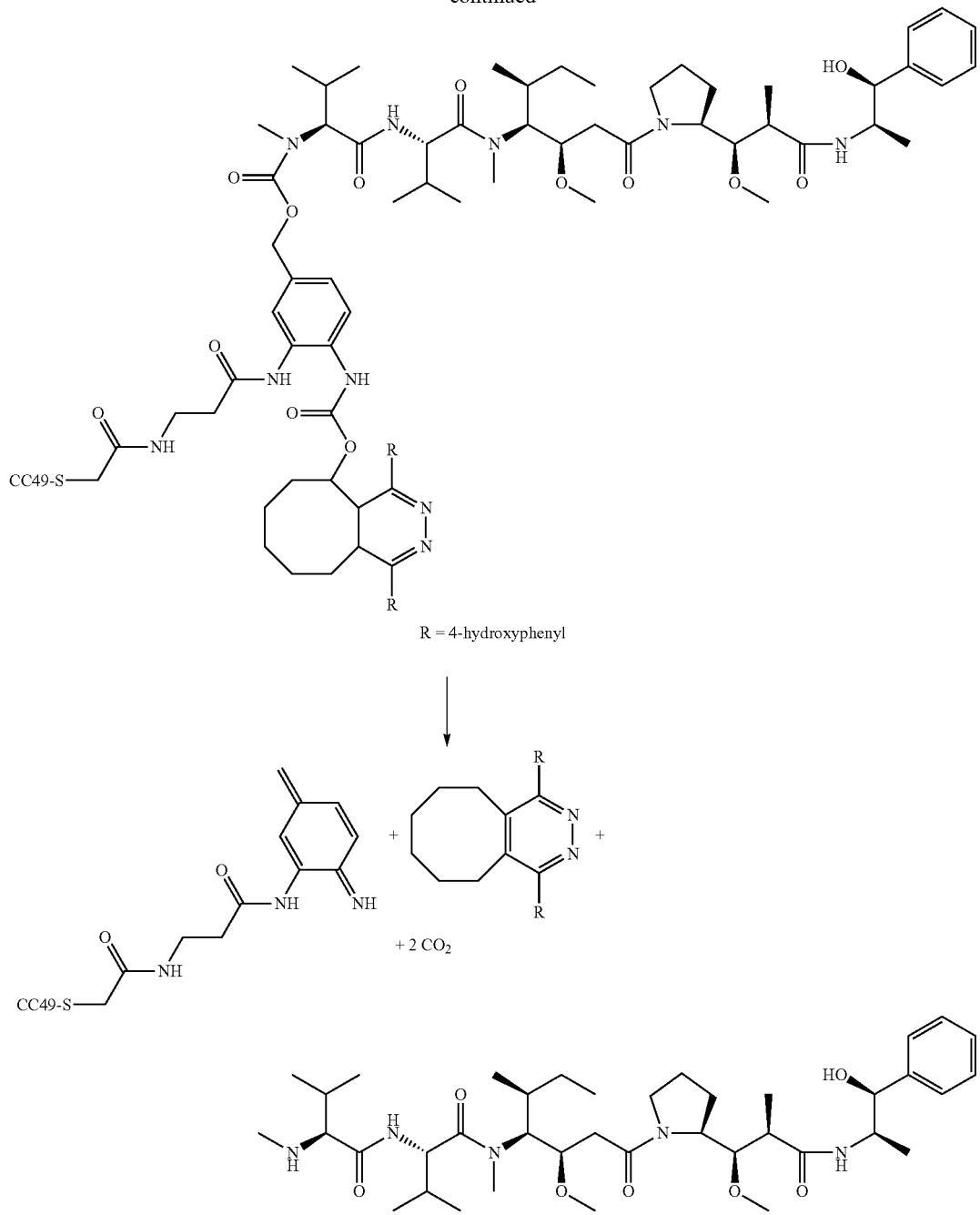

R = 4-hydroxyphenyl

Example 32

Activation of Tumor-Bound T-Cell Engaging Triabody

Figure 5:
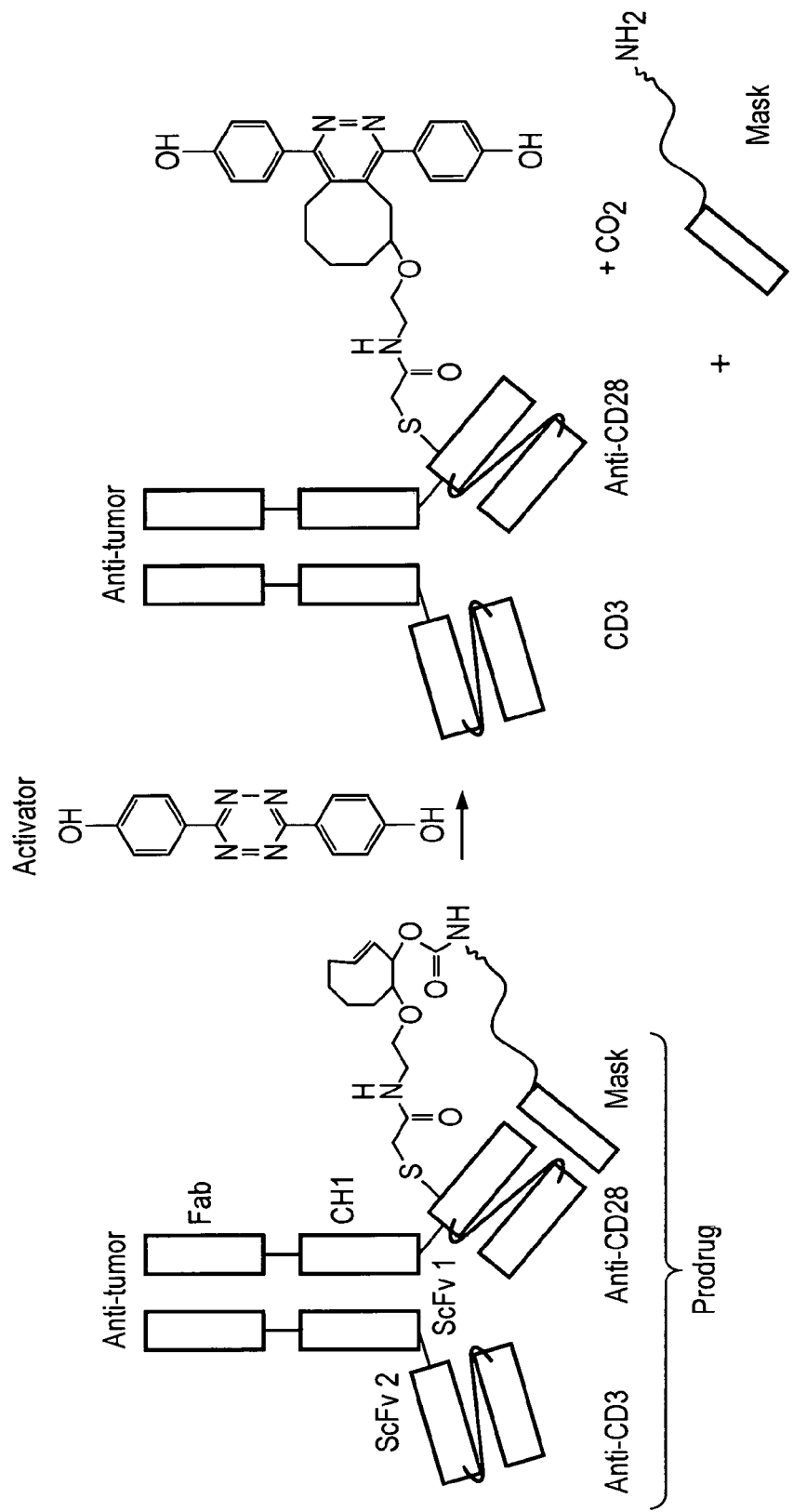
FIG. 5 shows the structure of an embodiment of a triabody prodrug, including a tumor-binding moiety, a CD3 T-cell engaging moiety, and a CD28 T-cell co-stimulatory moiety. The anti-CD28 domain can be blocked by a Masking Moiety $M^M$. After Prodrug administration, tumor binding and clearance from blood, the Activator is injected. The reaction of the Activator with the TCO trigger in the Prodrug results in release of the Masking Moiety from the anti-CD28 domain, enabling CD28 co-stimulation of T-cells, and boosting the T-cell mediated anticancer effect, while avoiding off target toxicity.

FIG. 5 shows the structure of an embodiment of a triabody prodrug, including a tumor-binding moiety, a CD3 T-cell engaging moiety, and a CD28 T-cell co-stimulatory moiety. The anti-CD28 domain can be blocked by a Masking Moiety $M^M$. After Prodrug administration, tumor binding and clearance from blood, the Activator is injected. The reaction of the Activator with the TCO trigger in the Prodrug results in release of the Masking Moiety from the anti-CD28 domain, enabling CD28 co-stimulation of T-cells, and boosting the T-cell mediated anticancer effect, while avoiding off target toxicity.

The triabody comprises a tumor-binding moiety, a CD3 T-cell engaging moiety, and a CD28 T-cell co-stimulatory moiety. As the CD3 and CD28 combined in one molecule will result in unacceptable toxic effect off target, the anti-CD28 domain is blocked by a Masking Moiety $M^M$, a peptide resembling the CD28 binding domain and which has affinity for the anti-CD28 moiety. This peptide is linked through a further peptide or a PEG chain $S^P$ to the TCO trigger which is itself conjugated to a site specifically engineered cysteine. After Prodrug administration, tumor binding and clearance from blood, the Activator is injected. The reaction of the Activator with the TCO trigger in the Prodrug results in release of the Masking Moiety from the anti-CD28 domain enabling CD28 co-stimulation of T-cells, boosting the T-cell mediated anticancer effect, while avoiding off target toxicity.

The invention claimed is:

1. A prodrug kit comprising a prodrug compound and an activator compound, wherein the prodrug compound comprises one or more drug moieties $D^D$ linked to a trigger moiety $T^R$ via a linker $L^D$ according to Formula 1(a), wherein the trigger moiety comprises a dienophile and the activator comprises a diene that reacts with the dienophile to release the drug moieties from the prodrug molecule, wherein the dienophile comprises a trans-cyclooctene ring;

wherein the dienophile comprises a structure according to formula (1a)

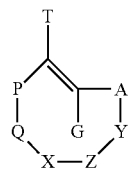

Formula (1a)

wherein A and P are independently $CR^a{}_2$ or $CR^aX^D$, provided that at least one is $CR^aX^D$, wherein $X^D$ is $O-C(O)-(L^D)_n-(D^D)$, $S-C(O)-(L^D)_n-(D^D)$, $O-C(S)-(L^D)_n-(D^D)$, $S-C(S)-(L^D)_n-(D^D)$, $NR^d-C(O)-(L^D)_n-(D^D)$, $NR^d-C(S)-(L^D)_n-(D^D)$, $C(O)-(L^D)_n-(D^D)$, $C(S)-(L^D)_n-(D^D)$, wherein $L^D$ is a linker and n=0 or 1, $D^D$ is the one or more drug moieties;

wherein $L^D$ is selected from

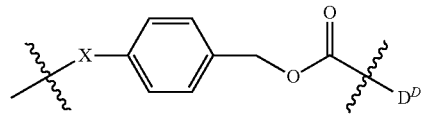

X = O or S or NH with R = alkyl or aryl

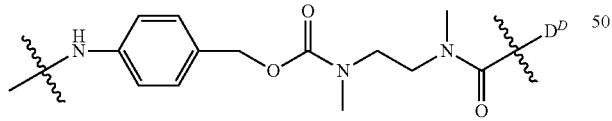

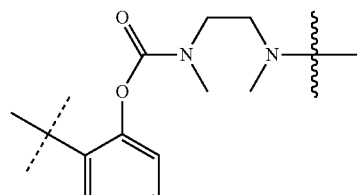

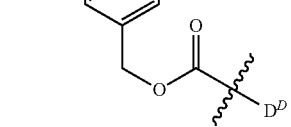

-continued

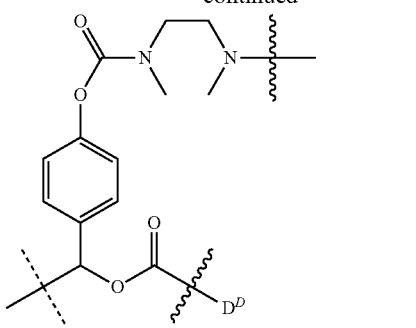

X = O, S, NH

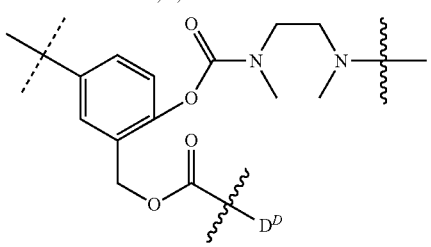

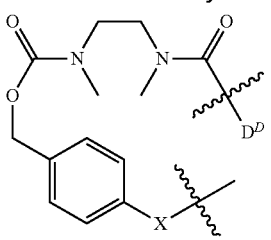

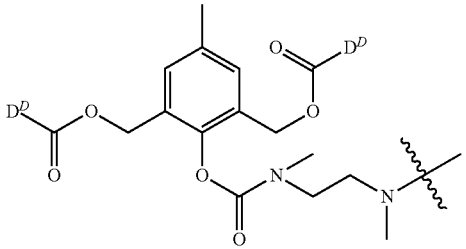

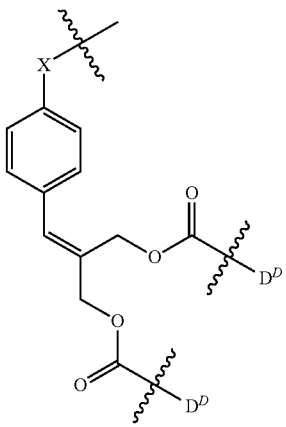

X = O, S, NH

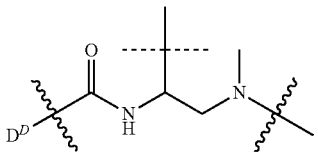

-continued

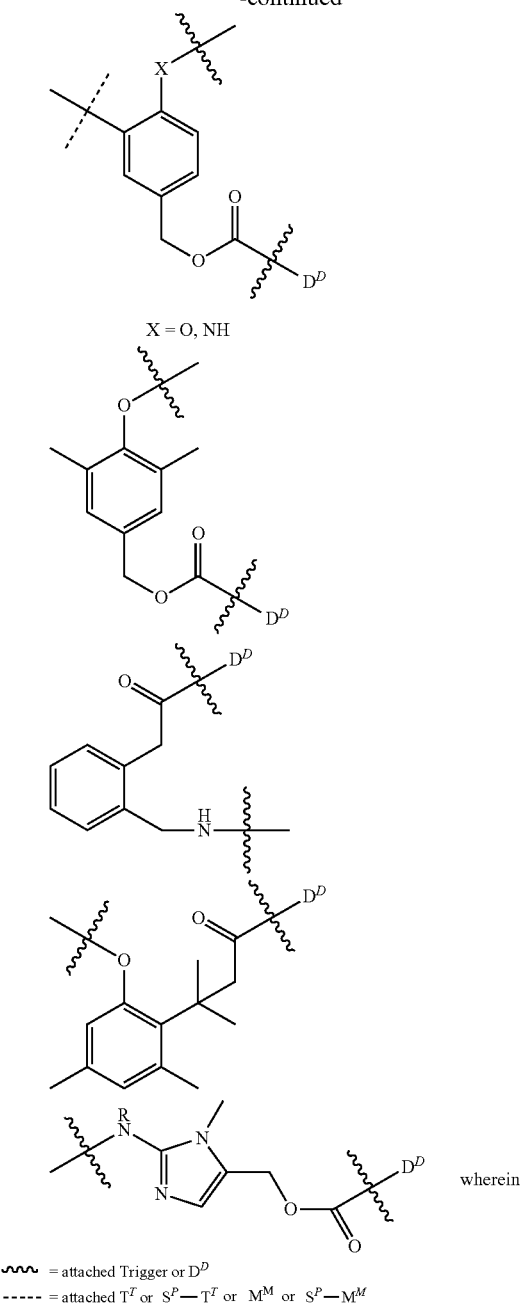

⌇⌇⌇⌇ = attached Trigger or $D^D$
- - - - = attached $T^T$ or $S^P$—$T^T$ or $M^M$ or $S^P$—$M^M$ wherein at least one of the drug $D^D$, the linker $L^D$ and the trigger moiety comprises a targeting agent $T^T$ or a masking moiety $M^M$;

wherein $S^P$ is an alkyl, a polyethylene glycol, a peptide or a polylactide spacer, $T^T$ is an antibody, antibody fragment, protein or peptide targeting agent, and $M^M$ is a protein, peptide, polymer, polyethylene glycol, or carbohydrate masking agent;

wherein T and G are H or a substituent selected from the group consisting of alkyl, F, Cl, Br, and I;

wherein Q, X, Z and Y are $CR^a_2$, $CR^e_2$, $C=CR^a_2$, $C=O$, $C=S$, $C=NR^b$, S, SO, $SO_2$, O, $NR^b$, and $SiR^e_2$, with at most three of Y, Z, X, and Q being selected from the group consisting of $C=CR^a_2$, $C=O$, $C=S$, and $C=NR^b$, wherein two R moieties together may form a ring, and with the proviso that no adjacent pairs of atoms are present selected from the group consisting of O—O, O—$NR^b$, S—$NR^b$, O—S, O—S(O), O—S(O)$_2$, and S—S, and such that Si is only adjacent to $CR^a_2$ or O;

wherein $R^a$ is selected from the group consisting of alkyl, aryl, OR', SR', S(=O)R''', S(=O)$_2$R''', S(=O)$_2$NR'R'', Si—R''', Si—O—R''', OC(=O)R''',SC(=O)R''', OC(=S)R''', SC(=S)R''', F, Cl, Br, I, N$_3$, SO$_2$H, SO$_3$H, SO$_4$H, PO$_3$H, PO$_4$H, NO, NO$_2$, CN, OCN, SCN, NCO, NCS, CF$_3$, CF$_2$—R', NR'R'', C(=O)R', C(=S)R', C(=O)O—R', C(=S)O—R', C(=O)S—R', C(=S)S—R', C(=O)NR'R'', C(=S)NR'R'', NR'C(=O)—R''', NR'C(=S)—R''', NR'C(=O)O—R''', NR'C(=S)O—R''', NR'C(=O)S—R''', NR'C(=S)S—R''', OC(=O)NR'—R''', SC(=O)NR'—R''', OC(=S)NR'—R''', SC(=S)NR'—R''', NR'C(=O)NR''—R''', NR'C(=S)NR''—R''', CR'NR'', with each R' and each R'' independently being H, aryl or alkyl and R''' independently being aryl or alkyl;

wherein each $R^b$ is independently selected from the group consisting of H, alkyl, aryl, O-aryl, O-alkyl, OH, C(=O)NR'R'' with R' and R'' each independently being H, aryl or alkyl, R'CO-alkyl with R' being H, alkyl, and aryl;

wherein each $R^c$ is independently selected from the group consisting of H, alkyl, aryl, O-alkyl, O-aryl, OH;

wherein $R^e$ is selected from the group consisting of H, alkyl, aryl, OR', SR', S(=O)R''', S(=O)$_2$R''', Si—R''', Si—O—R''', OC(=O)R''', SC(=O)R''', OC(=S)R''', SC(=S)R''', F, Cl, Br, I, N$_3$, SO$_2$H, SO$_3$H, PO$_3$H, NO, NO$_2$, CN, CF$_3$, CF$_2$—R', C(=O)R', C(=S)R', C(=O)O—R', C(=S)O—R', C(=O)S—R', C(=S)S—R', C(=O)NR'R'', C(=S)NR'R'', NR'C(=O)—R''', NR'C(=S)—R''', NR'C(=O)O—R''', NR'C(=S)O—R''', NR'C(=O)S—R''', NR'C(=S)S—R''', NR'C(=O)NR''—R''', NR'C(=S)NR''—R''', CR'NR'', with each R' and each R'' independently being H, aryl or alkyl and R''' independently being aryl or alkyl, wherein two or more $R^{a,e,b,c}$ groups can form a ring;

wherein the one or more drug moieties $D^D$ are selected from the group of auristatins, maytansines, calicheamicin, duocarmycins, maytansinoids DM1 and DM4, auristatin MMAE, duocarmycin CC1065, camptothecin, irinotecan SN-38, initomycins, bleomycins, taxanes, lexitropsins, pteridines, diynenes, podophyllotoxins, dolastatins, taxols, methotrexate, methopterin, dichloromethotrexate, 6-mercaptopurine, cytosine arabinoside, melphalan, leurosine, leurosideine, actinomycin, duanorubicin, doxorubicin, mitomycin C, mitomycin A, caminomycin, aminopterin, tallysomycin, etoposide, etoposide phosphate, vinblastine, vincristine, vindesine, taxotere, retinoic acid, butyric acid, N8-acetyl spermidine, and esperamicin;

wherein the activator comprises a diene selected from the dienes according to Formula 4

Formula 4

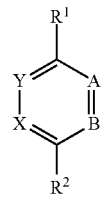

wherein R¹ and R² each independently are selected from the group consisting of H, alkyl, aryl, CF₃, CF₂—R', NO, NO₂, OR', SR', CN, C(=O)R', C(=S)R', OC(=O)R''', SC(=O)R''', OC(=S)R''', SC(=S)R''', S(=O)R', S(=O)₂R''', S(=O)₂OR', PO₃R'R'', S(=O)₂NR'R'', C(=O)O—R', C(=O)S—R', C(=S)O—R', C(=S)S—R', C(=O)NR'R'', C(=S)NR'R'', NR'R'', NR'C(=O)R'', NR'C(=S)R'', NR'C(=O)OR'', NR'C(=S)OR'', NR'C(=O)SR'', NR'C(=S)SR'', OC(=O)NR'R'', SC(=O)NR'R'', OC(=S)NR'R'', SC(=S)NR'R'', NR'C(=O)NR''R'', NR'C(=S)NR''R'' with each R' and each R'' independently being H, aryl or alkyl, and R''' independently being aryl or alkyl; wherein A is N; B is N; X is N; and Y is N.

2. A prodrug kit according to claim 1, wherein the dienophile is selected from the following structures:

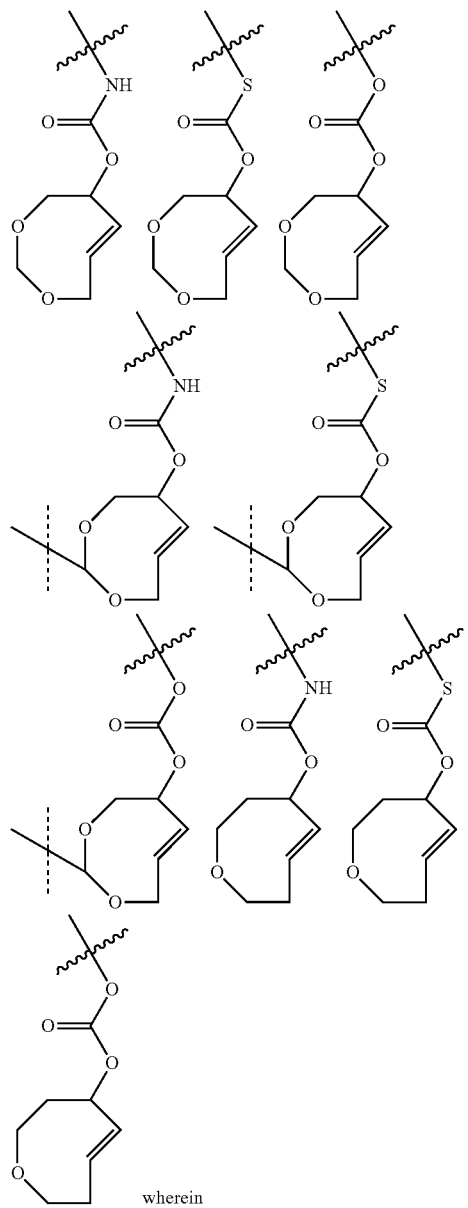

wherein
〜 = attached Trigger or D^D
---- = attached T^T or S^P—T^T or M^M or S^P—M^M.

3. A prodrug kit according to claim 1, wherein the diene is selected from the group consisting of:

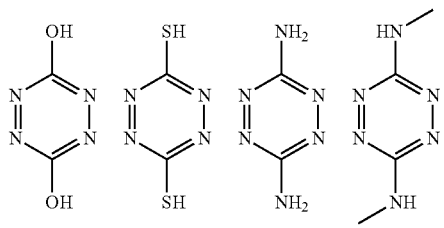

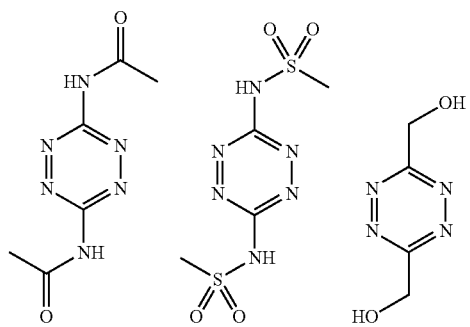

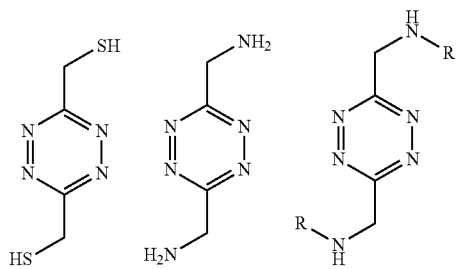

both R = methyl, or
both R = ethyl, or
both R = phenyl

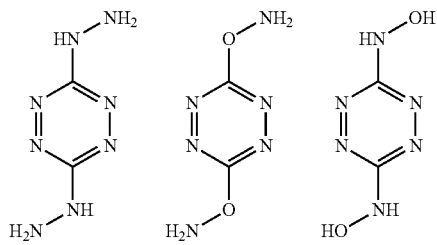

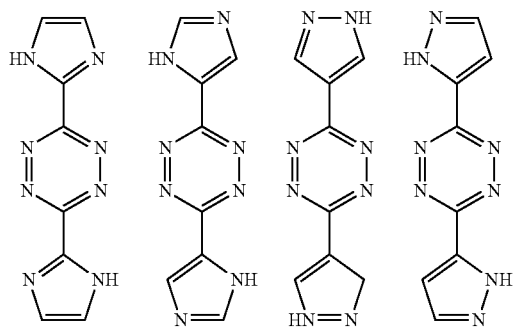

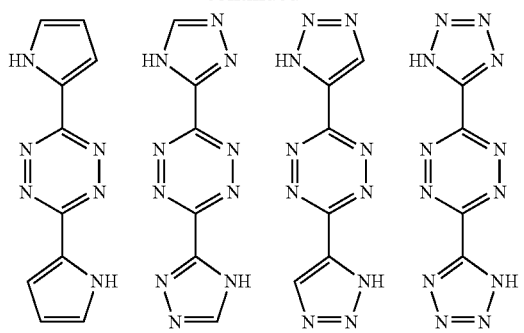
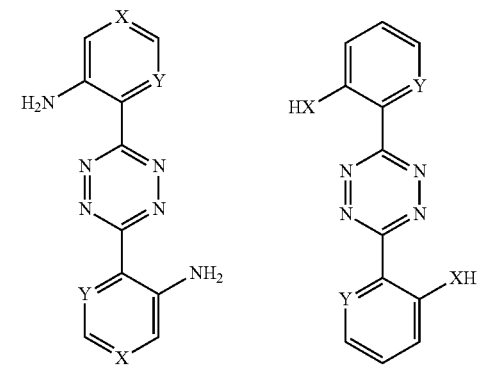

both Y = C and both X = C, or
both Y = C and both X = N, or
both Y = N and both X = C, or
both Y = N and both X = N both X = O and both Y = C, or
both X = O and both Y = N, or
both X = S and both Y = C, or
both X = S and both Y = N

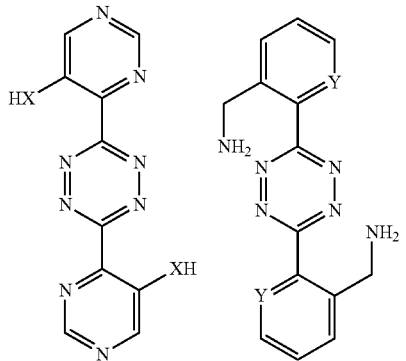

both X = O, or
both X = S both Y = C, or
both Y = N

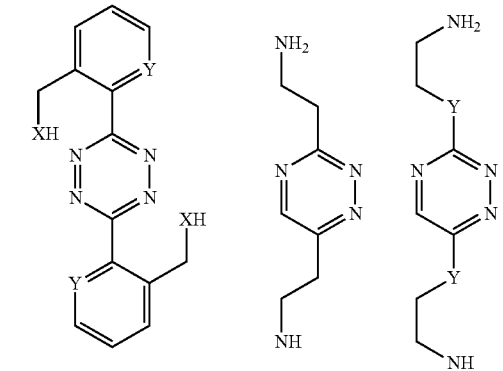

both X = O and both Y = C, or
both X = O and both Y = N, or
both X = S and both Y = C, or
both X = S and both Y = N both Y = O, or
both Y = S

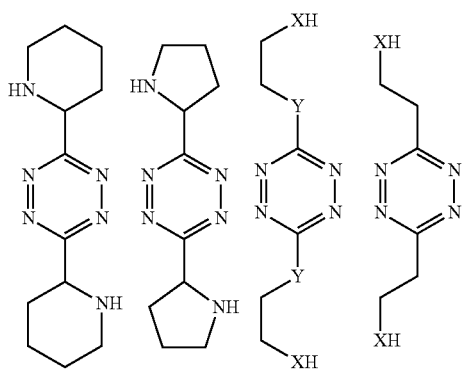
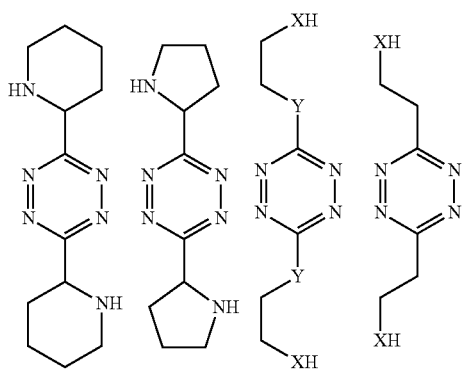

both X = O and both Y = O, or
both X = O and both Y = S, or
both X = S and both Y = O, or
both X = S and both Y = S

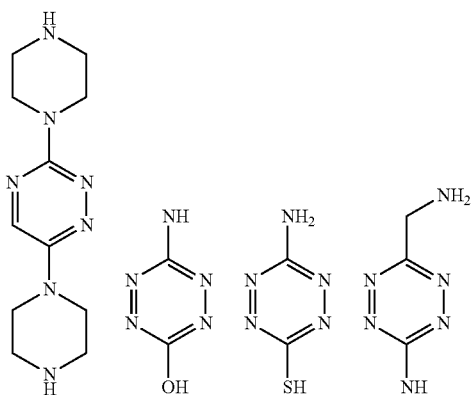
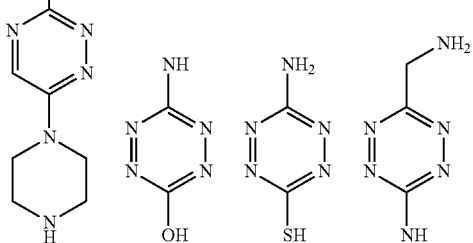

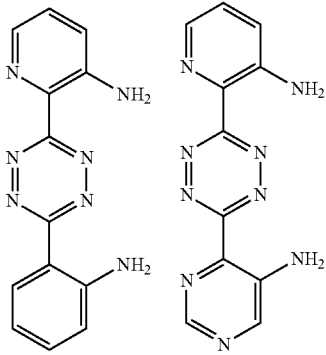
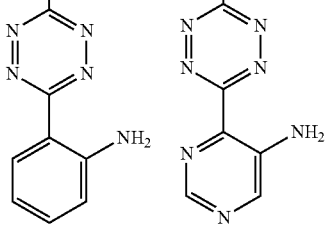

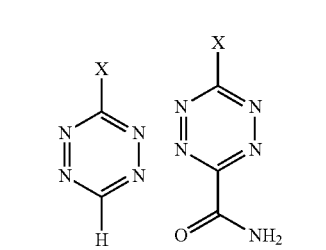
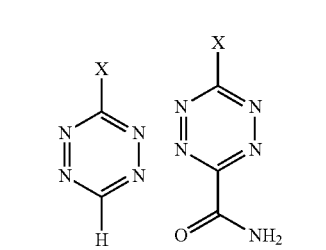

For all structures:
X = NH$_2$, or X = OH, or X = SH, or
X = CH$_2$NH$_2$, or X = 2,5-imidazyl, or
X = 2-aminophenyl, or X = (CH$_2$)$_2$—NH$_2$

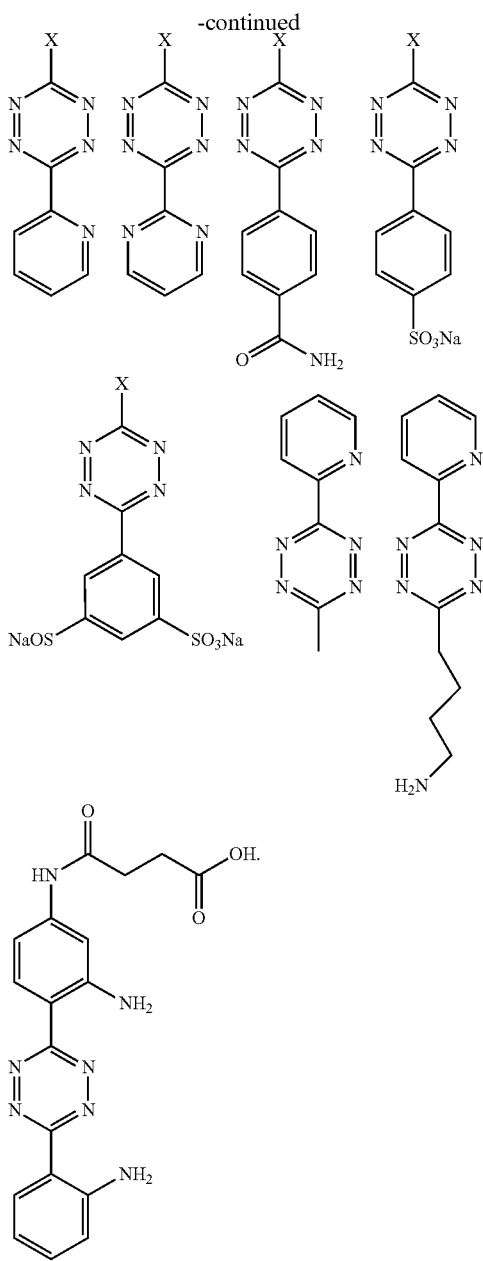

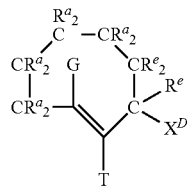

Formula (1b)

4. A prodrug kit according to claim 3, wherein the dienophile has the formula (1b):

wherein, in addition to the presence of zero to two exocyclic bonds fixed in the same plane, each $R^a$ independently denotes H, or, in at most four instances, a substituent selected from the group consisting of alkyl, aryl, OR', SR', S(=O)R''', S(=O)$_2$R''', S(=O)$_2$NR'R'', Si—R''', Si—O—R''', OC(=O)R''', SC(=O)R''', OC(=S)R''', SC(=S)R''', F, Cl, Br, I, N$_3$, SO$_2$H, SO$_3$H, SO$_4$H, PO$_3$H, PO$_4$H, NO, NO$_2$, CN, OCN, SCN, NCO, NCS, CF$_3$, CF$_2$—R', NR'R'', C(=O)R', C(=S)R', C(=O)O—R', C(=S)O—R', C(=O)S—R', C(=S)S—R', C(=O)NR'R'', C(=S)NR'R'', NR'C(=O)—R''', NR'C(=S)—R''', NR'C(=O)O—R''', NR'C(=S)O—R''', NR'C(=O)S—R''', NR'C(=S)S—R''', OC(=O)NR'—R''', SC(=O)NR'—R''', OC(=S)NR'—R''', SC(=S)NR'—R''', NR'C(=O)NR''—R''', NR'C(=S)NR''—R''', CR'NR'', with each R' and each R'' independently being H, aryl or alkyl and R''' independently being aryl or alkyl;

each $R^e$ as above indicated is independently selected from the group consisting of H, alkyl, aryl, OR', SR', S(=O)R''', S(=O)$_2$R''', Si—R''', Si—O—R''', OC(=O)R''', SC(=O)R''', OC(=S)R''', SC(=S)R''', F, Cl, Br, I, N$_3$, SO$_2$H, SO$_3$H, PO$_3$H, NO, NO$_2$, CN, CF$_3$, CF$_2$—R', C(=O)R', C(=S)R', C(=O)O—R', C(=S)O—R', C(=O)S—R', C(=S)S—R', C(=O)NR'R'', C(=S)NR'R'', NR'C(=O)—R''', NR'C(=S)—R''', NR'C(=O)O—R''', NR'C(=S)O—R''', NR'C(=O)S—R''', NR'C(=S)S—R''', NR'C(=O)NR''—R''', NR'C(=S)NR''—R''', CR'NR'', with each R' and each R'' independently being H, aryl or alkyl and R''' independently being aryl or alkyl: wherein two $R_{a,e}$ moieties together may form a ring;

with one $R^{a,e}$ comprised in a linker moiety to a targeting agent $T^T$ or a masking moiety $M_M$ and wherein T and G each independently denote H, or a substituent selected from the group consisting of alkyl, F, Cl, Br, and I, and $X^D$ is as defined above for formula (1a).

* * * * *